United States Patent
Ombrato et al.

(10) Patent No.: US 10,221,144 B2
(45) Date of Patent: Mar. 5, 2019

(54) ANTIBACTERIAL COMPOUNDS HAVING BROAD SPECTRUM OF ACTIVITY

(71) Applicant: AZIENDE CHIMICHE RIUNITE ANGELINI FRANCESCO A.C.R.A.F. S.p.A., Rome (IT)

(72) Inventors: Rosella Ombrato, Rome (IT); Barbara Garofalo, Rome (IT); Giorgina Mangano, Rome (IT); Alessandra Capezzone De Joannon, Rome (ID); Gaia Corso, Rome (IT); Claudia Cavarischia, Rome (IT); Guido Furlotti, Rome (IT); Tommaso Iacoangeli, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 15/533,594

(22) PCT Filed: Dec. 14, 2015

(86) PCT No.: PCT/EP2015/079528
§ 371 (c)(1),
(2) Date: Jun. 6, 2017

(87) PCT Pub. No.: WO2016/096686
PCT Pub. Date: Jun. 23, 2016

(65) Prior Publication Data
US 2017/0369450 A1    Dec. 28, 2017

(30) Foreign Application Priority Data
Dec. 17, 2014 (EP) .................................... 14198414

(51) Int. Cl.
| | | |
|---|---|---|
| *C07C 241/04* | (2006.01) |
| *C07D 241/04* | (2006.01) |
| *C07D 401/14* | (2006.01) |
| *C07D 405/14* | (2006.01) |
| *C07D 413/14* | (2006.01) |
| *C07D 471/04* | (2006.01) |
| *C07D 491/04* | (2006.01) |
| *C07D 493/04* | (2006.01) |
| *C07D 495/04* | (2006.01) |
| *C07D 497/04* | (2006.01) |
| *A61K 31/496* | (2006.01) |
| *C07D 211/94* | (2006.01) |
| *C07D 211/96* | (2006.01) |

(52) U.S. Cl.
CPC .......... *C07D 241/04* (2013.01); *A61K 31/496* (2013.01); *C07D 211/94* (2013.01); *C07D 211/96* (2013.01); *C07D 401/14* (2013.01); *C07D 405/14* (2013.01); *C07D 413/14* (2013.01); *C07D 471/04* (2013.01); *C07D 491/04* (2013.01); *C07D 493/04* (2013.01); *C07D 495/04* (2013.01); *C07D 497/04* (2013.01)

(58) Field of Classification Search
CPC .. C07D 241/04; C07D 211/94; C07D 211/96; C07D 401/14; C07D 405/14; C07D 413/14; C07D 471/04; C07D 491/04; C07D 493/04; C07D 497/04; A61K 31/496

See application file for complete search history.

(56) References Cited

U.S. PATENT DOCUMENTS

| | | | | |
|---|---|---|---|---|
| 2,679,481 A | * | 5/1954 | White ...................... C10M 1/08 252/401 |
| 3,585,193 A | * | 6/1971 | Renier .................. C07D 239/24 544/212 |
| 3,859,438 A | * | 1/1975 | Renth ................... A61K 31/495 514/254.11 |
| 3,928,358 A | * | 12/1975 | Renth ................ C07D 295/084 544/377 |
| 4,831,031 A | * | 5/1989 | Lowe, III ............. C07D 209/34 514/252.17 |
| 4,883,795 A | * | 11/1989 | Lowe, III ............. C07D 209/34 514/252.15 |
| 5,034,401 A | * | 7/1991 | Frost .................... C07D 401/06 514/212.02 |
| 5,294,619 A | * | 3/1994 | Nagel .................. C07D 211/14 514/259.41 |
| 5,767,128 A | * | 6/1998 | Guillaumet .......... C07D 471/04 514/228.2 |
| 6,008,352 A | * | 12/1999 | Chen .................... C07D 405/12 544/363 |
| 6,127,373 A | * | 10/2000 | Chappell .............. A61K 31/495 514/249 |

(Continued)

FOREIGN PATENT DOCUMENTS

| | | | | | |
|---|---|---|---|---|---|
| DE | 2429253 | A1 * | 1/1976 | ......... | C07D 205/085 |
| EP | 0281309 | A1 * | 9/1988 | ........... | C07D 209/34 |

(Continued)

OTHER PUBLICATIONS

CAS Abstract and Indexed Compounds U.S. Pat. No. 3,859,438 (1975).*

(Continued)

*Primary Examiner* — Alexander R Pagano
(74) *Attorney, Agent, or Firm* — Oblon, McClelland, Maier & Neustadt, L.L.P.

(57) ABSTRACT

The present invention relates to novel antibacterial compounds, pharmaceutical compositions containing them and their use as antimicrobials.

11 Claims, No Drawings

(56) References Cited

U.S. PATENT DOCUMENTS

| | | | | |
|---|---|---|---|---|
| 6,245,766 B1* | 6/2001 | Watsky | ............... | A61K 31/496 514/253.03 |
| 6,472,391 B2* | 10/2002 | Matsuno | ............... | A61K 31/496 514/218 |
| 6,921,821 B2* | 7/2005 | Blackburn | ............ | C07D 401/14 540/364 |
| 8,193,203 B2* | 6/2012 | Beard | ................. | C07D 401/12 514/266.1 |
| 8,680,114 B2* | 3/2014 | Mitchell | .............. | C07D 237/28 514/311 |
| 2005/0004137 A1* | 1/2005 | Romano | .............. | A61K 31/496 514/253.07 |
| 2009/0076274 A1* | 3/2009 | Bertani | ................ | C07D 265/36 544/363 |
| 2012/0040957 A1 | 2/2012 | Gaucher et al. | | |
| 2012/0115899 A1 | 5/2012 | Alemparte-Gallardo et al. | | |
| 2014/0221348 A1 | 8/2014 | Gaucher et al. | | |
| 2015/0051188 A1 | 2/2015 | Hubschwerlen et al. | | |
| 2015/0080373 A1 | 3/2015 | Gaucher et al. | | |
| 2017/0368017 A1* | 12/2017 | Ombrato | ................ | A61K 31/33 |

FOREIGN PATENT DOCUMENTS

| | | |
|---|---|---|
| WO | WO 96/10568 A1 | 4/1996 |
| WO | WO 02/072572 A1 | 9/2002 |
| WO | WO 2006/014580 A1 | 2/2006 |
| WO | WO 2006/021448 A1 | 3/2006 |
| WO | WO 2006/105289 A1 | 10/2006 |
| WO | WO-2008020306 A2 * 2/2008 ........... A61K 31/496 | |
| WO | WO 2008/139288 A2 | 11/2008 |
| WO | WO 2008/139288 A3 | 11/2008 |
| WO | WO 2010/081874 A1 | 7/2010 |
| WO | WO 2010/084152 A1 | 7/2010 |
| WO | WO 2012/003418 A2 | 1/2012 |
| WO | WO 2012/003418 A3 | 1/2012 |
| WO | WO 2012/012391 A2 | 1/2012 |
| WO | WO 2012/012391 A3 | 1/2012 |
| WO | WO 2013/068948 A1 | 5/2013 |
| WO | WO 2013/080156 A1 | 6/2013 |

OTHER PUBLICATIONS

P.R. Kym et al., 48 Journal of Medicinal Chemistry, 5888-5891 (2005).*

K.E. Hamlin et al., 71 Journal of the American Chemical Society, 2734-2736 (1949).*

G. Regnier et al., 11 Journal of Medicinal Chemistry, 1151-1155 (1968).*

International Search Report dated Feb. 15, 2016 in PCT/EP2015/079528.

George A. Jacoby, "Mechanisms of Resistance to Quinolones" CID, 2005:41, Suppl. 2, 2005, pp. S120-S126.

Mark J. Mitton-Fry, et al., "Novel Quinoline Derivatives as Inhibitors of Bacterial DNA Gyrase and Topoisomerase IV" Bioorganic 8 Medicinal Chemistry Letters, 23, 2010, pp. 2955-2961.

Jean-Philippe Surivet, et al., "Design, Synthesis, and Characterization of Novel Tetrahydropyran-Based Bacterial Topoisomerase Inhibitors with Potent Anti-Gram-Positive Activity" Journal of Medicinal Chemistry, 56, 2013, pp. 7396-7415.

Francis Blache, et al. "Differential Behaviors of *Staphylococcus aureus* and *Escherichia coli* Type II DNA Topoisomerases", Antimicrobial Agents Chemotherapy, vol. 40, No. 12, Dec. 1996, pp. 2714-2720.

* cited by examiner

ANTIBACTERIAL COMPOUNDS HAVING BROAD SPECTRUM OF ACTIVITY

CROSS REFERENCE TO RELATED APPLICATIONS

This application is a 371 of International Patent Application No. PCT/EP2015/079528, filed on Dec. 14, 2015, and claims priority to European Patent Application No. 14198414.6, filed on Dec. 17, 2014, both of which are incorporated herein by reference in their entireties.

FIELD OF THE INVENTION

The present invention relates to novel antibacterial compounds, pharmaceutical compositions containing them and their use as antimicrobials.

BACKGROUND OF THE INVENTION

DNA topoisomerases are enzymes involved in the modification of the DNA-supercoiling during replication or transcription. These enzymes bind to single-stranded or double-stranded DNA and cut the phosphate backbone of the DNA such that the DNA strand is untangled or unwound. At the end of the replication or transcription processes, the enzymes themselves reseal the DNA backbone.

DNA topoisomerases are classified as type I when cut a single strand of a DNA double helix and as type II when cut both strands of a DNA double helix.

Bacterial type II topoisomerases comprise DNA gyrase and topoisomerase IV (TopoIV), which are heterotetrameric enzymes concurrently present in almost all the prokaryotic cells. Both the enzymes are necessary for DNA replication and, hence, for bacterial cell growth and division.

Bacterial type II topoisomerases are a proven antibacterial target, in particular of compounds belonging to fluoroquinolone class.

Fluoroquinolones are broad-spectrum antibacterial drugs that play an important role in treatment of bacterial infections, especially hospital-acquired infections and infections in which resistance to other classes of antibacterial drugs is suspected. Fluoroquinolones act by inhibiting the DNA gyrase in Gram negative bacteria and the topoisomerase IV in Gram positive bacteria.

However, resistance to fluoroquinolones emerged in recent years due to mutations that altered either the active site of the drug targets DNA gyrase and topoisomerase IV or the drug accumulation. In addition, resistance to quinolones can be mediated by plasmids that produce the Qnr protein, which protects the quinolone targets from inhibition (G. A. Jacoby, CID, 2005:41, Suppl. 2, SD120-S126).

According to the World Health Organization, the antimicrobial resistance (AMR) is the resistance of a microorganism to an antimicrobial drug to which it was originally sensitive. Resistant bacteria are able to withstand attack by antibiotics and antibacterial drugs, so that standard treatments become ineffective and infections persist increasing risk of spread to others.

Mitton-Fry M. J. et al. (Bioorg. Med. Chem. Lett., 23, 2010, 2955-2961) developed novel quinolone derivatives as inhibitors of bacterial DNA gyrase and topoisomerase IV. Given the importance of stepwise target mutations in the clinical history of fluoroquinolones resistance, the authors felt strongly that providing inhibition of TopoIV alongside DNA gyrase was critically important. According to the authors, such dual-targeting activity should slow the rate of resistance emergence in the clinic, since organism which mutate DNA gyrase to avoid inhibition would still be susceptible to killing via TopoIV inhibition.

Surivet J. P. et al. (J. Med. Chem. 2013, 56, 7396-7415) reported the design of novel bacterial dual DNA gyrase and TopoIV inhibitors comprising a tetrahydropyran core and demonstrated that dual inhibition of DNA gyrase and TopoIV is required to minimize the rate of resistance development.

WO 2006/105289 relates to heterocyclic compounds, more particularly pyrazole compounds, which were tested for inhibition of both DNA gyrase and topoisomerase IV.

WO 02/072572, WO 2006/021448, WO 2008/139288, WO 2010/081874, WO 2010/084152, WO 2013/068948 and WO 2013/080156 disclose heterocyclic compounds endowed with antimicrobial activity.

WO 96/10568 and WO 2012/003418 disclose heterocyclic compounds endowed with other therapeutic activity.

SUMMARY OF THE INVENTION

The Applicant recognized that there is a strong and continuous need for antibacterial drugs that overcome the problem of resistant bacteria.

The Applicant faced the problem to develop new antibacterial compounds that allow to overcome the problem of antibacterial resistance.

More in particular, the Applicant faced the problem to develop new antibacterial compounds capable of concurrently inhibit bacterial type II topoisomerases, i.e. DNA gyrase and topoisomerase IV.

Also, the Applicant faced the problem to develop new antibacterial compounds having broad spectrum of activity, i.e. useful against Gram positive and/or Gram negative bacteria.

Thus, in a first embodiment, the present invention relates to a compound of formula (I):

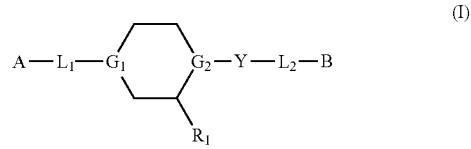

wherein $G_1$ and $G_2$, identical or different each other, are CH or N, provided that at least one of $G_1$ and $G_2$ is N;

$R_1$ is hydrogen atom, halogen atom, OH, $(C_{1-3})$alkyl, $(C_{1-3})$alkoxy, $(C_{1-3})$alkyl-OH, —COOR' or —CONR'R", wherein R' and R", identical or different each other, are hydrogen atom or $(C_{1-3})$alkyl;

$L_1$ is a σ bond, —$CH_2$—, —O— or —NH—;

Y is $(C_{1-6})$alkylenyl group, —NH—$(C_{1-6})$alkylenyl group or $(C_{4-5})$cycloalkylenyl group, said group being optionally substituted with a hydroxy group or an amino group or a formamido group (—NH—CHO);

$L_2$ is σ bond, —NH— or —NH—$(C_{1-6})$alkylenyl;

A is a fused bicyclic group having one of the following formulae (II) and (III)

(II)

(III)

wherein $G_3$ is N or C(R'), wherein R' is H or $(C_{1-3})$alkyl;

$G_4$, $G_5$, and $G_6$ identical or different each other, are CH, CF, C—CN, or N, $R_2$ is hydrogen atom, halogen atom, hydroxy, cyano, $(C_{1-3})$alkyl, $(C_{1-3})$alkoxy, $CF_3$, $OCF_3$ or NR'R", wherein R' and R", identical or different each other, are hydrogen atom or $(C_{1-3})$alkyl; and $R_3$ is hydrogen atom, halogen atom, hydroxy, cyano, $(C_{1-3})$alkyl, $(C_{1-3})$alkoxy, trifluoromethyl or NR'R", wherein R' and R" are hydrogen atom or $(C_{1-3})$alkyl;

and

B is a fused bicyclic group having one of the following formulae (IV), (V) and (VI), or a fused tricyclic group having the following formula (VII):

(IV)

(V)

(VI)

(VII)

wherein $P_1$ is N or CR', wherein R' is H, CN or $CF_3$;

$P_2$ is O, S, $SO_2$ or C(R')(R") wherein R' and R", identical or different each other, are hydrogen atom or $(C_{1-3})$alkyl;

$R_4$ and $R_5$ together form a 3- to 7-membered aromatic or aliphatic ring, optionally comprising at least one heteroatom selected from N, O and S;

n is 0 or 1; and $R_6$ is hydrogen atom, halogen atom, $CF_3$, hydroxy or NR'R". wherein R' and R", identical or different each other, are hydrogen atom or $(C_{1-3})$alkyl;

and salts of addition with pharmaceutically acceptable organic or inorganic acids or basis, enantiomers, N-oxides and quaternary ammonium salts of said compound of formula (I).

In a second embodiment, the present invention relates to a pharmaceutical composition comprising at least one compound of formula (I).

In a third embodiment, the present invention relates to the compounds of formula (I) for use in medicine.

In a fourth embodiment, the present invention relates to the compounds of formula (I) for use in the treatment of bacterial infections.

In a fifth embodiment, the present invention relates to a method for treating a bacterial infection, comprising the administration of a compound of formula (I) to a patient in need thereof.

According to a preferred aspect of the present invention, G3 is N, C(H) or $C(CH_3)$.

Preferably, $R_3$ is hydrogen atom, halogen atom, cyano, $(C_{1-3})$alkyl or NR'R", wherein R' and R" are hydrogen atom or $(C_{1-3})$alkyl.

More preferably, $R_3$ is hydrogen atom, F, Cl, cyano, $CH_3$, $NH_2$ or $N(CH_3)_2$.

Advantageously, $L_1$ is a σ bond or —NH—.

Preferably, $R_1$ is hydrogen atom, fluorine atom, chloride atom, OH, $(C_{1-3})$alkyl-OH, —COOR' or —CON(R')(R"), wherein R' and R", identical or different each other, are hydrogen atom or $(C_{1-3})$alkyl.

More preferably, $R_1$ is H, fluorine atom, OH, —$CH_2OH$, —$COOC_2H_5$ or —$CONH_2$.

Preferably, $R_2$ is hydrogen atom, halogen atom, hydroxy, cyano, $(C_{1-3})$alkyl, $(C_{1-3})$alkoxy, $OCF_3$, or NR'R", wherein R' and R", identical or different each other, are hydrogen atom or $(C_{1-3})$alkyl.

More preferably, $R_2$ is hydrogen atom, F, Cl, cyano, $CH_3$, $OCH_3$, $NH_2$ or $N(CH_3)_2$.

Preferably, Y is $(C_{1-4})$alkylenyl group, —NH—$(C_{1-4})$alkylenyl group or $(C_{4-5})$cycloalkylenyl group, said group being optionally substituted with one hydroxy group or an amino group.

More preferably, Y is $(C_{1-3})$alkylenyl group, —NH—$(C_{1-3})$alkylenyl group or $(C_{4-5})$cycloalkylenyl group, said group being optionally substituted with one hydroxy group or an amino group.

Preferably, $L_2$ is σ bond, —NH— or —NH—$(C_{1-3})$alkylenyl.

More preferably, $L_2$ is σ bond, —NH— or —NH—$CH_2$—.

Preferably, $P_2$ is O, S, $SO_2$ or $CH_2$.

Preferably, $R_4$ and $R_5$ together form a 5- or 6-membered aromatic or aliphatic ring, optionally comprising at least one heteroatom selected from N, O and S, wherein said ring optionally bears an oxo group.

More preferably, $R_4$ and $R_5$ together form a 5-membered ring comprising at least one heteroatom selected from N, O or S and optionally substituted with a keto group.

More preferably, $R_4$ and $R_5$ together form a 6-membered ring selected from benzene or pyridine.

Preferably, $R_6$ is hydrogen atom or halogen atom.

More preferably, $R_6$ is hydrogen atom, F or Cl.

According to a preferred aspect of the present invention, A is a fused bicyclic ring having one of the following formulas:

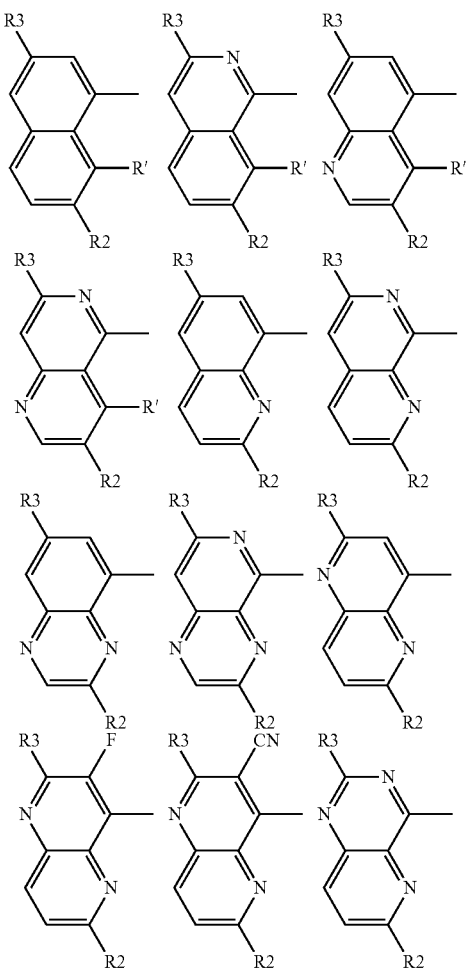

wherein R' is H or $(C_{1-3})$alkyl and $R_2$ and $R_3$ have the meaning explained above.

According to a preferred aspect of the present invention, B is a fused bicyclic or tricyclic group having one of the following formulae:

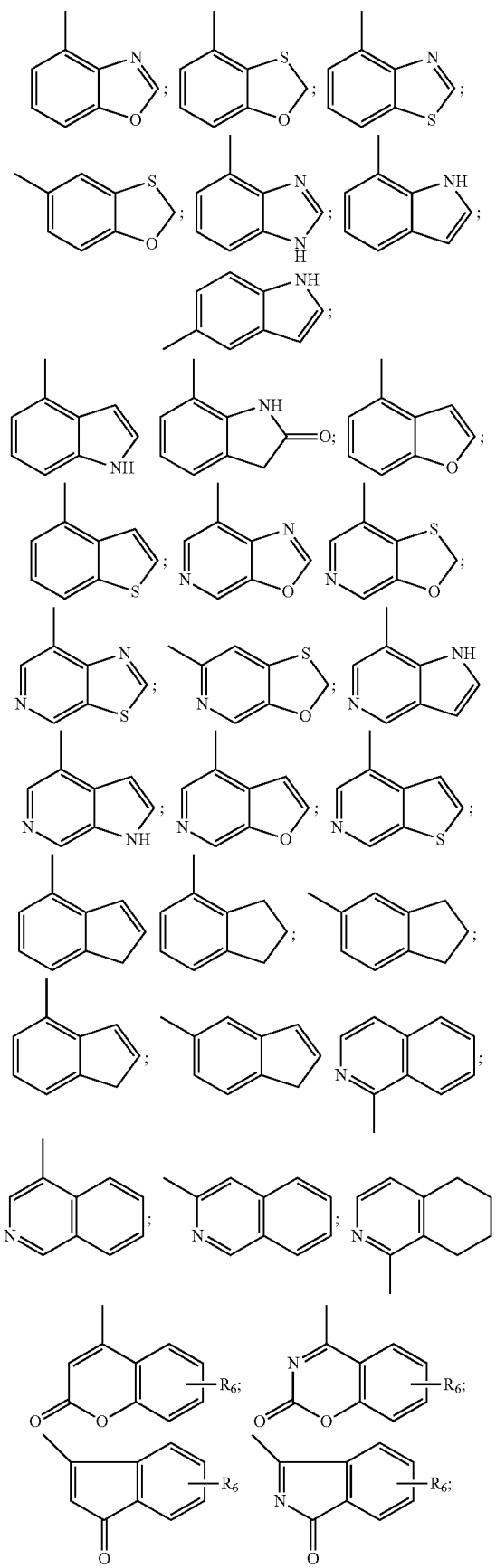

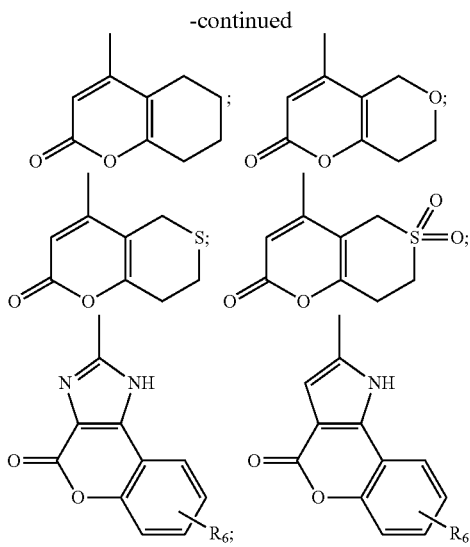

wherein R$_6$ has the meaning explained above.

In the present description and in the following claims, the term "(C$_{1-6}$)alkyl" means a linear or branched alkyl chain comprising from 1 to 6 carbon atoms, such as for example methyl, ethyl, propyl, isopropyl, n-butyl, isobutyl, sec-butyl, tert-butyl, pentyl, isopentyl, sec-pentyl, tert-pentyl, neopentyl, 3-pentyl, hexyl, isohexyl.

In the present description and in the following claims, the term "(C$_{1-3}$)alkyl" means a linear or branched alkyl chain comprising from 1 to 3 carbon atoms, such as for example methyl, ethyl, propyl, isopropyl.

In the present description and in the following claims, the term "(C$_{1-6}$)alkylenyl" means a divalent linear or branched alkyl chain comprising from 1 to 6 carbon atoms, such as for example methylenyl (—CH$_2$—), ethylenyl (—CH$_2$CH$_2$—), propylenyl (—CH$_2$CH$_2$CH$_2$—) or butylenyl (—CH$_2$CH$_2$CH$_2$CH$_2$—).

In the present description and in the following claims, the term "(C$_{4-5}$)cycloalkylenyl" means a divalent cycloalkyl group comprising 4 or 5 carbon atoms, such as cyclobutylenyl and cyclopentylenyl.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereomers by crystallization followed by liberation of the optically active bases from these salts. A different process for separation of optical isomers involves the use of a chiral chromatography column optimally chosen to maximize the separation of the enantiomers. Still another method involves synthesis of covalent diastereomers by reacting compounds of the invention with an optically pure acid in an activated form or an optically pure isocyanate. The synthesized diastereomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

The compounds of this invention can exist in radiolabeled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3$H, $^{14}$C, $^{32}$P, $^{35}$S, $^{18}$F and $^{36}$Cl, respectively. Compounds of this invention which contain those radioisotopes and/or other radioisotopes of other atoms are within the scope of this invention. Tritiated, i.e., $^3$H, and carbon-14, i.e., $^{14}$C, radioisotopes are particularly preferred for their ease of preparation and detectability.

Radiolabeled compounds of this invention can generally be prepared by methods well known to those skilled in the art. Conveniently, such radiolabeled compounds can be prepared by carrying out the procedures disclosed herein except substituting a readily available radiolabeled reagent for a non-radiolabelled reagent.

In a second embodiment, the present invention relates to a pharmaceutical composition comprising at least one compound of formula (I) as described above, a salt thereof with a pharmaceutically acceptable organic or inorganic acid or base, or an enantiomer thereof, or a N-oxide thereof, or a quaternary ammonium salt thereof, and at least one pharmaceutically acceptable excipient.

Preferably, the pharmaceutical composition of the present invention is prepared in suitable dosage forms.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions. Other suitable dosage forms are those with sustained release and those based on liposomes for oral, injectable or transdermal administration. The pharmaceutical compositions of this invention may also be administered by nasal aerosol or inhalation or delivered by implantation (e.g., surgically), such as with an implantable or indwelling device like a stent.

Other suitable dosage forms are those with sustained release and those based on liposomes for oral, injectable or transdermal administration.

The dosage forms of the pharmaceutical composition of the present invention can be prepared by techniques that are familiar to a pharmaceutical chemist, and comprise mixing, granulation, compression, dissolution, sterilization and the like.

Typically, the amount of compound of formula (I) or of the pharmaceutically acceptable quaternary ammonium salt, N-oxide and salt thereof in the pharmaceutical composition of the present invention will be between 0.01 mg to 1,500 mg, preferably between 0.1 mg and 500 mg and more preferably between 1 mg and 200 mg.

Typically, the amount of compound of formula (I) in the pharmaceutical composition of the present invention will be such to ensure a level of administration from 0.001 to 20 mg/kg/day. Preferably, the level of administration is from 0.01 to 7.5 mg/kg/day, more preferably from 0.1 to 5 mg/kg/day, and most preferably from 0.5 to 2.5 mg/kg/day.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The pharmaceutical compositions of this invention may be administered orally, parenterally, by inhalation spray, topically, rectally, nasally, buccally, vaginally or via an implanted reservoir. The term parenteral as used herein includes subcutaneous, intracutaneous, intravenous, intramuscular, intra-articular, intrasynovial, intrasternal, intrathecal, intralesional and intracranial injection or infusion techniques.

As mentioned above, depending on the nature of the substituents, the compound of formula (I) may form addition salts with a pharmaceutically acceptable organic or inorganic acid or base.

Typical examples of suitable physiologically acceptable inorganic acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

Typical examples of suitable physiologically acceptable inorganic bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)-piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

As described herein, the pharmaceutical composition of the present invention comprises a compound of the invention together with a pharmaceutically acceptable excipient, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, other non-toxic compatible lubricants such as sodium lauryl sulfate and magnesium stearate, coloring agents, releasing agents, coating agents, sweetening, flavoring and perfuming agents, preservatives and antioxidants.

The terms "pharmaceutically acceptable" and "physiologically acceptable" are intended to define, without any particular limitation, any material suitable for preparing a pharmaceutical composition to be administered to a living being.

In a third embodiment, the present invention relates to the compounds of formula (I) for use in medicine.

In a fourth embodiment, the present invention relates to the compounds of formula (I) for use in the treatment of bacterial infections.

In a fifth embodiment, the present invention relates to a method for treating a bacterial infection, comprising the administration of a compound of formula (I) to a patient in need thereof.

Preferably, said bacterial infection is a skin infection, a mucosal infection, a gynaecological infection, a respiratory tract infection (RTI), a CNS infections, a gastro-intestinal infection, a bone infection, a cardiovascular infection, a sexually transmitted infection, or a urinary tract infection.

More in particular, said bacterial infection is a acute exacerbation of chronic bronchitis (ACEB), an acute otitis media, an acute sinusitis, an infection caused by drug resistant bacteria, a catheter-related sepsis, a chancroid, a *chlamydia*, a community-acquired pneumonia (CAP), a complicated skin and skin structure infection, an uncomplicated skin and skin structure infection, an endocarditis, a febrile neutropenia, a gonococcal cervicitis, a gonococcal urethritis, a hospital-acquired pneumonia (HAP), a osteomyelitis, a sepsis, a syphilis, a ventilator-associated pneumonia, an intraabdominal infections, a *gonorrhoeae*, a meningitis, a tetanus, or a tuberculosis.

Even more, said bacterial infection can be an atherosclerosis or cardiovascular disease related to infection by *Helicobacter pylori* or *Chlamydia* pneumonia; a blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; bronchitis; catheter-related sepsis; chancroid; *chlamydia*; community-acquired pneumonia; disseminated *Mycobacterium avium* complex (MAC) disease related to infection by *Mycobacterium avium*, or *Mycobacterium intracellulare*; endocarditis; febrile neutropenia; gas gangrene related to infection by *Clostridium perfringens* or *Bacteroides* spp; gastroenteritis infection; glomerulonephritis related to infection by *Streptococcus pyogenes*, Groups C and G streptococci, *Corynebacterium diphtheriae*, or *Actinobacillus haemolyticum*; gonococcal cervicitis; gonococcal urethritis; gynaecological infection; hospital-acquired pneumonia (HAP); infection caused by drug resistant bacteria; infections caused by *Mycobacterium tuberculosis, M. leprae, M. paratuberculosis, M. kansasii*, or *M. chelonei*; intestinal protozoa related to infection by *Cryptosporidium* spp; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. injluenzae*, or *Listeria* spp.; mastoiditis related to infection by *Streptococcus pneumoniae, Haemophilus injluenzae, Moraxella catarrhalis, Staphylococcus aureus, Enterococ-* cus faecalis, E. faecium, E. casseliflavus, S. epidermidis, S. haemolyticus, or Peptostreptococcus spp; odontogenic infection related to infection by viridans streptococci; osteomyelitis; otitis media; persistent cough related to infection by Bordetella pertussis; pharyngitis; puerperal fever related to infection by Staphylococcus aureus, coagulase-negative staphylococci Streptococcus pyogenes, Streptococcus agalactiae, Streptococcal groups C-F (minute colony streptococci), viridans streptococci Corynebacterium minutissimum, Clostridium spp., or Bartonella henselae; respiratory tract infections related to infection by Mycoplasma pneumoniae, Legionella pneumophila, Streptococcus pneumoniae, Haemophilus injluenzae, or Chlamydia pneumoniae; rheumatic fever; sepsis; sexually transmitted diseases related to infection by Chlamydia trachomatis, Haemophilus ducreyi, Treponema pallidum, Ureaplasma urealyticum, or Neiseria gonorrhoeae; sinusitis; syphilis; systemic febrile syndromes related to infection by Borrelia recurrentis; tonsillitis; toxin diseases related to infection by S. aureus (food poisoning and toxic shock syndrome), or Groups A, B, and C streptococci; ulcers related to infection by Helicobacter pylori; uncomplicated acute urinary tract infections related to infection by Staphylococcus aureus coagulase-negative staphylococcal species, or Enterococcus spp; uncomplicated skin and soft tissue infections and abscesses; urethritis and cervicitis; urinary tract infection; central nervous system infections; device related infections caused by staphylococci; muscoleskeletal infection caused by staphylococci; Shiga toxin-producing E. coli; Haemophilus influenzae (invasive disease); legionellosis; psittacosis/ornithosis clamydia psittaci; salmonellosis caused by salmonella spp; shigellosis by shigella spp; streptococcal toxic shock syndrome; staphylococcal toxic shock syndrome; and typhoid fever caused by Salmonella typhi.

The bacterial infection can be an infection caused by Acinetobacter spp, Bacteroides spp, Burkholderia spp, Campylobacter spp, Chlamydia spp, Chlamydophila spp, Clostridium spp, Enterobacter spp, Enterococcus spp, Escherichia spp, Gardnerella spp, Haemophilus spp, Helicobacter spp, Klebsiella spp, Legionella spp, Moraxella spp, Morganella spp, Mycoplasma spp, Neisseria spp, Peptostreptococcus spp, Proteus spp, Pseudomonas spp, Salmonella spp, Serratia spp, Staphylococcus spp, Streptoccocus spp, Stenotrophomonas spp, Ureaplasma spp, aerobes, obligate anaerobes, facultative anaerobes, gram-positive bacteria, gram-negative bacteria, gram-variable bacteria, and atypical respiratory pathogens.

More in particular, the bacterial infection can be an infection caused by Acinetobacter baumanii, Acinetobacter haemolyticus, Acinetobacter junii, Acinetobacter johnsonii, Acinetobacter lwoffi, Bacteroides bivius, Bacteroides fragilis, Burkholderia cepacia, Campylobacter jejuni, Chlamydia pneumoniae, Chlamydia urealyticus, Chlamydophila pneumoniae, Clostridium difficile, Enterobacter aerogenes, Enterobacter cloacae, Enterococcus faecalis, Enterococcus faecium, Escherichia coli, Gardnerella vaginalis, Haemophilus parainfluenzae, Haemophilus influenzae, Helicobacter pylori, Klebsiella pneumoniae, Legionella pneumophila, Methicillin-resistant Staphylococcus aureus, Methicillin-susceptible Staphylococcus aureus, Moraxella catarrhalis, Morganella morganii, Mycoplasma pneumoniae, Neisseria gonorrhoeae, Penicillin-resistant Streptococcus pneumoniae, Penicillin-susceptible Streptococcus pneumoniae, Peptostreptococcus magnus, Peptostreptococcus micros, Peptostreptococcus anaerobius, Peptostreptococcus asaccharolyticus, Peptostreptococcus prevotii, Peptostreptococcus tetradius, Peptostreptococcus vaginalis, Proteus mirabilis, Pseudomonas aeruginosa, Quinolone-Resistant Staphylococcus aureus, Quinolone-Resistant Staphylococcus epidermis, Salmonella typhi, Salmonella paratyphi, Salmonella enteritidis, Salmonella typhimurium, Serratia marcescens, Staphylococcus aureus, Staphylococcus epidermidis, Staphylococcus saprophyticus, Streptococcus agalactiae, Streptococcus pneumoniae, Streptococcus pyogenes, Stenotrophomonas maltophilia, Ureaplasma urealyticum, Vancomycin-Resistant Enterococcus faecium, Vancomycin-Resistant Enterococcus faecalis, Vancomycin-Resistant Staphylococcus aureus, and Vancomycin-Resistant Staphylococcus epidermis.

Examples of compounds according to the present invention are provided in the following Table 1.

TABLE 1

| No. | A | $L_1$ | $G_1$ | $G_2$ | $R_1$ | Y | $L_2$ | B |
|---|---|---|---|---|---|---|---|---|
| 27 | (coumarin-like structure) | —NH— | CH | N | H | —(CH$_2$)$_3$— | σ bond | (benzoxazole structure) |
| 29 | (coumarin-like structure) | —NH— | CH | N | H | —(CH$_2$)$_3$— | σ bond | (isoquinoline structure) |

TABLE 1-continued

| No. | A | L₁ | G₁ | G₂ | R₁ | Y | L₂ | B |
|---|---|---|---|---|---|---|---|---|
| 40 | 4-methylcoumarin | —NH— | CH | N | H | —(CH₂)₃— | σ bond | 7-methyl-2-oxoindoline |
| 44 | 1-methylisoquinoline | σ bond | N | N | H | —(CH₂)₃— | —NH— | 4-methylcoumarin |
| 46 | 1-methylisoquinoline | σ bond | N | N | H | —(CH₂)₃— | —NH—CH₂— | [1,3]oxathiolo[5,4-c]pyridine |
| 51 | 7-chloro-1-methylisoquinoline | σ bond | N | N | H | —(CH₂)₃— | —NH— | 4-methylcoumarin |
| 52 | 7-cyano-1-methylisoquinoline | σ bond | N | N | H | —(CH₂)₃— | —NH— | 4-methylcoumarin |
| 54 | 1-methylisoquinoline | σ bond | N | N | H | cis-cyclobutane | —NH— | 4-methylcoumarin |
| 55 | 1-methylisoquinoline | σ bond | N | N | H | trans-cyclobutane | —NH— | 4-methylcoumarin |
| 56 | 1,3-dimethylisoquinoline | σ bond | N | N | H | —(CH₂)₃— | —NH— | 4-methylcoumarin |

TABLE 1-continued
| No. | A | $L_1$ | $G_1$ | $G_2$ | $R_1$ | Y | $L_2$ | B |
|---|---|---|---|---|---|---|---|---|
| 59 | 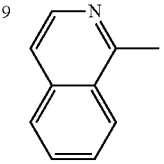 | σ bond | N | N | H | 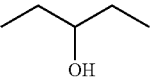 | —NH— | 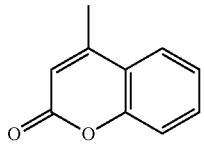 |
| 61 | 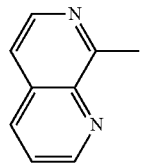 | σ bond | N | N | H | —(CH$_2$)$_3$— | —NH— | 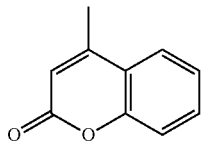 |
| 62 | 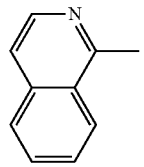 | σ bond | N | N | H | —(CH$_2$)$_2$— | —NH— | 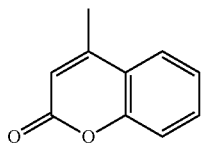 |
| 63 | 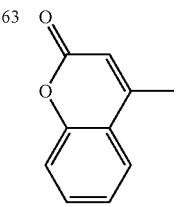 | σ bond | N | N | H | —(CH$_2$)$_3$— | —NH— | 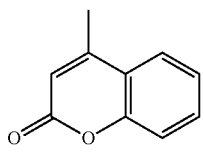 |
| 64 | 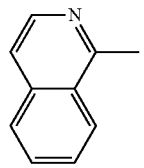 | σ bond | N | N | H | —(CH$_2$)$_3$— | —NH— | 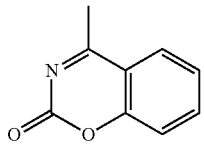 |
| 65 | 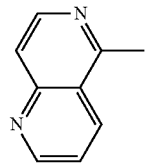 | σ bond | N | N | H | —(CH$_2$)$_3$— | —NH— | 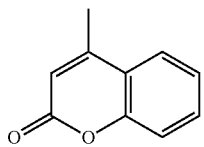 |
| 66 | 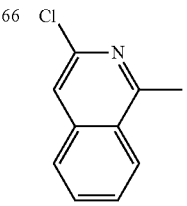 | σ bond | N | N | H | —(CH$_2$)$_3$— | —NH— | 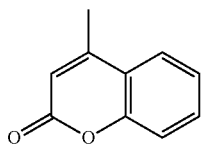 |
| 67 | 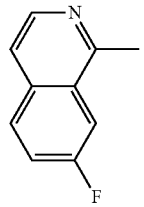 | σ bond | N | N | H | —(CH$_2$)$_3$— | —NH— | 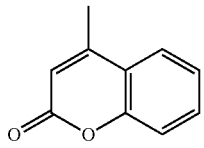 |

TABLE 1-continued

| No. | A | L₁ | G₁ | G₂ | R₁ | Y | L₂ | B |
|---|---|---|---|---|---|---|---|---|
| 69 | 1-methylisoquinoline | σ bond | N | N | H | —(CH₂)₃— | —NH— | 2-methylbenzofuran-3(2H)-one |
| 72 | 1,7-dimethylisoquinoline | σ bond | N | N | H | —(CH₂)₃— | —NH— | 4-methylcoumarin |
| 73 | 3-methoxy-1-methylisoquinoline | σ bond | N | N | H | —(CH₂)₃— | —NH— | 4-methylcoumarin |
| 77 | 1-methylisoquinoline | σ bond | N | N | H | cis-1,3-cyclopentylene | —NH— | 4-methylcoumarin |
| 78 | 1-methylisoquinoline | σ bond | N | N | H | trans-1,3-cyclopentylene | —NH— | 4-methylcoumarin |
| 79 | 1-methylisoquinoline | σ bond | N | N | H | —(CH₂)₃— | —NH— | 6-chloro-4-methylcoumarin |
| 80 | 1-methylisoquinoline | σ bond | N | N | H | —(CH₂)₃— | —NH— | 6-fluoro-4-methylcoumarin |
| 86 | 1-methylisoquinoline | σ bond | N | N | H | —(CH₂)₃— | —NH— | 4-methyl-5,6,7,8-tetrahydrocoumarin |

TABLE 1-continued

| No. | A | L₁ | G₁ | G₂ | R₁ | Y | L₂ | B |
|---|---|---|---|---|---|---|---|---|
| 88 | 1-methyl-7-methoxyisoquinoline | σ bond | N | N | H | —(CH₂)₃— | —NH— | 4-methylcoumarin |
| 89 | 1-methylisoquinoline | σ bond | N | N | —CONH₂ | —(CH₂)₃— | —NH— | 4-methylcoumarin |
| 90 | 1-methylisoquinoline | σ bond | N | N | —CH₂OH | —(CH₂)₃— | —NH— | 4-methylcoumarin |
| 91 | 3-fluoro-1-methylisoquinoline | σ bond | N | N | H | —(CH₂)₃— | —NH— | 4-methylcoumarin |
| 93 | 1-methylisoquinoline | σ bond | N | N | H | —CH(OH)(CH₂CH₃)— (pentan-3-ol linker) | —NH— | 4-methylcoumarin |
| 94 | 1-methylisoquinoline | σ bond | N | N | H | —CH(OH)(CH₂CH₃)— (pentan-3-ol linker) | —NH— | 4-methylcoumarin |
| 95 | 3-cyano-1-methylisoquinoline | σ bond | N | N | H | —(CH₂)₃— | —NH— | 4-methylcoumarin |
| 98 | 7-(dimethylamino)-1-methylisoquinoline | σ bond | N | N | H | —(CH₂)₃— | —NH— | 4-methylcoumarin |

TABLE 1-continued
| No. | A | L$_1$ | G$_1$ | G$_2$ | R$_1$ | Y | L$_2$ | B |
|---|---|---|---|---|---|---|---|---|
| 99 | 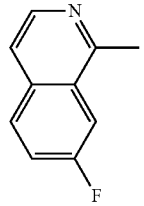 | σ bond | N | N | H | 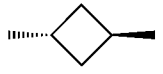 | —NH— | 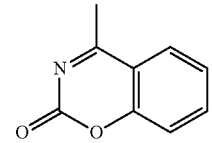 |
| 100 | 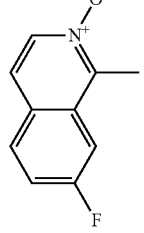 | σ bond | N | N | H | —(CH$_2$)$_3$— | —NH— | 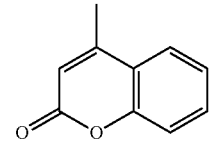 |
| 102 | 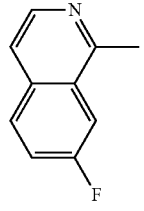 | σ bond | N | N | H | 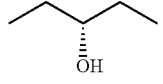 | —NH— | 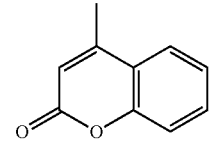 |
| 103 | 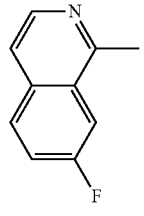 | σ bond | N | N | H | 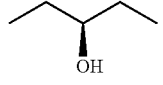 | —NH— | 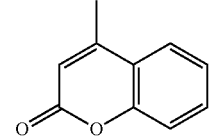 |
| 104 | 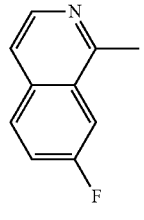 | σ bond | N | N | H | 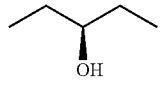 | —NH— | 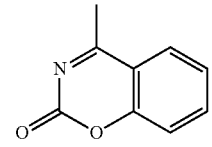 |
| 105 | 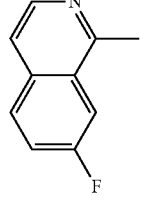 | σ bond | N | 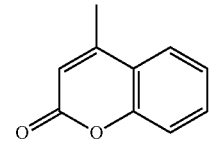 | H | —(CH$_2$)$_3$— | —NH— | 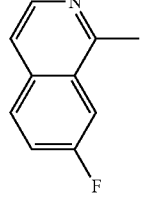 |
| 106 | 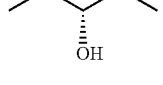 | σ bond | N | N | H | 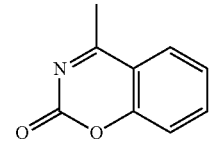 | —NH— | |

TABLE 1-continued

| No. | A | L₁ | G₁ | G₂ | R₁ | Y | L₂ | B |
|-----|---|-----|-----|-----|-----|-----|-----|---|
| 108 | 1-methyl-8-methylisoquinoline | σ bond | N | N | H | —(CH₂)₃— | —NH— | 4-methylcoumarin |
| 109 | 1-methylisoquinoline | σ bond | CH | N | H | —(CH₂)₃— | —NH— | 4-methylcoumarin |
| 124 | 1-methylisoquinoline | σ bond | N | N⁺(CH₃) | H | —(CH₂)₃— | —NH— | 4-methylcoumarin |
| 125 | 7-fluoro-1-methylisoquinoline | σ bond | N | N | H | —(CH₂)₃— | —NH— | 4-methyl-pyrano-pyran-2-one |
| 126 | 7-fluoro-1-methylisoquinoline | σ bond | N | N | H | —(CH₂)₃— | —NH— | 4-methyl-thiopyrano-pyran-2-one |
| 127 | 7-fluoro-1-methylisoquinoline | σ bond | N | N | H | —(CH₂)₃— | —NH— | 4-methyl-thiopyrano-pyran-2-one S,S-dioxide |
| 131 | 7-fluoro-1-methylisoquinoline | σ bond | N | CH | H | —NH—CH₂—CH₂— | —NH— | 6-fluoro-4-methylcoumarin |
| 134 | 7-fluoro-1-methylisoquinoline | σ bond | N | N | H | hexan-3-ol linker | σ bond | 4-methylcoumarin |

TABLE 1-continued
| No. | A | L₁ | G₁ | G₂ | R₁ | Y | L₂ | B |
|---|---|---|---|---|---|---|---|---|
| 143 | 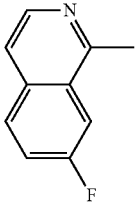 | σ bond | N | N | H | —(CH₂)₂— | σ bond | 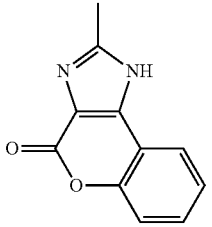 |
| 144 | 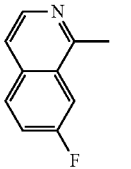 | σ bond | N | N | H | 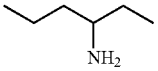 | σ bond | 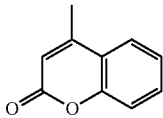 |
| 145 | 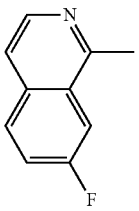 | σ bond | N | CH | H | —NH—CH₂— | σ bond | 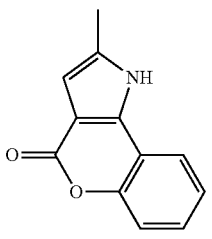 |
| 146 | 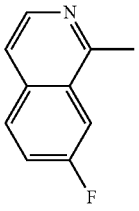 | σ bond | N | CH | H | —NH—CH₂— | σ bond | 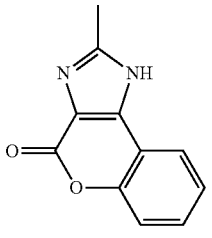 |
| 147 | 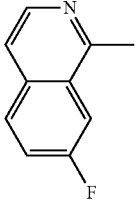 | σ bond | N | N | H | —(CH₂)₃— | σ bond | 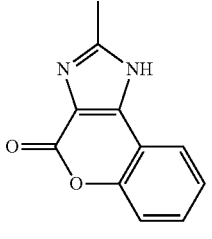 |
| 148 | 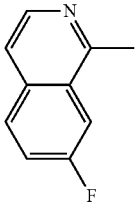 | σ bond | N | N | H | 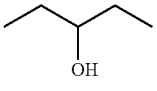 | —NH— | 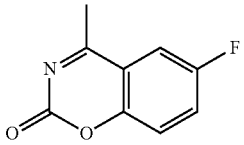 |
| 149 | 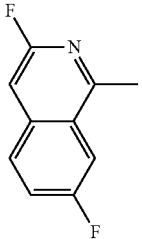 | σ bond | N | N | H | 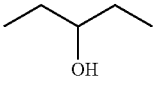 | —NH— | 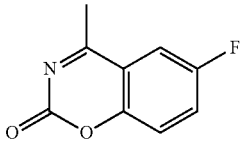 |

TABLE 1-continued
| No. | A | L$_1$ | G$_1$ | G$_2$ | R$_1$ | Y | L$_2$ | B |
|---|---|---|---|---|---|---|---|---|
| 150 |  | σ bond | N | N | H | —(CH$_2$)$_2$— | —NH—CH$_2$— | 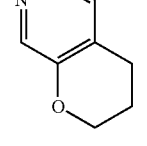 |
| 152 | 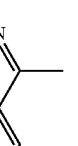 | σ bond | N | N | H | 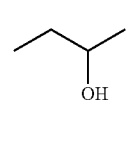 | σ bond | 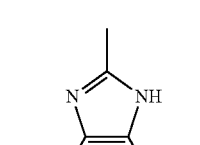 |
| 153 | 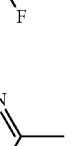 | σ bond | N | CH | H | —NH—CH$_2$— | σ bond | 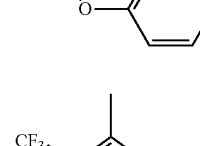 |
| 155 | 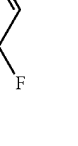 | σ bond | N | N | H |  | —NH— | 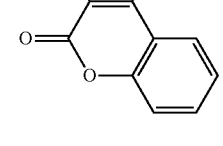 |
| 156 | 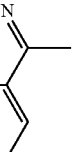 | σ bond | N | N | H | 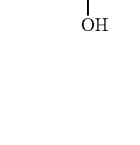 | —NH— | 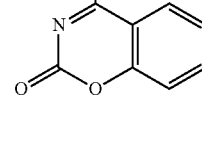 |
| 158 | 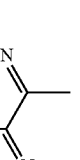 | σ bond | N | N | H | 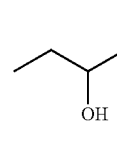 | σ bond | 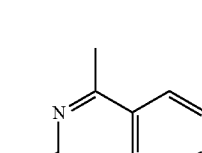 |

TABLE 1-continued
| No. | A | L₁ | G₁ | G₂ | R₁ | Y | L₂ | B |
|---|---|---|---|---|---|---|---|---|
| 159 | 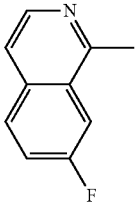 | σ bond | N | N | H | 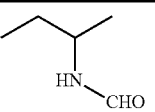 | σ bond | 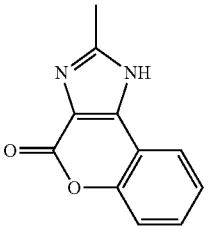 |
| 162 | 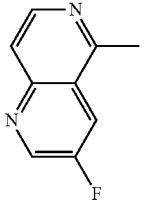 | σ bond | N | N | H | 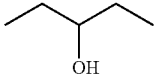 | —NH— | 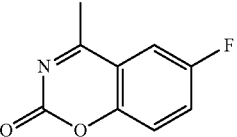 |
| 163 | 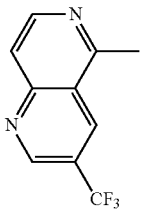 | σ bond | N | N | H | 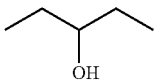 | —NH— | 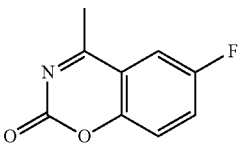 |
| 166 | 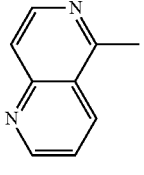 | σ bond | N | N | H | 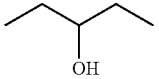 | —NH— | 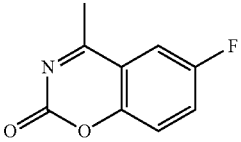 |
| 171 | 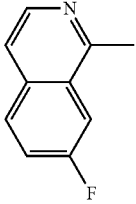 | σ bond | N | CH | —OCH₃ | —NH—CH₂— | σ bond | 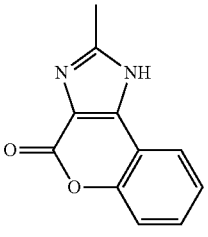 |
| 172 | 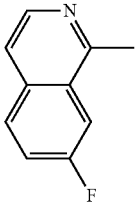 | σ bond | N | CH | F | —NH—CH₂— | σ bond | 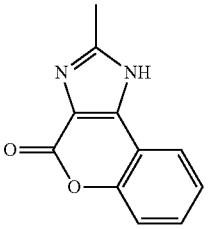 |
| 177 | 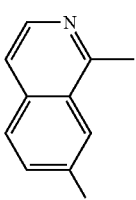 | σ bond | N | CH | —CH₃ | —NH—CH₂— | σ bond | 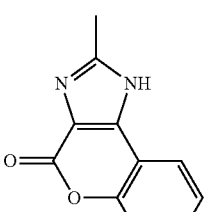 |

TABLE 1-continued

| No. | A | L₁ | G₁ | G₂ | R₁ | Y | L₂ | B |
|-----|---|----|----|----|----|---|----|---|
| 184 | 1-methyl-7-fluoroisoquinoline | σ bond | N | CH | —COO—C₂H₅ | —NH—CH₂— | σ bond | 2-methyl chromeno-imidazolone |
| 186 | 1-methyl-7-fluoroisoquinoline | σ bond | N | CH | —OH | —NH—CH₂— | σ bond | 2-methyl chromeno-imidazolone |
| 187 | 1-methyl-1,6-naphthyridine | σ bond | N | CH | H | —NH—CH₂— | σ bond | 2-methyl-8-fluoro chromeno-imidazolone |
| 188 | 8-methyl-2-methoxy-1,5-naphthyridine | σ bond | N | CH | H | —NH—CH₂— | σ bond | 2-methyl-8-fluoro chromeno-imidazolone |
| 192 | 7-fluoro-8-methyl-2-methoxy-1,5-naphthyridine | σ bond | N | CH | H | —NH—CH₂— | σ bond | 2-methyl-8-fluoro chromeno-imidazolone |
| 195 | 7-cyano-8-methyl-2-methoxy-1,5-naphthyridine | σ bond | N | CH | H | —NH—CH₂— | σ bond | 2-methyl-8-fluoro chromeno-imidazolone |

TABLE 1-continued

| No. | A | L$_1$ | G$_1$ | G$_2$ | R$_1$ | Y | L$_2$ | B |
|---|---|---|---|---|---|---|---|---|
| 196 | (pyrido-pyrazine with methyl) | σ bond | N | CH | H | —NH—CH$_2$— | σ bond | (methyl-imidazo-chromenone with F) |
| 199 | (pyrido-pyrazine with methyl, OCH$_3$) | σ bond | N | CH | H | —NH—CH$_2$— | σ bond | (methyl-pyrrolo-chromenone with F) |
| 203 | (F-isoquinoline with methyl, OCH$_3$) | σ bond | N | N | H | (2-butanol CH$_3$CH(OH)CH(CH$_3$)) | —NH— | (4-methyl-6-fluoro-coumarin) |

The above compounds can be prepared as explained in the synthetic examples below.

The man skilled in the art has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for A L$_1$, B, L$_2$, Y, L$_3$ and C.

Various synthetic approaches may be used to produce the compounds described herein, including those approaches depicted schematically below. The man skilled in the art will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art.

Also, one may chose reagents enriched for a desired isotope, e.g. tritium in place of hydrogen, to create compounds of this invention containing such isotope(s). Compounds containing tritium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The compounds of the this invention can be synthesized using the methods described below, together with synthetic methods known in the art of synthetic organic chemistry, or by a variation thereon as appreciated by those skilled in the art. Preferred methods include, but are not limited to those described below. The reactions are performed in a solvent appropriate to the reagents and materials employed and suitable for the transformation being effected. It will be understood by those skilled in the art of organic synthesis that the functionality present on the molecule should be consistent the transformations proposed. This will sometimes required some judgment to modify the order of the synthetic steps or to select one particular process scheme over another in order to obtain a desired compound of the invention.

A compound of the present invention could be prepared as outlined in the synthetic pathways described hereinafter and via standard methods known to those skilled in the art.

EXAMPLES

List of the abbreviations used in the synthetic pathways described hereinafter:
Boc: tert-butyl carbamate
cHex cyclohexane CV column volume
DBU: 1,5-diazabiciclo[5.4.0]undec-5-ene
DCM: dichloromethane
DIPEA N,N-diisopropylethylamine
DME: 1,2-dimethoxyethane
DMF: N,N-dimethylformamide
$Et_2O$: diethyl ether
EtOAc: ethylacetate
MS: mass spectroscopy
TEA: triethylamine
TFA: trifluoroacetic acid
THF: tetrahydrofuran
Pd/C: palladium on activated charcoal
$Pd(OH)_2$/C: palladium hydroxide on activated charcoal
r.t.: room temperature
UPLC: Ultra High Performance Liquid Chromatography Preparation of Compounds 27, 29 and 40

Compounds 27, 29 and 40 were prepared as described hereinbelow, following the synthetic pathway A.

then separated, dried over sodium sulfate and evaporated in vacuum. The crude material was purified by trituration with methanol to obtain the tert-butyl 4-[(2-oxo-2H-chromen-4-yl)amino]piperidine-1-carboxylate intermediate compound A2 (1.51 g, Y=73%). LC-MS (M–H⁺): 345.2

Step 3

The intermediate compound A2 (1 g) was dissolved in DCM (10 ml), TFA (3 ml) was added drop wise at 0° C. and the solution was left stirring for 2 hours. The solution was then concentrated in vacuum, washed with toluene and diethyl ether to obtain the trifluoroacetic acid salt of the 4-(piperidin-4-ylamino)-2H-chromen-2-one intermediate compound A3 (1.2 g, Y=quant.). LC-MS (M–H⁺): 245.1

Step 4

The intermediate compound A3 (50 mg) and potassium carbonate (38.7 mg) were mixed in DMF (2 ml). 3-bromoprop-1-yne (20.8 mg) was added subsequently at room temperature and the reaction was left stirring overnight. The suspension was filtered and the filtrate concentrated. The residue was purified by Si-column, eluting with EtOAc to

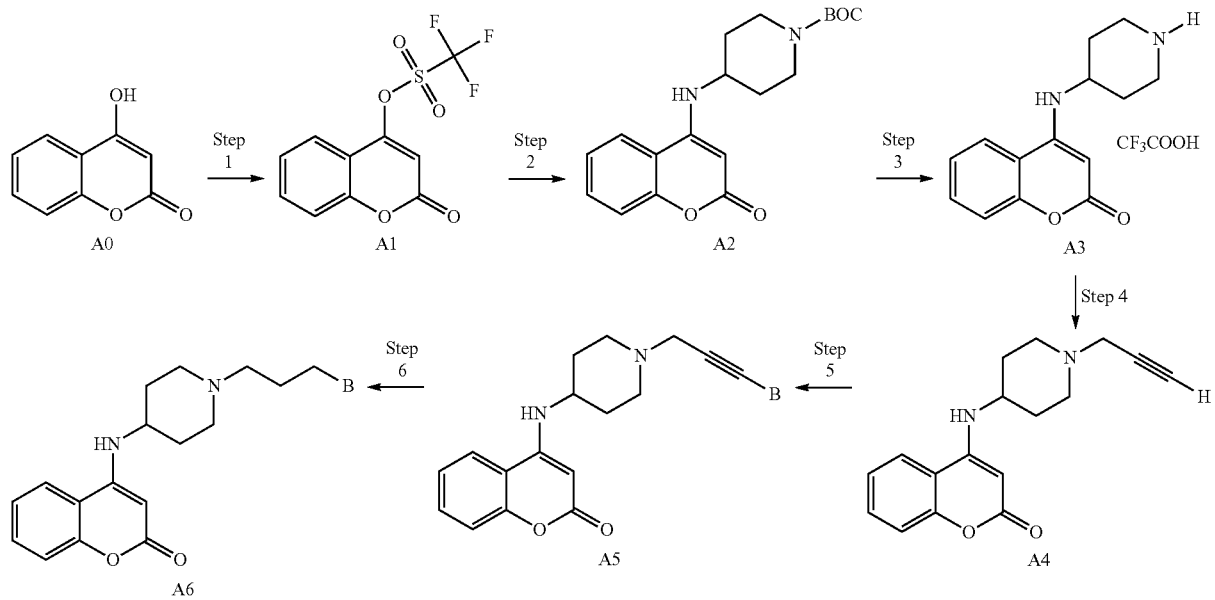

EtOAc/Methanol 8:2 to give the 4-{[1(prop-2-yn-1-yl)piperidin-4-yl]amino}-2H-chromen-2-one intermediate compound A4 (25.6 mg, Y=76%). LC-MS (M–H⁺): 283.1

Step 5

The intermediate compound A4 (50 mg, 1 eq.), the desired halogen-heteroaromatic compound B-hal (1.1 eq.) represented in the table below, and copper iodide (CuI, 3.42 mg, 0.1 eq.) were dissolved in DMF (1 ml). DIPEA (0.125 ml, 4 eq.) was added. The mixture was degassed by alternatively applying vacuum and nitrogen, then bis(triphenylphosphine)palladium(II) dichloride (12.6 mg, 0.1 eq.) was added and the mixture was heated at 60° C. After 3 hours, when the reaction was complete, water was added and the mixture was extracted with ethyl acetate. The organic phase was washed with brine, dried over $Na_2SO_4$, filtered and concentrated in vacuum to give crude material. After purification by Si-column eluting with EtOAc to EtOAc/Methanol 8:2 was obtained the corresponding desired intermediate compounds A5, described in the table below:

Step 1

4-hydroxycoumarine A0 (1 g) was dissolved in DCM (30 ml) with triethylamine (1.72 ml) and trifluoromethanesulfonic anhydride (1.25 ml) was added drop wise at –10° C. in DCM and the solution was let stirring at –10° C. for 2 hours. The resulting reddish brown solution, warmed to room temperature, was diluted with cyclohexane/diethyl ether 1/1 and filtered through a pad of silica gel using cyclohexane/diethyl ether 1/1. The solvent was removed in vacuum to obtain the 2-oxo-2H-chromen-4-yltrifluoromethanesulfonate intermediate compound A1 (1.76 g, Y=97%). LC-MS (M–H⁺): 295.0

Step 2

Triethylamine (1 ml) in acetonitrile (2 ml) was added drop wise to a stirred solution of the intermediate compound A1 (1.76 g) and 1-Boc-4-aminopiperidine (1.2 g) in dry acetonitrile (20 ml). Once the addition was complete, the solution was heated at reflux for 2 hours. The reaction mixture was cooled to room temperature, diluted with DCM and washed with saturated $NaHCO_3$ and water. The organic phase was

| Compound No. | B-hal | Intermediate A5 | LC-MS |
|---|---|---|---|
| 27 | (4-bromo-1,3-benzoxazole) | 4-({1-[3-(1,3-benzoxazol-4-yl)prop-2-yn-1-yl]piperidin-4-yl}amino)-2H-chromen-2-one | LC-MS (M − H$^+$): 400.1 |
| 29 | (1-chloroisoquinoline) | 4-({1-[3-(isoquinolin-1-yl)prop-2-yn-1-yl]piperidin-4-yl}amino)-2H-chromen-2-one | LC-MS (M − H$^+$): 410.3 |
| 40 | (7-iodo-1,3-dihydro-2H-indol-2-one) | 7-(3-{4-[(2-oxo-2H-chromen-4-yl)amino]piperidin-1-yl}prop-1-yn-1-yl)-1,3-dihydro-2H-indol-2-one | LC-MS (M − H$^+$): 414.1 |

Step 6

Each of the above intermediate compounds A5 (0.09 mmoles, 1 eq.) were placed in EtOAc (5 ml). Pd/C 10% (0.05 eq.) was added to each solution and the mixture was stirred under hydrogen (3.5 atm) at room temperature. After 3 hours DCM was added, the mixture was then filtered and concentrated in vacuum to give crude material, which was purified by Si-column eluting with DCM to DCM/Methanol 8:2 to give the corresponding compound A6, described below:

| Compound No. | A6 IUPAC name | LC-MS |
|---|---|---|
| 27 | 4-({1-[3-(1,3-benzoxazol-4-yl)propyl]piperidin-4-yl}amino)-2H-chromen-2-one | LC-MS (M − H$^+$): 404.2 |
| 29 | 4-({1-[3-(isoquinolin-1-yl)propyl]piperidin-4-yl}amino)-2H-chromen-2-one | LC-MS (M − H$^+$): 414.1 |
| 40 | 7-(3-{4-[(2-oxo-2H-chromen-4-yl)amino]piperidin-1-yl}propyl)-1,3-dihydro-2H-indol-2-one | LC-MS (M − H$^+$): 418.1 |

Compound 29 was dissolved in DCM. 1 M HCl in diethyl ether was added drop-wise at 0° C. and the solutions were left under stirring for 2 hours. Each solution was then concentrated in vacuum to obtain, after trituration from diethyl ether, the final compound as hydrochloride salt:

| Compound No. | IUPAC name | LC-MS |
|---|---|---|
| 29 | 4-({1-[3-(isoquinolin-1-yl)propyl]piperidin-4-yl}amino)-2H-chromen-2-one hydrochloride | LC-MS (M − H$^+$): 414.1 |

Compound 29: 1H NMR (400 MHz, DMSO-d6) δ 10.62 (br. s., 1H), 8.62 (br. s., 1H), 8.55 (d, J=6.3 Hz, 1H), 8.21 (d, J=8.5 Hz, 3H), 8.09 (br. s., 1H), 7.95 (br. s., 1H), 7.64-7.56 (m, 1H), 7.49 (br. s., 1H), 7.35-7.26 (m, 2H), 5.36 (s, 1H), 3.82 (br. s., 2H), 3.75-3.41 (m, 4H), 3.26 (br. s., 2H), 3.12 (br. s., 2H), 2.40-2.25 (m, 2H), 2.20-1.94 (m, 4H)

Compound 40: 1H NMR (400 MHz, DMSO-d6) δ 10.67 (br. s., 1H), 7.59-7.51 (m, 2H), 7.35 (d, J=7.8 Hz, 1H), 7.30 (t, J=7.5 Hz, 1H), 7.10 (d, J=7.0 Hz, 1H), 7.05-7.00 (m, 1H), 6.96 (t, J=7.3 Hz, 1H), 5.47-5.32 (m, 2H), 3.63-3.52 (m, 3H), 3.07 (d, J=11.0 Hz, 2H), 2.64 (t, J=5.9 Hz, 2H), 2.35 (t, J=5.9 Hz, 2H), 2.31-2.13 (m, 4H), 2.06-1.93 (m, 2H), 1.87 (td, J=6.1, 12.1 Hz, 2H)

Preparation of Compound 46

Compound 46 was prepared as described herein below, following the synthetic pathway B.

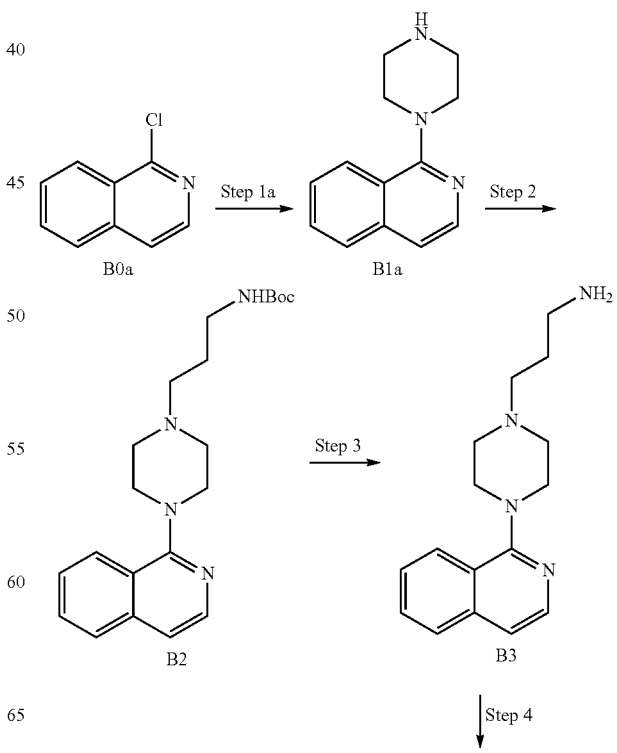

-continued

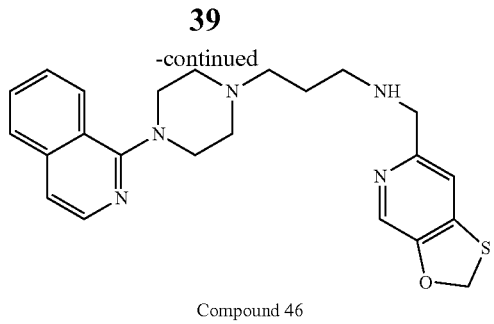

Compound 46

Step 1a

2-Chloroisoquinole B0a (3 g) was dissolved in CH₃CN (150 ml) with piperazine (23.7 g) and potassium carbonate (3.8 g) and the solution was heated to reflux for 48 h. The solution was concentrated, diluted with DCM and washed with saturated NaHCO₃ and brine. The organic phase was then separated, dried with sodium sulfate and evaporated in vacuum to obtain the 1-(piperazin-1-yl)isoquinoline intermediate compound B1a (3.9 g, Y=94%). LC-MS (M-H$^+$): 214.1

Step 1b

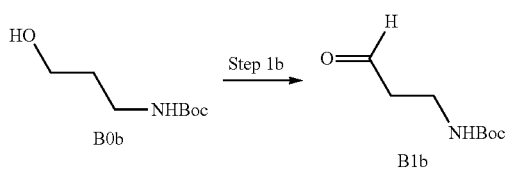 [SMILES: CC(C)(C)OC(=O)NCCCO ; CC(C)(C)OC(=O)NCCC=O]

To a solution of 3-(Boc-amino)-1-propanol of formula B0b (3.9 ml) in DCM (140 ml) was added Dess-Martin periodinane (12.4 g) and the resultant mixture was stirred at room temperature for 2 hours. The mixture was then diluted with diethyl ether and washed with a 1M aqueous solution of Na₂S₂O₃ and sat. NaHCO₃. The organic phase was then separated, dried with sodium sulfate and evaporated in vacuum to provide the tert-butyl (3-oxopropyl)carbamate intermediate compound B1 b (3.9 g, Y=quant.). LC-MS (M-H$^+$): 174.0

Step 2

The intermediate compound B1a (4 g) was dissolved in DCM (75 ml) and the intermediate compound B1b (4.9 g) and five drops of acetic acid were added subsequently at room temperature. After ten minutes sodium triacetoxyborohydride (6 g) was also added and the solution was left stirring overnight. The solution was diluted with DCM and washed with 1 M of sodium hydroxide, dried with sodium sulfate, filtered and evaporated in vacuum.

The crude material was purified firstly with a Si-Column, eluting with ethyl acetate and then another Si-Column eluting with DCM/ethyl acetate/MeOH 7/2.5/0.5, to obtain the tert-butyl-{3-[4-(isoquinolin-1-yl)piperazin-1-yl]propyl}carbamate intermediate compound B2 (3.5 g, Y=50%). LC-MS (M-H$^+$)=371.2

Step 3

The intermediate compound B2 (3.5 g) was dissolved in DCM (25 ml), TFA (10 ml) was added drop wise at 0° C. and the solution was left stirring for 2 hours. The solution was concentrated in vacuum, washed with toluene and diethyl ether to obtain the 3-[4-(isoquinolin-1-yl)piperazin-1-yl] propan-1-amine intermediate compound B3 as TFA salt (6.35 g, Y=93%). LC-MS (M-H$^+$)=271.2

Step 4

The intermediate compound B3 as TFA salt (1.3 g) was dissolved in DCM (12 ml) and TEA (1 ml), one drop of acetic acid and [1,3]oxathiolo[5,4-c]pyridine-6-carbaldehyde (150 mg), prepared as described in Preparation of naphthyridine derivatives as antibacterial agents; Miller, William Henry; Rouse, Meagan B.; Seefeld, Mark Andrew, PCT Int. Appl., 2006014580, 9 Feb. 2006), were added subsequently at r.t. After ten minutes sodium triacetoxyborohydride (382 mg) was added and the solution was left stirring overnight. The solution was diluted with DCM and washed with brine, dried with sodium sulfate, filtered and evaporated in vacuum. The crude material was purified firstly by Si-column (NH), eluting with ethyl acetate to ethyl acetate/MeOH 9:1, then by Si-column eluting with DCM to DCM/MeOH 7:3 to obtain the desired compound 46, 3-[4-(isoquinolin-1-yl)piperazin-1-yl]-N-([1,3]oxathiolo-[5,4-c]pyridin-6-ylmethyl)propan-1-amine (290 mg, Y=28%). 1H NMR (400 MHz, DMSO-d6) δ 8.15 (d, J=5.8 Hz, 1H), 8.10 (d, J=8.5 Hz, 1H), 8.03 (s, 1H), 7.75 (d, J=8.0 Hz, 1H), 7.61 (ddd, J=1.3, 7.0, 8.1 Hz, 1H), 7.51 (ddd, J=1.3, 7.0, 8.3 Hz, 1H), 7.24 (d, J=5.8 Hz, 1H), 7.22 (s, 1H), 5.74 (s, 2H), 5.31 (s, 1H), 3.83 (s, 2H), 3.55-3.38 (m, 4H), 2.82-2.68 (m, 6H), 2.56 (t, J=7.3 Hz, 2H), 1.81 (quin, J=7.1 Hz, 2H)

Preparation of compounds 44, 51, 52, 56, 62, 66, 67, 69, 72, 73, 79, 80, 86, 88, 91, 95, 98, 108 and 124

Compounds 44, 51, 52, 56, 62, 66, 67, 69, 72, 73, 79, 80, 86, 88, 91, 95, 98, 108 and 124 were prepared as described herein below, following the synthetic pathway C.

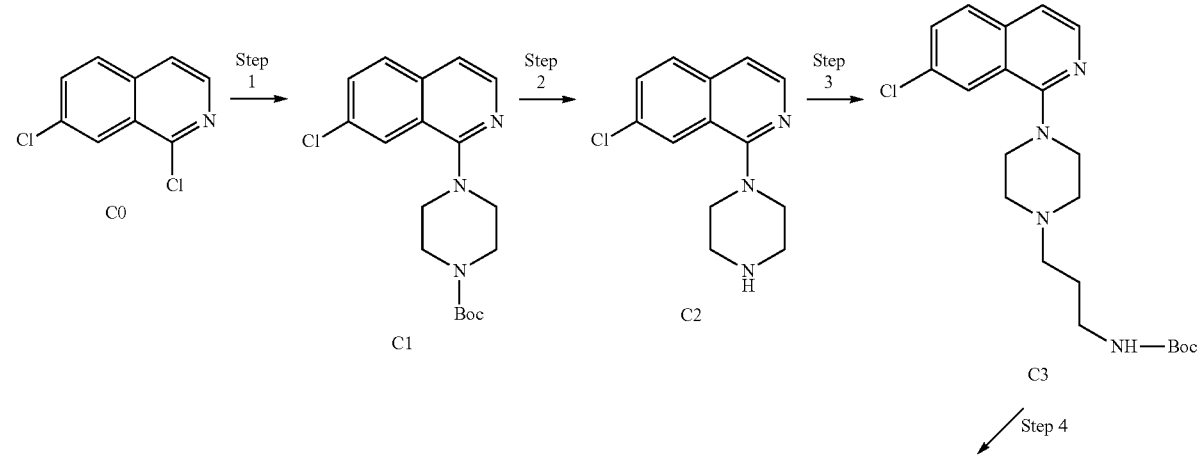

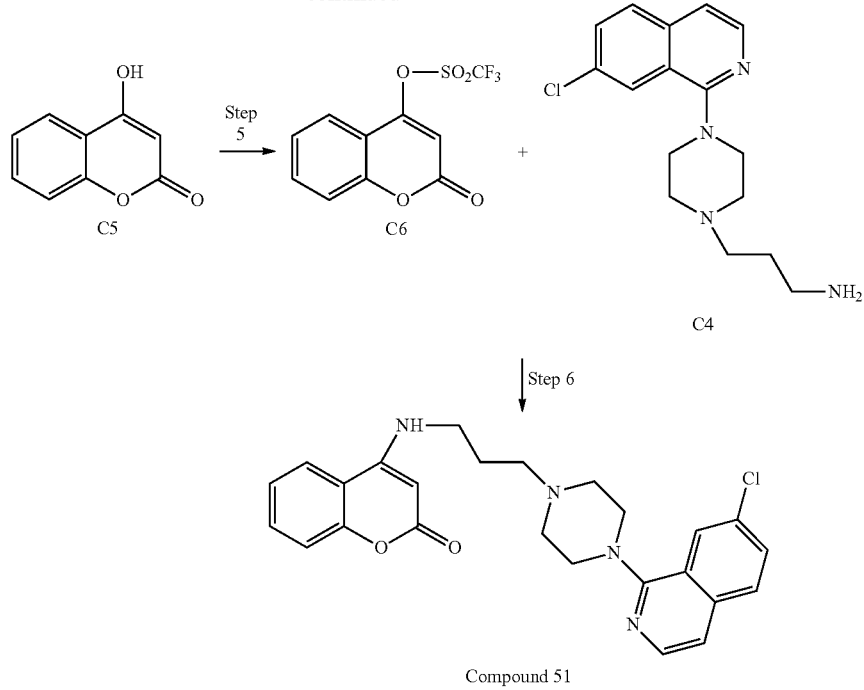

Compound 51

Synthetic Method Used to Prepare Compound 51

Step 1

A mixture of 1,7-dichloroisoquinoline C0 (350 mg), $K_2CO_3$ (390 mg) and tert-butyl piperazine-1-carboxylate (700 mg) were put together in a flask and three cycles of vacuum/$N_2$ were performed. DMSO (10 ml) was added and the suspension was heated to 120° C. and stirred for 5.5 h. The reaction was then allowed to cool, diluted with water and extracted with EtOAc. The organic phase was separated and washed with brine, dried over sodium sulphate and evaporated under reduced pressure to obtain the crude material as brown oil. It was purified by SNAP 50 g Si cartridge, eluting mixture cHex/EtOAc (10/0, 2 CV—from 10/0 to 7/3, 8 CV—7/3, 2 CV), to obtain a colorless sticky gum, tert-butyl 4-(7-chloroisoquinolin-1-yl)piperazine-1-carboxylate intermediate compound C1. (Y=73%). LC-MS (M−H$^+$)=348.3

Step 2

TFA (1 mL) was added to a solution of intermediate compound C1 (480 mg) in dichloromethane (3 mL) at room temperature and the resulting mixture stirred for 60 minutes. The reaction was evaporated under reduced pressure. The residue was twice dissolved in dichloromethane (10 mL) and evaporated under reduced pressure then the residue dissolved in MeOH (4 mL) and loaded onto a preconditioned SCX cartridge (5 g). The SCX was eluted with MeOH and then a 2M solution of ammonia in methanol. The basic fractions were evaporated under reduced pressure to give 330 mg of a thick colorless oil, 7-chloro-1-(piperazin-1-yl)isoquinoline intermediate compound C2. (Y=quant.). LC-MS (M−H$^+$)=248.2

Step 3

A mixture of intermediate compound C2 (325 mg), tert-butyl N-(3-bromopropyl)carbamate (297 mg), potassium iodide (109 mg) and potassium carbonate (362 mg) in DMF (4 mL) was stirred overnight at room temperature. The reaction was partitioned between EtOAc (50 mL) and half saturated brine (50 mL). The organic phase was separated then washed with half-saturated brine (50 mL) and brine (50 mL), dried over sodium sulfate and evaporated under reduced pressure. The residue was chromatographed on silica gel (SNAP 25) eluting with a gradient of 50-100% of mixture A in cyclohexane, where A is EtOAc/MeOH (97:3) to give 465 mg of a colorless sticky gum, tert-butyl N-{3-[4-(7-chloroisoquinolin-1-yl)piperazin-1-yl]propyl}carbamate intermediate compound C3 (Y=92%). LC-MS (M−H$^+$)=405.4

Step 4

TFA (2 mL) was added to a solution of intermediate compound C3 (462 mg) in dichloromethane (6 mL) at room temperature and the resulting mixture stirred for 60 minutes. The volatiles were evaporated under reduced pressure. The residue was dissolved twice in dichloromethane (10 mL) and evaporated under reduced pressure then the residue dissolved in MeOH (4 mL) and loaded onto a preconditioned SCX cartridge (5 g). The SCX was eluted with MeOH and then a 2M solution of ammonia in methanol. The basic fractions were evaporated under reduced pressure to give 336 mg of a yellow gum, 3-[4-(7-chloroisoquinolin-1-yl)piperazin-1-yl]propan-1-amine intermediate compound C4 (Y=96%). LC-MS (M−H$^+$)=305.3

Step 5

A solution of trifluoromethanesulfonic anhydride (2.5 mL) in dichloromethane (10 mL) was added drop-wise to a stirred solution of 4-hydroxy-2H-chromen-2-one intermediate compound C5 (2.00 g) and triethylamine (3.44 mL) in dichloromethane (60 mL) at −10° C. The reaction was stirred at −10° C. for 2 hours then allowed to warm to 0° C. and diluted with cyclohexane/diethyl ether (3:1, 100 mL). The mixture was filtered over a silica gel plug washing with further cyclohexane/diethyl ether (3:1). Washings containing the desired product were evaporated under reduced pressure to give 3.80 g of a brown solid, 2-oxo-2H-chromen- 4-yl trifluoromethanesulfonate intermediate compound C6 (Y=97%). LC-MS (M–H⁺)=295.1

Step 6

A solution of intermediate compound C4 (114 mg), triethylamine (70 microL) and intermediate compound C6 (100 mg) in acetonitrile (4 mL) was heated to 70° C. for 1 hour. The reaction mixture was concentrated under reduced pressure and the residue was partitioned between dichloromethane (15 mL) and a brine/sodium bicarbonate mixture (1:1, 15 mL). The mixture was filtered through a hydrophobic frit (Phase Separator) washing with dichloromethane (10 mL). The organic phase was evaporated under reduced pressure and the residue was chromatographed on silica gel (2×SNAP 10 in series) eluting with a 10-100% gradient of A in cyclohexane, where A is MeOH/EtOAc (20:80), to give 63 mg of 4-({3-[4-(7-chloroisoquinolin-1-yl)piperazin-1-yl]propyl}amino)-2H-chromen-2-one (Compound 51) as a white foam.

4-({3-[4-(7-chloroisoquinolin-1-yl)piperazin-1-yl]propyl}amino)-2H-chromen-2-one (Compound 51) (60 mg) was dissolved in dichloromethane (3 mL) and treated with 1 M HCl solution in diethyl ether (0.35 mL) causing precipitation. The resulting mixture was evaporated under reduced pressure and the residue was triturated with diethyl ether. The solids were dried to give 69 mg of an off white solid, 4-({3-[4-(7-chloroisoquinolin-1-yl)piperazin-1-yl]propyl}amino)-2H-chromen-2-one hydrochloride (Y=35%). LC-MS (M–H⁺)=449.3

Compounds 44, 52, 56, 66, 67, 72, 88, 91, 95, 98 and 108 were prepared in a similar way by replacing the 1,7-dichloroisoquinoline (C0) of step 1 with the following compounds, respectively.

| Compound | Intermediate C0 | LC-MS of the final compound |
|---|---|---|
| 44 | 1-chloroisoquinoline | LC-MS (M – H⁺) = 415.2 |
| 52 | 7-cyano-1-chloroisoquinoline | LC-MS (M – H⁺) = 440.3 |
| 56 | 3-methyl-1-chloroisoquinoline | LC-MS (M – H⁺) = 429.4 |
| 66 | 1,3-dichloroisoquinoline | LC-MS (M – H⁺) = 449.3 |
| 67 | 7-fluoro-1-chloroisoquinoline | LC-MS (M – H⁺) = 433.3 |
| 72 | 7-methyl-1-chloroisoquinoline | LC-MS (M – H⁺) = 429.4 |
| 73 | 3-methoxy-1-chloroisoquinoline | LC-MS (M – H⁺) = 445.4 |
| 88 | 7-methoxy-1-chloroisoquinoline | LC-MS (M – H⁺) = 445.4 |
| 91 | 3-fluoro-1-chloroisoquinoline | LC-MS (M – H⁺) = 433.3 |
| 95 | 3-cyano-1-chloroisoquinoline | LC-MS (M – H⁺) = 440.3 |
| 98 | 7-dimethylamino-1-chloroisoquinoline | LC-MS (M – H⁺) = 458.4 |
| 108 | 8-methyl-1-chloroisoquinoline | LC-MS (M – H⁺) = 429.4 |

Compound 44: 1H NMR (400 MHz, DMSO-d6) δ 11.07 (br. s., 1H), 8.19 (d, J=8.5 Hz, 1H), 8.15 (d, J=8.3 Hz, 1H), 8.08 (d, J=6.0 Hz, 1H), 8.00 (d, J=8.3 Hz, 1H), 7.95 (t, J=5.5 Hz, 1H), 7.85 (t, J=7.5 Hz, 1H), 7.73-7.67 (m, 1H), 7.63-7.58 (m, 1H), 7.57 (d, J=6.0 Hz, 1H), 7.39-7.28 (m, 2H), 5.27 (s, 1H), 4.23 (br. s., 2H), 4.00 (d, J=13.3 Hz, 2H), 3.65 (d, J=10.5 Hz, 4H), 3.50-3.34 (m, 4H), 3.30 (td, J=4.8, 9.4 Hz, 2H), 2.14 (quin, J=7.3 Hz, 2H)

Compound 51: 1H NMR (400 MHz, DMSO-d6) δ 10.72 (br. s., 1H), 8.18 (d, J=5.5 Hz, 1H), 8.15-8.09 (m, 2H), 8.01 (d, J=8.8 Hz, 1H), 7.89 (t, J=5.9 Hz, 1H), 7.79 (dd, J=1.9, 8.7 Hz, 1H), 7.63-7.57 (m, 1H), 7.55 (d, J=5.5 Hz, 1H), 7.38-7.28 (m, 2H), 5.78 (br. s., 1H), 5.27 (s, 1H), 3.90-3.75 (m, 2H), 3.62 (d, J=10.0 Hz, 2H), 3.53-3.34 (m, 6H), 3.33-3.22 (m, 2H), 2.14 (quin, J=7.0 Hz, 2H)

Compound 52: 1H NMR (400 MHz, DMSO-d6) δ 10.73 (br. s., 1H), 8.65 (s, 1H), 8.30 (d, J=5.8 Hz, 1H), 8.16-8.07 (m, 2H), 8.03 (dd, J=1.5, 8.5 Hz, 1H), 7.89 (t, J=5.1 Hz, 1H), 7.69-7.52 (m, 2H), 7.41-7.25 (m, 2H), 5.28 (s, 1H), 4.75 (br. s., 1H), 3.89 (d, J=11.5 Hz, 2H), 3.62 (d, J=9.3 Hz, 2H), 3.55-3.36 (m, 6H), 3.35-3.17 (m, 2H), 2.14 (quin, J=7.0 Hz, 2H)

Compound 56: 1H NMR (400 MHz, DMSO-d6) δ 10.06 (br. s., 2H), 8.08 (d, J=8.3 Hz, 2H), 7.83 (d, J=7.8 Hz, 2H), 7.70 (t, J=7.2 Hz, 1H), 7.66-7.60 (m, 1H), 7.59-7.50 (m, 1H), 7.41-7.27 (m, 3H), 5.31 (s, 1H), 3.88 (d, J=11.0 Hz, 2H), 3.75-3.17 (m, 13H), 2.21-2.02 (m, 2H)

Compound 72: 1H NMR (400 MHz, DMSO-d6) δ (CHLOROFORM-d) 8.14 (d, J=5.5 Hz, 1H), 7.93 (br. s., 2H), 7.84 (s, 1H), 7.71 (d, J=8.5 Hz, 1H), 7.55-7.44 (m, 2H), 7.34-7.28 (m, 3H), 5.25 (s, 1H), 3.70 (br. s., 4H), 3.49 (br. s., 2H), 3.04 (br. s., 4H), 2.92 (br. s., 2H), 2.59-2.49 (m, 3H), 2.18-2.04 (m, 2H)

Compound 73: 1H NMR (400 MHz, DMSO-d6) δ 11.07 (br. s., 1H), 8.17 (d, J=5.8 Hz, 1H), 7.97 (br. s., 2H), 7.76 (d, J=6.8 Hz, 1H), 7.59 (br. s., 2H), 7.32 (br. s., 3H), 6.77 (br. s., 1H), 5.26 (br. s., 1H), 3.90 (br. s., 6H), 3.70-3.05 (m, 10H), 2.15 (br. s., 2H)

Compound 88: 1H NMR (400 MHz, DMSO-d6) δ 11.07 (br. s., 1H), 8.16 (d, J=7.8 Hz, 1H), 8.00 (d, J=6.0 Hz, 1H), 7.97-7.89 (m, 2H), 7.65-7.56 (m, 1H), 7.56-7.45 (m, 2H), 7.40-7.27 (m, 3H), 5.27 (s, 1H), 4.64 (br. s., 1H), 4.03-3.84 (m, 5H), 3.73-3.52 (m, 4H), 3.50-3.35 (m, 4H), 3.30 (br. s., 2H), 2.16 (quin, J=7.2 Hz, 2H)

Compound 91: 1H NMR (400 MHz, DMSO-d6) δ 10.52 (br. s., 1H), 8.14-8.07 (m, 2H), 7.93 (d, J=8.3 Hz, 1H), 7.86 (t, J=5.5 Hz, 1H), 7.74 (t, J=7.5 Hz, 1H), 7.64-7.58 (m, 1H), 7.58-7.52 (m, 1H), 7.40-7.28 (m, 2H), 7.15 (s, 1H), 5.28 (s, 1H), 3.96 (d, J=13.3 Hz, 2H), 3.68 (br. s., 1H), 3.63 (d, J=11.5 Hz, 2H), 3.52-3.24 (m, 8H), 2.17-2.04 (m, 2H)

Compound 95: 1H NMR (400 MHz, DMSO-d6) δ 10.57 (br. s., 1H), 8.24 (s, 1H), 8.21 (d, J=8.3 Hz, 1H), 8.09 (dd, J=8.0, 13.1 Hz, 2H), 7.94-7.88 (m, 1H), 7.88-7.80 (m, 2H), 7.65-7.57 (m, 1H), 7.38-7.28 (m, 2H), 5.28 (s, 1H), 3.98 (d, J=13.3 Hz, 2H), 3.63 (d, J=11.0 Hz, 2H), 3.55-3.45 (m, 2H), 3.44-3.24 (m, 6H), 2.12 (quin, J=7.1 Hz, 2H)

Compound 98: 1H NMR (400 MHz, DMSO-d6) δ 11.12 (br. s., 1H), 8.14 (d, J=7.8 Hz, 1H), 7.93 (d, J=8.5 Hz, 2H), 7.78 (d, J=6.3 Hz, 1H), 7.68-7.49 (m, 3H), 7.38-7.27 (m, 2H), 6.96 (br. s., 1H), 5.28 (s, 1H), 4.69-3.86 (m, 6H), 3.69 (d, J=12.3 Hz, 2H), 3.52-3.35 (m, 4H), 3.30 (br. s., 2H), 3.11 (s, 6H), 2.23-2.08 (m, 2H)

Compound 108: 1H NMR (400 MHz, DMSO-d6) δ ppm 1.90-2.27 (m, 2H), 2.92 (s, 3H), 3.06-4.06 (m, 12H), 5.27 (s, 1H), 7.18-8.01 (m, 8H), 8.03-8.19 (m, 2H), 10.59 (br. s., 1H)

Compound 62 was prepared like compound 44, but employing tert-butyl N-(3-bromoethyl)carbamate instead of tert-butyl N-(3-bromopropyl)carbamate in step 3. LC-MS (M–H⁺)=401.3

Compound 62: 1 H NMR (400 MHz, DMSO-d6) δ 11.28 (br. s., 1H), 8.23 (d, J=7.5 Hz, 1H), 8.19 (d, J=8.3 Hz, 1H), 8.11 (d, J=5.8 Hz, 1H), 8.04 (t, J=5.3 Hz, 1H), 7.99 (d, J=8.0 Hz, 1H), 7.83 (t, J=7.4 Hz, 1H), 7.73-7.66 (m, 1H), 7.65-7.58 (m, 1H), 7.56 (d, J=5.8 Hz, 1H), 7.39-7.28 (m, 2H), 5.39 (s, 1H), 4.86 (br. s., 1H), 3.99 (d, J=11.8 Hz, 2H), 3.87-3.73 (m, 4H), 3.64 (t, J=11.4 Hz, 2H), 3.51 (br. s., 4H)

Compound 69 was prepared like compound 44, but employing 1H-Indene-1,3(2H)-dione instead of 2-oxo-2H-chromen-4-yl trifluoromethanesulfonate in step 6. LC-MS (M–H⁺)=399.3

Compound 69: 1H NMR (400 MHz, DMSO-d6) δ 8.40 (t, J=5.3 Hz, 1H), 8.10 (d, J=5.8 Hz, 1H), 8.08 (d, J=8.3 Hz, 1H), 7.87 (d, J=8.0 Hz, 1H), 7.70 (t, J=7.3 Hz, 1H), 7.63-7.55 (m, 2H), 7.43-7.33 (m, 3H), 7.28-7.23 (m, 1H), 4.84 (s, 1H), 3.39 (q, J=6.5 Hz, 2H), 3.36-3.25 (m, 6H), 2.67 (br. s., 4H), 1.87 (quin, J=6.5 Hz, 2H)

Compound 79 was prepared like compound 44, but employing 2-oxo-6-chloro-2H-chromen-4-yl trifluoromethanesulfonate instead of 2-oxo-2H-chromen-4-yl trifluoromethanesulfonate in step 6. LC-MS (M−H⁺)=449.3

Compound 79: 1H NMR (400 MHz, DMSO-d6) δ 10.86 (br. s., 1H), 8.28 (d, J=1.8 Hz, 1H), 8.17 (d, J=8.3 Hz, 1H), 8.11 (d, J=5.8 Hz, 1H), 7.97 (d, J=8.0 Hz, 1H), 7.95-7.88 (m, J=5.0, 5.0 Hz, 1H), 7.81 (t, J=7.4 Hz, 1H), 7.73-7.60 (m, 2H), 7.54 (d, J=5.8 Hz, 1H), 7.37 (d, J=9.0 Hz, 1H), 5.32 (s, 1H), 4.31 (br. s., 1H), 3.94 (d, J=13.3 Hz, 2H), 3.75-3.50 (m, 4H), 3.48-3.12 (m, 6H), 2.25-2.03 (m, 2H)

Compound 80 was prepared like compound 44, but employing 2-oxo-6-fluoro-2H-chromen-4-yl trifluoromethanesulfonate instead of 2-oxo-2H-chromen-4-yl trifluoromethanesulfonate in step 6. LC-MS (M−H⁺)=433.3

Compound 80: 1H NMR (400 MHz, DMSO-d6) δ 11.07 (br. s., 1H), 8.18 (d, J=8.3 Hz, 1H), 8.14-8.05 (m, 2H), 7.99 (d, J=8.3 Hz, 1H), 7.92 (t, J=5.3 Hz, 1H), 7.83 (t, J=7.4 Hz, 1H), 7.74-7.65 (m, 1H), 7.55 (d, J=6.0 Hz, 1H), 7.49 (dt, J=2.8, 8.5 Hz, 1H), 7.43-7.32 (m, 1H), 5.31 (s, 1H), 4.72 (br. s., 1H), 3.98 (d, J=13.3 Hz, 2H), 3.65 (d, J=11.5 Hz, 4H), 3.48-3.35 (m, 4H), 3.30 (br. s., 2H), 2.24-2.06 (m, 2H)

Compound 86 was prepared like compound 44, but employing 2-oxo-5,6,7,8-tetrahydro-2H-chromen-4-yl trifluoromethane sulfonate instead of 2-oxo-2H-chromen-4-yl trifluoromethanesulfonate in step 6. LC-MS (M−H⁺)=419.4

Compound 86: 1H NMR (400 MHz, DMSO-d6) δ 11.16 (br. s., 1H), 8.19 (d, J=8.3 Hz, 1H), 8.07 (d, J=6.0 Hz, 1H), 8.00 (d, J=8.0 Hz, 1H), 7.94-7.79 (m, 1H), 7.77-7.66 (m, 1H), 7.57 (d, J=5.8 Hz, 1H), 6.80 (br. s., 1H), 4.92 (s, 1H), 4.01 (d, J=13.3 Hz, 1H), 4.06 (br. s., 3H), 3.68 (d, J=10.0 Hz, 1H), 3.62 (d, J=12.0 Hz, 2H), 3.39 (d, J=10.0 Hz, 2H), 3.30-3.12 (m, 4H), 2.42-2.32 (m, 2H), 2.30-2.17 (m, 2H), 2.03 (quin, J=7.0 Hz, 2H), 1.78-1.53 (m, 4H)

2-oxo-6-chloro-2H-chromen-4-yl trifluoromethanesulfonate, 2-oxo-6-fluoro-2H-chromen-4-yl trifluoromethanesulfonate and 2-oxo-5,6,7,8-tetrahydro-2H-chromen-4-yl trifluoromethane are prepared with the procedure of step 5, using 4-hydroxy-6-chloro-2H-chromen-2-one, 4-hydroxy-6-fluoro-2H-chromen-2-one and 4-hydroxy-5,6,7,8-tetrahydro-2H-chromen-2-one, respectively.

Preparation of Compound 124

To a solution of 4-({3-[4-(isoquinolin-1-yl)piperazin-1-yl]propyl}amino)-2H-chromen-2-one (compound 44) (110 mg, 0.265 mmoles, 1 eq.) in THF (5 mL), at 0° C., CH₃I (33 μl, 0.53 mmoles, 2 eq.) was added. The mixture temperature was raised spontaneously to r.t. and then heated to 70° C. for two days. Solvent was removed by vacuum and the crude material is purify by preparative HPLC-MS to obtain 4-(isoquinolin-1-yl)-1-methyl-1-{3-[(2-oxo-2H-chromen-4-yl)amino]propyl}piperazin-1-ium iodide (compound 124) (52 mg, Y=32%). LC-MS (M−H⁺)=429.2

¹H NMR (300 MHz, DMSO-d6+D₂O) δ=8.20-8.09 (m, 2H), 8.03 (dd, J=1.3, 8.0 Hz, 1H), 7.95 (d, J=7.6 Hz, 1H), 7.77 (dt, J=1.0, 7.5 Hz, 1H), 7.72-7.58 (m, 2H), 7.52 (d, J=5.8 Hz, 1H), 7.41-7.30 (m, 2H), 5.33 (s, 1H), 3.87-3.58 (m, 10H), 3.42 (t, J=6.6 Hz, 2H), 3.22 (s, 3H), 2.26-2.05 (m, 2H).

Preparation of Compound 64

Compound 64 was prepared as compound 44 by replacing the 2-oxo-2H-chromen-4-yl-trifluoromethane-sulfonate of step 6 with the 4-chloro-3,4-dihydro-2H-1,3-benzoxazin-2-one intermediate compound D1, prepared as described below. LC-MS (M−H⁺)=416.3

Synthetic Method Used to Prepare Compound 64

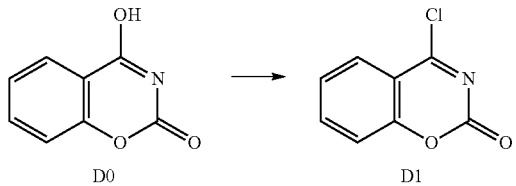

Phosphorus pentachloride (293 mg) was added to a stirred mixture of 4-hydroxy-1,3-benzoxazin-2-one intermediate compound D0 (100 mg) in phosphorus(V) oxychloride (0.335 mL) at room temperature. The reaction mixture was heated to 110° C. and stirred 4 h. The reaction mixture was cooled and evaporated under reduced pressure. Then, for 3 times, the residue was dissolved in toluene and concentrated under reduced pressure to remove the excess of POCl₃. The crude product was chromatographed on a silica gel cartridge eluting with EtOAc to give 108 mg of 4-chloro-3,4-dihydro-2H-1,3-benzoxazin-2-one intermediate compound D1 (Y=99%).

Compound 64: 1H NMR (400 MHz, DMSO-d6) δ 10.62 (br. s., 1H), 9.49 (br. s., 1H), 8.24 (d, J=8.0 Hz, 1H), 8.17 (d, J=8.3 Hz, 1H), 8.11 (d, J=6.0 Hz, 1H), 7.97 (d, J=8.0 Hz, 1H), 7.81 (t, J=7.7 Hz, 1H), 7.77-7.71 (m, 1H), 7.71-7.64 (m, 1H), 7.54 (d, J=6.0 Hz, 1H), 7.37 (t, J=7.7 Hz, 1H), 7.32 (d, J=8.5 Hz, 1H), 4.11 (br. s., 1H), 3.95 (d, J=11.8 Hz, 2H), 3.66 (q, J=6.1 Hz, 4H), 3.56 (br. s., 2H), 3.41 (br. s., 2H), 3.31 (br. s., 2H), 2.16 (quin, J=7.4 Hz, 2H)

Preparation of Compounds 61, 63, 65, 66, 67, 72, 88 and 100

Compounds 61, 63, 65, 66, 67, 72, 88 and 100 were prepared as described herein below, following the synthetic pathway E.

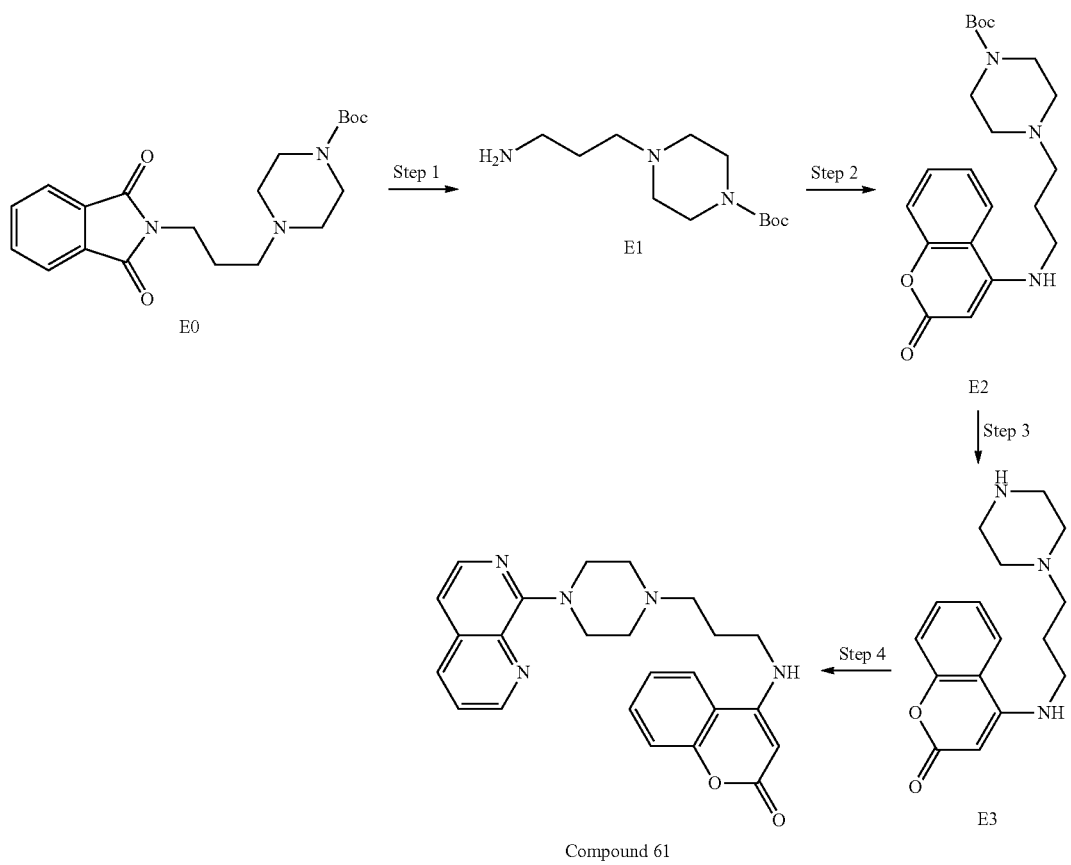 [SMILES: CC(C)(C)OC(=O)N1CCN(CCCN2C(=O)c3ccccc3C2=O)CC1 ; CC(C)(C)OC(=O)N1CCN(CCCN)CC1 ; CC(C)(C)OC(=O)N1CCN(CCCNc2cc(=O)oc3ccccc23)CC1 ; O=c1cc(NCCCN2CCN(c3nccc4cccnc34)CC2)c2ccccc2o1 ; O=c1cc(NCCCN2CCNCC2)c2ccccc2o1]

Compound 61

Synthetic Method Used to Prepare Compound 61

Step 1

Tert-butyl-4-[3-(1,3-dioxoisoindol-2-yl)propyl]piperazine-1-carboxylate intermediate compound E0 (1.9 g) was dissolved in methylamine (33% in absolute ethanol, 20 mL) and heated at 40° C. for 4 h. The solvent was evaporated and the residue was dissolved in diethyl ether and filtered. The filtrate was evaporated to give tert-butyl 4-(3-aminopropyl) piperazine-1-carboxylate intermediate compound E1 as a colourless oil (1.1 g, Y=89%). LC-MS (M−H$^+$)=244.3

Step 2

A solution of intermediate compound E1 (1.1 g), triethylamine (0.674 mL) and 2-oxo-2H-chromen-4-yl trifluoromethanesulfonate (1.2 g), prepared as described in step 5 of the preparation of compound 51, in acetonitrile (20 mL) was heated to 70° C. for 1 hour. The reaction mixture was concentrated under reduced pressure and the residue was partitioned between dichloromethane and a brine/sodium bicarbonate mixture (1:1). The mixture was filtered through a hydrophobic frit (Phase Separator) washing with dichloromethane. The organic phase was evaporated under reduced pressure and the residue was chromatographed on silica gel (SNAP50) eluting with a gradient of EtOAc in cyclohexane to give 700 mg of tert-butyl 4-{3-[(2-oxo-2H-chromen-4-yl)amino]propyl}piperazine-1-carboxylate intermediate compound E2 (700 mg, Y=44%). LC-MS (M−H$^+$)=388.3

Step 3

TFA (2 mL) was added to a solution of intermediate compound E2 (700 mg) in dichloromethane (6 mL) at room temperature and the resulting mixture stirred for 20 minutes. The residue was evaporated under reduced pressure, dissolved in MeOH and loaded onto a preconditioned SCX cartridge. The SCX was eluted with MeOH and then a 2M solution of ammonia in methanol. The basic fractions were evaporated under reduced pressure to give 4-{[3-(piperazin-1-yl)propyl]amino}chromen-2-one intermediate compound E3 (456 mg) (Y=88%). LC-MS (M−H$^+$)=288.3

Step 4

A mixture of intermediate compound E3 (40 mg), 8-chloro-1,7-naphthyridine (19 mg) and potassium carbonate (23 mg) in DMSO (1 mL) was stirred overnight at 110° C. The mixture was diluted with EtOAc. The organic phase was washed with sodium bicarbonate solution, water and brine. The organic phase was dried over sodium sulfate and evaporated under reduced pressure. The residue was chromatographed on silica gel (SNAP10) eluting with a gradient of 0-100% of A in EtOAc where A is MeOH/EtOAc (10:90) to give 20 mg of the desired product 4-({3-[4-(1,7-naphthyridin-8-yl)piperazin-1-yl]propyl}amino)-2H-chromen-2-one (compound 61). LC-MS (M−H$^+$)=416.3 4-({3-[4-(1,7-naphthyridin-8-yl)piperazin-1-yl]propyl}amino)-2H-chromen-2-one was dissolved in dichloromethane (1.5 mL) and treated with 1 M HCl solution in diethyl ether (0.12 mL) causing precipitation. The resulting mixture was evaporated under reduced pressure and was triturated with diethyl ether. The solids were dried to give 14.8 mg of 4-({3-[4-(1,7-naphthyridin-8-yl)piperazin-1-yl]propyl}amino)-2H-chromen-2-one hydrochloride salt as a yellow solid. LC-MS (M−H$^+$)=416.3

Compound 61: 1H NMR (400 MHz, DMSO-d6) δ 10.56 (br. s., 1H), 8.91 (dd, J=1.8, 4.3 Hz, 1H), 8.35 (dd, J=1.8, 8.3

Hz, 1H), 8.15-8.04 (m, 2H), 7.85 (t, J=5.4 Hz, 1H), 7.76 (dd, J=4.0, 8.3 Hz, 1H), 7.64-7.55 (m, 1H), 7.43-7.25 (m, 3H), 5.26 (s, 1H), 5.04 (d, J=14.1 Hz, 2H), 3.71-3.48 (m, 6H), 3.46-3.35 (m, 2H), 3.34-3.16 (m, 4H), 2.11 (quin, J=7.2 Hz, 2H)

Compounds 63, 65, 66, 67, 72, 88 and 100 were also prepared in a similar way by replacing the 8-chloro-1,7-naphthyridine of step 4 with the following compounds, respectively.

| Compound | Replacement compound | LC-MS |
|---|---|---|
| 63 | 4-chloro-2H-chromen-2-one | LC-MS (M − H$^+$) = 432.4 |
| 65 | 5-chloro-1,6-naphthyridine | LC-MS (M − H$^+$) = 416.3 |
| 66 | 1,3-dichloroisoquinoline | LC-MS (M − H$^+$) = 449.3 |
| 67 | 7-fluoro-1-chloroisoquinoline | LC-MS (M − H$^+$) = 433.3 |
| 72 | 7-methyl-1-chloroisoquinoline | LC-MS (M − H$^+$) = 429.4 |
| 88 | 7-methoxy-1-chloroisoquinoline | LC-MS (M − H$^+$) = 445.4 |
| 100 | 1-chloro-7-fluoroisoquinolin-2-ium-2-olate | LC-MS (M − H$^+$) = 449.3 |

Compound 63: 1H NMR (400 MHz, DMSO-d6) δ 10.74 (br. s., 1H), 8.10 (d, J=7.8 Hz, 1H), 7.91-7.82 (m, 1H), 7.73 (d, J=7.5 Hz, 1H), 7.61 (q, J=7.7 Hz, 2H), 7.40 (d, J=8.0 Hz, 1H), 7.38-7.28 (m, 3H), 5.87 (s, 1H), 5.27 (s, 1H), 3.78 (d, J=9.0 Hz, 2H), 3.59 (br. s., 7H), 3.45-3.22 (m, 8H), 2.18-2.04 (m, 2H)

Compound 65: 1H NMR (400 MHz, DMSO-d6) δ 10.10 (br. s., 1H), 9.06 (dd, J=1.6, 4.1 Hz, 1H), 8.54 (d, J=8.3 Hz, 1H), 8.35 (d, J=6.0 Hz, 1H), 8.07 (d, J=8.0 Hz, 1H), 7.81 (t, J=5.5 Hz, 1H), 7.68-7.57 (m, 2H), 7.53 (d, J=6.0 Hz, 1H), 7.40-7.28 (m, 2H), 5.28 (s, 1H), 3.92 (d, J=11.5 Hz, 2H), 3.63 (d, J=10.0 Hz, 2H), 3.37-3.18 (m, 8H), 2.18-2.01 (m, 2H)

Compound 66: 1H NMR (400 MHz, DMSO-d6) δ 9.99 (br. s., 1H), 8.11 (d, J=8.3 Hz, 1H), 8.05 (d, J=8.3 Hz, 1H), 7.91 (d, J=7.8 Hz, 1H), 7.85-7.72 (m, 2H), 7.69-7.56 (m, 3H), 7.41-7.28 (m, 2H), 5.29 (s, 1H), 3.96 (d, J=9.3 Hz, 2H), 3.64 (d, J=6.5 Hz, 2H), 3.48-3.34 (m, 8H), 2.16-2.01 (m, 2H)

Compound 67: 1H NMR (400 MHz, DMSO-d6) δ 10.27 (br. s., 1H), 8.16 (d, J=5.8 Hz, 1H), 8.11-8.03 (m, 2H), 7.88-7.80 (m, 2H), 7.70 (dt, J=2.5, 8.8 Hz, 1H), 7.64-7.58 (m, 1H), 7.56 (d, J=5.8 Hz, 1H), 7.39-7.26 (m, 2H), 5.29 (s, 1H), 3.81 (d, J=12.0 Hz, 2H), 3.68-3.58 (m, 2H), 3.57-3.22 (m, 9H), 2.12 (quin, J=7.6 Hz, 2H)

Compound 72: 1H NMR (400 MHz, DMSO-d6) δ (CHLOROFORM-d) 8.14 (d, J=5.5 Hz, 1H), 7.93 (br. s., 2H), 7.84 (s, 1H), 7.71 (d, J=8.5 Hz, 1H), 7.55-7.44 (m, 2H), 7.34-7.28 (m, 3H), 5.25 (s, 1H), 3.70 (br. s., 4H), 3.49 (br. s., 2H), 3.04 (br. s., 4H), 2.92 (br. s., 2H), 2.59-2.49 (m, 3H), 2.18-2.04 (m, 2H)

Compound 88: 1H NMR (400 MHz, DMSO-d6) δ 11.07 (br. s., 1H), 8.16 (d, J=7.8 Hz, 1H), 8.00 (d, J=6.0 Hz, 1H), 7.97-7.89 (m, 2H), 7.65-7.56 (m, 1H), 7.56-7.45 (m, 2H), 7.40-7.27 (m, 3H), 5.27 (s, 1H), 4.64 (br. s., 1H), 4.03-3.84 (m, 5H), 3.73-3.52 (m, 4H), 3.50-3.35 (m, 4H), 3.30 (br. s., 2H), 2.16 (quin, J=7.2 Hz, 2H)

Compound 100: 1H NMR (400 MHz, DMSO-d6) δ 9.97 (br. s., 1H), 8.12 (d, J=7.3 Hz, 2H), 8.07 (dd, J=5.6, 8.9 Hz, 1H), 8.00-7.81 (m, 3H), 7.65-7.52 (m, 2H), 7.39-7.29 (m, 2H), 5.28 (s, 1H), 4.31-3.71 (m, 3H), 3.57 (d, J=11.3 Hz, 2H), 3.52-3.35 (m, 4H), 3.34-3.24 (m, 2H), 3.13 (br. s., 2H), 2.12 (quin, J=7.3 Hz, 2H)

The synthesis of 1-chloro-7-fluoroisoquinolin-2-ium-2-olate, the intermediate X0 used in the preparation of compound 100, is described below.

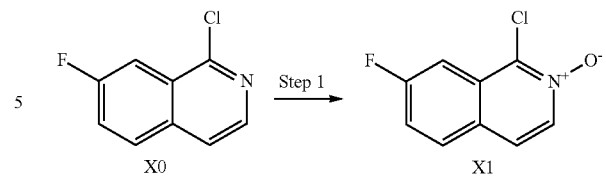

3-Chloroperoxybenzoic acid (0.10 g) was added to a solution of 1-chloro-7-fluoroisoquinoline X0 (50 mg) in dry dichloromethane (1.5 ml). The mixture was stirred at room temperature for 2 days. The mixture was then diluted with dichloromethane and washed with a aqueous 1 M NaOH solution (2×) and brine. The organic phase was dried over Na$_2$SO$_4$, filtered and concentrated in vacuum to give crude 1-chloro-7-fluoroisoquinolin-2-ium-2-olate as a white solid (0.049 g, Y=80%). This product was used without further purification. LC-MS (M−H$^+$)=198.0

Preparation of Compounds 54, 55, 77, 78 and 99

Compounds 54, 55, 77, 78 and 99 were prepared as described herein below, following the synthetic pathway F.

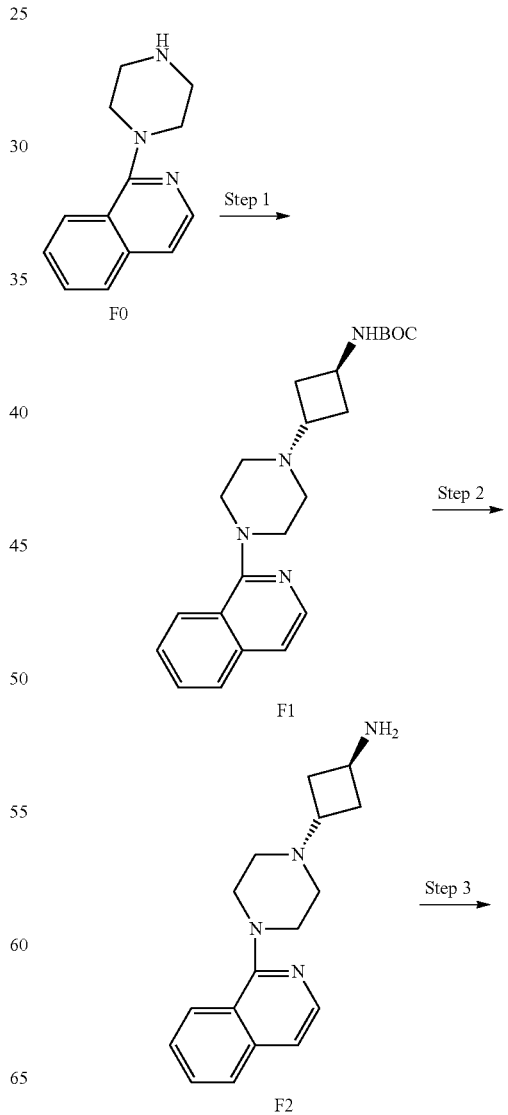

-continued

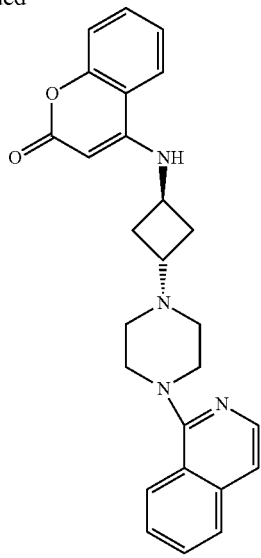

Compound 55

Synthetic Method Used to Prepare Compounds 54 and 55

Step 1

Sodium triacetoxyborohydride (597 mg) was added to a stirred solution of the 1-(piperazin-1-yl)isoquinoline intermediate compound F0 (200 mg), prepared as described in step 1 of the preparation of compound 46, and tert-butyl N-(3-oxocyclobutyl)carbamate (174 mg) in dichloromethane (5 mL) at room temperature. The reaction was stirred at room temperature for 2 hours. The reaction was diluted with dichloromethane (15 mL) and quenched with water (20 mL). The mixture was filtered through a hydrophobic frit (Phase Separator) and the organic phase was washed with a mixture of brine and sodium bicarbonate solution (1:1, 20 mL) then filtered through a hydrophobic frit (Phase Separator). The organic phase was evaporated under reduced pressure. The residue was chromatographed on silica gel (SNAP 25) eluting with a gradient of A in cyclohexane, where A is MeOH/EtOAc (3:97), to give 84 mg of the cis-tert-butyl {3-[4-(isoquinolin-1-yl)piperazin-1-yl]cyclobutyl}-carbamate as a yellow gum (Y=23%), and 175 mg of the trans-tert-butyl-{3-[4-(isoquinolin-1-yl)piperazin-1-yl]cyclobutyl}-carbamate (intermediate compound F1) as white foam (Y=49%) both have LC-MS (M–H$^+$)=383.3.

The following steps have been made using the trans intermediate compound F1 in order to get compound 55. The same steps can be repeated using the cis intermediate compound F1 in order to get compound 54.

Step 2

TFA (1 mL) was added to a solution of trans intermediate compound F1 (175 mg) in dichloromethane (3 mL) at room temperature and the resulting mixture was stirred for 60 minutes. The volatiles were evaporated under reduced pressure. The residue was dissolved twice in dichloromethane (5 mL) and evaporated under reduced pressure. Then the residue was dissolved in MeOH (2 mL) and loaded onto a preconditioned SCX cartridge (1 g). The SCX was eluted with MeOH and then with a 2M solution of ammonia in methanol. The basic fractions were evaporated under reduced pressure to give 127 mg of the trans-3-[4-(isoquinolin-1-yl)piperazin-1-yl]cyclobutanamine intermediate compound F2 as a colorless sticky oil (Y=98%). LC-MS (M–H$^+$)=283.2

Step 3

A solution of the trans intermediate compound F2 (120 mg), triethylamine (81 microL) and 2-oxo-2H-chromen-4-yl trifluoromethanesulfonate (114 mg), prepared as described in step 5 of the preparation of compound 51, in acetonitrile (4 mL) was heated to 70° C. for 1 hour. The reaction mixture was cooled and filtered, washing the solid with acetonitrile (2×1 mL). The solid was further purified by chromatography on silica gel (2×SNAP 10 in series) eluting with a gradient of 1-10% MeOH in dichloromethane to give 148 mg of trans-4-({3-[4-(isoquinolin-1-yl)piperazin-1-yl]cyclobutyl}amino)-2H-chromen-2-one (compound 55) as a white foam (Y=79%). LC-MS (M–H$^+$)=427.4

Trans-4-({3-[4-(isoquinolin-1-yl)piperazin-1-yl]cyclobutyl}amino)-2H-chromen-2-one was dissolved in dichloromethane (5 mL) and a minimum quantity of MeOH and treated with 1 M HCl solution in diethyl ether (0.87 mL) causing precipitation. The resulting mixture was evaporated under reduced pressure and the residue was triturated with diethyl ether. The solid was dried to give 152 mg of trans-4-({3-[4-(isoquinolin-1-yl)piperazin-1-yl]cyclobutyl}amino)-2H-chromen-2-one hydrochloride salt as a white solid (Y=79%). LC-MS (M–H$^+$)=427.4.

Compound 55

1H NMR (500 MHz, DMSO-d6) δ ppm 2.55-2.69 (m, 2H), 2.89-3.05 (m, 2H), 3.19-3.37 (m, 2H), 3.58-3.79 (m, 4H), 3.94-4.10 (m, 3H), 4.31 (br. s., 1H), 4.98 (s, 1H), 7.30-7.39 (m, 2H), 7.55-7.65 (m, 2H), 7.72 (t, J=7.58 Hz, 1H), 7.82-7.89 (m, 1H), 7.94 (br. s., 1H), 8.01 (d, J=7.60 Hz, 1H), 8.06-8.13 (m, 1H), 8.17-8.27 (m, 2H), 11.84 (br. s., 1H).

Compound 54

LC-MS (M–H$^+$)=427.4.

$^1$H NMR (500 MHz, DMSO-d6) δ ppm 2.60-2.70 (m, 2H), 2.83-2.94 (m, 2H), 3.27-3.38 (m, 2H), 3.56 (d, J=11.74 Hz, 2H), 3.60-3.75 (m, 3H), 3.86-3.96 (m, 1H), 4.04 (d, J=12.23 Hz, 2H), 5.10 (s, 1H), 7.30-7.38 (m, 2H), 7.55-7.64 (m, 2H), 7.72 (t, J=7.58 Hz, 1H), 7.86 (t, J=7.34 Hz, 1H), 7.97-8.04 (m, 2H), 8.08 (d, J=6.36 Hz, 1H), 8.17-8.27 (m, 2H), 11.85 (br. s., 1H).

Compound 99 was prepared in a similar way by replacing the 1-(piperazin-1-yl)isoquinoline of step 1 with 7-fluoro-1-(piperazin-1-yl)isoquinoline (Y=50%) LC-MS (M–H$^+$)=401.3.

Compounds 99: 1H NMR (400 MHz, DMSO-d6) δ 10.82 (br. s., 1H), 9.37 (d, J=5.8 Hz, 1H), 8.29 (d, J=7.0 Hz, 1H), 8.18 (d, J=5.8 Hz, 1H), 8.08 (dd, J=5.8, 9.0 Hz, 1H), 7.87 (dd, J=2.5, 10.3 Hz, 1H), 7.79-7.68 (m, 2H), 7.58 (d, J=5.8 Hz, 1H), 7.39 (t, J=8.0 Hz, 1H), 7.33 (d, J=8.3 Hz, 1H), 4.96 (br. s., 1H), 4.78 (br. s., 1H), 4.01 (d, J=7.3 Hz, 1H), 3.86 (d, J=12.3 Hz, 2H), 3.65 (d, J=10.8 Hz, 2H), 3.47-3.17 (m, 4H), 3.02-2.81 (m, 2H), 2.74-2.57 (m, 2H)

Preparations of Compounds 77 and 78.

Compounds 77 and 78 were prepared in a similar way of compounds 55 and 54 but in step 1, tert-butyl N-(3-oxocyclooentyl)carbamate having the following formula (ii) was used in place of tert-butyl N-(3-oxocyclobutyl)carbamate. Both compounds have LC-MS (M–H$^+$)=441.4.

Compounds 77: 1 H NMR (400 MHz, DMSO-d6) δ 11.51 (br. s., 1H), 8.43 (d, J=7.3 Hz, 1H), 8.20 (d, J=8.5 Hz, 1H), 8.12 (d, J=5.8 Hz, 1H), 7.99 (d, J=8.3 Hz, 1H), 7.83 (t, J=7.7 Hz, 1H), 7.75-7.66 (m, 2H), 7.65-7.51 (m, 2H), 7.37-7.26 (m, 2H), 5.25 (s, 1H), 4.68 (br. s., 1H), 4.17-4.05 (m, 1H), 3.97 (d, J=11.5 Hz, 2H), 3.81-3.65 (m, 3H), 3.65-3.51 (m, 2H), 3.50-3.35 (m, 2H), 2.72-2.60 (m, 1H), 2.27-2.08 (m, 3H), 2.06-1.91 (m, 2H)

Compounds 78: 1 H NMR (400 MHz, DMSO-d6) δ 11.27 (br. s., 1H), 8.19 (t, J=7.8 Hz, 2H), 8.11 (d, J=6.0 Hz, 1H), 7.98 (d, J=8.0 Hz, 1H), 7.82 (t, J=7.5 Hz, 1H), 7.73-7.65 (m, 1H), 7.64-7.58 (m, 1H), 7.55 (d, J=6.0 Hz, 1H), 7.47 (d, J=6.3 Hz, 1H), 7.39-7.25 (m, 2H), 5.24 (s, 1H), 4.84 (br. s., 1H), 4.25-4.13 (m, 1H), 4.01-3.92 (m, 2H), 3.91-3.81 (m, 1H), 3.74-3.64 (m, 2H), 3.58 (t, J=12.5 Hz, 2H), 3.49-3.32 (m, 2H), 2.48-2.40 (m, 1H), 2.37-2.14 (m, 3H), 2.08-1.95 (m, 1H), 1.94-1.81 (m, 1H)

Tert-butyl N-(3-oxocyclooentyl)carbamate of formula (ii) was prepared as follows.

Step 1a

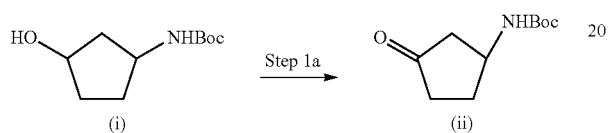

Dess-Martin periodinane (2.53 g) was added portion-wise to a solution of tert-butyl (3-hydroxycyclopentyl)carbamate (1 g) of formula (i) in dichloromethane (26 mL) at 0° C. After complete addition, the reaction mixture was stirred for 1 hour at 0° C., then, allowed to warm up to room temperature and stirred for 18 hours. The reaction mixture was quenched with a 50/50 of a saturated aqueous solution of sodium bicarbonate and a saturated aqueous solution of sodium thiosulfate. The aqueous layer was extracted 3 times with dichloromethane. The combined organic layers were washed with brine, dried over magnesium sulfate and concentrated in vacuum. The residue was purified on silica gel by flash column chromatography eluting with cHex to cHex/ethyl acetate 1:1 to give 980 mg of the intermediate compound tert-butyl (3-oxocyclopentyl)carbamate of formula (ii). (Y=99%). LC-MS (M–H$^+$)=200.1.

Preparation of Compounds 59, 93, 94, 102, 103, 104, 106

Compounds 59, 93, 94, 102, 103, 104, 106 were prepared as described herein below, following the synthetic pathway G.

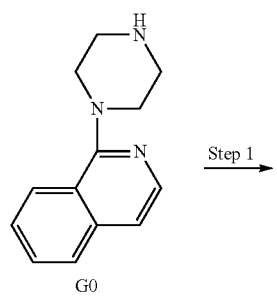

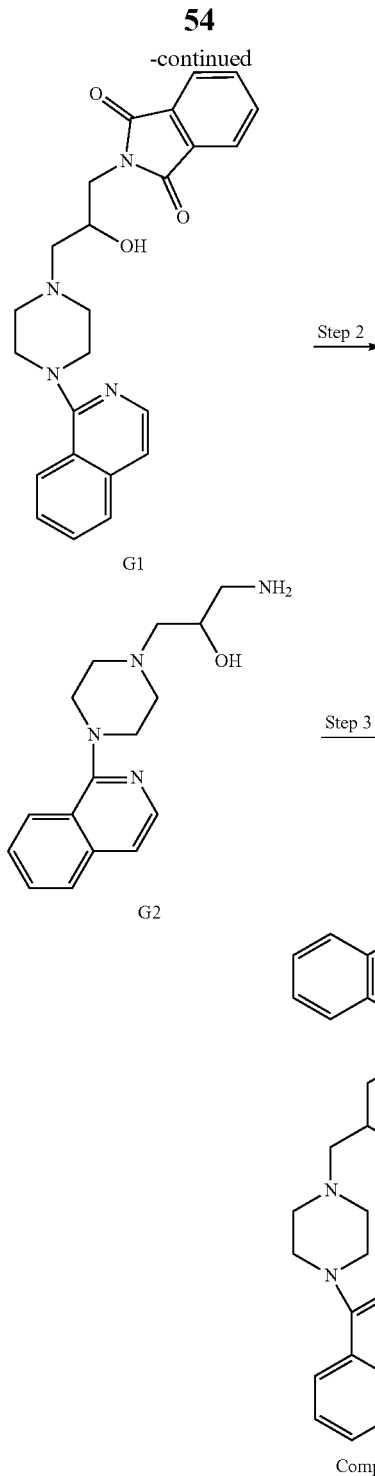

Synthetic Method Used to Prepare Compound 59
Step 1

A mixture of 1-(piperazin-1-yl)isoquinoline, intermediate compound G0 (150 mg), prepared as described in step 1 of the preparation of compound 61, and 2-(oxiran-2-ylmethyl)-2,3-dihydro-1H-isoindole-1,3-dione (136 mg) in CH$_3$CN (3 mL) was heated with shaking to 60° C. for two days. The reaction mixture was evaporated under reduced pressure and the residue was chromatographed on silica gel (SNAP 25) eluting with a gradient of 50-100% EtOAc in cyclohexane to give 203 mg of the intermediate compound 2-{2-hydroxy- 3-[4-(isoquinolin-1-yl)piperazin-1-yl]propyl}-2,3-dihydro-1H-isoindole-1,3-dione, intermediate compound G1 as a white sticky foam (Y=73%). LC-MS (M–H$^+$)=417.3

Step 2

The intermediate compound G1 (202 mg) was dissolved in ethanol methylamine solution (5 mL, 33% solution in EtOH) and heated to 50° C. for 2 hours. The reaction mixture was concentrated under reduced pressure and the residue was triturated with diethyl ether/EtOAc (1:1, ~10 mL). The mixture was filtered, washing the solid with a small quantity of the same solvent mixture. The residue was loaded onto an SCX cartridge (1 g) and eluted with MeOH and then with a 2M solution of NH$_3$ in MeOH. The basic fractions were collected to give 125 mg of the 1-amino-3-[4-(isoquinolin-1-yl)piperazin-1-yl]propan-2-ol, intermediate compound G2 as a colorless sticky gum (Y=90%). LC-MS (M–H$^+$)=287.2

Step 3

A solution of the intermediate compound G2 (123 mg), triethylamine (82 microL) and 2-oxo-2H-chromen-4-yl-trifluoromethane-sulfonate (115 mg), prepared as described in step 1 of the preparation of compound 27, in acetonitrile (4 mL) was heated to 60° C. for 1 hour. The reaction mixture was concentrated under reduced pressure and the residue was partitioned between dichloromethane (20 mL) and a brine/sodium bicarbonate mixture (1:1, 20 mL). The mixture was filtered through a hydrophobic frit (Phase Separator) washing with dichloromethane (10 mL). The organic phase was evaporated under reduced pressure and the residue was chromatographed on silica gel (SNAP 25) eluting with a gradient of 1-10% MeOH in dichloromethane to give 113 mg of the racemic mixture of the desired product 4-({2-hydroxy-3-[4-(iso-quinolin-1-yl)piperazin-1-yl]propyl}amino)-2H-chromen-2-one (compound 59) as a colorless foam. LC-MS (M–H$^+$)=431.3.

The compound 59 was dissolved in dichloromethane (3 mL) and the minimum amount of MeOH and treated with 1 M HCl solution in diethyl ether (0.66 mL) causing precipitation. The resulting mixture was evaporated under reduced pressure and the residue was triturated with diethyl ether. The solids were dried to give 117 mg of the 4-({2-hydroxy-3-[4-(isoquinolin-1-yl)piperazin-1-yl]propyl}amino)-2H-chromen-2-one hydrochloric salt as an off-white solid (Y=60%). LC-MS (M–H$^+$)=431.3

Compound 59: 1H NMR (400 MHz, DMSO-d6) δ 10.23 (br. s., 1H), 8.28-8.04 (m, 3H), 8.03-7.75 (m, 3H), 7.74-7.45 (m, 3H), 7.40-7.26 (m, 2H), 6.06 (br. s., 1H), 5.36 (s, 1H), 4.76 (br. s., 1H), 4.39 (br. s., 1H), 3.95 (br. s., 2H), 3.82-3.42 (m, 7H), 3.40-3.17 (m, 3H)

Compounds 93 and 94, i.e., the R and S stereoisomers of compound 59 were resolved by using a chiral preparative HPLC-MS. Both have LC-MS (M–H$^+$)=431.3.

Compound 93: 1H NMR (400 MHz, DMSO-d6) δ 9.89 (br. s., 1H), 8.18-8.06 (m, 3H), 7.94 (d, J=8.0 Hz, 1H), 7.85 (t, J=5.9 Hz, 1H), 7.76 (t, J=7.8 Hz, 1H), 7.69-7.57 (m, 2H), 7.49 (d, J=5.8 Hz, 1H), 7.40-7.29 (m, 2H), 6.01 (br. s., 1H), 5.38 (s, 1H), 4.33 (d, J=7.8 Hz, 1H), 4.19-3.77 (m, 4H), 3.70 (br. s., 1H), 3.61 (d, J=10.3 Hz, 1H), 3.54-3.31 (m, 6H), 3.30-3.19 (m, 1H)

Compound 94: 1H NMR (400 MHz, DMSO-d6) δ 9.89 (br. s., 1H), 8.19-8.06 (m, 3H), 7.94 (d, J=8.3 Hz, 1H), 7.85 (t, J=6.0 Hz, 1H), 7.76 (t, J=7.4 Hz, 1H), 7.68-7.58 (m, 2H), 7.49 (d, J=5.8 Hz, 1H), 7.39-7.29 (m, 2H), 6.01 (br. s., 1H), 5.38 (s, 1H), 4.43-4.24 (m, 1H), 3.96-3.81 (m, 2H), 3.64 (br. s., 3H), 3.52-3.16 (m, 8H)

Compounds 102 and 103 were prepared in a similar way by replacing the 1-(piperazin-1-yl)isoquinoline of step 1 with the 7-fluoro-1-(piperazin-1-yl)isoquinoline. Both have LC-MS (M–H$^+$)=449.1.

Compound 102: H NMR (400 MHz, DMSO-d6) δ 10.23 (br. s., 1H), 8.19 (d, J=8.0 Hz, 1H), 8.14 (d, J=5.8 Hz, 1H), 8.07 (dd, J=5.8, 9.0 Hz, 1H), 7.94 (t, J=5.5 Hz, 1H), 7.85 (dd, J=2.3, 10.3 Hz, 1H), 7.72 (dt, J=2.5, 8.8 Hz, 1H), 7.65-7.52 (m, 2H), 7.40-7.26 (m, 2H), 5.36 (s, 1H), 4.65-3.17 (m, 15H)

Compound 103: H NMR (400 MHz, DMSO-d$_6$) δ=10.17 (br. s., 1H), 8.18 (d, J=7.8 Hz, 1H), 8.15 (d, J=5.8 Hz, 1H), 8.07 (dd, J=5.6, 8.9 Hz, 1H), 7.92 (t, J=5.7 Hz, 1H), 7.84 (d, J=10.3 Hz, 1H), 7.71 (dt, J=2.3, 8.8 Hz, 1H), 7.64-7.59 (m, 1H), 7.56 (d, J=6.0 Hz, 1H), 7.39-7.30 (m, 2H), 5.37 (s, 1H), 4.51-3.93 (m, 3H), 3.82 (t, J=13.0 Hz, 2H), 3.71 (d, J=10.8 Hz, 1H), 3.61 (d, J=10.8 Hz, 1H), 3.55-3.19 (m, 8H).

Compound 104 and 106 were prepared in a similar way as compound 103 and 102 by replacing the 2-oxo-2H-chromen-4-yl-trifluoromethane-sulfonate of step 3 with the 4-chloro-3,4-dihydro-2H-1,3-benzoxazin-2-one, prepared as described in the preparation of compound 64. Both have LC-MS (M–H$^+$)=450.3

Compound 104: 1H NMR (400 MHz, DMSO-d6) δ 10.05 (br. s., 1H), 9.41 (br. s., 1H), 8.27 (br. s., 1H), 8.15 (d, J=5.8 Hz, 1H), 8.05 (dd, J=5.6, 8.7 Hz, 1H), 7.82 (d, J=10.3 Hz, 1H), 7.78-7.64 (m, 2H), 7.55 (d, J=5.8 Hz, 1H), 7.43-7.25 (m, 2H), 4.51-4.31 (m, 1H), 4.07-3.31 (m, 13H), 3.29-3.17 (m, 1H)

Compound 106: 1H NMR (400 MHz, DMSO-d6) δ 9.94 (br. s., 1H), 9.38 (t, J=5.4 Hz, 1H), 8.25 (d, J=7.8 Hz, 1H), 8.15 (d, J=5.8 Hz, 1H), 8.06 (dd, J=5.6, 8.9 Hz, 1H), 7.82 (dd, J=2.1, 10.2 Hz, 1H), 7.77-7.72 (m, 1H), 7.69 (dt, J=2.8, 8.8 Hz, 1H), 7.55 (d, J=5.8 Hz, 1H), 7.37 (t, J=7.7 Hz, 1H), 7.33 (d, J=8.3 Hz, 1H), 4.45-4.35 (m, J=7.0 Hz, 1H), 3.87-3.67 (m, 5H), 3.66-3.57 (m, 3H), 3.55-3.31 (m, 5H), 3.24 (t, J=11.4 Hz, 1H)

Preparation of Compound 90

Compound 90 was prepared as described herein below, following the synthetic pathway I.

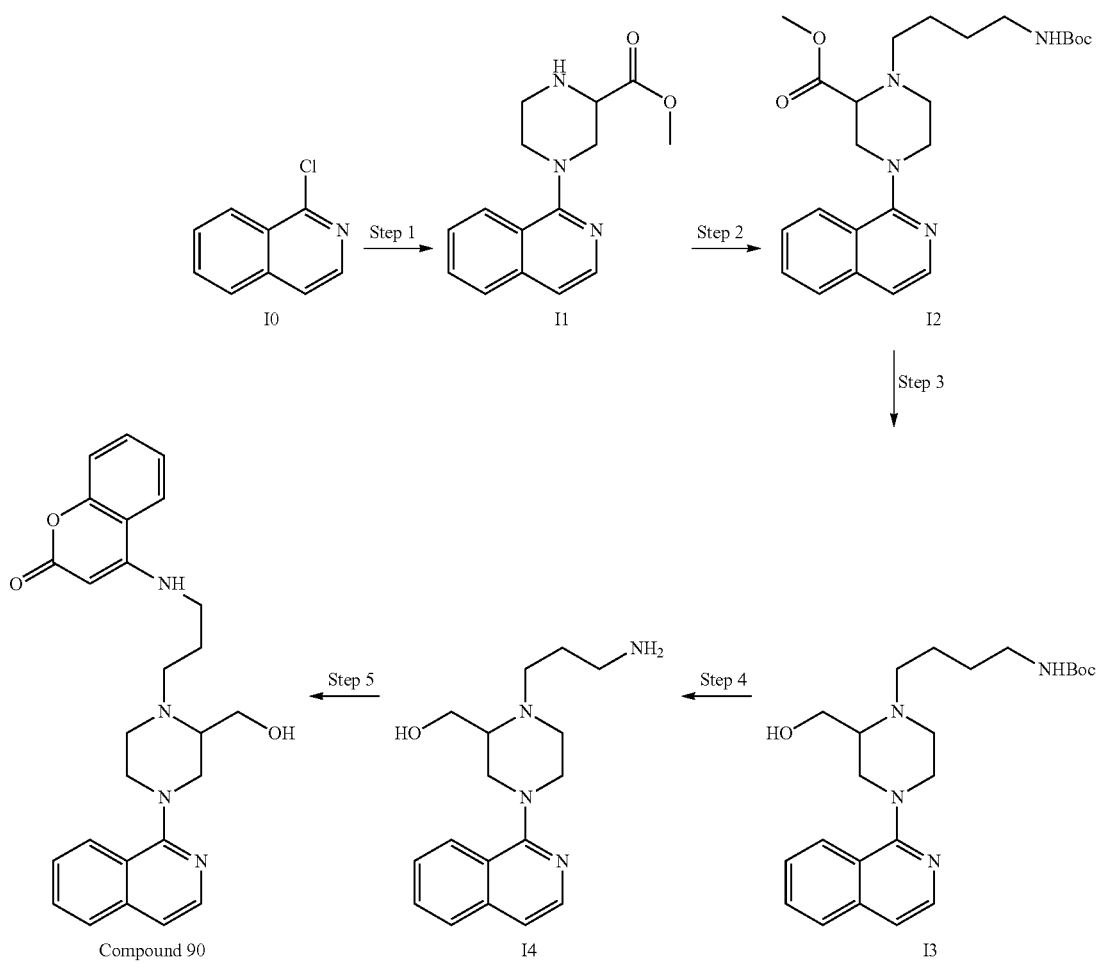

Step 1

1-chloroisoquinoline, intermediate compound 10 (905 mg) was dissolved in $CH_3CN$ (72 ml). Potassium carbonate (796 mg) was added followed by piperazine-2-carboxylic acid methyl ester di-hydrochloride (1.8 g). The mixture was stirred at 100° C. for 7 days. DCM was added and the mixture washed with water. The organic phase was separated, dried and evaporated by vacuum. The crude material was purified by Si-column eluting with cHex/Ethyl acetate 3:7 to ethyl acetate/MeOH 9:1 to obtain 570 mg of the methyl 4-(isoquinolin-1-yl)piperazine-2-carboxylate, intermediate compound 11 (Y=38%). LC-MS (M–H$^+$)=272.2.

Step 2

A mixture of intermediate compound 11 (570 mg), tert-butyl N-(3-bromopropyl)carbamate (475 mg), potassium iodide (174 mg) and potassium carbonate (579 mg) in DMF (20 ml) was stirred at 60° C. overnight.

The reaction was partitioned between EtOAc and semi-saturated brine. The organic phase was separated then washed with semi-saturated brine and brine, dried over sodium sulfate and evaporated under reduced pressure. The residue was chromatographed on silica gel (SNAP 50) eluting with a gradient of 30-100% EtOAc in cyclohexane to give 470 mg of the methyl 1-{3-[(tert-butoxycarbonyl)amino]propyl}-4-(isoquinolin-1-yl)piperazine-2-carboxylate, intermediate compound 12 (Y=52%). LC-MS (M–H$^+$)= 429.4.

Step 3

The intermediate compound 12 (200 mg) was dissolved in THF (2 ml), the mixture was cooled to 0° C. and 2M lithium borohydride solution in THF (0.259 ml) was added drop-wise under $N_2$ atmosphere. The mixture was stirred at room temperature for 7 hours, cooled to 0° C. and quenched with water. Ethyl acetate was added and the organic phase washed with brine. The solvent was evaporated by vacuum to obtain the crude material purified by Si-column (NH) eluting with cyclohexane to ethyl acetate to obtain 102 mg of the tert-butyl N-{3-[2-(hydroxymethyl)-4-(isoquinolin-1-yl)piperazin-1-yl]propyl}carbamate, intermediate compound 13 (Y=54%). LC-MS (M–H$^+$)=401.4

Step 4

The intermediate compound 13 (100 mg) was dissolved in DCM (5 ml), cooled to 0° C. and TFA (1 ml) was added drop-wise. The mixture was stirred at room temperature for 2 hours. The solvent was removed by vacuum and the crude purified by SCX column to obtain 70 mg of the 1-(3-aminopropyl)-4-(isoquinolin-1-yl)piperazine-2-carboxamide intermediate compound 14 (Y=93%). LC-MS (M–H$^+$)= 301.3

Step 5

A solution the intermediate compound 14 (70 mg), triethyl amine (0.726 ml) and 2-oxo-2H-chromen-4-yl trifluoromethanesulfonate (62 mg) in acetonitrile (2 mL) was heated to 70° C. for 1 hour. The reaction mixture was concentrated under reduced pressure. The residue was purified by Si-column (NH) eluting with cyclohexane to ethyl acetate to obtain 40 mg of the desired product 4-({3-[2-(hydroxymethyl)-4-(isoquinolin-1-yl)piperazin-1-yl]-propyl}amino)-2H-chromen-2-one (compound 90). LC-MS (M–H$^+$)=445.4

This product was dissolved in DCM, cooled to 0° C. and 1 M HCl in Et$_2$O (3 eq) was added. After 30 minutes, the solution was evaporated in vacuum and triturated with Et$_2$O to obtain 28 mg of the 4-({3-[2-(hydroxymethyl)-4-(isoquinolin-1-yl)piperazin-1-yl]propyl}amino)-2H-chromen-2-one hydrochloride salt. LC-MS (M−H$^+$)=445.4

Compound 90: 1H NMR (400 MHz, DMSO-d6) δ 9.92 (br. s., 1H), 8.21-8.04 (m, 3H), 7.95 (d, J=8.0 Hz, 1H), 7.87 (t, J=5.8 Hz, 1H), 7.77 (t, J=7.5 Hz, 1H), 7.69-7.57 (m, 2H), 7.51 (d, J=5.8 Hz, 1H), 7.37-7.27 (m, 2H), 5.30 (s, 1H), 4.12 (br. s., 2H), 3.98-3.83 (m, 3H), 3.77 (d, J=12.3 Hz, 1H), 3.67 (br. s., 1H), 3.56 (br. s., 3H), 3.49-3.36 (m, 4H), 3.31 (br. s., 1H), 2.22-2.00 (m, 2H)

Preparation of Compound 105

Compound 105 was prepared as described hereinbelow, following the synthetic pathway L.

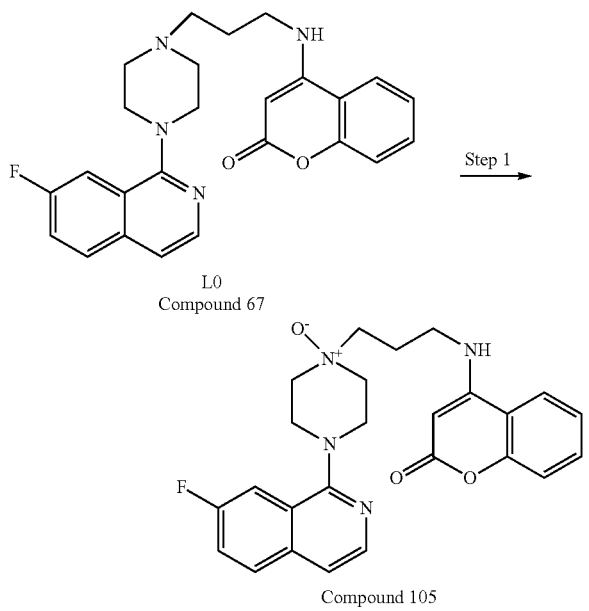

Step 1

3-chloroperoxybenzoic acid (26 mg) was added at 0° C. to a solution of 4-({3-[4-(7-fluoroisoquinolin-1-yl)piperazin-1-yl]propyl}amino)chromen-2-one L0 (compound 67) (60 mg) in dry dichloromethane (3 ml). The mixture was stirred at 0° C. The mixture was then diluted with dichloromethane and washed with a 1 M aqueous NaOH solution (2×) and brine. The organic phase was dried over Na$_2$SO$_4$, filtered and concentrated in vacuum. The residue (59 mg) was purified by flash chromatography (Biotage KP-Sil 10 g SNAP cartridge, eluent A: dichloromethane, eluent B: dichloromethane/MeOH 80/20, gradient A/B from 90/10 to 0/100 in 15CV, then 5CV at 0/100, fraction size 9 mL) to give (0.054 g) of the desired product 4-({3-[4-(7-fluoroisoquinolin-1-yl)-1-oxidopiperazin-1-yl]propyl}amino)-2H-chromen-2-one (compound 105). LC-MS (M−H$^+$)=449.3.

This compound (29.5 mg) was dissolved in dichloromethane and a 1 M HCl solution in diethyl ether (0.14 mL, 2 eq) was added at room temperature. The mixture thus obtained was concentrated under nitrogen and the residue was triturated with diethyl ether (2×) to give the 4-({3-[4-(7-fluoroisoquinolin-1-yl)-1-oxidopiperazin-1-yl]propyl}amino)-2H-chromen-2-one hydrochloride salt as a yellow solid (0.028 g, Y=52%). LC-MS (M−H$^+$)=449.3

Compound 105: 1H NMR (400 MHz, DMSO-d6) δ 12.44 (br. s., 1H), 8.17 (d, J=5.8 Hz, 1H), 8.12 (d, J=7.5 Hz, 1H), 8.08 (dd, J=5.8, 9.0 Hz, 1H), 7.87 (d, J=7.8 Hz, 2H), 7.71 (dt, J=2.5, 8.8 Hz, 1H), 7.64-7.54 (m, 2H), 7.39-7.27 (m, 2H), 5.30 (s, 1H), 4.18-3.73 (m, 8H), 3.68-3.55 (m, 2H), 3.45 (q, J=6.4 Hz, 2H), 2.26 (quin, J=7.0 Hz, 2H)

Preparation of Compound 109

Compound 109 was prepared as described herein below, following the synthetic pathway M.

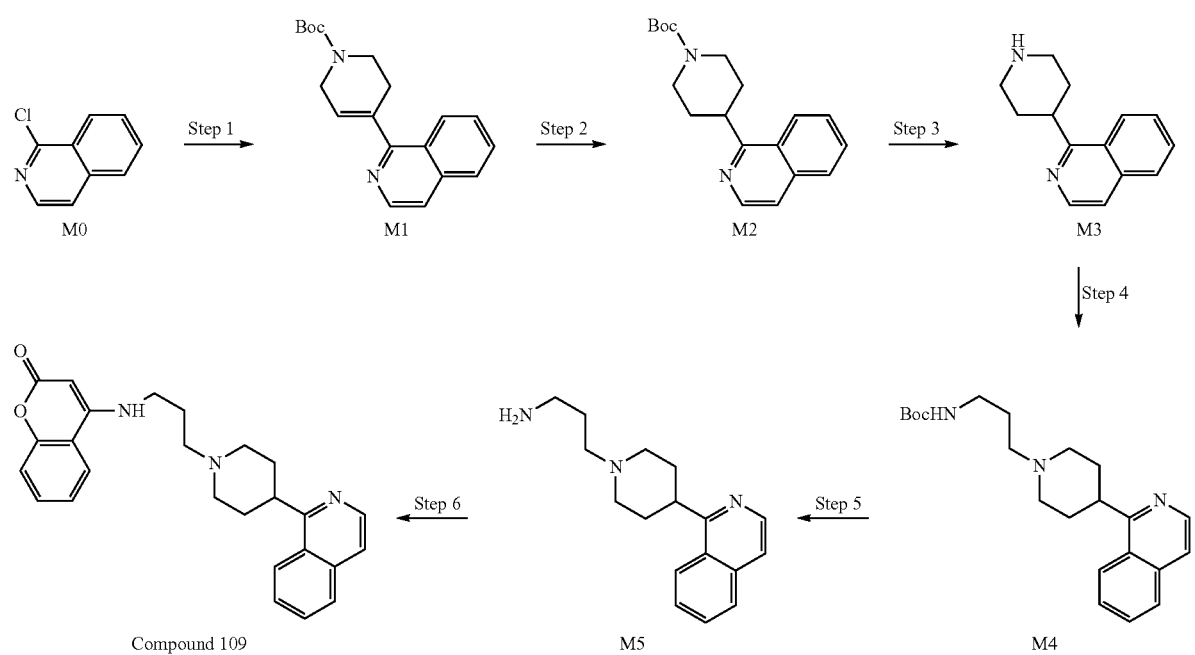

Step 1

A flask charged with 1-chloroisoquinoline, intermediate compound M0 (2.2 g) and N-Boc-1,2,3,6-tetrahydropyridine-4-boronic acid pinacol ester (4 g) was placed under nitrogen. DME (80 mL) and EtOH (24 mL) were added to give a solution. A solution of monobasic potassium phosphate (1.2 g) and tribasic potassium phosphate (1.9 mg) in water (40 mL) was added. The mixture was de-oxygenated via several vacuum/$N_2$ cycles before the addition of $PdCl_2$ (dbpf) (548 mg). The resulting reaction mixture was then stirred at 60° C. overnight. The reaction mixture was partially evaporated under reduced pressure to remove volatiles, then the residue was partitioned between half-saturated sodium bicarbonate solution and EtOAc. The aqueous phase was further extracted with EtOAc. The combined organic phases were washed with brine, dried over $Na_2SO_4$ and evaporated under reduced pressure. The residue was chromatographed on silica gel (SNAP 100) eluting with a gradient of 20-80% EtOAc in cyclohexane to give 2.8 g of tert-butyl 4-(isoquinolin-1-yl)-3,6-dihydro-2H-pyridine-1-carboxylate, intermediate compound M1 (Y=67%). LC-MS (M–$H^+$)=311.5.

Step 2

To a solution of the intermediate compound M1 (2.8 g) in EtOH (90 mL), ammonium formate (3.9 g) and Pd(OH)$_2$/C (644 mg) were added at r.t. The mixture was heated to 80° C. and left stirring at that temperature for 1 hour, then cooled to r.t. and filtered over a pad of celite, washing with EtOH. Solvent was eliminated under reduce pressure. The residue was chromatographed on silica gel (SNAP 100) eluting with a gradient of 10-80% EtOAc in cyclohexane to give 1.66 g of the tert-butyl 4-(isoquinolin-1-yl)piperidine-1-carboxylate, intermediate compound M2 (Y=59%). LC-MS (M–$H^+$)= 313.3

Step 3

TFA (2 mL) was added to a solution of the intermediate compound M2 (658 mg) in dichloromethane (6 mL) at room temperature and the resulting mixture was stirred for 20 minutes. The residue was evaporated under reduced pressure, dissolved in MeOH and loaded onto a preconditioned SCX cartridge. The SCX was eluted with MeOH and then with a 2M solution of ammonia in methanol. The basic fractions were evaporated under reduced pressure to give the 1-(piperidin-4-yl)isoquinoline, intermediate compound M3 (447 mg, Y=quant.). LC-MS (M–$H^+$)=213.2

Step 4

A mixture of the intermediate compound M3 (447 mg), tert-butyl N-(3-bromopropyl)carbamate (476 mg), potassium iodide (174 mg) and potassium carbonate (580 mg) in DMF (10 mL) was stirred overnight at room temperature. The reaction was partitioned between EtOAc and half-saturated brine. The organic phase was separated, then washed with half-saturated brine and brine, dried over sodium sulfate and evaporated under reduced pressure. The residue was chromatographed on silica gel (SNAP 25) eluting with a gradient of 30-100% A in EtOAc, where A is MeOH/EtOAc (20:80) to give 665 mg of the tert-butyl {3-[4-(isoquinolin-1-yl)piperidin-1-yl]propyl}carbamate, intermediate compound M4 (Y=85%). LC-MS (M–$H^+$)= 370.4

Step 5

The intermediate compound M4 (665 mg) was dissolved in DCM (100 ml) and cooled at 0° C. TFA (18 ml) was added and the reaction was stirred at r.t. overnight. The solution was concentrated under vacuum and the residue was loaded on 5 g SCX and eluted with MeOH/$NH_3$ 1M in MeOH. Fractions in MeOH were loaded again on 5 g SCX and eluted with MeOH/$NH_3$ 1M in MeOH. Fractions in $NH_3$ were combined to obtain the 3-[4-(isoquinolin-1-yl)piperidin-1-yl]propan-1-amine intermediate compound M5 (410 mg), as a light yellow oil (Y=85%). LC-MS (M–$H^+$)=270.4

Step 6

A solution of the intermediate compound M5 (167 mg), TEA (130 µL) and 4-chloro-2H-chromen-2-one (100 mg) in $CH_3CN$ (5 ml) was stirred at r.t. for 2 hours. The solution was heated to 40° C., stirred for 1.5 hours, then cooled to r.t. and stirred overnight. The day after, the solution was heated to 60° C. and stirred for 2 hours, then the reaction was stopped. The reaction solution was concentrated and the residue was dissolved in EtOAc, washed with $NaHCO_3$ and brine, dried over $Na_2SO_4$ and concentrated to obtain a crude product (237 mg), as a yellow foam. Such crude product was purified by 25 g Si cartridge, eluting with a mixture DCM/MeOH (from 10/0 to 9/1) to obtain the desired product 4-({3-[4-(isoquinolin-1-yl)piperidin-1-yl]propyl}amino)-2H-chromen-2-one 110 mg (Compound 109), as a white foam. LC-MS (M–$H^+$)=414.4

83 mg of the compound 109 were dissolved in DCM, cooled to 0° C. and then 1M HCl in $Et_2O$ (0.6 mmol, 600 microL) was added. After 15 minutes, the solution was evaporated with $N_2$ and triturated with $Et_2O$ to obtain 4-({3-[4-(isoquinolin-1-yl)piperidin-1-yl]propyl}amino)-2H-chromen-2-one hydrochloride salt, as a light yellow solid (123 mg, Y=44%). LC-MS (M–$H^+$)=414.4

1H NMR (500 MHz, CHLOROFORM-d) δ ppm 1.65 (br. s., 2H), 1.92-2.15 (m, 4H), 2.31 (br. s., 2H), 2.45 (d, J=12.23 Hz, 2H), 2.76 (br. s., 2H), 3.27-3.50 (m, 4H), 3.62-3.78 (m, 1H), 5.22 (s, 1H), 7.32 (d, J=8.80 Hz, 1H), 7.46-7.56 (m, 2H), 7.59 (d, J=5.38 Hz, 1H), 7.63 (t, J=8.30 Hz, 1H), 7.70 (t, J=7.34 Hz, 1H), 7.88 (d, J=7.83 Hz, 1H), 7.91-8.01 (m, 1H), 8.22 (d, J=7.83 Hz, 2H), 8.54-8.72 (m, 2H).

Preparation of Compounds 125, 126 and 127

Compounds 125, 126 and 127 were prepared as described hereinbelow, following the synthetic pathway N.

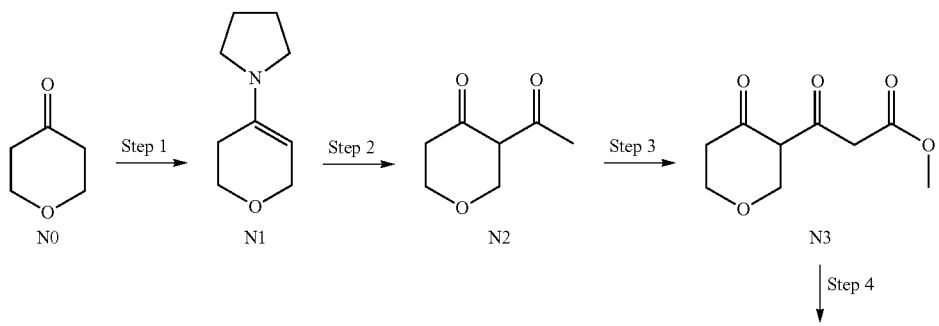

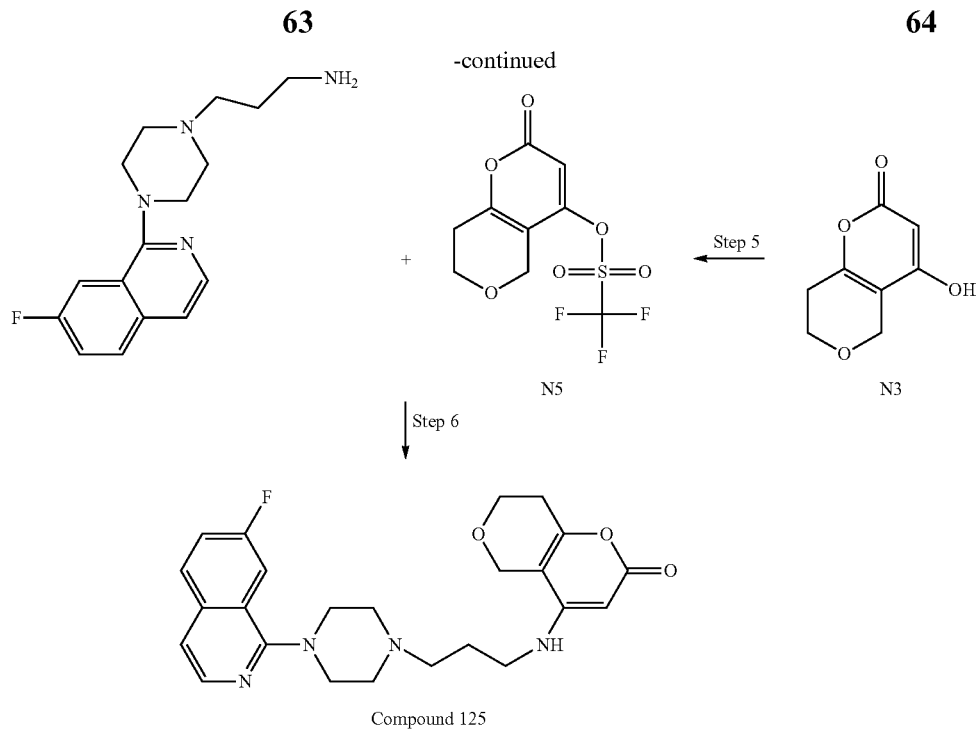

Compound 125

Synthetic Method Used to Prepare Compound 125

Step 1

Pyrrolidine (22 ml) was added to a solution of tetrahydro-4H-pyran-4-one, intermediate compound N0 (10 g) in toluene (120 ml). The mixture was heated at reflux with a Dean-Stark apparatus (bath temperature 120-130° C.). After 1 hour and 30 minutes the reaction was complete, as the formation of the stoichiometric quantity of water was observed. The mixture was then concentrated in vacuum to give a brown oil 1-(3,6-dihydro-2H-pyran-4-yl)pyrrolidine, intermediate compound N1 (17.5 g). The compound was used in the following synthesis without further purification.

Step 2

To a solution of the intermediate compound N1 (9.16 g) in 1,4-dioxane (60 ml) at 00° C., acetic anhydride (12.4 ml) was added and the resulting mixture was allowed to stir at room temperature under nitrogen overnight. Water (15 ml) was added, the resulting mixture was refluxed for 1 hour, then cooled to room temperature and concentrated by vacuum. Water (60 ml) was added and the aqueous phase was extracted twice with EtOAc (60 ml). The combined organics extracts were washed with a 5% w/w HCl aqueous solution (60 ml), dried over $Na_2SO_4$ and concentrated by vacuum to give 7.6 g of crude material. This crude material was purified by flash chromatography (Biotage KP-Sil 340 g SNAP cartridge, gradient cyclohexane/ethyl acetate from 90/10 to 20/80 in 10 CV, fraction size 100 mL) to give the 2-acetyloxan-4-one, intermediate compound N2 as a colorless oil (1.34 g, Y=16%). LC-MS (M–H$^+$)=143.0

Steps 3

The intermediate compound N2 (1.34 g), in THF (47 ml) was cooled to −78° C. and LiHMDS (28.2 ml) was added drop-wise. After stirring for 1 hour at the same temperature, dimethyl carbonate was added. The resulting mixture was allowed to warm up slowly to −10° C. and stirred at this temperature. After 5 hours the reaction mixture was quenched at 0° C. with aqueous 1 M HCl to pH 6. Ethyl acetate was added and the organic phase was separated. The aqueous phase was extracted again with ethyl acetate. The mixed organic phases were washed with brine, dried over $Na_2SO_4$, filtered and evaporated in vacuum to obtain 1.7 g of crude methyl 3-oxo-3-(4-oxotetrahydro-2H-pyran-3-yl)propanoate, intermediate compound N3, which was used for the next step without further purification. LC-MS (M–H$^+$)=183.1

Step 4

The intermediate compound N3 (1.7 g) was dissolved in toluene. DBU (1.4 ml) was added and the mixture stirred at reflux. The reaction was cooled to 0° C. and quenched with aqueous 1M HCl. Ethyl acetate was added and the organic phase was separated. The aqueous phase was extracted again with ethyl acetate. The mixed organic phases were washed with brine, dried over $Na_2SO_4$, filtered and evaporated in vacuum to obtain 1.2 g of crude material. The crude material was purified by flash chromatography (Biotage KP-Sil 50 g SNAP cartridge, eluent A: dichloromethane, eluent B: dichloromethane/MeOH 9/1, gradient A/B from 70/30 to 0/100 in 10CV, fraction size 9 mL) to give the 4-hydroxy-2,5,7,8-tetrahydropyrano[3,2-c]pyran-2-one, intermediate compound N4 as a yellow foam (553 mg, Y=35%). LC-MS (M–H$^+$)=169.0

Step 5

A solution of trifluoromethanesulfonic anhydride (0.664 ml) in dichloromethane (5 mL) was added drop-wise to a stirred solution of the intermediate compound N4 (553 mg) and triethylamine (0.915 ml) in dichloromethane (10 mL) at −10° C. The reaction was stirred at −10° C. for 1 hour, then allowed to warm to 0° C. and diluted with cyclohexane/diethyl ether (3:1, 60 mL). The mixture was filtered over a silica gel plug washing with further cyclohexane/diethyl ether (3:1). The washings containing the desired product were evaporated under reduced pressure to give 425 mg of the 2-oxo-2,5,7,8-tetrahydropyrano[3,2-c]pyran-4-yl trifluoromethanesulfonate, inter-mediate compound N5 as a yellow oil (Y=43%). LC-MS (M+H$^+$)=301.1

Step 6

A solution of 3-[4-(7-fluoroisoquinolin-1-yl)piperazin-1-yl]propan-1-amine (intermediate compound C4 in the synthesis of compound 67) (164 mg), triethylamine (0.145 ml) and intermediate compound N5 (150 mg) in acetonitrile (4 mL) was stirred at room temperature for 2 hours. DCM was added and the organic phase washed with brine. The solvent was removed in vacuum to obtain 130 mg of crude material. The reaction mixture was concentrated under reduced pressure. The residue was purified by Si-column eluting with ethyl acetate to ethyl acetate/methanol 8:2 and then with DCM to DCM/Methanol 9:1 to obtain 58 mg of the desired product 4-({3-[4-(7-fluoroisoquinolin-1-yl)piperazin-1-yl]propyl}amino)-7,8-dihydro-2H,5H-pyrano[4,3-b]pyran-2-one (compound 125) (Y=25%). LC-MS (M−H$^+$)=439.3

Compound 125: 1H NMR (400 MHz, DMSO-d6) δ 10.07 (br. s., 1H), 8.17 (d, J=5.5 Hz, 1H), 8.06 (dd, J=5.8, 9.0 Hz, 1H), 7.84 (dd, J=2.4, 10.4 Hz, 1H), 7.70 (dt, J=2.5, 8.8 Hz, 1H), 7.56 (d, J=5.8 Hz, 1H), 6.75 (t, J=5.4 Hz, 1H), 4.99 (s, 1H), 4.35 (s, 2H), 3.91-3.75 (m, 5H), 3.46-3.28 (m, 5H), 3.27-3.14 (m, 5H), 2.07-1.92 (m, 2H)

This product was dissolved in DCM to 0° C. and 2N HCl in diethyl ether (3 eq) was added. After 10 minutes the solvent was evaporated in vacuum and the solid triturated with diethyl ether to afford 20 mg of 4-({3-[4-(7-fluoroisoquinolin-1-yl)piperazin-1-yl]propyl}amino)-7,8-dihydro-2H,5H-pyrano[4,3-b]pyran-2-one hydrochloride salt (Y=7.5%). LC-MS (M−H$^+$)=439.3

Compounds 126 and 127 were prepared in a similar way by replacing the tetrahydro-4H-pyran-4-one (NO) of step 1 with the following compounds, respectively.

| Compound | Intermediate NO | LC-MS |
|---|---|---|
| 126 | Tetrahydro-4H-thiopyran-4-one | LC-MS (M − H$^+$) = 455.3 |
| 127 | Tetrahydro-4H-thiopyran-4-one 1,1-dioxide | LC-MS (M − H$^+$) = 487.3 |

Compound 126: 1H NMR (400 MHz, DMSO-d6) δ 10.30 (br. s., 1H), 8.16 (d, J=5.8 Hz, 1H), 8.07 (dd, J=5.9, 9.2 Hz, 1H), 7.90-7.78 (m, 1H), 7.71 (t, J=8.8 Hz, 1H), 7.56 (d, J=5.5 Hz, 1H), 6.97-6.84 (m, 1H), 5.00 (s, 1H), 3.93 (br. s., 1H), 3.81 (d, J=10.0 Hz, 2H), 3.68-3.52 (m, 2H), 3.48-3.31 (m, 6H), 3.26 (d, J=6.0 Hz, 4H), 2.85 (t, J=5.5 Hz, 2H), 2.74-2.61 (m, 2H), 2.12-1.90 (m, 2H)

Compound 127: 1H NMR (400 MHz, DMSO-d6) δ 10.49 (br. s., 1H), 8.16 (d, J=5.8 Hz, 1H), 8.07 (dd, J=5.6, 8.9 Hz, 1H), 7.85 (dd, J=2.1, 10.2 Hz, 1H), 7.71 (dt, J=2.5, 8.8 Hz, 1H), 7.57 (d, J=5.8 Hz, 1H), 6.92 (t, J=5.4 Hz, 1H), 5.06 (s, 1H), 4.16 (br. s., 1H), 4.07 (s, 2H), 3.82 (d, J=9.3 Hz, 2H), 3.60 (d, J=5.8 Hz, 2H), 3.51 (t, J=6.4 Hz, 2H), 3.46-3.32 (m, 4H), 3.24 (q, J=6.4 Hz, 4H), 3.02 (t, J=6.1 Hz, 2H), 2.02 (quin, J=7.0 Hz, 2H)

Preparation of Compound 131

Compound 131 was prepared as described hereinbelow, following the synthetic pathway O.

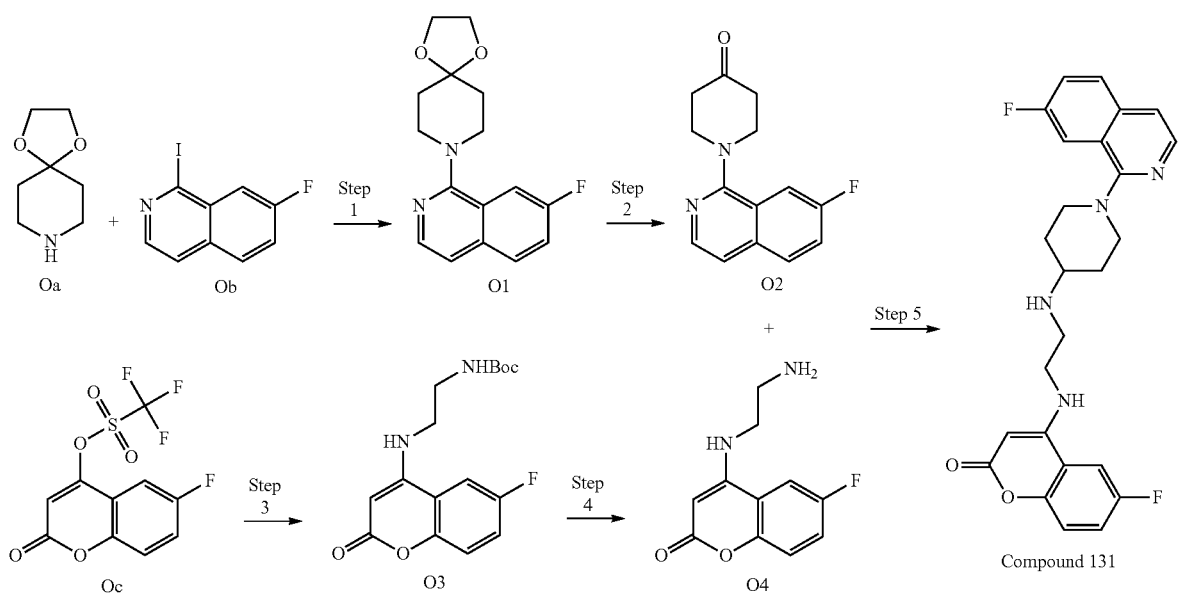

Step 1

A mixture of 1,4-dioxa-8-azaspiro[4.5]decane, intermediate compound Oa (723 mg), 7-fluoro-1-iodoisoquinoline intermediate compound Ob (1.15 g) and potassium carbonate (872 mg) in DMSO (13 mL) was stirred overnight at 110° C. The mixture was diluted with EtOAc. The organic phase was washed with sodium bicarbonate solution and brine. The organic phase was dried over sodium sulfate, filtered and evaporated under reduced pressure to give 1.3 g of 1-(1,4-dioxa-8-azaspiro[4.5]dec-8-yl)-7-fluoroisoquinoline, intermediate compound O1 as a yellow oil (Y=92%). LC-MS (M−H+)=289.1

Step 2

To a solution of 1-(1,4-dioxa-8-azaspiro[4.5]dec-8-yl)-7-fluoroisoquinoline, intermediate compound O1 (1.1 g) in THF (3 mL) 2N HCl (5 mL) was added at r. t. and left stirring overnight. The red solution obtained was then heated to 60° C. for 8 h and overnight at r.t. The reaction mixture was made basic with a solution of 10% NaOH and extracted with EtOAc. The organic phase was washed with brine, dried over sodium sulphate, filtered and evaporated under reduced pressure. The residue was chromatographed on silica gel eluting CHCl₃ to CHCl₃/MeOH (99:1) to obtain 1-(7-fluoroisoquinolin-1-yl)piperidin-4-one, intermediate compound O2 (Y=78%). LC-MS (M–H+)=245.1

Step 3

Tert-butyl {2-[(6-fluoro-2-oxo-2H-chromen-4-yl)amino]ethyl}carbamate, intermediate compound O3, was prepared as described in step 6 of the preparation of compound 51, using tert-butyl (2-aminoethyl)carbamate and 6-fluoro-2-oxo-2H-chromen-4-yl trifluoromethanesulfonate as starting reagents (Y=50%). LC-MS (M–H+)=323.1

Step 4

4-[(2-aminoethyl)amino]-6-fluoro-2H-chromen-2-one, intermediate compound O4, was prepared as described in step 4 of the preparation of compound 51, using tert-butyl {2-[(6-fluoro-2-oxo-2H-chromen-4-yl)amino]ethyl} carbamate as reagent (Y=90%). LC-MS (M–H+)=223.1

Step 5

To a suspension of 4-[(2-aminoethyl)amino]-6-fluoro-2H-chromen-2-one, intermediate compound O4 (300 mg) in CHCl₃ (35 ml), a solution of 1-(7-fluoroisoquinolin-1-yl)piperidin-4-one O2 (213 mg) in CHCl₃ (15 ml) was added at r.t. Two drops of acetic acid and, after ten minutes, sodium triacetoxyborohydride (210 mg) were added to the mixture. This was left stirring for two days at r.t. The suspension was diluted with DCM and washed with sodium bicarbonate solution. The phases were separated and the organic phase was washed with brine, dried over sodium sulphate, filtered and evaporated under reduced pressure. The residue was chromatographed on silica gel eluting with CHCl₃ to CHCl₃/MeOH (9:1) to obtain 6-fluoro-4-[(2-{[1-(7-fluoroisoquinolin-1-yl)piperidin-4-yl]amino}ethyl)amino]-2H-chromen-2-one (compound 131) (35 mg, Y=10%). LC-MS (M–H⁺)=451.19

¹H NMR (300 MHz, DMSO-d₆) δ=8.09 (d, J=5.8 Hz, 1H), 8.04-7.94 (m, 2H), 7.70-7.54 (m, 3H), 7.48 (ddd, J=3.0, 8.0, 9.0 Hz, 1H), 7.41 (d, J=5.8 Hz, 1H), 7.37 (dd, J=4.9, 9.1 Hz, 1H), 5.27 (s, 1H), 3.66 (td, J=3.0, 13.1 Hz, 2H), 3.42-3.22 (m, 2H), 3.03-2.83 (m, 4H), 2.79-2.66 (m, 1H), 2.00 (dd, J=2.4, 12.6 Hz, 2H), 1.59 (dq, J=3.4, 11.3 Hz, 2H).

Preparation of Compound 134

Compound 134 was prepared as described hereinbelow, following the synthetic pathway P.

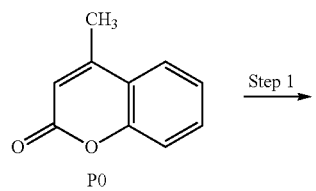

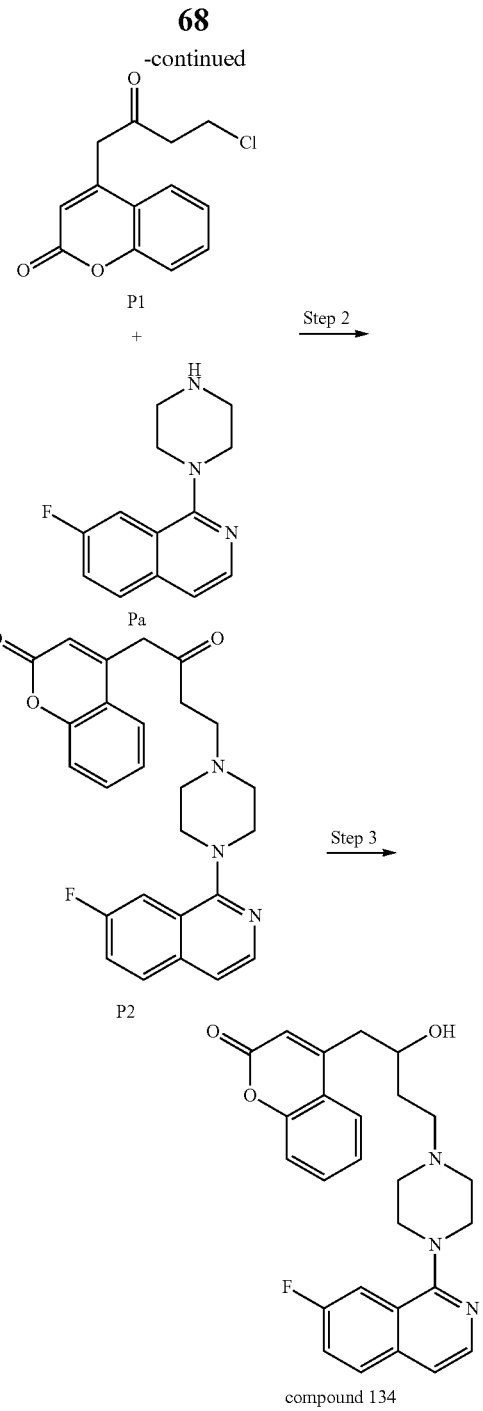

Step 1

4-methyl-2H-chromen-2-one, intermediate compound P0 (300 mg) was dissolved in dry THF (4 ml) under N₂ and chilled at −30° C. 1M solution of lithium bis(trimethylsilyl)amide (1.87 ml) was added drop-wise and the red solution was stirred 30 min at −30° C. The temperature was the lowered to −78° C. and chloropropionyl chloride (0.35 ml) was added drop-wise. The temperature was allowed to reach r.t. After 2 h the reaction was partitioned between EtOAc and NH₄Cl and the organic phase was evaporated by vacuum. The residual crude material was triturated in a pentane/Et₂O mixture to obtain 4-(4-chloro-2-oxobutyl)-2H-chromen-2-one, intermediate compound P1 (200 mg) used for the subsequent reaction without further purification.

Step 2

4-(4-chloro-2-oxobutyl)-2H-chromen-2-one, intermediate compound P1 (200 mg) and 7-fluoro-1-(piperazin-1-yl)isoquinoline, intermediate compound Pa (184 mg) were dissolved in dry CH$_3$CN (10 ml). K$_2$CO$_3$ (330 mg) was added and the mixture was stirred at 45° C. for 1 h. After cooling, the inorganic salts were filtered off and the filtrate was evaporated by vacuum. The crude product was preliminary purified by flash chromatography (eluent cHex:EtOAc: MeOH=6:3:1) to obtain 4-{4-[4-(7-fluoroisoquinolin-1-yl)piperazin-1-yl]-2-oxobutyl}-2H-chromen-2-one, intermediate compound P2 (135 mg) as a pale yellow powder. LC-MS (M−H+)=446.4

Step 3

To a solution of 4-{4-[4-(7-fluoroisoquinolin-1-yl)piperazin-1-yl]-2-oxobutyl}-2H-chromen-2-one, intermediate compound P2 (50 mg) in MeOH (4 ml), NaBH$_4$ (9 mg) was added and the mixture was stirred at room temperature overnight. The volatiles were evaporated in vacuum and the crude product purified by C-18 reversed phase chromatography using the mixture of H$_2$O/MeCN+1% HCOOH as eluent. 4-{4-[4-(7-fluoroisoquinolin-1-yl)piperazin-1-yl]-2-hydroxybutyl}-2H-chromen-2-one (compound 134) (26 mg, Y=37%) was obtained as formate salt. LC-MS (M−H+)=448.4

1H-NMR (500 MHz, DMSO-d6) δ ppm 1.67-1.81 (m, 2H), 2.53-2.58 (m, 1H), 2.59-2.82 (m, 6H), 3.09 (dd, J=13.45, 3.18 Hz, 1H), 3.30 (br. s., 4H), 3.85-4.03 (m, 1H), 6.38 (s, 1H), 7.34-7.43 (m, 2H), 7.45 (d, J=5.87 Hz, 1H), 7.59-7.67 (m, 2H), 7.68-7.73 (m, 1H), 7.95 (d, J=7.83 Hz, 1H), 8.01 (dd, J=8.80, 5.87 Hz, 1H), 8.12 (d, J=5.38 Hz, 1H), 8.15 (s, 1H).

Preparation of Compound 143

Compound 143 was prepared as described hereinbelow, following the synthetic pathway Q

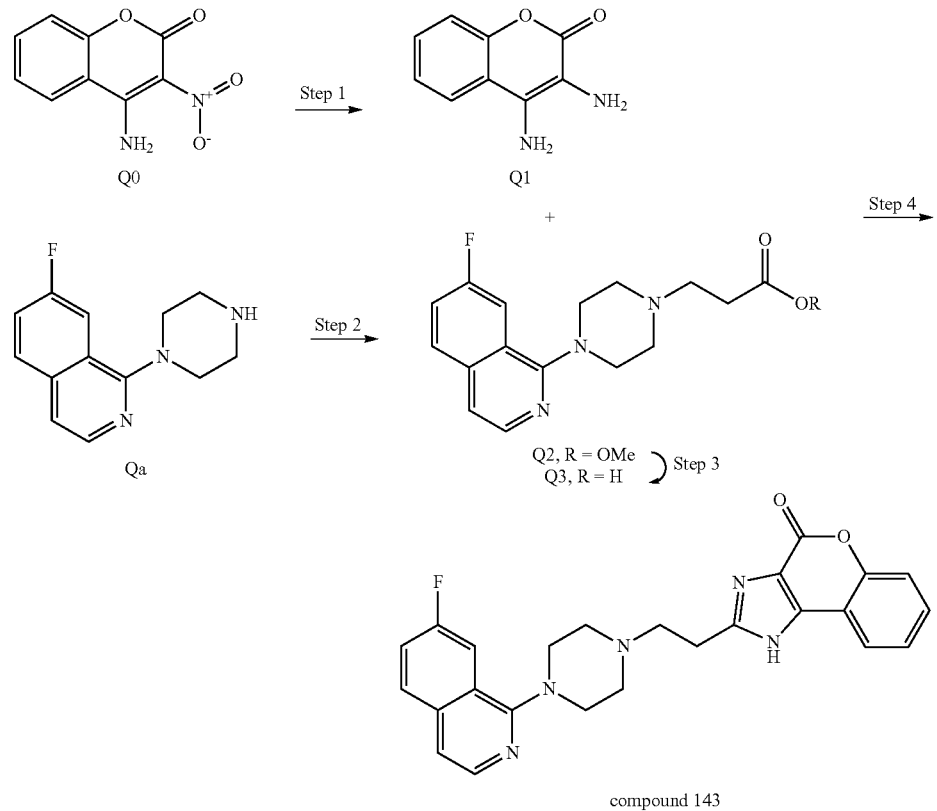

compound 143

Step 1

To a suspension of 4-amino-3-nitro-2H-chromen-2-one, intermediate compound Q0 (100 mg) in isopropyl alcohol (6 ml), zinc powder (1.2 g) and 3M HCl aqueous solution (6.4 ml) were added. The mixture was stirred 40 min. at r.t. and then it was poured into Na$_2$CO$_3$ saturated aqueous solution. The product was extracted twice with Et$_2$O, dried on dry Na$_2$SO$_4$, filtered and evaporated to recover 55 mg of pure 3,4-diamino-2H-chromen-2-one, intermediate compound Q1, used without further purification for the subsequent step. LC-MS (M−H+)=177.1

Step 2

7-fluoro-1-(piperazin-1-yl)isoquinoline, intermediate was compound Qa (400 mg) was dissolved in MeOH dry (20 ml), N,N-diisopropylethylamine (0.82 ml) was added followed by methyl acrylate (0.356 ml). The mixture was stirred at 60-70° C. for 1 h. Solvents were evaporated under reduced pressure and product was isolated by column chromatography (gradient of 20 to 80% ethyl acetate in cyclohexane), to obtain methyl 3-[4-(7-fluoroisoquinolin-1-yl)piperazin-1-yl]propanoate, intermediate compound Q2 (410 mg, Y=75%). LC-MS (M−H+)=318.3

Step 3

A solution of methyl 3-[4-(7-fluoroisoquinolin-1-yl)piperazin-1-yl]propanoate, intermediate compound Q2 (300 mg) was dissolved in THF/water (1:1) and LiOH (68 mg) was added, The mixture was stirred at r.t. for 2 hours. The reaction mixture was concentrated under reduced pressure, the residue obtained purified by SCX cartridge (eluting the desired product with solution 3M of TEA in MeOH), to obtain 3-[4-(7-fluoroisoquinolin-1-yl)piperazin-1-yl]propanoic acid, intermediate compound Q3 as triethylamine salt (330 mg, Y=65%). LC-MS (M−H+)=304.2

Step 4

3,4-diamino-2H-chromen-2-one, intermediate compound Q1 (50 mg) and 3-[4-(7-fluoroisoquinolin-1-yl)piperazin-1-yl]propanoic acid, intermediate compound Q3 as triethylamine salt (50 mg) were suspended in polyphosphoric acid (1.5 ml) and the mixture was heated at 140° C. for 4 h. The reaction mixture was poured into saturated $Na_2CO_3$ aqueous solution and the product extracted twice with EtOAc. The organic phase was purified by flash chromatography using a mixture of cHex/EtOAc/MeOH (6:3:1) as eluent. 30 mg of recovered compound was dissolved in DCM (1 ml) and treated with an excess of 1 M HCl in $Et_2O$ (1 ml). The cloudy mixture was concentrated and dried in oven (50° C.) for 1 h to obtain 2-{2-[4-(7-fluoroisoquinolin-1-yl)piperazin-1-yl]ethyl}chromeno[3,4-d]imidazol-4(1H)-one (compound 143) as hydrochloride salt. LC-MS (M−H+)=444.4

$^1$H NMR (500 MHz, METHANOL-d4) δ ppm 3.63 (t, J=6.85 Hz, 2H), 3.92 (br. s., 4H), 3.93-3.98 (m, 2H), 4.20 (br. s., 4H), 7.45 (t, J=7.34 Hz, 1H), 7.50 (d, J=7.83 Hz, 1H), 7.56-7.63 (m, 1H), 7.82 (d, J=6.36 Hz, 1H), 7.89-7.95 (m, 1H), 7.97-8.03 (m, 2H), 8.08 (d, J=9.29 Hz, 1H), 8.23 (dd, J=9.29, 5.38 Hz, 1H).

Preparation of Compound 144

Compound 144 was prepared as described herein below.

Step 1—Synthesis of tert-butyl 4-(7-fluoroisoquinolin-1-yl)piperazine-1-carboxylate

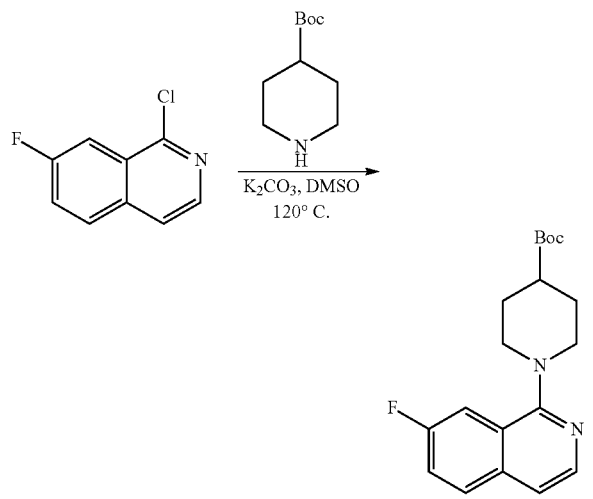

Potassium carbonate (2.9 g, 21 mmol) was added to a stirred solution of 1-chloro-7-fluoroisoquinoline (2.6, 14 mmol) and tert-butyl piperazine-1-carboxylate (5.2 g, 28 mmol) in DMSO (20 mL) at room temperature. The resulting mixture was heated to 120° C. overnight. UPLC check showed the reaction was complete. The mixture was then allowed to cool to room temperature and was partitioned between EtOAc (300 mL) and water (300 mL). The organic phase was separated, washed with 1 M citric acid solution (100 mL) and brine (70 mL) and dried over sodium sulphate. The solvents were evaporated under reduced pressure and the resulting residue was purified by flash chromatography on silica gel (SNAP 100, from Cy to Cy/Ethyl acetate 8:2) to obtain tert-butyl 4-(7-fluoroisoquinolin-1-yl)piperazine-1-carboxylate (4.3 g, 13 mmol, 93% yield). LC-MS (M−H+)= 332.3

Step 2—Synthesis of 7-fluoro-1-(piperazin-1-yl)isoquinoline

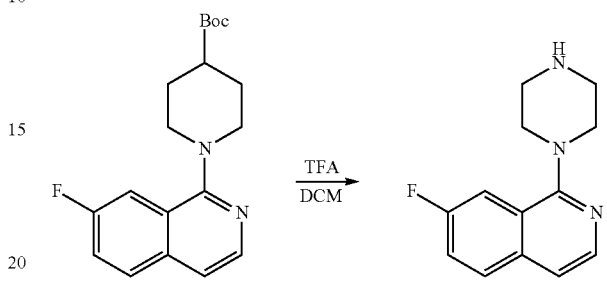

TFA (10 mL) was added to a solution of tert-butyl 4-(7-fluoroisoquinolin-1-yl)piperazine-1-carboxylate (4.3 g, 13 mmol) in dichloromethane (30 mL) and the resulting mixture was stirred overnight at room temperature. UPLC check showed the reaction was complete. The volatiles were evaporated under reduced pressure, the residue was dissolved in dichloromethane (20 mL) and evaporated under reduced pressure twice. The resulting residue was dissolved in MeOH and loaded onto a preconditioned SCX cartridge (50 g). The SCX was eluted with MeOH and then a 2M solution of ammonia in methanol. Finally, the basic fraction was evaporated under reduced pressure to give 3.1 g (Y=quant.) of 7-fluoro-1-(piperazin-1-yl)isoquinoline as a yellow sticky gum. LC-MS (M−H+)=232.2

Step 3—Synthesis of 4-(4-chloro-2-oxobutyl)-2H-1-benzopyran-2-one

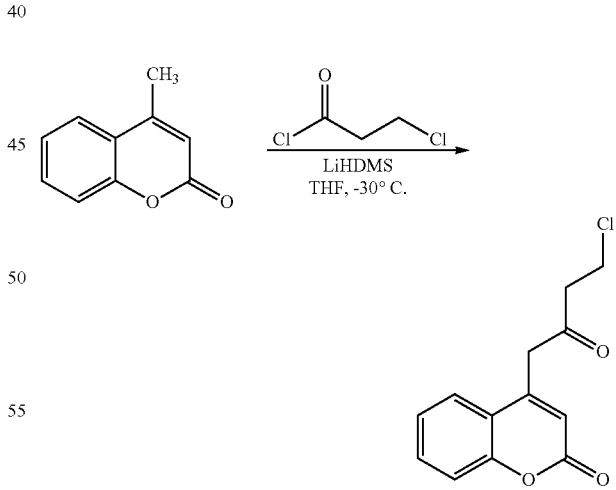

4-methyl-2H-1-benzopyran-2-one (200 mg, 1.25 mmol) was dissolved in dry THF (4 mL) under $N_2$ and chilled at −30° C. LiHDMS (1 M solution in THF, 1.25 mL, 1.25 mmol) was added dropwise and the red solution was stirred 30 min at −30° C. The temperature was then lowered to −78° C. and chloropropionyl chloride (0.24 mL, 2.5 mmol) was added dropwise. The reaction mixture was allowed to reach room temperature then was partitioned between EtOAc and NH₄Cl. The organic phase was evaporated in vacuum and the residual crude material was treated with a pentane/Et₂O mixture to give 270 mg (1.1 mmol, 88% yield) of 4-(4-chloro-2-oxobutyl)-2H-1-benzopyran-2-one. LC-MS (M−H⁺)=251.2

Step 4—Synthesis of 4-{4-[4-(7-fluoroisoquinolin-1-yl)piperazin-1-yl]-2-oxobutyl}-2H-1-benzopyran-2-one

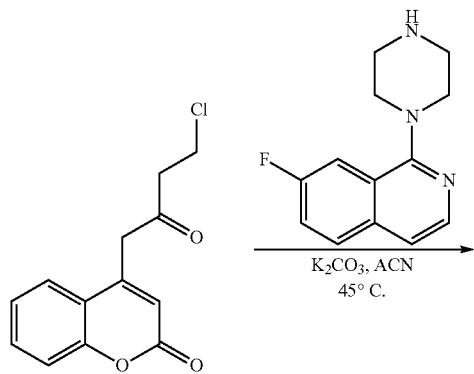

Step 5—Synthesis of 4-{4-[4-(7-fluoroisoquinolin-1-yl)piperazin-1-yl]-2-hydroxybutyl}-2H-1-benzopyran-2-one (compound 144)

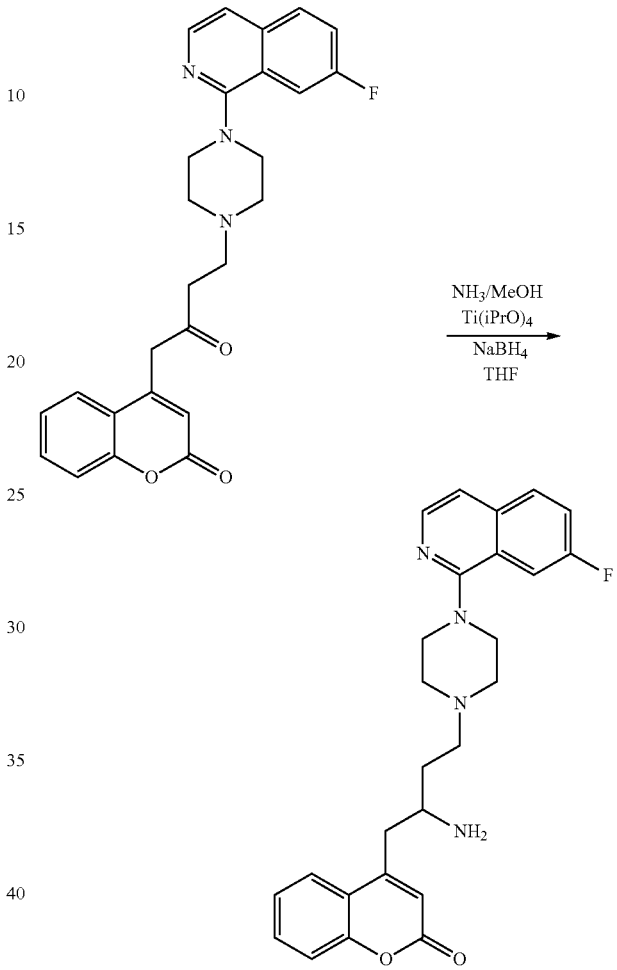

4-(4-chloro-2-oxobutyl)-2H-1-benzopyran-2-one (270 mg, 1.1 mmol) and 7-fluoro-1-(piperazin-1-yl)isoquinoline (244 mg, 1.1 mmol) were dissolved in dry MeCN (10 mL). K₂CO₃ (434 mg, 2.4 mmol) was added and the mixture was stirred at 45° C. for 1 h. After cooling, the inorganic salts were filtered off and the filtrate was evaporated in vacuum. The crude was purified by FC (Cy:EtOAc:MeOH 6:3:1) to recover 188 mg (0.42 mmol, 38% yield) of 4-{4-[4-(7-fluoroisoquinolin-1-yl)piperazin-1-yl]-2-oxobutyl}-2H-1-benzopyran-2-one as a pale yellow powder (Y=39%). LC-MS (M−H⁺)=446.4

4-{4-[4-(7-fluoroisoquinolin-1-yl)piperazin-1-yl]-2-oxobutyl}-2H-1-benzopyran-2-one (80 mg, 0.18 mmol) was dissolved in dry THF (0.5 mL). 2M NH₃ in MeOH (0.9 mL, 1.8 mmol) was added followed by Ti(iPrO)₄ (212 μL, 0.72 mmol). The reaction mixture was heated at 50° C. in a closed vial for 3 hours and then was left to reach room temperature overnight. The volatiles were evaporated in vacuum, the residue was dissolved in THF/MeOH and cooled in an ice bath. NaBH₄ (127 mg) was added quickly. After 10 minutes the reaction was quenched with 4M HCl in dioxane to reach pH 4, the solvent was evaporated in vacuum and the crude material was purified by preparative HPLC under basic conditions to obtain 25 mg (Y=31%) of 4-{4-[4-(7-fluoroisoquinolin-1-yl)piperazin-1-yl]-2-hydroxybutyl}-2H-1-benzopyran-2-one. LC-MS (M−H⁺)=447.2. ¹H NMR (400 MHz, DMSO-d6) δ ppm 1.67-1.88 (m, 2H) 2.50 (dt, J=3.70, 1.79 Hz, 7H) 3.09-3.95 (m, 6H) 6.44 (s, 1H) 7.35-7.44 (m, 2H) 7.46 (d, J=5.77 Hz, 1H) 7.61-7.76 (m, 3H) 7.97-8.04 (m, 2H) 8.13 (d, J=5.77 Hz, 1H).

Preparation of Compound 145

Compound 145 was prepared as described herein below.

Step 1—Synthesis of tert-butyl [1-(7-fluoroisoquinolin-1-yl)piperidin-4-yl]carbamate

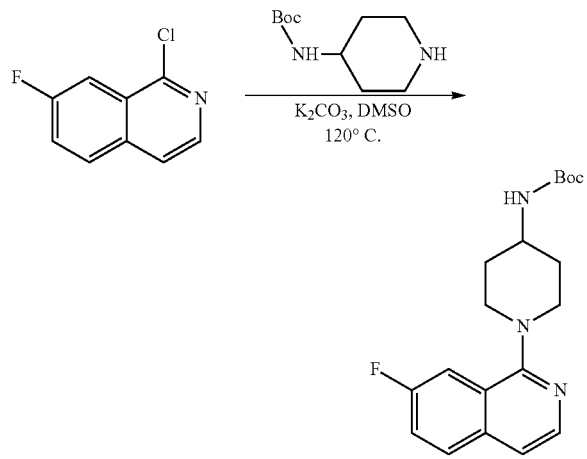

Intermediate tert-butyl [1-(7-fluoroisoquinolin-1-yl)piperidin-4-yl]carbamate was prepared according to the procedure described for the synthesis of tert-butyl 4-(7-fluoroisoquinolin-1-yl)piperazine-1-carboxylate (see compound 144) using tert-butyl piperidin-4-ylcarbamate. Y=71%. LC-MS (M–H+)=346.5

Step 2—Synthesis of 1-(7-fluoroisoquinolin-1-yl)piperidin-4-amine

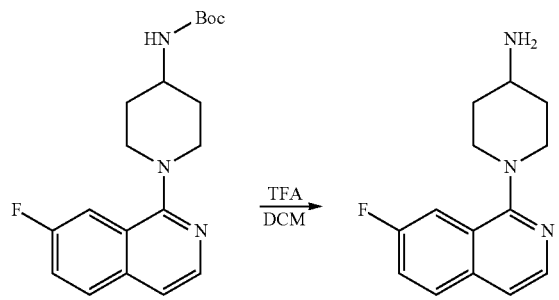 [SMILES: CC(C)(C)OC(=O)NC1CCN(c2nccc3ccc(F)cc23)CC1 ; NC1CCN(c2nccc3ccc(F)cc23)CC1]

Intermediate 1-(7-fluoroisoquinolin-1-yl)piperidin-4-amine was prepared according to the procedure described for the synthesis of 7-fluoro-1-(piperazin-1-yl)isoquinoline (see compound 144) using tert-butyl [1-(7-fluoroisoquinolin-1-yl)piperidin-4-yl]carbamate. Y=quant. LC-MS (M–H+)=246.3

Step 3—Synthesis of ethyl 4-oxo-1,4-dihydro[1]benzopyrano[4,3-b]pyrrole-2-carboxylate

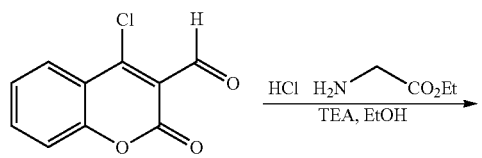

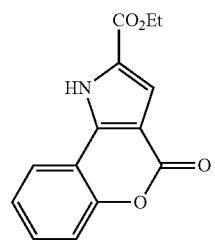

4-chloro-3-formylcoumarin (0.5 g, 2.4 mmol) and ethyl glycinate hydrochloride (353 mg, 2.5 mmol) were suspended in absolute ethanol. The mixture was cooled to 0° C. then TEA (1.1 mL, 7.2 mmol) was added. The mixture was stirred 2 h at 0° C. and then heated at 80° C. for 12 h. The crude mixture was charged on a C-18 cartridge and eluted with $H_2O$/MeCN (+0.1% HCOOH) from 100/0 to 0/100 to recover 400 mg of ethyl 4-oxo-1,4-dihydro[1]benzopyrano[4,3-b]pyrrole-2-carboxylate (400 mg, 1.5 mmol, 64% yield). LC-MS (M–H+)=258.2

Step 4—Synthesis of 2-(hydroxymethyl)[1]benzopyrano[4,3-b]pyrrol-4(1H)-one

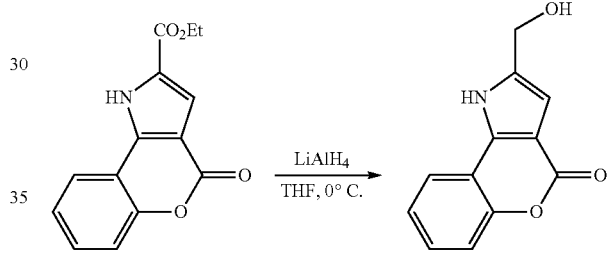

Ethyl 4-oxo-1,4-dihydro[1]benzopyrano[4,3-b]pyrrole-2-carboxylate (170 mg, 0.66 mmol) was dissolved in dry THF (6 mL). 1M $LiAlH_4$ in THF (1.33 mL, 1.33 mmol) was added dropwise at 0° C. The solution was stirred 4 h at 0° C. then was quenched by adding $Na_2SO_4$*$10H_2O$. The inorganic salts were filtered off and the solvents were evaporated. The crude residue was purified by flash chromatography (Cy:EtOAc:MeOH 6:3:1) to obtain 2-(hydroxymethyl)[1]benzopyrano[4,3-b]pyrrol-4(1H)-one (80 mg, 0.37 mmol, 56% yield). LC-MS (M–H+)=216.2

Step 5—Synthesis of 4-oxo-1,4-dihydro[1]benzopyrano[4,3-b]pyrrole-2-carbaldehyde

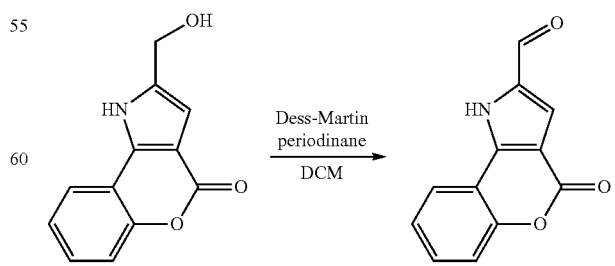

2-(hydroxymethyl)[1]benzopyrano[4,3-b]pyrrol-4(1H)-one (80 mg, 0.37 mmol) was suspended in dry DCM (15 mL) and treated with Dess-Martin Periodinane (100 mg, 0.44 mmol). The reaction mixture was stirred 45 min at room temperature then the suspension was partitioned between DCM and an aq. solution of sat. NaHCO$_3$/10% Na$_2$S$_2$O$_3$ 1:1. The organic phase was dried over Na$_2$SO$_4$, filtered and evaporated to recover 40 mg (0.19 mmol, Y=51%) of 4-oxo-1,4-dihydro[1]benzopyrano[4,3-b]pyrrole-2-carbaldehyde, that was progressed in the next step without any purification. LC-MS (M−H$^+$)=214.2

Step 6—Synthesis of 2-({[1-(7-fluoroisoquinolin-1-yl)piperidin-4-yl]amino}methyl)[1]benzopyrano[4,3-b]pyrrol-4(1H)-one (formate salt, compound 145)

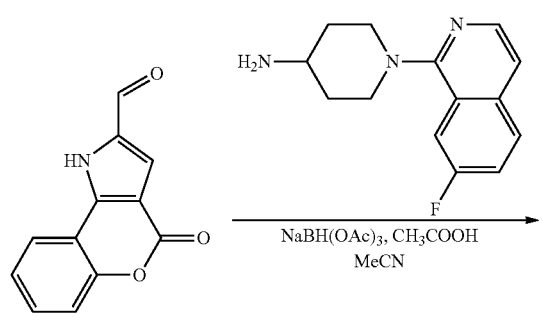

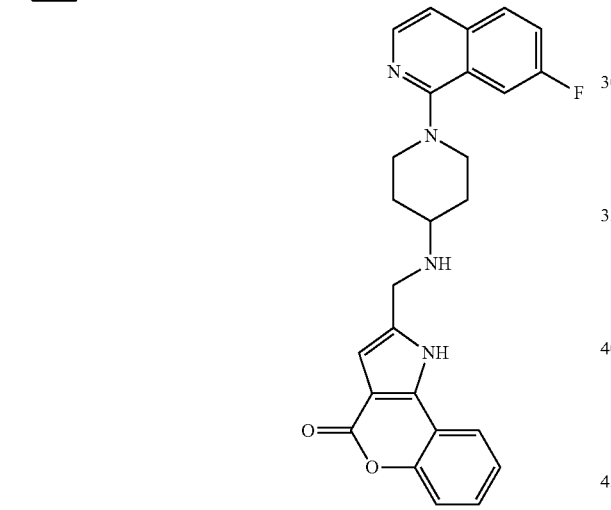

To a suspension of 4-oxo-1,4-dihydro[1]benzopyrano[4,3-b]pyrrole-2-carbaldehyde (40 mg, 0.19 mmol) in dry MeCN (40 mL), 1-(7-fluoroisoquinolin-1-yl)piperidin-4-amine (60 mg, 0.24 mmol) was added followed by 3 drops of acetic acid. The cloudy mixture was stirred 1 h at room temperature then NaBH(OAc)$_3$ (100 mg, 0.47 mmol) was added in one portion. The heterogeneous mixture was stirred overnight then the volatiles were evaporated in vacuum. The residue was charged on a C-18 reversed phase column and eluted with H$_2$O/MeOH+1% HCOOH (from 95/5 to 70/30) to give 32 mg (0.066 mmol, 34% yield) of 2-({[1-(7-fluoroisoquinolin-1-yl)piperidin-4-yl]amino}methyl)[1]benzopyrano[4,3-b]pyrrol-4(1H)-one as formate salt. LC-MS (M−H$^+$)=443.4.

$^1$H NMR (500 MHz, METHANOL-d4) δ ppm 1.99 (qd, J=12.06, 3.42 Hz, 2H), 2.31 (d, J=10.76 Hz, 2H), 3.06 (t, J=12.23 Hz, 2H), 3.31-3.35 (m, 2H), 3.84 (d, J=13.21 Hz, 2H), 4.37 (s, 2H), 6.93 (s, 1H), 7.37-7.46 (m, 3H), 7.48-7.58 (m, 2H), 7.76 (dd, J=10.03, 2.20 Hz, 1H), 7.91-7.99 (m, 2H), 8.07 (d, J=5.87 Hz, 1H).

Preparation of Compound 146

Compound 146 was prepared as described herein below.

Step 1—Synthesis of 3,4-diamino-2H-1-benzopyran-2-one

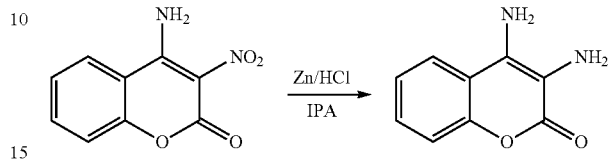

4-amino-3-nitro-2H-1-benzopyran-2-one (500 mg, 2.4 mmol) was suspended in IPA (30 mL). Zinc powder (6 g, 92 mmol) was added followed by 3M HCl solution (32 ml, 96 mmol). The mixture was stirred at room temperature for 40 min then was poured into sat. Na$_2$CO$_3$. The product was extracted twice with Et$_2$O, the organic phases were dried over Na$_2$SO$_4$, filtered and concentrated to dryness to give 330 mg of 3,4-diamino-2H-1-benzopyran-2-one (330 mg, 78% yield), which was used without further purification. LC-MS (M−H$^+$)=177.2

Step 2—Synthesis of 2-(chloromethyl)[1]benzopyrano[3,4-d]imidazol-4(1H)-one

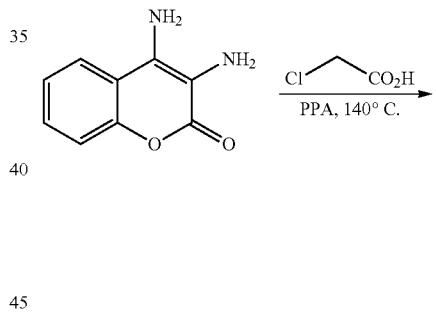

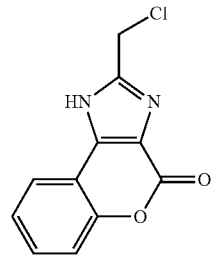

To a suspension of 3,4-diamino-2H-1-benzopyran-2-one (120 mg, 0.68 mmol) in polyphosphoric acid (2.5 mL) chloroacetic acid (96 mg, 1 mmol) was added. The suspension was heated at 140° C. for 45 min then was cooled an the crude was partitioned between H$_2$O and Et$_2$O. The organic phase was dried over Na$_2$SO$_4$, filtered and concentrated to give 90 mg (0.38 mmol, 56% yield) of 2-(chloromethyl)[1]benzopyrano[3,4-d]imidazol-4(1H)-one. LC-MS (M−H$^+$)=235.1

Step 3—Synthesis of 2-({[1-(7-fluoroisoquinolin-1-yl)piperidin-4-yl]amino}methyl)[1]benzopyrano[3,4-d]imidazol-4(1H)-one (compound 146)

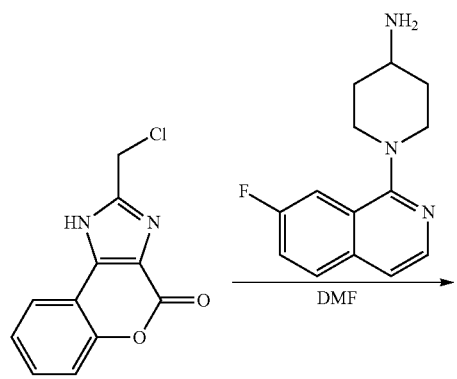

1-(7-fluoroisoquinolin-1-yl)piperidin-4-amine (370 mg, 1.5 mmol, see compound 145) was dissolved in dry DMF (2 mL) and cooled in an ice bath. Solid 2-(chloromethyl)[1]benzopyrano[3,4-d]imidazol-4(1H)-one (90 mg, 0.38 mmol) was added portion wise and the mixture was stirred for 10 min. The crude reaction was charged directly on a C-18 reverse phase chromatography and eluted with $H_2O$/MeCN+ 1% HCOOH (from 100/0 to 85/15) to recover 38 mg (0.09 mmol, 23% yield) of 2-({[1-(7-fluoroisoquinolin-1-yl)piperidin-4-yl]amino}methyl)[1]benzopyrano[3,4-d]imidazol-4(1H)-one. LC-MS (M−H$^+$)=444.4.

$^1$H NMR (500 MHz, METHANOL-d4) δ ppm 1.84-1.97 (m, 2H), 2.25 (d, J=11.74 Hz, 2H), 3.03 (t, J=11.74 Hz, 2H), 3.11-3.21 (m, 1H), 3.80 (d, J=12.72 Hz, 2H), 4.34 (s, 2H), 7.40 (d, J=5.87 Hz, 1H), 7.43 (t, J=7.58 Hz, 1H), 7.48 (d, J=7.83 Hz, 1H), 7.50-7.60 (m, 2H), 7.75 (dd, J=10.03, 2.20 Hz, 1H), 7.92 (dd, J=9.05, 5.62 Hz, 1H), 8.03 (dd, J=7.83, 1.47 Hz, 1H), 8.05 (d, J=5.87 Hz, 1H), 8.24-8.29 (m, 1H).

Preparation of Compound 147

Compound 147 was prepared as described herein below.

Step 1—Synthesis of 2-(3-bromopropyl)[1]benzopyrano[3,4-d]imidazol-4(1H)-one

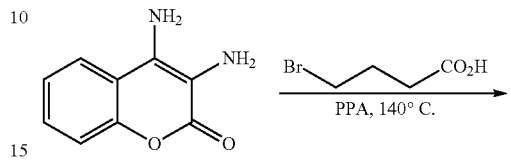

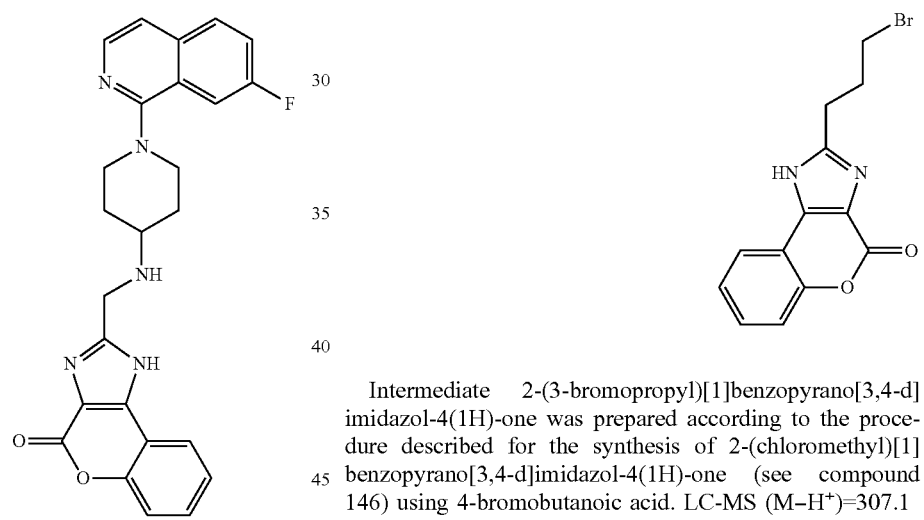

Intermediate 2-(3-bromopropyl)[1]benzopyrano[3,4-d]imidazol-4(1H)-one was prepared according to the procedure described for the synthesis of 2-(chloromethyl)[1]benzopyrano[3,4-d]imidazol-4(1H)-one (see compound 146) using 4-bromobutanoic acid. LC-MS (M−H$^+$)=307.1

Step 2—Synthesis of 2-{3-[4-(7-fluoroisoquinolin-1-yl)piperazin-1-yl]propyl}[1]benzopyrano[3,4-d]imidazol-4(1H)-one (formate salt, compound 147)

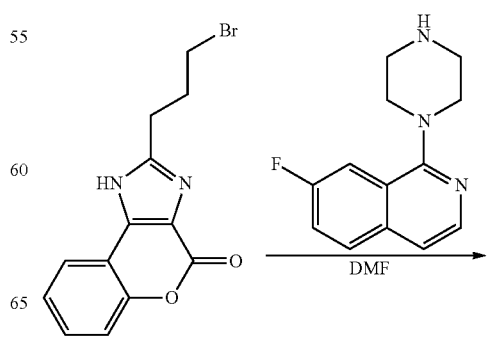

-continued

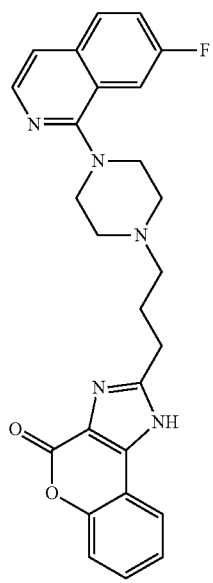

To a suspension of 2-(3-bromopropyl)[1]benzopyrano[3,4-d]imidazol-4(1H)-one (160 mg, 0.7 mmol) in dry DMF (2 mL) solid 7-fluoro-1-(piperazin-1-yl)isoquinoline (70 mg, 0.30 mmol, see compound 144) was added portion wise. The mixture was stirred for 2 h then 1M HCl 1 (8 mL) was added. The aqueous phase was washed with DCM twice then was charged on a C-18 reversed phase chromatography and eluted with H$_2$O/MeCN+1% HCOOH (from 100/0 to 75/25) to give 39 mg (0.09 mmol, 30% yield) of 2-{3-[4-(7-fluoroisoquinolin-1-yl)piperazin-1-yl]propyl}[1]benzopyrano[3,4-d]imidazol-4(1H)-one as formate salt. LC-MS (M–H$^+$)=458.4.

$^1$H NMR (500 MHz, METHANOL-d4) δ ppm 2.29 (quin, J=7.09 Hz, 2H), 3.02-3.17 (m, 4H), 3.28 (s, 4H), 3.61 (br. s., 4H), 7.36-7.50 (m, 3H), 7.51-7.62 (m, 2H), 7.79 (dd, J=9.78, 2.45 Hz, 1H), 7.88-8.01 (m, 2H), 8.11 (d, J=5.38 Hz, 1H).

Preparation of Compound 148

Compound 148 was prepared as described herein below.

Step 1—Synthesis of tert-butyl 4-(7-fluoroisoquinolin-1-yl)piperazine-1-carboxylate

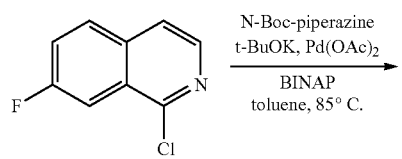

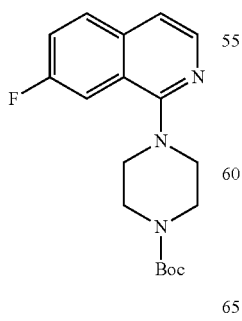

A solution of 1-chloro-7-fluoroisoquinoline (0.5 g, 2.76 mmol) and N-Boc-piperazine (1.54 g, 8.3 mmol) in toluene was degassed for 10 min. Then potassium tert-Butoxide (626 mg, 5.6 mmol), BINAP (174 mg, 0.28 mmol) and palladium acetate (61 mg 0.28 mmol) were added at room temperature. The mixture was stirred at 85° C. for 4 h monitoring the reaction by LCMS. The reaction mixture was cooled to room temperature, diluted with EtOAc, washed with water and brine and dried over sodium sulfate. The solvent was concentrated under reduced pressure and the resulting crude was purified on silica gel (60-120 mesh) column chromatography (0-20% ethyl acetate in hexane) to obtain tert-butyl 4-(7-fluoroisoquinolin-1-yl)piperazine-1-carboxylate (310 mg, 34%) as a pale yellow color solid. LS-MS m/z: 331.2 (M+1). $^1$HNMR (DMSO d6): δ ppm 1.44 (s, 9H), 3.21-3.24 (m, 4H), 3.60 (m, 4H), 7.48-7.49 (m, 1H), 7.64-7.69 (m, 1H), 7.75-7.78 (m, 1H), 7.97-8.04 (m, 1H), 8.13-8.14 (m, 1H).

Step 2—Synthesis of 7-fluoro-1-(piperazine-1-yl)isoquinoline trifluoroacetate

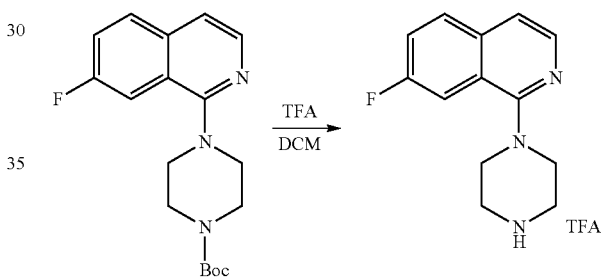

To a solution of tert-butyl 4-(7-fluoroisoquinolin-1-yl) piperazine-1-carboxylate (300 mg, 0.9 mmol) in DCM (5 mL) TFA (5 mL) was added slowly at room temperature. The reaction mixture was stirred for 4 h then was concentrated under reduced pressure and the resulting crude (brown liquid) was used as such in the next step (310 mg, quant.). LS-MS m/z: 231.2 (M+1). $^1$HNMR (DMSO d6): δ ppm 3.38 (m, 4H), 3.46-3.47 (m, 4H), 7.52 (d, J=5.7 Hz, 1H), 7.67-7.72 (m, 1H), 7.83 (d, J=9.9 Hz, 1H), 8.03-8.07 (m, 1H), 8.15 (d, J=5.7 Hz, 1H), 8.83 (br. s, 1H).

Step 3—Synthesis of 1-chloro-3-[4-(7-fluoroisoquinolin-1-yl)piperazin-1-yl]propan-2-ol

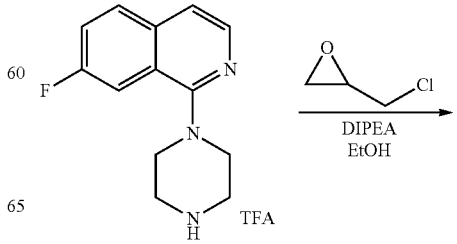

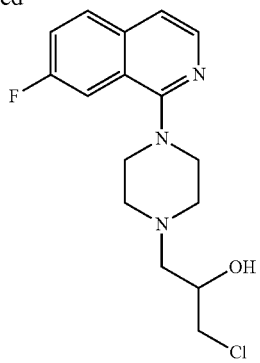

A solution of 7-fluoro-1-(piperazine-1-yl)isoquinoline trifluoroacetate (200 mg, 0.87 mmol), DIPEA (398 mg, 43 mmol) and epichlorohydrine (398 mg, 4.8 mmol) in ethanol (5 mL) was stirred for 5 h at room temperature. The reaction was monitored by LCMS. After completion of the reaction the mixture was concentrated under reduced pressure. The resulting crude was dissolved in EtOAc (50 mL) and washed with water and brine. The organic layer was dried and concentrated to obtain 1-chloro-3-[4-(7-fluoroisoquinolin-1-yl)piperazin-1-yl]propan-2-ol (220 mg, 79%) as a gummy liquid which was used in the next step without further purification. LS-MS m/z: 324.2 (M+1).

Step 4—Synthesis of 1-azide-3-(4-(7-fluoroisoquinolin-1-yl) piperazin-1-yl)propan-2-ol

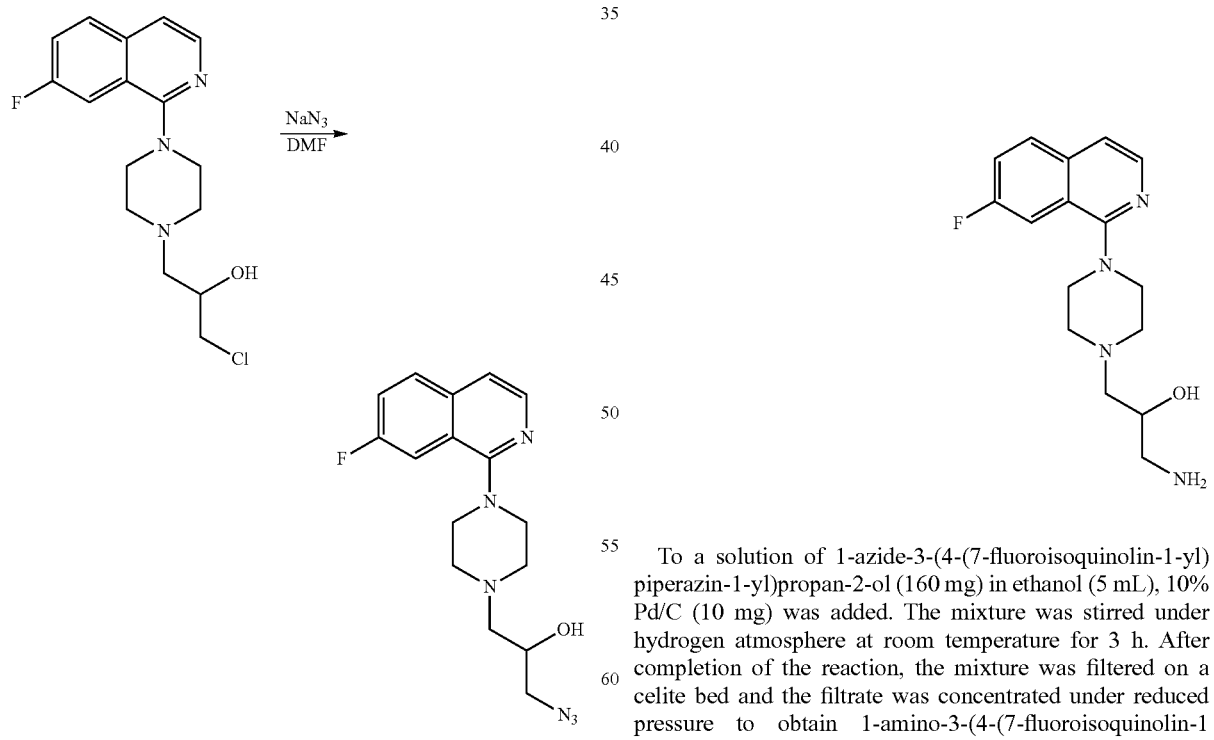

To a solution of 1-chloro-3-(4-(7-fluoroisoquinolin-1-yl) piperazin-1-yl)propan-2-ol (210 mg, 0.65 mmol) in DMF (4 mL), sodium azide (65 mg, 1 mmol) was added. The suspension was stirred at 85° C. for 5 h then was cooled to room temperature and partitioned between water and EtOAc. The organic layer was dried over sodium sulfate and concentrated under reduced pressure. The resulting crude was purified on silica gel (60-120 mesh, 0-10% MeOH in DCM) column chromatography to obtain 1-azide-3-(4-(7-fluoroisoquinolin-1-yl) piperazin-1-yl)propan-2-ol (160 mg, 74%) as a pale yellow color gum. LS-MS m/z: 331.2 (M+1). $^1$HNMR (DMSO d6): δ ppm 2.49-2.52 (m, 2H), 2.50-2.71 (m, 4H), 2.86-2.87 (m, 2H), 3.19-3.20 (m, 4H), 3.88-3.89 (m, 1H), 5.14 (br. s, 1H), 7.44 (d, J=7.7 Hz, 1H), 7.61-7.70 (m, 2H), 7.98-8.03 (m, 1H), 8.11 (d, J=7.6 Hz, 1H).

Step 5—Synthesis of 1-amino-3-(4-(7-fluoroisoquinolin-1 yl)piperazine-1-yl)propan-2-ol To a solution of 1-azide-3-(4-(7-fluoroisoquinolin-1-yl) piperazin-1-yl)propan-2-ol (160 mg) in ethanol (5 mL), 10% Pd/C (10 mg) was added. The mixture was stirred under hydrogen atmosphere at room temperature for 3 h. After completion of the reaction, the mixture was filtered on a celite bed and the filtrate was concentrated under reduced pressure to obtain 1-amino-3-(4-(7-fluoroisoquinolin-1 yl)piperazine-1-yl)propan-2-ol (125 mg, 85%) as a pale yellow color solid. LS-MS m/z: 305.2 (M+1). $^1$HNMR (CDCl3): δ ppm 2.27-2.28 (m, 2H), 2.45-2.57 (m, 2H), 2.70-2.91 (m, 4H), 3.40 (m, 4H), 3.81 (m, 1H), 7.25-7.45 (m, 2H), 7.56-8.12 (m, 2H), 8.42-8.44 (m, 1H).

Step 6—Synthesis of methyl 5-fluoro-2-hydroxybenzoate

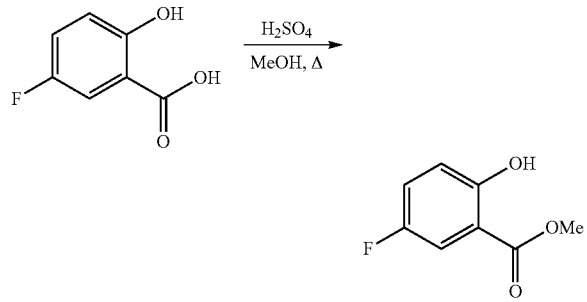

To a stirred solution of 5-fluoro salicylic acid (25 g, 160 mmol) in MeOH (250 mL), conc. sulfuric acid (20 mL) was added slowly at 0° C. The resulting reaction mixture was refluxed for 48 h then was concentrated under reduced pressure and the resulting crude was basified to pH 8.0 with sat. NaHCO$_3$. Then it was neutralized by 1.5 N HCl solution and extracted with EtOAc. The organic layer was dried over anhydrous Na$_2$SO$_4$ and concentrated to afford methyl 5-fluoro-2-hydroxybenzoate as a light brown liquid (22.8 g, 83%). GCMS: (AcqMethod HP-1MS.M) 170.1 (M). $^1$H NMR (400 MHz, DMSO-d6): δ ppm 10.29 (s, 1H), 7.51-7.49 (m, 1H), 7.42-7.41 (m, 1H), 57.03-7.01 (m, 1H), 3.89 (s, 3H).

Step 7—Synthesis of 5-fluoro-2-hydroxybenzamide

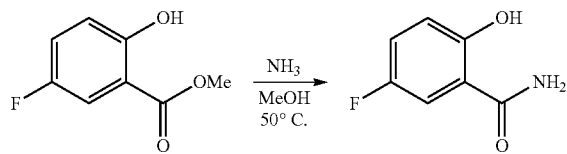

A mixture of methyl 5-fluoro-2-hydroxybenzoate (22 g, 129 mmol) and methanolic ammonia (250 mL) was heated at 50° C. in an autoclave for 10 h. The reaction mixture was concentrated under reduced pressure, the resulting crude was codistilled with toluene and dried to give 5-fluoro-2-hydroxybenzamide as a brown solid (18.5 g, 92%). LS-MS m/z: 154.0 (M–H). $^1$H NMR (400 MHz, DMSO-d6): δ ppm 12.74 (s, 1H), 8.40 (s, 1H), 8.03 (s, 1H), 7.73-7.71 (m, 1H), 7.31-7.29 (m, 1H), 6.91-6.90 (m, 1H).

Step 8—Synthesis of 6-fluoro-2H-1,3-benzoxazine-2,4(3H)-dione

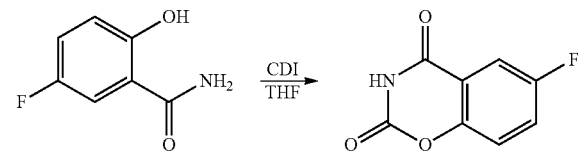

To a stirred solution of 5-fluoro-2-hydroxybenzamide (8.0 g, 51.6 mmol) in dry THF (80 mL), 1,1'-carbonyldiimidazole (10.9 g, 67.09 mmol) was added at 0° C. The mixture was stirred at room temperature for 14 h then was concentrated under reduced pressure. The resulting crude was treated with MeOH and washed with diethyl ether. The resulting white solid was dried and used in the next step without further purification (5.1 g, 55% white solid). LS-MS m/z: 180.0 (M–H): $^1$H NMR (400 MHz, DMSO-d6): δ ppm 12.19 (s, 1H), 7.68-7.67 (m, 2H), 7.50-7.48 (m, 1H).

Step 9—Synthesis of 4-chloro-6-fluoro-2H-1,3-benzoxazin-2-one

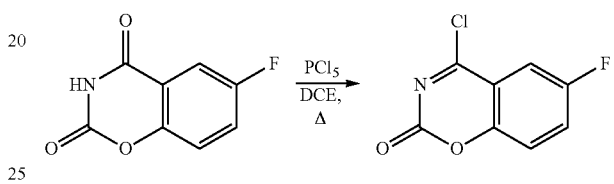

To a stirred solution of 6-fluoro-2H-1,3-benzoxazine-2,4(3H)-dione (0.5 g, 2.76 mmol) in dry 1,2-dichloroethane (2.5 mL), phosphorous pentachloride (0.69 g, 3.31 mmol) was added at 0° C. The resulting mixture was refluxed for 6 h then was concentrated under reduced pressure. DCM (15 mL) was added to the resulting crude, washed with water (2 mL) and dried over anhydrous Na$_2$SO$_4$. The solvent was concentrated under reduced pressure to afford 4-chloro-6-fluoro-2H-1,3-benzoxazin-2-one as an off-white solid (0.46 g, 84%). $^1$H NMR (400 MHz, DMSO-d6): δ ppm 7.69-7.67 (m, 2H), 7.50-7.49 (m, 1H).

Step 10—Synthesis of 6-fluoro-4-({3-[4-(7-fluoroisoquinolin-1-yl)piperazin-1-yl]-2-hydroxypropyl}amino)-2H-1,3-benzoxazin-2-one (Compound 148)

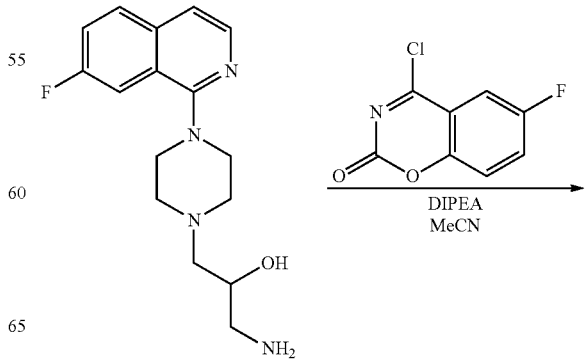

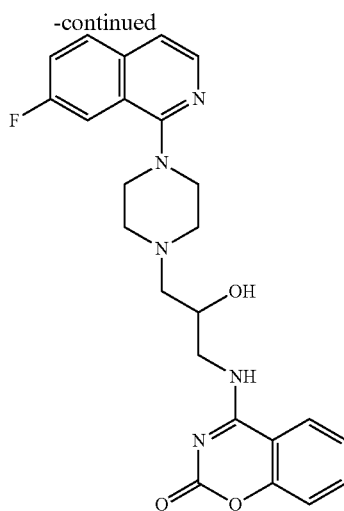

To a suspension of 4-chloro-6-fluoro-2H-1,3-benzoxazin-2-one (235 mg, 1.2 mmol) in acetonitrile (5 mL) DIPEA (402 mg, 3.1 mmol) and 1-amino-3-[4-(7-fluoroisoquinolin-1-yl)piperazin-1-yl]propan-2-ol (120 mg, 0.39 mmol) were added at 0° C. The mixture was stirred at room temperature for 15 h then the resulted solid was filtered, washed with water and dried. The crude product was purified on silica gel column chromatography eluting with (0-20% MeOH in DCM) to obtain 6-fluoro-4-({3-[4-(7-fluoroisoquinolin-1-yl)piperazin-1-yl]-2-hydroxypropyl}amino)-2H-1,3-benzoxazin-2-one (90 mg, 74%) as an off-white solid. LCMS m/z: 468.2 (M+1).

$^1$HNMR (DMSO d6): δ ppm 2.48-2.49 (m, 2H), 2.71 (m, 2H), 2.76 (m, 2H), 3.26 (m, 4H), 3.40-3.43 (m, 1H), 3.70-3.75 (m, 1H), 4.07 (d, J=5.9 Hz, 1H), 5.00 (d, J=4.5 Hz, 1H) 7.35-7.39 (m, 1H), 7.43 (d, J=5.6 Hz, 1H), 7.59-7.70 (m, 3H), 7.98 (dd, J=8.6, 5.6 Hz, 1H), 8.09-8.12 (m, 2H), 9.11-9.14 (m, 1H).

Preparation of Compound 149

Compound 149 was prepared as described herein below.

Step 1—Synthesis of 2-(cyanomethyl)-5-fluorobenzonitrile

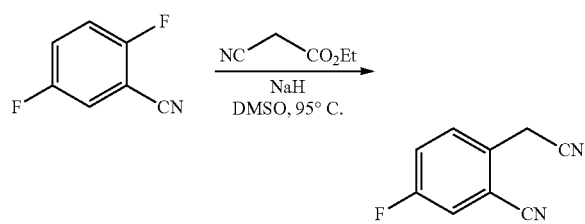

To a stirred solution of NaH (2.58 g, 60% in mineral oil, 64.74 mmol) in DMSO (30 mL) ethyl cyanoacetate (7.3 g, 64.7 mmol) was added slowly at 0° C. and stirred at the same temperature for 20 min. Then 2,5-difluoro benzonitrile (3 g, 21.5 mmol) in DMSO (10 mL) was added. The mixture was heated at 95° C. overnight then water (20 mL) was added and the solution was heated to 120° C. for 12 h. Completion of the reaction was monitored by LCMS. 0.1 N HCl (30 mL) was added to the reaction mixture at 0° C., after stirring 10 min the solid was filtered and washed with water and petroleum ether. The crude was purified by flash chromatography (24% EtOAc in petroleum ether) to give the title compound (1.8 g, 53.0%) as an off-white solid. LCMS m/z: 159.2 (M-1). $^1$HNMR (DMSO d6): δ ppm 4.2 (s, 2H), 7.64-7.73 (m, 2H), 7.96 (dd, J=8.5, 2.5 Hz, 1H).

Step 2—Synthesis of 1-bromo-7-fluoroisoquinolin-3-amine

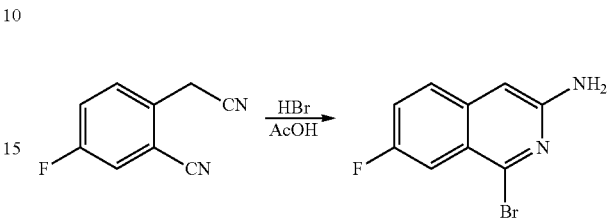

To a stirred solution of HBr in AcOH (14 mL, 33%) 2-(cyanomethyl)-5-fluorobenzonitrile (1.4 g, 87.5 mmol) was added slowly at 0° C. The mixture was stirred at room temperature for 1 h then was diluted with water (15 mL) and basified by using sat. Na$_2$CO$_3$. The solution was extracted with EtOAc, the organic layer was washed with brine and dried over sodium sulfate. The solvent was removed under reduced pressure to give 1-bromo-7-fluoroisoquinolin-3-amine as yellow solid (1.5 g, 75%). LCMS m/z: 241.0 (M+1). $^1$HNMR (DMSO d6): δ ppm 6.30 (s, 2H), 6.70 (s, 1H), 7.48-7.54 (m, 2H), 7.70 (dd, J=9.1, 5.5 Hz, 1H).

Step 3—Synthesis of 1-bromo-3,7-difluoroisoquinoline

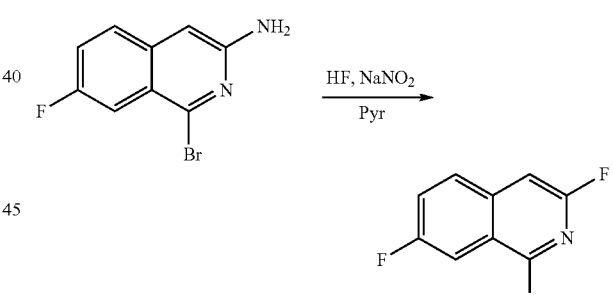

To a stirred solution of 1-bromo-7-fluoroisoquinolin-3-amine (0.5 g, 20.7 mmol) in pyridine (2 mL) HF.pyridine (2 mL) was added slowly at 0° C. followed by sodium nitrite (0.171 g, 24 mmol). The reaction mixture was stirred for 3 days at room temperature then was poured slowly into a saturated sodium carbonate solution to adjust pH to 8 and extracted with EtOAc. The combined organic layers were washed with brine and dried over sodium sulfate. The solvent was removed under reduced pressure and the resulting crude was purified by flash chromatography (25% EtOAc in petroleum ether) to give 1-bromo-3,7-difluoroisoquinoline as a yellow solid (0.250 g, 50%). LCMS m/z: 244.0 (M+1). $^1$HNMR (DMSO d6): δ ppm 7.83 (s, 1H), 7.86-7.94 (m, 2H), 7.20 (dd, J=9.1, 5.5 Hz, 1H).

Step 4—Synthesis of tert-butyl 4-(3,7-difluoroiso-quinolin-1-yl)piperazine-1-carboxylate

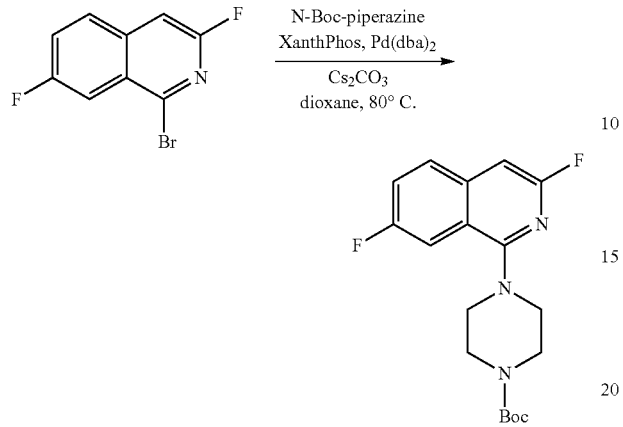

A solution of 1-bromo-3,7-difluoroisoquinoline (400 mg, 1.6 mmol) and N-Boc-piperazine (610 mg, 3.2 mmol) in dioxane (10 mL) was degassed for 10 min. Then Cs$_2$CO$_3$ (1.04 g, 3.2 mmol), XanthPhos (138 mg, 0.24 mmol) and Pd(dba)$_2$ (61 mg, 0.28 mmol) were added at room temperature. The reaction mixture was stirred at 80° C. overnight then was filtered onto a celite pad and washed with DCM. The combined organic layers were concentrated under reduced pressure and the resulting crude was purified on silica gel (60-120 mesh) column chromatography (25-20% ethyl acetate in hexane) to obtain tert-butyl 4-(3,7-difluor-oisoquinolin-1-yl)piperazine-1-carboxylate (200 mg, 35%) as a pale yellow color solid. ES-MS m/z: 294.2 (−tBu+1). $^1$HNMR (DMSO d6): δ ppm 1.43 (s, 9H), 2.27-2.49 (m, 4H), 3.58-3.59 (m, 4H), 7.41 (s, 1H), 7.65-7.77 (m, 2H), 7.97-8.02 (m, 1H).

Step 5—Synthesis of 3,7-difluoro-1-(piperazin-1-yl)isoquinoline hydrochloride

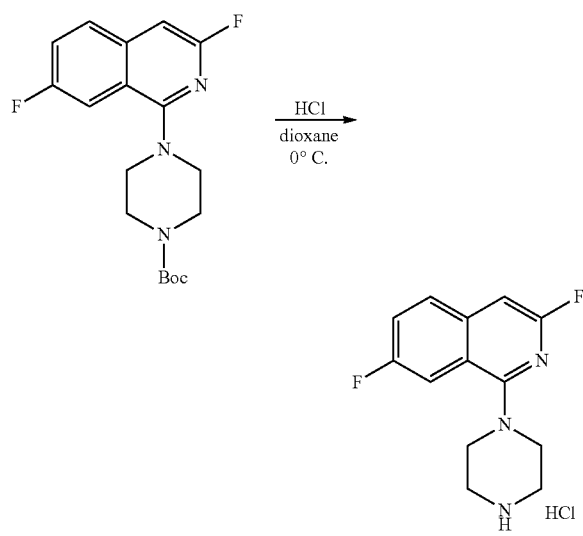

To a solution of tert-butyl 4-(3,7-difluoroisoquinolin-1-yl)piperazine-1-carboxylate (280 mg, 0.8 mmol) in dioxane (1 mL), dioxane.HCl (5 mL, 4.5 M) was added slowly at 0° C. After stirring for 2 h at ° O the reaction mixture was concentrated under reduced pressure and the resulting brown color thick liquid (160 mg) was used in the next step without further purification. ES-MS m/z: 250.2 (M+1). $^1$HNMR (DMSO d6): δ ppm 3.32-3.38 (m, 4H), 3.53-3.54 (m, 4H), 7.24 (s, 1H), 7.69-7.73 (m, 1H), 7.86 (dd, J=10.4, 2.6 Hz, 1H), 8.03 (dd, J=8.8, 5.6 Hz, 1H), 9.09 (br.s, 1H).

Step 6—Synthesis of 1-chloro-3-[4-(3,7-difluoroiso-quinolin-1-yl)piperazin-1-yl]propan-2-ol

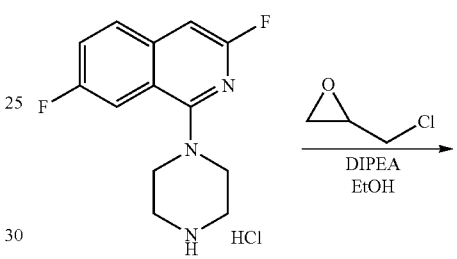

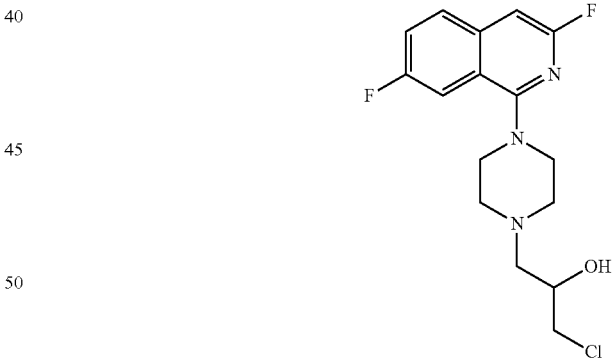

The title intermediate was prepared following the procedure described for the synthesis of 1-chloro-3-[4-(7-fluor-oisoquinolin-1-yl)piperazin-1-yl]propan-2-ol (see compound 148) using 3,7-difluoro-1-(piperazin-1-yl) isoquinoline hydrochloride (99% yield). ES-MS m/z: 342.2 (M+1). $^1$HNMR (DMSO d6): δ ppm 2.68-2.71 (m, 2H), 2.80-2.83 (m, 2H), 2.97-3.10 (m, 2H), 3.55-3.77 (m, 6H), 4.07-4.09 (m, 1H), 6.82 (s, 1H), 7.40 (td, J=8.4, 2.1 Hz, 1H), 7.63 (dd, J=9.7, 2.1 Hz, 1H), 7.60-7.72 (m, 1H).

Step 7—Synthesis of 1-azido-3-[4-(3,7-difluoroiso-quinolin-1-yl)piperazin-1-yl]propan-2-ol

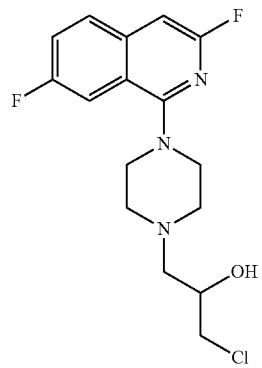

The title intermediate was prepared following the procedure described for 1-azide-3-(4-(7-fluoroisoquinolin-1-yl)piperazin-1-yl)propan-2-ol (see compound 148) using 1-chloro-3-[4-(3,7-difluoroisoquinolin-1-yl)piperazin-1-yl]propan-2-ol (89% yield). ES-MS m/z: 349.2 (M+1). ¹HNMR (DMSO d6): δ ppm 2.64-2.69 (m, 2H), 2.68-2.73 (m, 4H), 3.22-3.25 (m, 2H), 3.31-3.36 (m, 4H), 3.82-3.89 (m, 1H), 5.10 (d, J=4.9 Hz, 1H), 7.10 (s, 1H), 7.65-7.90 (m, 1H), 7.96-8.00 (m, 1H).

Step 8—Synthesis of 1-amino-3-[4-(3,7-difluoroiso-quinolin-1-yl)piperazin-1-yl]propan-2-ol

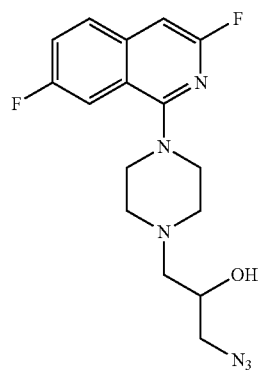

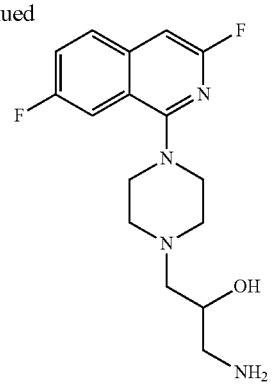

The title intermediate was prepared following the procedure described for 1-amino-3-(4-(7-fluoroisoquinolin-1-yl)piperazine-1-yl)propan-2-ol (see compound 148) using 1-azido-3-[4-(3,7-difluoroisoquinolin-1-yl)piperazin-1-yl]propan-2-ol (99% yield). ES-MS m/z: 323.2 (M+1). ¹HNMR (DMSO d6): δ ppm 1.90 (br. s, 2H), 2.33-2.48 (m, 4H), 2.51-2.68 (m, 4H), 3.17-3.33 (m, 4H), 3.60-3.62 (m, 1H), 4.50 (s, 1H), 7.10 (s, 1H), 7.66-7.70 (m, 2H), 7.98 (dd, J=8.8, 6.6 Hz, 1H).

Step 9—Synthesis of 4-({3-[4-(3,7-difluoroisoqui-nolin-1-yl)piperazin-1-yl]-2-hydroxypropyl}amino)-6-fluoro-2H-1,3-benzoxazin-2-one (compound 149)

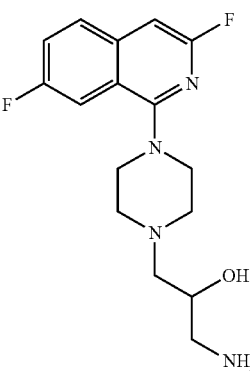 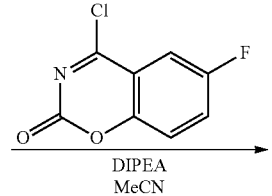

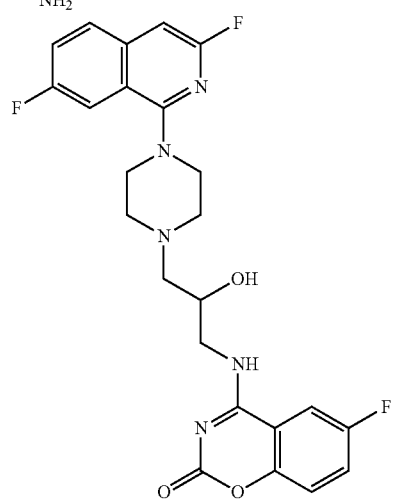

The title compound was prepared following the procedure described for compound 148 using 1-amino-3-[4-(3,7-difluoroisoquinolin-1-yl)piperazin-1-yl]propan-2-ol (23% yield). ES-MS m/z: 486.2 (M+1).

$^1$HNMR (DMSO d6). δ ppm 2.69-2.75 (m, 4H), 2.71 (m, 2H), 3.32-3.36 (m, 4H), 3.71-3.72 (m, 1H), 4.06 (s, 1H), 4.01 (s, 1H), 7.09 (s, 1H) 7.38 (s, 1H), 7.62-7.70 (m, 2H), 7.97 (s, 1H), 8.10 (d, J=8.4 Hz, 1H), 9.13 (s, 1H).

Preparation of Compound 150

Compound 150 was prepared as described herein below.

Step 1—Synthesis of N-boc-2-[4-(7-fluoroisoquinolin-1-yl)piperazin-1-yl]ethanamine

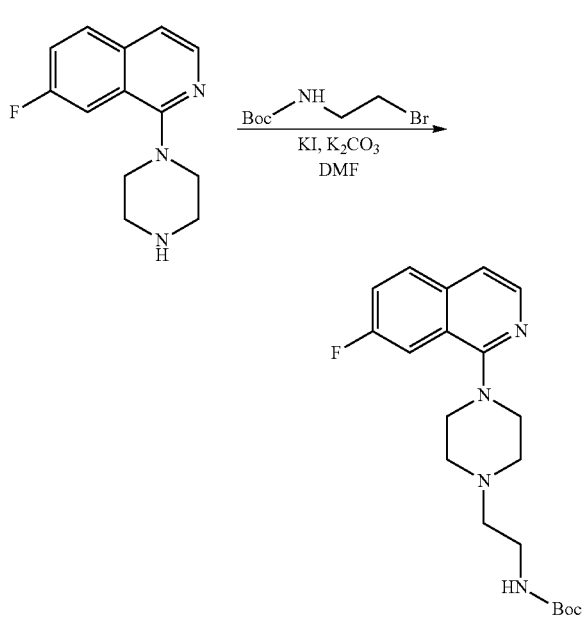

The title compound was prepared according to the procedure described for the synthesis of intermediate C$_3$ (compound 51) by using 7-fluoro-1-(piperazin-1-yl)isoquinoline and tert-butyl-(2-bromoethyl)carbamate (82% yield). LC-MS (M–H$^+$)=375.2

Step 2—Synthesis of 2-[4-(7-fluoroisoquinolin-1-yl)piperazin-1-yl]ethan-1-amine trifluoroacetate

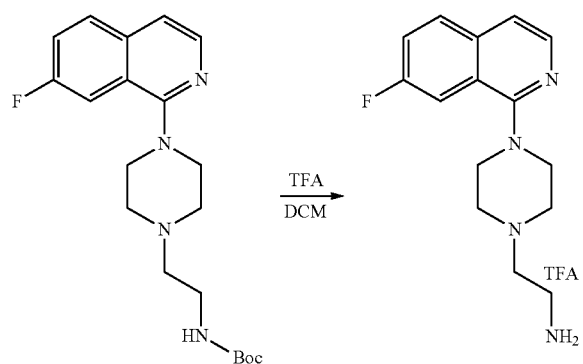 [SMILES: CC(C)(C)OC(=O)NCCN1CCN(c2nccc3ccc(F)cc23)CC1 ; NCCN1CCN(c2nccc3ccc(F)cc23)CC1]

The title intermediate was prepared according to the procedure described for the synthesis of 7-fluoro-1-(piperazin-1-yl)isoquinoline (see compound 144) using N-boc-2-[4-(7-fluoroisoquinolin-1-yl)piperazin-1-yl]ethanamine (91% yield). LC-MS (M–H+)=275.2

Step 3—Synthesis of N-[(3,4-dihydro-2H-pyrano[2,3-c]pyridin-6-yl)methyl]-2-[4-(7-fluoroisoquinolin-1-yl)piperazin-1-yl]ethan-1-amine (compound 150)

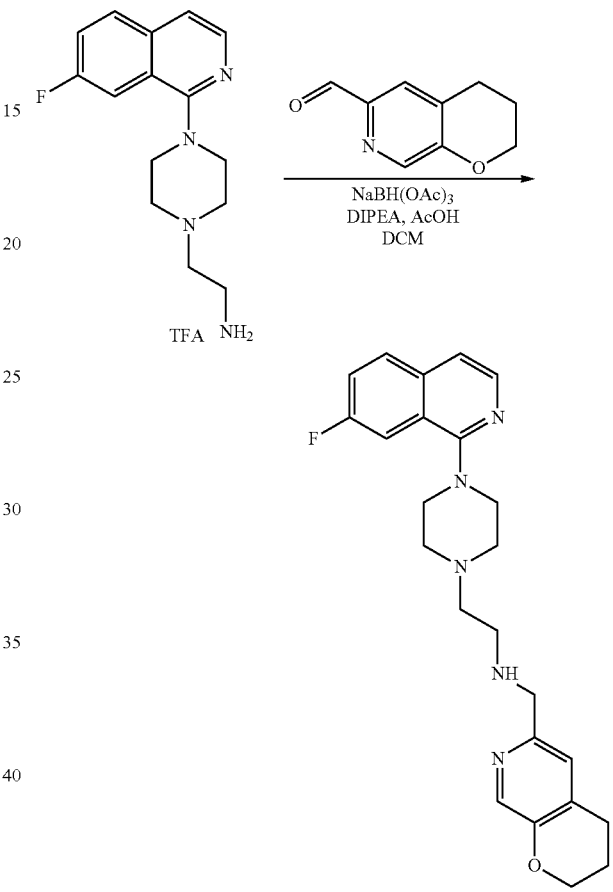

To a solution of 3,4-dihydro-2H-pyrano[2,3-c]pyridine-6-carbaldehyde (prepared as described in WO2012012391, 218 mg, 1.33 mmol) and DIPEA (0.25 mL) in DCM (3 mL), 2-[4-(7-fluoroisoquinolin-1-yl)piperazin-1-yl]ethan-1-amine trifluoroacetate (1.6 g, 5.8 mmol) in DCM (5 mL) and 2 drops of AcOH were added. After stirring 10 min NaBH(OAc)$_3$ (446 mg, 2 mmol) was added. The mixture was stirred at room temperature for 4 h then DCM (35 mL) and sat. NaHCO$_3$ (25 mL) were added. The organic phase was separated, washed with sat. NaCl, dried over Na$_2$SO$_4$ and concentrated. The residue was purified by flash chromatography (silica gel, DCM/MeOH 9/1) to give N-[(3,4-dihydro-2H-pyrano[2,3-c]pyridin-6-yl)methyl]-2-[4-(7-fluoro isoquinolin-1-yl)piperazin-1-yl]ethan-1-amine (139 mg, 0.33 mmol, 25% yield). LC-MS (M–H+)=422.2.

$^1$H NMR (300 MHz, CHLOROFORM-d) δ=8.13 (d, J=5.8 Hz, 1H), 8.09 (s, 1H), 7.76 (dd, J=5.6, 9.0 Hz, 1H), 7.69 (dd, J=2.6, 10.2 Hz, 1H), 7.39 (dt, J=2.6, 8.6 Hz, 1H), 7.24 (d, J=5.8 Hz, 1H), 7.01 (s, 1H), 4.21 (t, J=5.1 Hz, 2H), 3.87 (s, 2H), 3.40 (t, J=4.9 Hz, 4H), 2.84 (t, J=6.2 Hz, 2H), 2.80-2.64 (m, 8H), 2.55 (br. s., 1H), 2.08-1.95 (m, 2H).

Preparation of Compound 152

Compound 152 was prepared as described herein below.

Step 1—Synthesis of [1]benzopyrano[3,4-d]imidazol-4(1H)-one

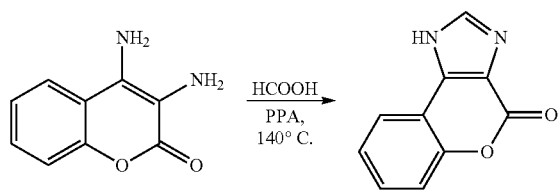 [SMILES: Nc1c(N)c2ccccc2oc1=O ; "HCOOH" ; O=c1oc2ccccc2c2[nH]cnc12]

Intermediate [1]benzopyrano[3,4-d]imidazol-4(1H)-one was prepared according to the procedure described for the synthesis of 2-(chloromethyl)[1]benzopyrano[3,4-d]imidazol-4(1H)-one (see compound 146) using formic acid. Y=67%. LC-MS (M–H$^+$)=187.1

Step 2—Synthesis of 1-{[2-(trimethylsilyl)ethoxy]methyl}[1]benzopyrano [3,4-d]imidazol-4(1H)-one

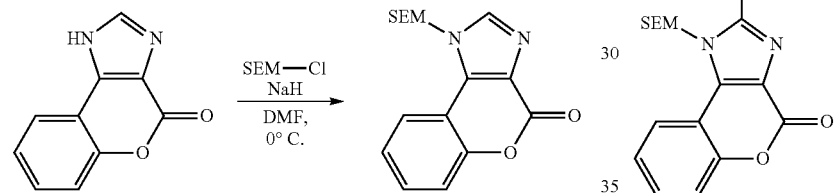

A solution of [1]benzopyrano[3,4-d]imidazol-4(1H)-one (274 mg, 1.5 mmol) in dry DMF (10 mL) was cooled to 0° C. NaH (60% dispersion in mineral oil, 117 mg, 2.9 mmol) was added and the mixture was stirred 15 min at 0° C. SEM-Cl (294 mg, 1.8 mmol) was added and the mixture was stirred for further 2 h. UPLC analysis showed that reaction was complete so water was added at 0° C. followed by ethyl acetate. The organic phase was separated and washed with brine, dried over Na$_2$SO$_4$ and evaporated in vacuum. The crude material was purified by Si-column eluting with Cy to Cy/ethyl acetate 1:1 to obtain 265 mg of 1-{[2-(trimethylsilyl)ethoxy]methyl}[1]benzopyrano [3,4-d]imidazol-4 (1H)-one as a mix of regioisomers. LC-MS (M–H$^+$)=317.3

Step 3—Synthesis of 2-bromo-1-{[2-(trimethylsilyl)ethoxy]methyl}[1] benzo pyrano[3,4-d]imidazol-4 (1H)-one

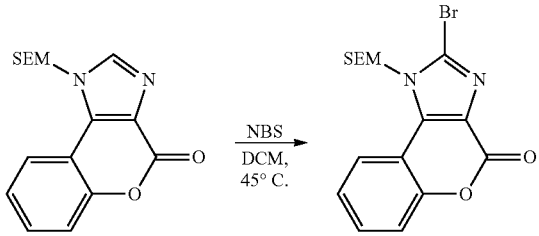

1-{[2-(trimethylsilyl)ethoxy]methyl}[1]benzopyrano[3,4-d]imidazol-4(1H)-one (150 mg, 0.47 mmol) was dissolved in DCM. N-bromosuccinimide (88 mg, 0.5 mmol) and cat. AIBN were added and the mixture was stirred at 45° C. for 4 h. UPLC analysis showed that reaction was complete so water was added and the organic phase was separated and evaporated in vacuum. The crude material was purified by Si-column eluting with Cy to Cy/ethyl acetate 85:15 to obtain 104 mg (Y=56%) of 2-bromo-1-{[2-(trimethylsilyl)ethoxy]methyl}[1]benzopyrano[3,4-d] imidazol-4(1H)-one as a mixture of regioisomers. LC-MS (M–H$^+$)=396.2

Step 4—Synthesis of 2-(1-ethoxyethenyl)-1-{[2-(trimethylsilyl)ethoxy]methyl}[1]benzopyrano[3,4-d]imidazol-4(1H)-one

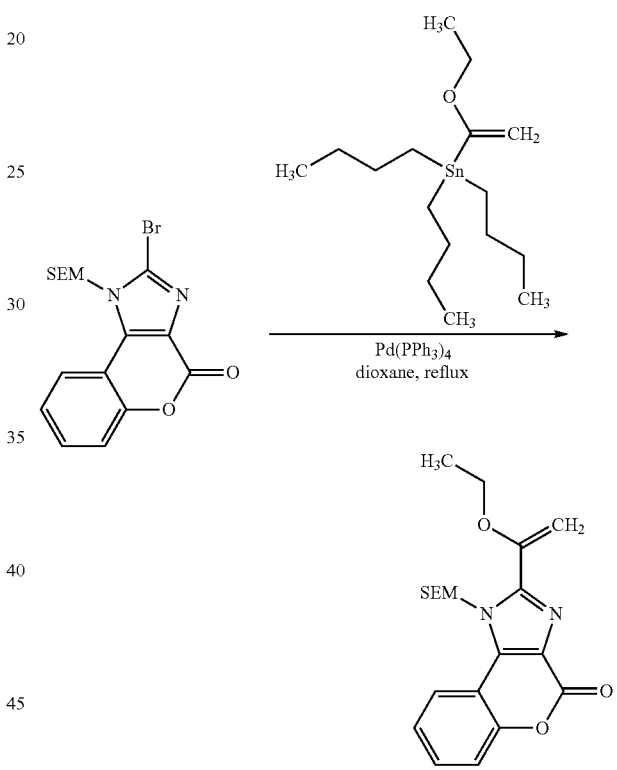

2-bromo-1-{[2-(trimethylsilyl)ethoxy]methyl}[1]benzopyrano[3,4-d]imidazol-4(1H)-one (104 mg, 0.26 mmol) was dissolved in dioxane (2 mL), tributyl(1-ethoxyvinyl)tin (140 mg, 0.39 mmol) was added and the mixture was purged with N$_2$ for 20 minutes. Tetrakis(triphenylphosphine)palladium (0) (30 mg, 0.026 mmol) was added and the mixture was stirred at reflux for 6 h then was cooled to 0° C., diluted with water and extracted with ethyl acetate. The organic phase was washed with aqueous solution of KF, dried over Na$_2$SO$_4$ and concentrated in vacuum. The crude material was purified by NH2-column eluting with Cy to Cy/ethyla acetate 8:2 to obtain 100 mg (0.25 mmol) of 2-(1-ethoxyethenyl)-1-{[2-(trimethylsilyl)ethoxy]methyl}[1]benzopyrano [3,4-d]imidazol-4(1H)-one, which was used in the next step without further purification. LC-MS (M–H$^+$)=387.4

Step 5—Synthesis of 2-(bromoacetyl)-1-{[2-(trimethylsilyl)ethoxy]methyl}[1]benzopyrano[3,4-d]imidazol-4(1H)-one

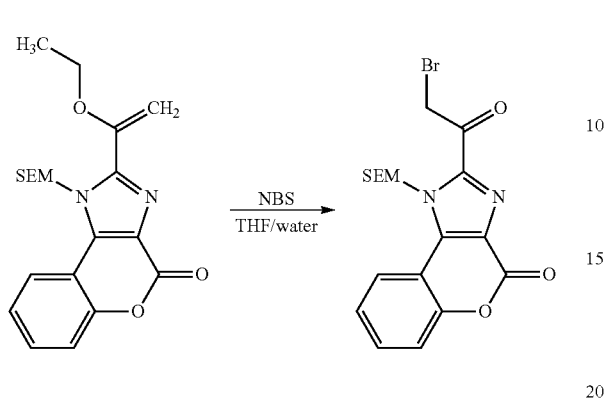

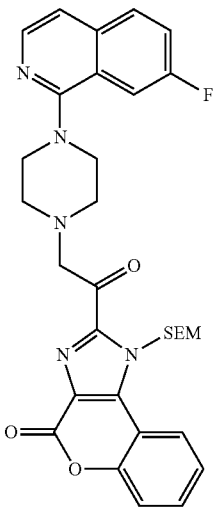

A solution of 2-(1-ethoxyethenyl)-1-{[2-(trimethylsilyl)ethoxy]methyl}[1]benzopyrano[3,4-d]imidazol-4(1H)-one (100 mg, 0.25 mmol) in THF/water (10 mL) was cooled to 0° C. N-bromosuccinimide (76 mg, 0.43 mmol) was added and the mixture was stirred at room temperature for 1 h. UPLC analysis showed the completion of the reaction. DCM was added followed by water. The organic phase was separated, dried over Na₂SO₄ and concentrated in vacuum. The crude material was purified by Si-column eluting with Cy to Cy/ethyl acetate 9:1 to obtain 70 mg (0.16 mmol, 64% yield) of 2-(bromoacetyl)-1-{[2-(trimethylsilyl)ethoxy]methyl}[1]benzopyrano[3,4-d]imidazol-4(1H)-one, which was used without any further purification and characterization.

Step 6—Synthesis of 2-{[4-(7-fluoroisoquinolin-1-yl)piperazin-1-yl]acetyl}-1-{[2-(trimethylsilyl)ethoxy]methyl}[1]benzopyrano[3,4-d]imidazol-4(1H)-one

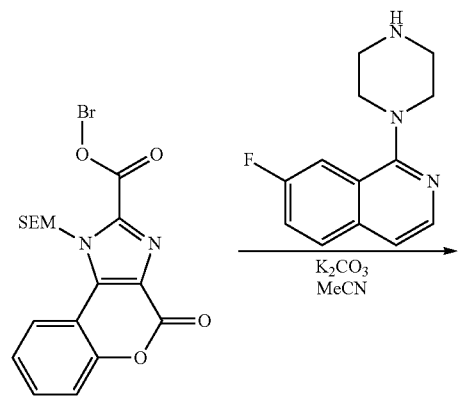

2-(bromoacetyl)-1-{[2-(trimethylsilyl)ethoxy]methyl}[1]benzopyrano[3,4-d]imidazol-4(1H)-one (70 mg, 0.16 mmol), 7-fluoro-1-(piperazin-1-yl)isoquinoline (37 mg, 0.16 mmol, see compound 144) and potassium carbonate (33 mg, 0.24 mmol) were dissolved in MeCN. The mixture was stirred at room temperature for 30 min then ethyl acetate was added followed by water. The organic phase was separated, dried over Na₂SO₄ and concentrated in vacuum. The resulting crude material was purified by Si-column eluting with Cy to Cy/ethyl acetate 1:1 to obtain 61 mg (0.1 mmol, 65% yield) of 2-{[4-(7-fluoroisoquinolin-1-yl)piperazin-1-yl]acetyl}-1-{[2-(trimethylsilyl)ethoxy]methyl}[1]benzopyrano[3,4-d]imidazol-4(1H)-one. LC-MS (M−H⁺)=588.4

Step 7—Synthesis of 2-{2-[4-(7-fluoroisoquinolin-1-yl)piperazin-1-yl]-1-hydroxyethyl}-1-{[2-(trimethylsilyl)ethoxy]methyl}[1]benzopyrano[3,4-d]imidazol-4(1H)-one

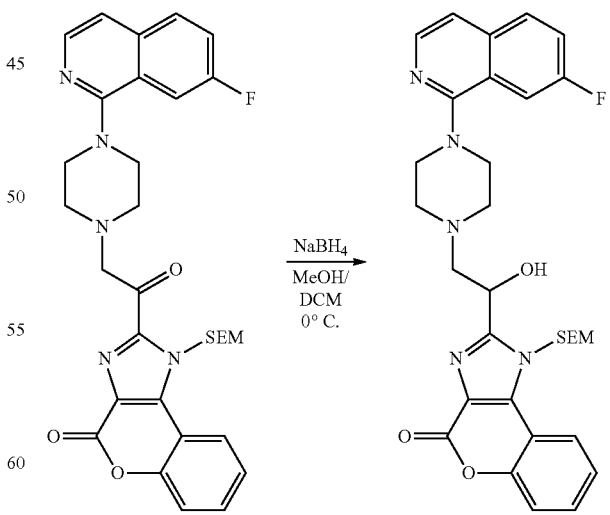

A solution of 2-{[4-(7-fluoroisoquinolin-1-yl)piperazin-1-yl]acetyl}-1-{[2-(trimethylsilyl)ethoxy]methyl}[1]benzopyrano[3,4-d]imidazol-4(1H)-one (61 mg, 0.1 mmol) in methanol/DCM 10:1 (11 mL) was cooled to 0° C. then NaBH$_4$ (19 mg, 0.5 mmol) was added. The mixture was stirred for 30 min at 0° C. then the solvent was evaporated in vacuum, ethyl acetate was added and the organic phase was washed with water, dried over Na$_2$SO$_4$ and concentrated in vacuum to obtain 51 mg (0.086 mmol, 86% yield) of 2-{2-[4-(7-fluoroisoquinolin-1-yl)piperazin-1-yl]-1-hydroxyethyl}-1-{[2-(trimethylsilyl)ethoxy]methyl}[1]benzopyrano[3,4-d]imidazol-4(1H)-one, that was used in the next step without further purification. LC-MS (M–H$^+$)=590.4

Step 8—Synthesis of 2-{2-[4-(7-fluoroisoquinolin-1-yl)piperazin-1-yl]-1-hydroxyethyl}[1]benzopyrano[3,4-d]imidazol-4(1H)-one hydrochloride (compound 152)

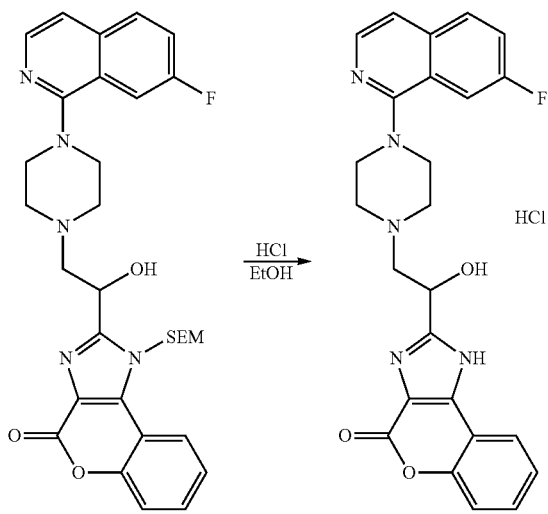 [SMILES: "EtOH" ; C[Si](C)(C)CCOCn1c(C(O)CN2CCN(c3nccc4ccc(F)cc34)CC2)nc2c(=O)oc3ccccc3c21 ; Cl ; O=c1oc2ccccc2c2[nH]c(C(O)CN3CCN(c4nccc5ccc(F)cc45)CC3)nc12 ; Cl]

2-{2-[4-(7-fluoroisoquinolin-1-yl)piperazin-1-yl]-1-hydroxyethyl}-1-{[2-(trimethylsilyl)ethoxy]methyl}-1H,4H-chromeno[3,4-d]imidazol-4-one (51 mg, 0.086 mmol) was dissolved in ethanol (8 mL), 1 M HCl in ethanol was added (10 mL, 10 mmol) and the mixture was stirred at room temperature for 4 h. After removal of the solvent in vacuum the resulting crude was purified by C18 rev. chromatography eluting with water/acetonitrile 95:5 to acetonitrile 100% to obtain 60 mg of the product. The compound was dissolved in DCM and the solution was cooled to 0° C. 1 M HCl in diethyl ether was added (5 mL), the mixture was concentrated in vacuum and the crude solid was treated with diethyl ether to obtain 30 mg of 2-{2-[4-(7-fluoroisoquinolin-1-yl)piperazin-1-yl]-1-hydroxyethyl}[1]benzopyrano[3,4-d]imidazol-4(1H)-one as hydrochloride salt. LC-MS (M–H$^+$) =460.4.

$^1$H NMR (500 MHz, DMSO-d6) δ ppm 3.42-3.90 (m, 8H), 5.51 (dd, J=10.03, 2.69 Hz, 1H), 6.95 (d, J=8.80 Hz, 1H), 7.37-7.48 (m, 1H), 7.50-7.54 (m, 1H), 7.55-7.62 (m, 2H), 7.73 (td, J=8.68, 2.69 Hz, 1H), 7.87 (dd, J=10.03, 2.20 Hz, 1H), 8.08 (dd, J=9.05, 5.62 Hz, 1H), 8.14-8.28 (m, 2H), 10.55 (br. s., 1H).

Preparation of Compound 153

Compound 153 was prepared as described herein below.

Step 1—Synthesis of 4-chloro-3-(trifluoroacetyl)-2H-1-benzopyran-2-one

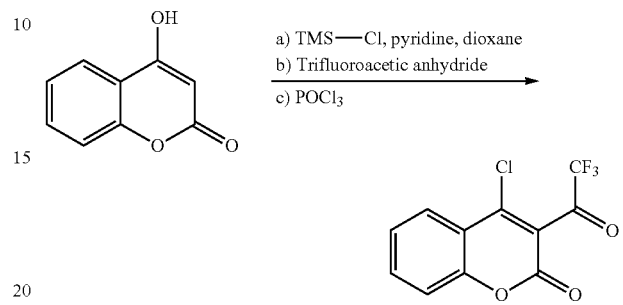

The reaction was conducted in a pressure tube. To a suspension of 4-hydroxycoumarin (2.5 g, 15.4 mmol) in dry 1,4-dioxane, dry pyridine 2.56 g (2.6 mL, 32.4 mmol) was added. When the mixture became completely homogeneous, trimethylsilylchloride (2 g, 18.5 mmol) was added. The reaction mixture was stirred for 1 h at room temperature. Trifluoroacetic anhydride (2.8 mL, 20 mmol) was then added and the mixture was stirred for 2 h at 90° C. To the cooled reaction mass phosphorus oxychloride (1.4 mL, 15.4 mmol) was added and the mixture was stirred at 60° C. for 2 h then it was diluted with ice water and extracted with DCM (3×50 mL). The combined organic layers were dried over sodium sulfate and concentrated to give 4-chloro-3-(trifluoroacetyl)-2H-1-benzopyran-2-one (3.1 g, 73% yield). The compound was used without further purification and characterization.

Step 2—Synthesis of ethyl 4-oxo-3-(trifluoromethyl)-1,4-dihydro[1]benzopyrano[4,3-b]pyrrole-2-carboxylate

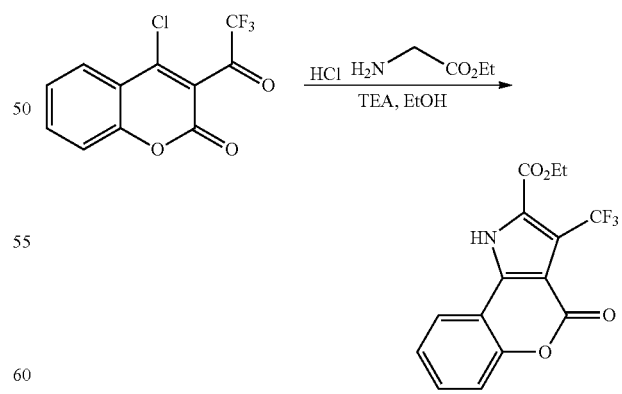

The title intermediate was prepared according to the procedure described for the synthesis of ethyl 4-oxo-1,4-dihydro[1]benzopyrano[4,3-b]pyrrole-2-carboxylate (see compound 145) using 4-chloro-3-(trifluoroacetyl)-2H-1-benzopyran-2-one (Y=74%). LC-MS (M–H$^+$)=326.1

Step 3-4—Synthesis of 4-oxo-3-(trifluoromethyl)-1,4-dihydro[1]benzopyrano[4,3-b]pyrrole-2-carbaldehyde

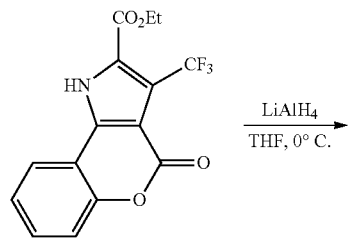

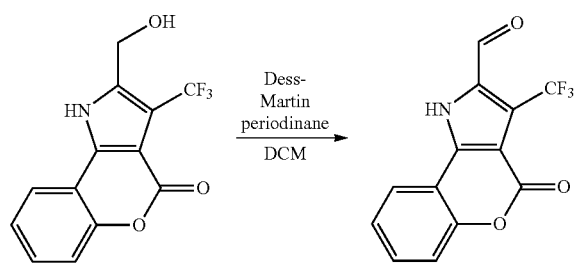

The title intermediate was prepared according to the procedure described for the synthesis of 4-oxo-1,4-dihydro[1]benzopyrano[4,3-b]pyrrole-2-carbaldehyde (see compound 145) using ethyl 4-oxo-3-(trifluoromethyl)-1,4-dihydro[1]benzopyrano[4,3-b]pyrrole-2-carboxylate (Y=35% over two steps), that was used in the next step without further purification. LC-MS (M−H$^+$)=282.1

Step 5—Synthesis of 2-({[1-(7-fluoroisoquinolin-1-yl)piperidin-4-yl]amino}methyl)-3-(trifluoromethyl)[1]benzopyrano[4,3-b]pyrrol-4(1H)-one (formate salt, compound 153)

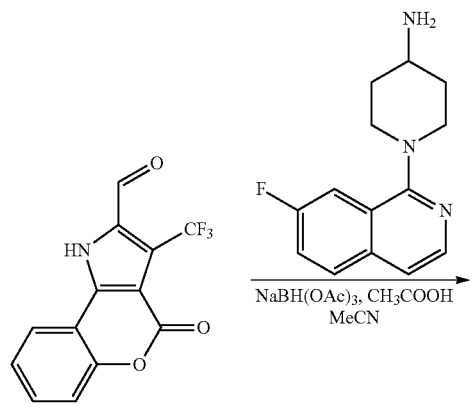

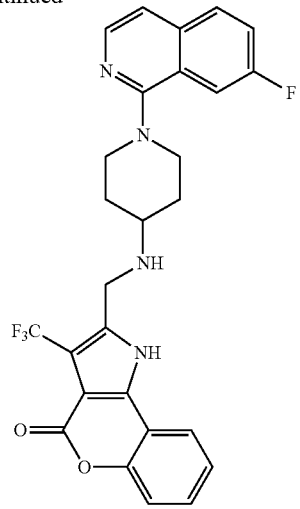

Compound 153 was prepared according to the procedure described for the synthesis of compound 145 using 4-oxo-3-(trifluoromethyl)-1,4-dihydro[1]benzopyrano[4,3-b]pyrrole-2-carbaldehyde (Y=8%). LC-MS (M−H$^+$)=511.3.

$^1$H NMR (500 MHz, DMSO-d6) δ ppm 1.60-1.73 (m, 2H), 1.98-2.08 (m, 2H), 2.69-2.80 (m, 1H), 2.93 (t, J=11.60 Hz, 2H), 3.67 (d, J=11.60 Hz, 2H), 4.06 (s, 2H), 7.38-7.44 (m, 2H), 7.44-7.48 (m, 1H), 7.49-7.56 (m, 1H), 7.60-7.69 (m, 2H), 7.99 (dd, J=8.80, 5.87 Hz, 1H), 8.09 (d, J=5.87 Hz, 1H), 8.17 (s, 1H), 8.22 (dd, J=7.83, 0.98 Hz, 1H).

Preparation of Compound 155

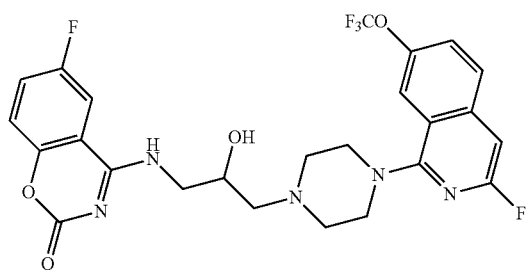 [SMILES: O=c1nc(NCC(O)CN2CCN(c3nc(F)cc4ccc(OC(F)(F)F)cc34)CC2)c2cc(F)ccc2o1]

Compound 155 6-fluoro-4-[(3-{4-[3-fluoro-7-(trifluoromethoxy) isoquinolin-1-yl]piperazin-1-yl}-2-hydroxypropyl)amino]-2H-1,3-benzoxazin-2-one was prepared following the procedure described for the synthesis of compound 149 starting from 2-fluoro-5-trifluromethoxybenzonitrile. LCMS m/z: 552.2 (M+1).

$^1$HNMR (400 MHz, CDCl$_3$+MeOH-d4): δ ppm 2.48-2.54 (m, 1H), 2.62-2.65 (m, 1H), 2.74-2.75 (m, 2H), 2.87-2.89 (m, 2H), 3.33 (s, 1H), 3.45-3.55 (m, 4H), 3.88 (dd, J=14.0, 3.6 Hz, 1H), 4.05-4.06 (m, 1H), 6.78 (s, 1H) 7.23-7.27 (m, 2H), 7.34 (dd, J=8.8, 2.3 Hz, 1H), 7.43 (d, J=8.8 Hz, 1H), 7.61 (dd, J=8.4, 2.4 Hz, 1H), 7.23 (d, J=8.8 Hz, 1H), 7.78 (s, 1H).

Preparation of Compound 156

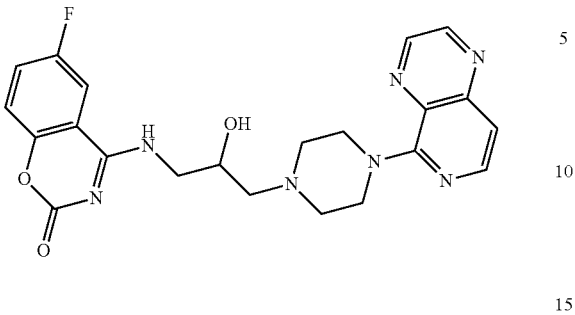

Compound 156 6-fluoro-4-((2-hydroxy-3-(4-(pyrido[3,4-b]pyrazin-5-yl)piperazin-1-yl)propyl)amino)-2H-benzo[e][1,3]oxazin-2-one was prepared according to the synthesis of compound 149 using 5-chloropyrido[3,4-b]pyrazine, prepared as described for compound 196. LCMS m/z: 452.2 (M+1).

¹HNMR (DMSO-d6): δ ppm 2.49-2.50 (m, 4H), 3.31-3.34 (m, 3H), 3.37-3.75 (m, 1H), 3.98-3.99 (m, 4H), 4.08-4.09 (m, 1H), 5.00 (d, J=4.4 Hz, 1H) 7.23 (d, J=5.6 Hz, 1H), 7.38 (dd, J=8.8, 4.6 Hz, 1H), 7.60-7.64 (m, 1H), 8.10 (d, J=8.4 Hz, 1H), 8.25 (d, J=5.6 Hz, 1H), 8.84 (s, 1H), 8.99 (s, 1H), 9.13-9.14 (m, 1H).

Preparation of Compound 158 and 159

Compound 158 was prepared as described herein below.

Step 1—Synthesis of 2-{1-azido-2-[4-(7-fluoroisoquinolin-1-yl)piperazin-1-yl]ethyl}-1-{[2-(trimethylsilyl)ethoxy]methyl}[1]benzopyrano[3,4-d]imidazol-4(1H)-one

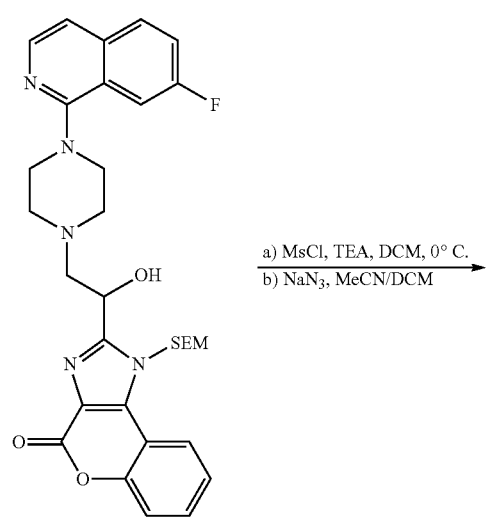

a) MsCl, TEA, DCM, 0° C.
b) NaN₃, MeCN/DCM

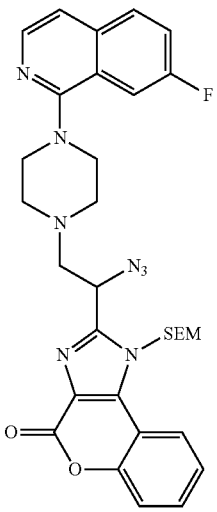

2-{2-[4-(7-fluoroisoquinolin-1-yl)piperazin-1-yl]-1-hydroxyethyl}-1-{[2-(trimethylsilyl)ethoxy]methyl}[1]benzopyrano[3,4-d]imidazol-4(1H)-one (279 mg, 0.47 mmol, see compound 152) was dissolved in dry DCM (30 mL), TEA (98 µL, 0.7 mmol) was added and the mixture was cooled to 0° C. MsCl (40 µL, 0.52 mmol) was added and the mixture was stirred for 1 h at 0° C. Sodium azide (244 mg, 3.8 mmol) and MeCN (16 mL) were then added. The mixture was stirred at room temperature overnight then was dilute with DCM. The organic phase was washed with water and concentrated in vacuum. The crude material was purified by Si-column (from 100% Cy to cy/ethyl acetate 6:4) to obtain 134 mg (0.22 mmol, 46% yield) of 2-{1-azido-2-[4-(7-fluoroisoquinolin-1-yl)piperazin-1-yl]ethyl}-1-{[2-(trimethylsilyl)ethoxy]methyl}[1]benzopyrano[3,4-d]imidazol-4(1H)-one. LC-MS (M–H⁺)=615.3

Step 2—Synthesis of 2-{1-amino-2-[4-(7-fluoroisoquinolin-1-yl)piperazin-1-yl]ethyl}-1-{[2-(trimethylsilyl)ethoxy]methyl}[1]benzopyrano[3,4-d]imidazol-4(1H)-one

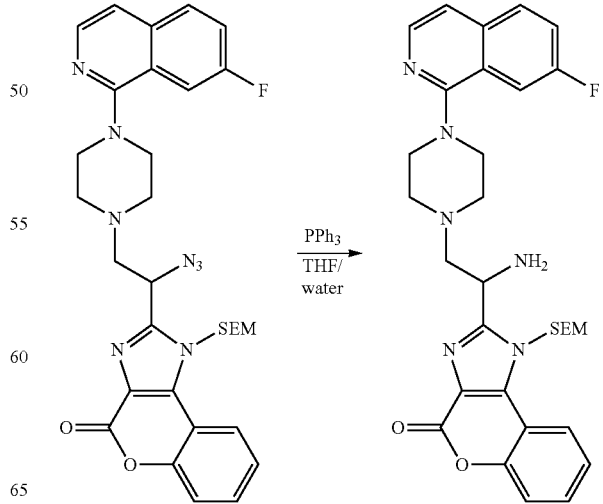

To a solution of 2-{1-azido-2-[4-(7-fluoroisoquinolin-1-yl)piperazin-1-yl]ethyl}-1-{[2-(trimethylsilyl)ethoxy]methyl}[1]benzopyrano[3,4-d] imidazol-4(1H)-one (134 mg, 0.22 mmol) in THF/H$_2$O 3:1 (44 mL), triphenylphosphine (69 mg, 0.26 mmol) was added. The mixture was stirred at room temperature overnight then DCM was added followed by water. The organic phase was separated and evaporated in vacuum. The crude material was purified by Si-column (DCM/methanol 98:2) to obtain 124 mg (0.21 mmol, 96% yield) of 2-{1-amino-2-[4-(7-fluoroisoquinolin-1-yl)piperazin-1-yl]ethyl}-1-{[2-(trimethylsilyl)ethoxy]methyl}[1]benzo pyrano[3,4-d]imidazol-4(1H)-one. LC-MS (M–H$^+$)=589.5

Step 3—Synthesis of 2-{1-amino-2-[4-(7-fluoroisoquinolin-1-yl)piperazin-1-yl]ethyl}[1]benzopyrano[3,4-d]imidazol-4(1H)-one hydrochloride (compound 158) and N-{2-[4-(7-fluoroisoquinolin-1-yl)piperazin-1-yl]-1-(4-oxo-1,4-dihydro[1]benzopyrano[3,4-d]imidazol-2-yl)ethyl}formamide hydrochloride (compound 159)

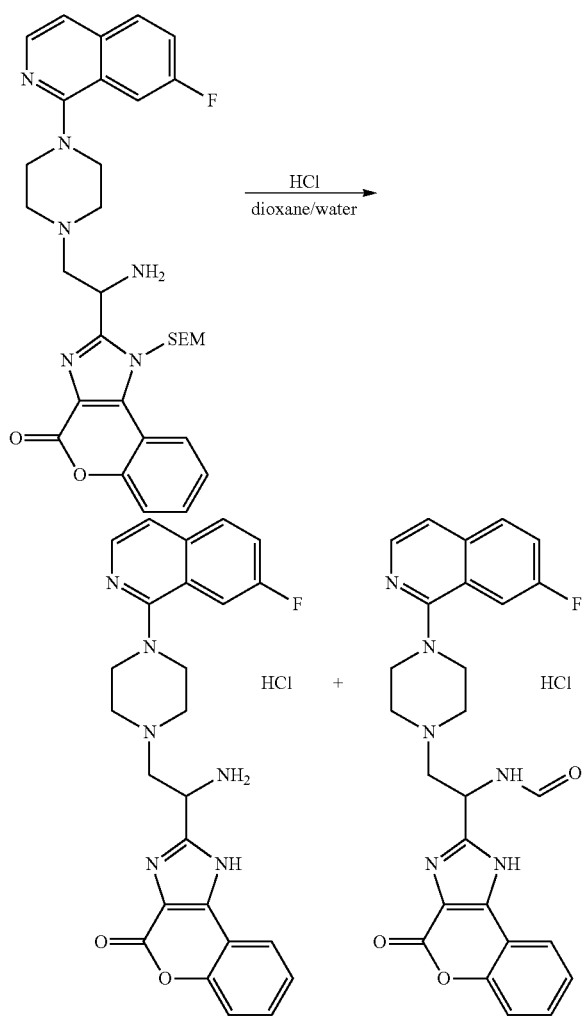

2-{1-amino-2-[4-(7-fluoroisoquinolin-1-yl)piperazin-1-yl]ethyl}-1-{[2-(trimethylsilyl)ethoxy]methyl}[1]benzopyrano[3,4-d]imidazol-4(1H)-one (124 mg, 0.21 mmol) was dissolved in 4 M HCl in dioxane (10 mL). Water (1 mL) was added and the mixture was stirred at room temperature for 2 h. The solvent was removed in vacuum, the resulting solid was purified by C-18 reverse chromatography eluting with (water+0.1% formic acid/methanol+0.1% formic acid). Both 2-{1-amino-2-[4-(7-fluoroisoquinolin-1-yl)piperazin-1-yl]ethyl}[1]benzopyrano[3,4-d]imidazol-4(1H)-one (compound 158) and the corresponding N-{2-[4-(7-fluoroisoquinolin-1-yl)piperazin-1-yl]-1-(4-oxo-1,4-dihydro[1]benzopyrano[3,4-d]imidazol-2-yl)ethyl}formamide (compound 159) were recovered.

Compound 158: the product was dissolved in DCM and 1 M HCl in diethyl ether was added to obtain 39 mg of the title compound as hydrochloride salt. LC-MS (M–H$^+$)=459.3.

$^1$H NMR. (500 MHz, METHANOL-d4) δ ppm 2.87-2.98 (m, 2H), 3.04-3.12 (m, 2H), 3.20 (d, J=6.85 Hz, 2H), 3.83-4.03 (m, 4H), 4.88-4.99 (m, 1H), 7.46 (t, J=7.60 Hz, 1H), 7.51 (d, J=7.60 Hz, 1H), 7.58-7.63 (m, 1H), 7.66 (d, J=6.85 Hz, 1H), 7.80 (d, J=6.85 Hz, 1H), 7.88 (td, J=8.80, 2.00 Hz, 1H), 7.99 (dd, J=9.78, 1.96 Hz, 1H), 8.05 (d, J=7.60 Hz, 1H), 8.16 (dd, J=8.80, 5.38 Hz, 1H).

Compound 159: the product was dissolved in DCM and 1 M HCl in diethyl ether was added to obtain 3.3 mg of the title compound as hydrochloride salt. LC-MS (M–H$^+$)= 487.3.

$^1$H NMR (500 MHz, METHANOL-d4) δ ppm 3.70-4.01 (m, 9H), 4.14 (dd, J=13.30, 6.02 Hz, 1H), 5.98 (t, J=6.90 Hz, 1H), 7.45 (t, J=7.53 Hz, 1H), 7.49-7.54 (m, 1H), 7.57-7.63 (m, 1H), 7.66 (d, J=6.27 Hz, 1H), 7.74 (td, J=8.66, 2.30 Hz, 1H), 7.95 (dd, J=9.79, 2.26 Hz, 1H), 8.01-8.15 (m, 3H), 8.38 (s, 1H).

Preparation of Compound 162

Compound 162 was prepared as described herein below.

Step 1—Synthesis of 2-chloro-5-fluoronicotinamide

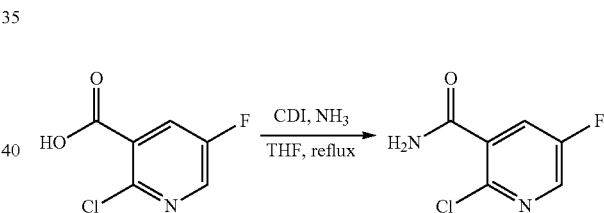

To a solution of 2-chloro-5-fluoro nicotinic acid (5.0 g, 28.5 mmol) in THF (50 mL), 1,1'-carbonyl diimidazole (5.38 g, 39 mmol) was added at 0° C. The mixture was refluxed for 3 h then was cooled to 0° C. and THF*ammonia (60 mL) was added. After stirring for 12 h at room temperature the reaction mixture was concentrated under reduced pressure and the resulting crude was purified by flash chromatography (5% MeOH in DCM) to give 2-chloro-5-fluoronicotinamide (4.4 g, 88%) as a white solid. LC-MS m/z: 175.2 (M+1). $^1$HNMR (300 MHz, DMSO-d6): δ ppm 7.87 (br. s, 1H), 8.00 (d, J=8.0 Hz, 1H), 8.10 (br. s, 1H), 8.53 (d, J=2.9 Hz, 1H).

Step 2—Synthesis of 5-fluoro-2-methylnicotinamide

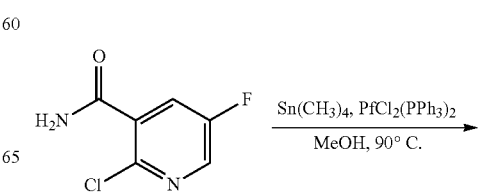

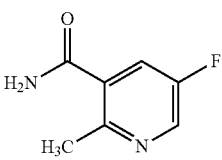

A solution of 2-chloro-5-fluoronicotinamide (4.2 g, 24.0 mmol) in DMF (42 mL) was purged for 15 min under argon. Tin tetramethyl (8.58 g, 48 mmol) and bis(triphenylphosphine)palladium(II) dichloride (0.84 g, 1.2 mmol) were added and the resulting mixture was stirred at 90° C. for 6 h and then filtered through a celite bed. The filtrate was concentrated under reduced pressure and the resulting crude was purified by flash chromatography (5% MeOH in DCM) to give 5-fluoro-2-methylnicotinamide (2.15 g, 58%) as a pale brown solid. LC-MS m/z: 155.2 (M+1). $^1$HNMR (400 MHz, DMSO-d6): δ ppm 2.53 (s, 3H), 7.71-7.68 (m, 2H), 7.98 (s, 1H), 8.49 (d, J=2.9 Hz, 1H).

Step 3—Synthesis of
3-fluoro-1,6-naphthyridin-5(6H)-one

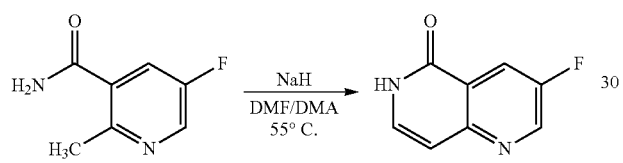

A mixture of 5-fluoro-2-methylnicotinamide (1.6 g, 10 mmol) in anhydrous DMF/DMA (3.2 mL) was heated at 55° C. for 3 h. The reaction mixture was concentrated under reduced pressure and anhydrous DMF (10 mL) was added to the resulting crude. Then NaH (60% in mineral oil, 620 mg, 15.5 mmol) was added at 0° C. and the mixture was heated at 85° C. for 3 h, cooled, diluted with water and neutralized by using conc. HCl. The reaction mass was concentrated under reduced pressure and the resulting crude was purified by flash chromatography (5% MeOH.NH$_3$ in DCM) to give 3-fluoro-1,6-naphthyridin-5(6H)-one as an off-white solid (150 mg, 9%). LCMS m/z: 165.2 (M+1). $^1$HNMR (300 MHz, DMSO-d6): δ ppm 6.66 (d, J=7.5 Hz, 1H), 7.46-7.40 (m, 1H), 8.27-8.21 (m, 1H), 8.96 (d, J=3 Hz, 1H), 11.7 (br.s, 1H).

Step 4—Synthesis of
5-chloro-3-fluoro-1,6-naphthyridine

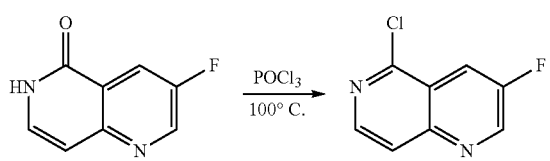

A mixture of 3-fluoro-1,6-naphthyridin-5(6H)-one (150 mg, 0.9 mmol) and phosphorous oxychloride (3.48 g, 23 mmol) was heated to 100° C. for 3 h. The reaction mixture was cooled to room temperature and concentrated under reduced pressure to remove excess POCl$_3$. The resulting crude was dissolved in EtOAc and washed with sat. NaHCO$_3$ and water. The organic layer was dried over sodium sulfate and concentrated to obtain 5-chloro-3-fluoro-1,6-naphthyridine (152 mg, 91.5%) as a pale brown solid. This was used as such in the next step without further purification. LC-MS m/z: 183.2 (M+1).

Step 5—Synthesis of 6-fluoro-4-({3-[4-(3-fluoro-1,6-naphthyridin-5-yl)piperazin-1-yl]-2-hydroxypropyl}amino)-2H-1,3-benzoxazin-2-one
(compound 162)

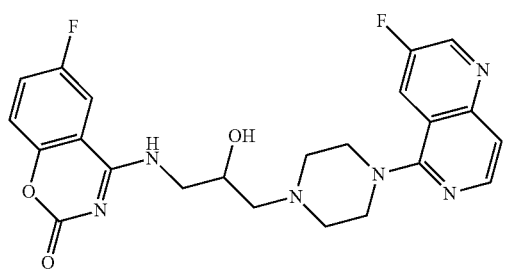 [SMILES: O=c1nc(NCC(O)CN2CCN(c3nccc4ncc(F)cc34)CC2)c2cc(F)ccc2o1]

The title compound was prepared according to the synthesis described for compound 149 using 5-chloro-3-fluoro-1,6-naphthyridine. LCMS m/z: 469.2 (M+1).

$^1$HNMR (400 MHz, DMSO-d6): δ ppm 2.78-2.58 (m, 6H), 3.44-3.34 (m, 5H), 3.73-3.71 (m, 1H), 4.08-4.06 (m, 1H), 5.04-5.02 (m, 1H), 7.41-7.37 (m, 1H), 7.49 (d, J=5.6 Hz, 1H), 7.65-7.61 (m, 1H), 8.18-8.11 (m, 2H), 8.31 (d, J=8 Hz, 1H), 9.17-9.10 (m, 2H).

Preparation of Compound 163

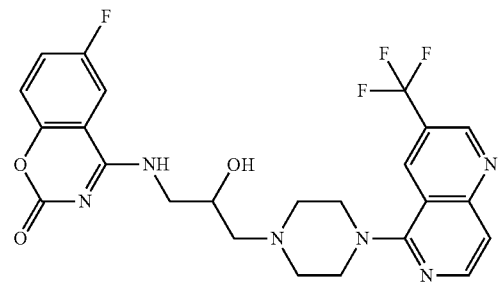 [SMILES: O=c1nc(NCC(O)CN2CCN(c3nccc4ncc(C(F)(F)F)cc34)CC2)c2cc(F)ccc2o1]

Compound 163 6-fluoro-4-[(2-hydroxy-3-{4-[3-(trifluoromethyl)-1,6-naphthyridin-5-yl]piperazin-1-yl}propyl)amino]-2H-1,3-benzoxazin-2-one was prepared according to the synthesis described for compound 162 starting from 2-chloro-5-(trifluromethyl)pyridine-3-carboxylic acid. LCMS m/z: 519.2 (M+1).

$^1$HNMR (DMSO d6): δ ppm 2.26-2.18 (m, 4H), 3.62-3.72 (m, 8H), 4.24 (br. s, 1H), 7.18-7.21 (m, 1H), 7.21-7.34 (m, 2H), 7.51 (d, J=6.0 Hz, 1H), 7.74-7.75 (m, 1H), 8.35 (d, J=6.0 Hz, 1H), 8.52 (s, 1H), 9.09 (s, 1H).

Preparation of Compound 166
Compound 166 was prepared as described herein below.

Step 1—Synthesis of tert-butyl 4-[3-(1,3-dioxo-1,3-dihydro-2H-isoindol-2-yl)-2-hydroxypropyl]piperazine-1-carboxylate

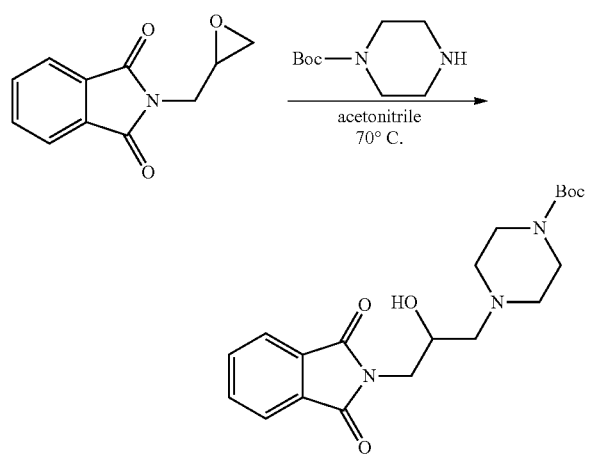

A mixture of N-Boc-piperazine (15 g, 81 mmol) and N-(2,3-epoxypropyl)phthalimide (16.4 g, 81 mmol) in acetonitrile (100 mL) was heated at 70° C. for 6 h. The reaction mixture was cooled to room T, concentrated under vacuum and the residue was purified via flash chromatography (silica gel, CHCl$_3$/MeOH 9/1) to give 20.4 g of a brown solid (52 mmol, Y=64%). LC-MS (M−H+)=390.1

Step 2—Synthesis of tert-butyl 4-(3-amino-2-hydroxypropyl)piperazine-1-carboxylate

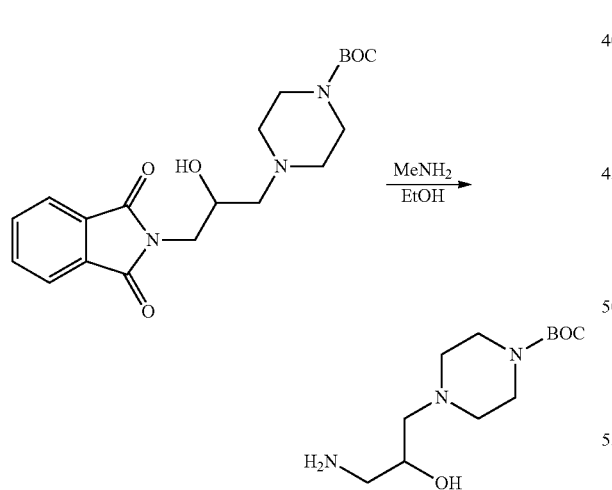

A solution of tert-butyl 4-[3-(1,3-dioxo-1,3-dihydro-2H-isoindol-2-yl)-2-hydroxypropyl]piperazine-1-carboxylate (20.4 g, 52 mmol) and 30% methylamine in EtOH (215 mL) was heated at 50° C. in a sealed tube overnight. The mixture was cooled to room temperature and filtered. The filtrate was concentrated under vacuum and purified by flash chromatography (silica gel, CHCl$_3$/MeOH 9/1) to give tert-butyl 4-(3-amino-2-hydroxypropyl)piperazine-1-carboxylate (6.2 g, 24 mmol, Y=46%). LC-MS (M−H+)=260.1

Step 3—Synthesis of 6-fluoro-2-oxo-2H-chromen-4-yl trifluoromethanesulfonate

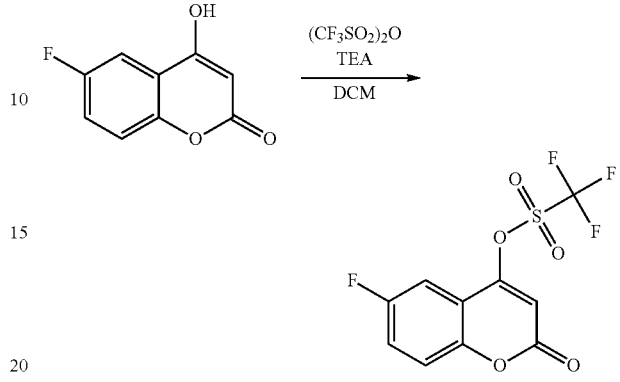

A solution of 6-fluoro-4-hydroxy-2H-chromen-2-one (10 g, 55.5 mmol) and TEA (15.5 mL, 111 mmol) in DCM (150 mL) was cooled at −10° C. Trifluoromethanesulfonic anhydride (10.3 mL, 61.1) in DCM (10 mL) was added drop wise. The mixture was stirred at −10° C. for 2 h and at room temperature overnight. The mixture was diluted with hexane/diethyl ether 1/1, the solid was filtered through a silica bed and concentrated to give a solid (11.2 g, 35 mmol, Y=63%) that was used without any further purification. GCMS=312.0

Step 4—Synthesis of tert-butyl 4-{3-[(7-fluoro-2-oxo-2H-1-benzopyran-4-yl)amino]-2-hydroxypropyl}piperazine-1-carboxylate

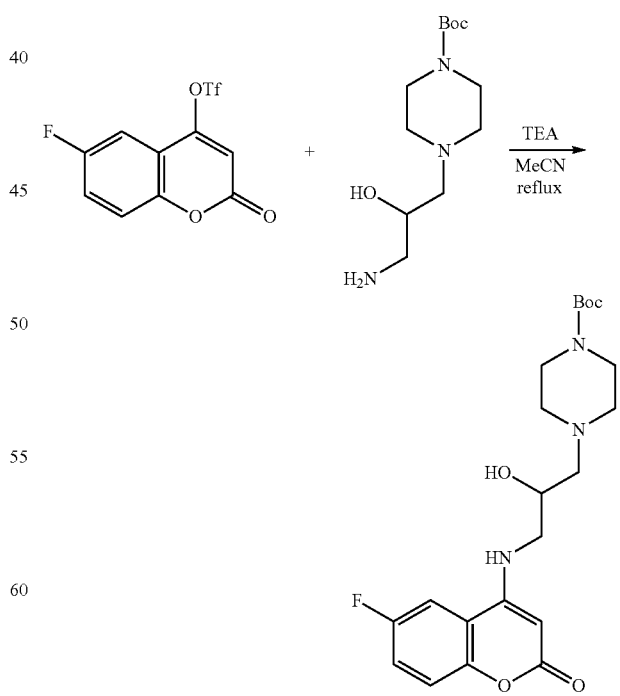

Triethylamine (4 mL, 28.7 mmol) in acetonitrile (20 mL) was added drop wise to a stirred solution of 6-fluoro-2-oxo- 2H-chromen-4-yl trifluoromethanesulfonate (7.5 g, 23.9 mmol) and tert-butyl 4-(3-amino-2-hydroxypropyl)piperazine-1-carboxylate (6.2 g, 23.9 mmol) in dry acetonitrile (50 ml). Once the addition was complete, the solution was heated at reflux for 2 hours. The reaction mixture was cooled to room temperature, diluted with DCM and washed with saturated NaHCO₃ and water. The organic phase was then separated, dried over sodium sulfate and evaporated in vacuum. The crude material was purified by flash chromatography (silica gel, from 100% CHCl₃ to CHCl₃/MeOH 85/15) to obtain tert-butyl 4-{3-[(7-fluoro-2-oxo-2H-1-benzopyran-4-yl)amino]-2-hydroxypropyl}piperazine-1-carboxylate (4.2 g, 10 mmol, Y=42%). LC-MS (M−H+): 422.2

Step 5—Synthesis of 7-fluoro-4-{[2-hydroxy-3-(piperazin-1-yl)propyl]amino}-2H-1-benzopyran-2-one hydrochloride

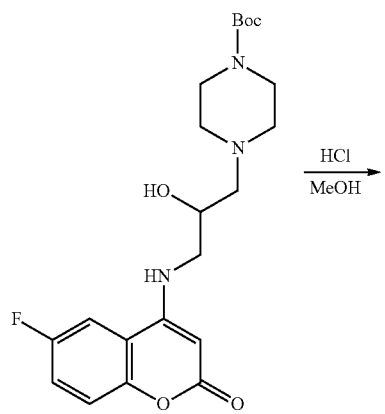

tert-butyl-4-{3-[(7-fluoro-2-oxo-2H-1-benzopyran-4-yl)amino]-2-hydroxy propyl}piperazine-1-carboxylate (4 g, 9.5 mmol) was dissolved in MeOH (30 mL), 1.25 M HCl in MeOH (4.5 mL) was added and the mixture was refluxed for 2 h. After cooling the white solid was filtered and dried to give 7-fluoro-4-{[2-hydroxy-3-(piperazin-1-yl)propyl] amino}-2H-1-benzopyran-2-one hydrochloride (3.4 g, Y=quant.) that was progressed without further purification. LC-MS (M−H+): 322.2

Step 6—Synthesis of 6-fluoro-4-({2-hydroxy-3-[4-(1,6-naphthyridin-5-yl)piperazin-1-yl] propyl}amino)-2H-1-benzopyran-2-one (compound 166)

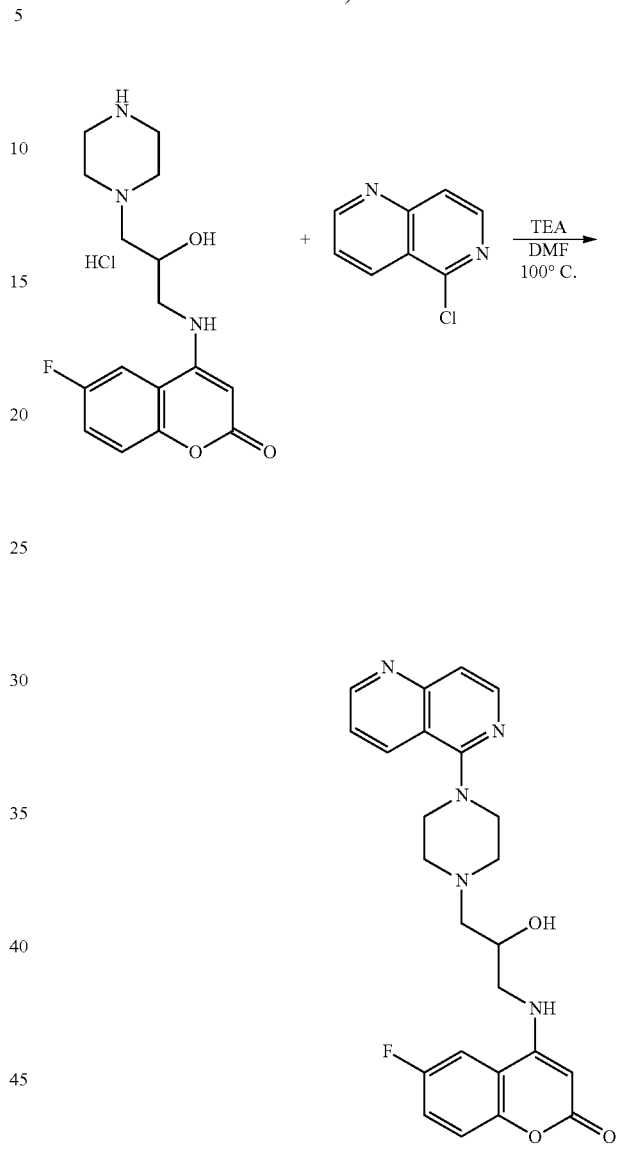

To a solution of 7-fluoro-4-{[2-hydroxy-3-(piperazin-1-yl)propyl]amino}-2H-1-benzopyran-2-one hydrochloride (261 mg, 0.73 mmol) and TEA (0.2 mL, 1.46 mmol) in DMF (3 mL) 5-chloro-1,6-naphthyridine (80 mg, 0.49 mmol) was added. The mixture was stirred at 100° C. for 18 h then was cooled, diluted with water and extracted with EtOAc. The organic layer was dried over sodium sulfate, concentrated under vacuum and the crude residue was purified by flash chromatography (silica gel, CHCl₃/MeOH 95/5) to obtain 95 mg (0.21 mmol, Y=29%) of the title compound. LC-MS (M−H+): 450.2.

¹H NMR (300 MHz, CHLOROFORM-d) δ=9.01 (dd, J=1.2, 4.3 Hz, 1H), 8.42-8.33 (m, 2H), 7.53 (d, J=5.9 Hz, 1H), 7.45 (dd, J=4.3, 8.4 Hz, 1H), 7.36-7.19 (m, 4H), 5.78 (t, J=4.3 Hz, 1H), 5.36 (s, 1H), 4.26-4.10 (m, 1H), 3.50 (s, 6H), 3.28-3.15 (m, 1H), 3.05-2.93 (m, 2H), 2.81-2.70 (m, 2H), 2.62 (d, J=6.8 Hz, 2H).

Preparation of Compound 171

Compound 171 was prepared as described herein below.

Step 1—Synthesis of 3-methoxypiperidin-4-amine dihydrochloride

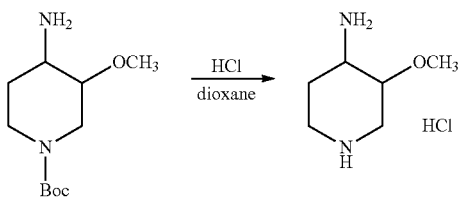 [SMILES: COC1CN(C(=O)OC(C)(C)C)CCC1N ; Cl ; COC1CNCCC1N ; Cl]

A solution of tert-butyl 4-amino-3-methoxypiperidine-1-carboxylate (900 mg, 3.9 mmol) in 1,4-dioxane (10 mL) was cooled to 0-5° C. 4M HCl in dioxane (9 mL) was added. After stirring 2 h at room temperature the reaction mixture was concentrated under reduced pressure. The resulting crude was triturated with petroleum ether (3×25 mL), filtered and dried under reduced pressure to afford 3-methoxypiperidin-4-amine dihydrochloride (700 mg, crude) as an off-white solid. LS-MS (ELSD) m/z: 131.2 (M+H).

Step 2—Synthesis of 1-(7-fluoroisoquinolin-1-yl)-3-methoxypiperidin-4-amine

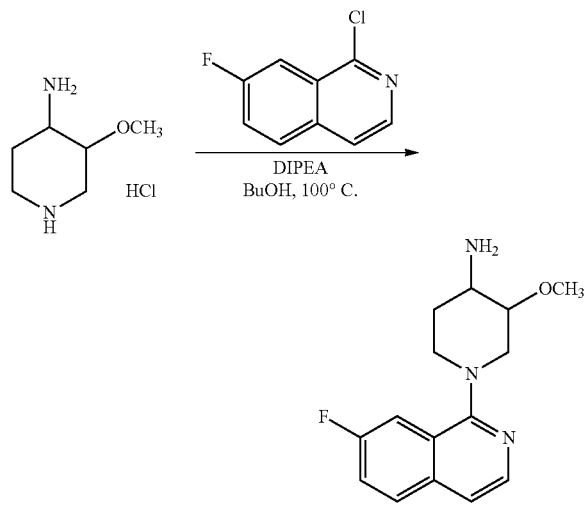

To a stirred solution of 3-methoxypiperidin-4-amine dihydrochloride (700 mg, 3.4 mmol) in 1-butanol (3 mL), DIPEA (1.07 g, 8.28 mmol) was added. After stirring 15 min at room temperature 1-chloro-7-fluoroisoquinoline (300 mg, 1.6 mmol) was added. The mixture was stirred at 100° C. for 48 h then was cooled and concentrated at under reduced pressure. The residue was diluted with water (25 mL) and extracted with EtOAc (3×50 mL). The combined organic layers were washed with brine (20 mL), dried over sodium sulfate and evaporated under vacuum. The resulting crude was purified by flash chromatography (silica gel, 8-10% MeOH in DCM) to afford 1-(7-fluoroisoquinolin-1-yl)-3-methoxypiperidin-4-amine (150 mg, 32.9%) as a pale yellow solid. LS-MS m/z: 276.1 (M+H).

Step 3—Synthesis of 2-({[1-(7-fluoroisoquinolin-1-yl)-3-methoxypiperidin-4-yl]amino}methyl)[1]benzopyrano[4,3-b]pyrrol-4(1H)-one (compound 171)

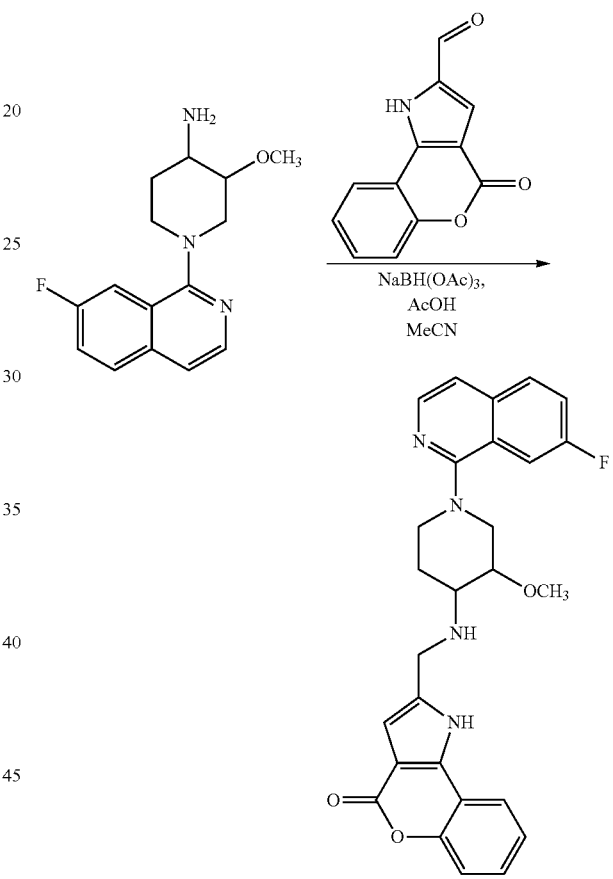

The title compound was prepared according to the procedure described for the synthesis of compound 145 using 1-(7-fluoroisoquinolin-1-yl)-3-methoxypiperidin-4-amine. A purification by flash chromatography (silica gel, 5% MeOH in DCM) followed by chiral SFC separation afforded 2-({[1-(7-fluoroisoquinolin-1-yl)-3-methoxypiperidin-4-yl]amino}methyl)[1]benzopyrano[4,3-b]pyrrol-4(1H)-one (unassigned stereo-isomer, Y=11%). LC-MS (M−H$^+$)=473.2.

$^1$H NMR (DMSO d6): δ ppm 12.60 (brs, 1H), 8.08 (d, J=5.6 Hz, 2H), 8.07-7.97 (m, 1H), 7.77-7.74 (m, 1H), 7.66-7.62 (m, 1H), 7.45-7.34 (m, 4H), 6.58 (s, 1H), 3.92-3.91 (m, 2H), 3.72-3.63 (m, 3H), 3.33-3.29 (m, 3H), 3.11-3.08 (m, 2H), 2.93-2.91 (m, 1H), 1.91-1.83 (m, 2H).

Preparation of Compound 172

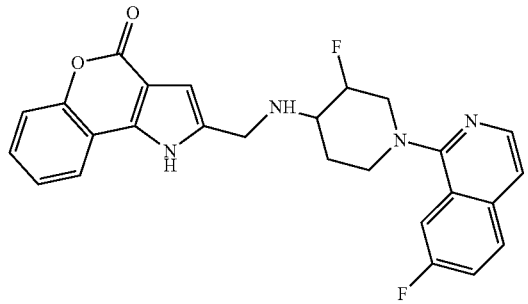 [SMILES: O=c1oc2ccccc2c2[nH]c(CNC3CCN(c4nccc5ccc(F)cc45)CC3F)cc12]

Compound 172 was prepared according to the procedure described for the synthesis of compound 171 using tert-butyl 4-amino-3-fluoropiperidine-1-carboxylate. A purification by flash chromatography (silica gel, 5% MeOH in DCM) followed by chiral SFC separation afforded 2-({[3-fluoro-1-(7-fluoroisoquinolin-1-yl)piperidin-4-yl]amino} methyl) [1]benzopyrano[4,3-b]pyrrol-4(1H)-one (unassigned stereoisomer, Y=7%). LS-MS m/z: 461.2 (M+1).

$^1$H NMR (400 MHz, DMSO-d6): δ ppm 12.56 (brs, 1H), 8.11-8.08 (m, 2H), 8.02-7.98 (m, 1H), 7.75 (d, J=10.4 Hz, 1H), 7.67-7.62 (m, 1H), 7.46-7.34 (m, 4H), 6.60 (s, 1H), 5.07-4.95 (m, 1H), 3.99-3.93 (m, 3H), 3.74-3.71 (m, 1H), 3.22-2.99 (m, 1H), 2.97-2.78 (m, 2H), 1.98-1.97 (m, 2H).

Preparation of Compound 177

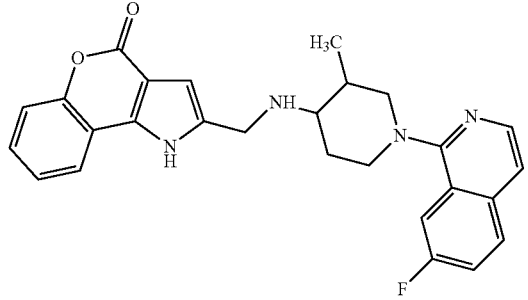 [SMILES: CC1CN(c2nccc3ccc(F)cc23)CCC1NCc1cc2c(=O)oc3ccccc3c2[nH]1]

2-({[1-(7-fluoroisoquinolin-1-yl)-3-methylpiperidin-4-yl]amino}methyl) [1]benzopyrano[4,3-b]pyrrol-4(1H)-one was prepared according to the procedure described for the synthesis of compound 171 using tert-butyl 4-amino-3-methylpiperidine-1-carboxylate. A purification by flash chromatography (silica gel, 0-6% MeOH in DCM) followed by chiral SFC separation afforded the title compound (unassigned stereoisomer, Y=7%). LS-MS m/z: 457.2 (M+H).

$^1$HNMR (DMSO d6): δ ppm 12.55 (brs, 1H), 8.09-8.06 (m, 2H), 8.01-7.97 (m, 1H), 7.67-7.62 (m, 2H), 7.45-7.35 (m, 4H), 6.59 (s, 1H), 4.01-3.98 (m, 1H), 3.90-3.86 (m, 1H), 3.72-3.69 (m, 1H), 3.62-3.59 (m, 1H), 2.89 (t, J=12 Hz, 1H), 2.68-2.60 (m, 1H), 2.33-2.15 (m, 2H), 1.86-1.80 (m, 1H), 1.65-1.60 (m, 1H), 1.01 (d, J=6.8 Hz, 3H).

Preparation of Compound 184

Compound 184 was prepared as described herein below.

Step 1—Synthesis of ethyl 4-amino-1-benzylpiperidine-3-carboxylate

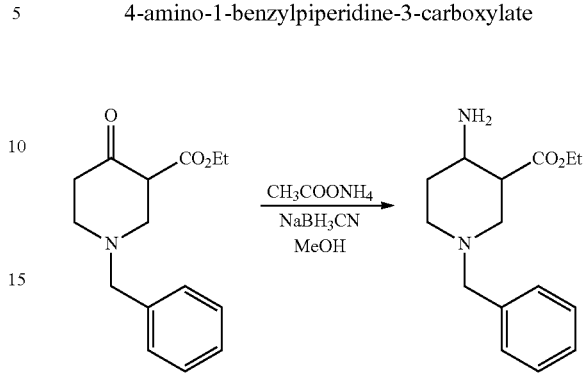

The title compound as syn/anti racemic mixture was prepared according to the procedure described for intermediate tert-butyl 4-amino-3-(benzyloxy)piperidine-1-carboxylate (see compound 186) using ethyl 1-benzyl-4-oxopiperidine-3-carboxylate (Y=65%). LS-MS m/z: 263.2 (M+H).

Step 2—Synthesis of ethyl 1-benzyl-4-[(tert-butoxycarbonyl)amino]piperidine-3-carboxylate

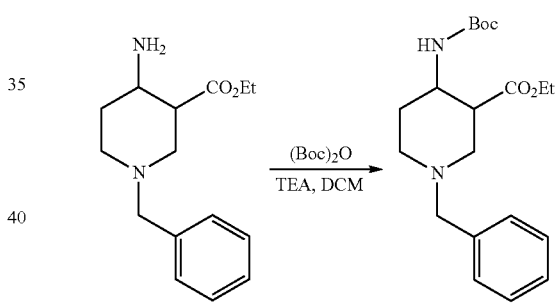

To a cool (0-5° C.) solution of ethyl 4-amino-1-benzylpiperidine-3-carboxylate (6 g, 22.87 mmol) in DCM (20 mL) TEA (9.5 mL, 68.61 mmol) and Boc anhydride (5.98 g, 27.4 mmol) were added slowly. After stirring for 4 h at room temperature the mixture was diluted with water (25 mL) and extracted with DCM (3×30 mL). The combined organic layers were washed with water (25 mL) and brine solution (25 mL), dried over sodium sulfate and concentrated under vacuum. The resulting crude was purified by flash chromatography (silica gel, 30-35% EtOAc in pet ether) to give the title compound as syn/anti racemic mixture (1.4 g). LS-MS m/z: 363.2 (M+H). $^1$H NMR (400 MHz, CDCl$_3$): δ ppm 7.31-7.28 (m, 5H), 5.32 (brs, 1H), 4.17-4.12 (m, 3H), 3.90-3.80 (m, 1H), 3.60-3.31 (m, 2H), 3.15-3.08 (m, 1H), 2.79-2.76 (m, 1H), 2.24-2.20 (m, 3H), 2.09-2.06 (m, 1H), 1.61-1.59 (m, 1H), 1.45 (s, 9H), 1.22-1.18 (m, 2H).

Step 3—Synthesis of ethyl 4-[(tert-butoxycarbonyl)amino]piperidine-3-carboxylate

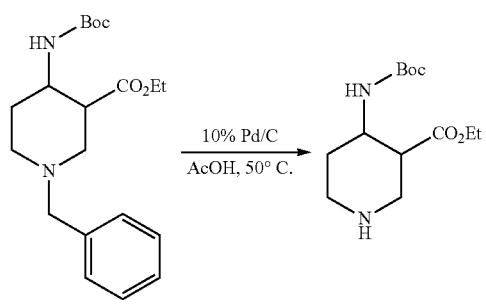 [SMILES: CCOC(=O)C1CN(Cc2ccccc2)CCC1NC(=O)OC(C)(C)C ; CCOC(=O)C1CNCCC1NC(=O)OC(C)(C)C]

To a stirred solution of ethyl 1-benzyl-4-[(tert-butoxycarbonyl)amino]piperidine-3-carboxylate (1.4 g, 3.86 mmol) in AcOH (30 mL) 10% Pd/C (140 mg, 50% wet) was added at room temperature under nitrogen atmosphere. The reaction mixture was hydrogenated at 50° C. for 24 h then was filtered on a celite bed and the filtrate was concentrated under reduced pressure to afford ethyl 4-[(tert-butoxycarbonyl)amino]piperidine-3-carboxylate (900 mg, 85% yield) as syn/anti racemic mixture. LS-MS (ELSD) m/z: 273.2 (M+H). $^1$H NMR (400 MHz, CDCl$_3$): δ ppm 5.56-5.45 (m, 1H), 4.33-4.12 (m, 2H), 3.90-3.78 (m, 1H), 3.45-3.33 (m, 1H), 3.15-3.01 (m, 1H), 2.86-2.68 (m, 3H), 1.88-1.76 (m, 3H), 1.45 (s, 9H), 1.32-1.23 (m, 3H).

Step 4—Synthesis of ethyl 4-[(tert-butoxycarbonyl)amino]-1-(7-fluoroisoquinolin-1-yl)piperidine-3-carboxylate

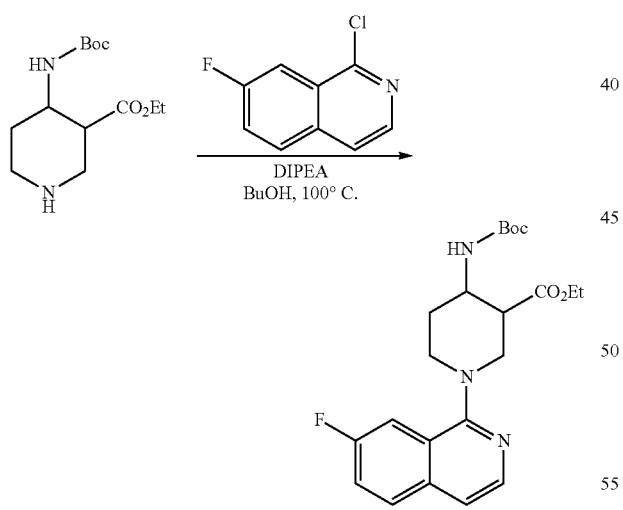

The title compound as syn/anti racemic mixture was prepared according to the procedure described for intermediate 1-(7-fluoroisoquinolin-1-yl)-3-methoxypiperidin-4-amine (see compound 171) using ethyl 4-[(tert-butoxycarbonyl)amino]piperidine-3-carboxylate (Y=24%). LS-MS m/z: 418.2 (M+H). $^1$HNMR (CDCl$_3$): δ ppm 8.18-8.16 (m, 1H), 7.91-7.88 (m, 1H), 7.87-7.85 (m, 1H), 7.52-7.44 (m, 1H), 7.35-7.30 (m, 1H), 5.67 (brs, 1H), 4.29-4.01 (m, 4H), 3.35-3.33 (m, 1H), 3.20-3.18 (m, 1H), 2.45-2.42 (m, 2H), 2.08-1.98 (m, 2H), 1.45 (s, 9H), 1.25-1.17 (m, 3H).

Step 5—Synthesis of ethyl 4-amino-1-(7-fluoroisoquinolin-1-yl)piperidine-3-carboxylate hydrochloride

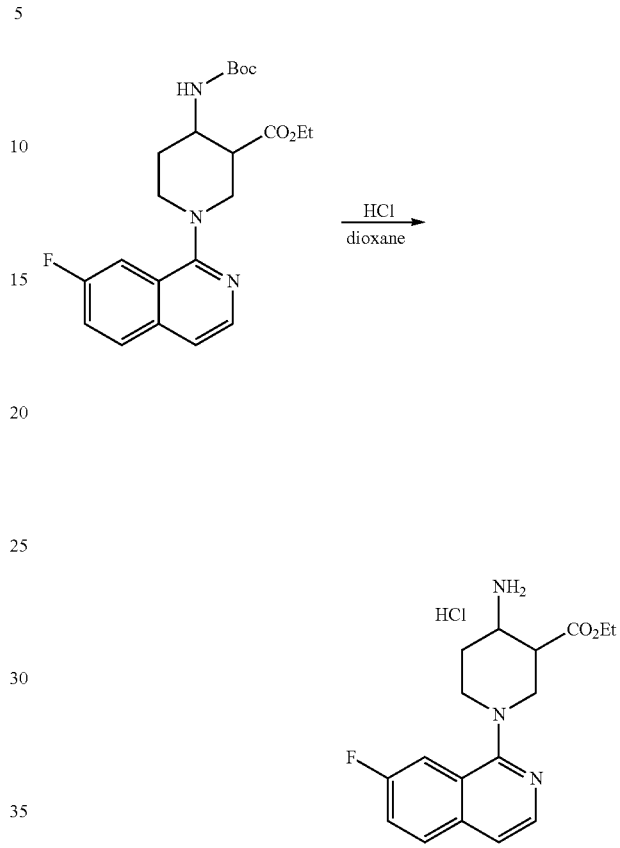

The title compound as syn/anti racemic mixture was prepared according to the procedure described for intermediate 3-methoxypiperidin-4-amine dihydrochloride (see compound 171) using ethyl 4-[(tert-butoxycarbonyl)amino]-1-(7-fluoroisoquinolin-1-yl)piperidine-3-carboxylate (Y=88%). LS-MS m/z: 318.1 (M+H).

Step 6—Synthesis of ethyl 1-(7-fluoroisoquinolin-1-yl)-4-{[(4-oxo-1,4-dihydro[1]benzopyrano[4,3-b]pyrrol-2-yl)methyl]amino}piperidine-3-carboxylate (compound 184)

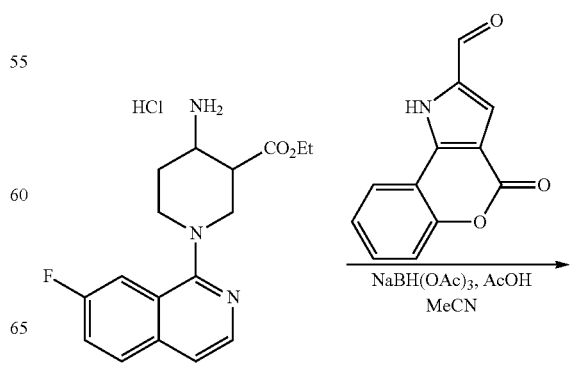

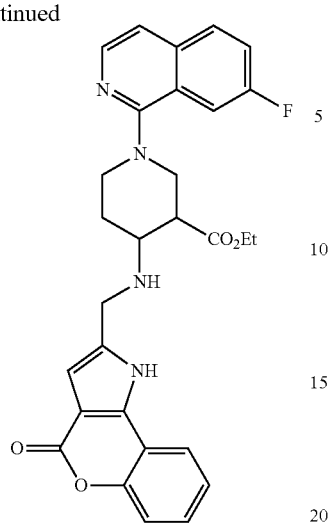

The title compound as syn/anti racemic mixture was prepared according to the procedure described for the synthesis of compound 145 using ethyl 4-amino-1-(7-fluoroisoquinolin-1-yl)piperidine-3-carboxylate hydrochloride (Y=9%). LS-MS m/z: 515.2 (M+H).

$^1$H NMR (400 MHz, DMSO-d6): δ ppm 12.48 (brs, 1H), 8.12 (d, J=5.6 Hz, 1H), 8.06 (d, J=7.6 Hz, 1H), 8.03-7.98 (m, 1H), 7.71-7.63 (m, 2H), 7.46-7.24 (m, 4H), 6.59 (s, 1H), 4.07-3.84 (m, 5H), 3.59-3.11 (m, 5H), 2.08-1.92 (m, 2H), 1.04-1.03 (m, 3H).

Preparation of Compound 186

Compound 186 was prepared as described herein below.

Step 1—Synthesis of tert-butyl 4-amino-3-(benzyloxy)piperidine-1-carboxylate

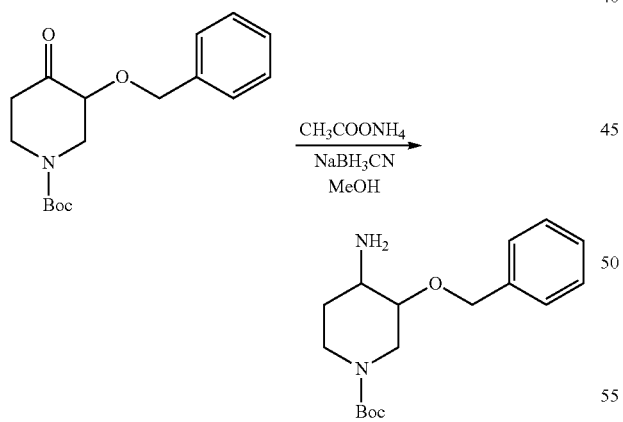

A solution of tert-butyl 3-(benzyloxy)-4-oxopiperidine-1-carboxylate (1.9 g, 6.2 mmol) and ammonium acetate (3.35 g, 43.5 mmol) in methanol (100 mL) was stirred 2 h at room temperature then was cooled to 10° C. Sodium cyanoborohydride (580 mg, 9.3 mmol) was added and the mixture was stirred at room temperature for 18 h. The reaction mixture was concentrated under vacuum, diluted with water (20 mL) and extracted with EtOAc (3×50 mL). The combined organic layers were washed with brine (40 mL), dried over sodium sulfate and concentrated in vacuum to afford crude tert-butyl 4-amino-3-(benzyloxy)piperidine-1-carboxylate (1.6 g) as a pale green gummy. This crude was progressed as such to the next step without further purification. LS-MS m/z: 307.1 (M+H).

Step 2—Synthesis of 3 3-(benzyloxy)piperidin-4-amine dihydrochloride

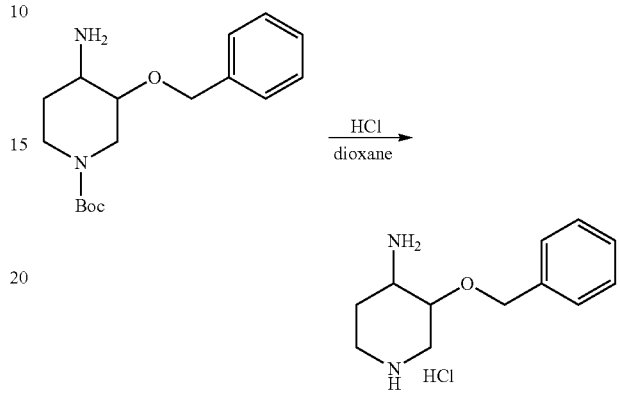

A stirred solution of tert-butyl 4-amino-3-(benzyloxy)piperidine-1-carboxylate (1.6 g, 5.2 mmol) in 1,4,Dioxane (5 mL) was cooled to 0-5° C. HCl (4 M in 1,4 dioxane, 16 mL) was added and the mixture was stirred at room temperature for 2 h. The solvent was removed under reduced pressure, the resulting crude was triturated with petroleum ether (3×25 mL) and filtered. The off-white solid was dried under reduced pressure to afford 3-(benzyloxy)piperidin-4-amine dihydrochloride (1.5 g, crude), which was progressed as such to next step without further purification. LS-MS m/z: 207.1 (M+H-2HCl).

Step 3—Synthesis of 3-(benzyloxy)-1-(7-fluoroisoquinolin-1-yl)piperidin-4-amine

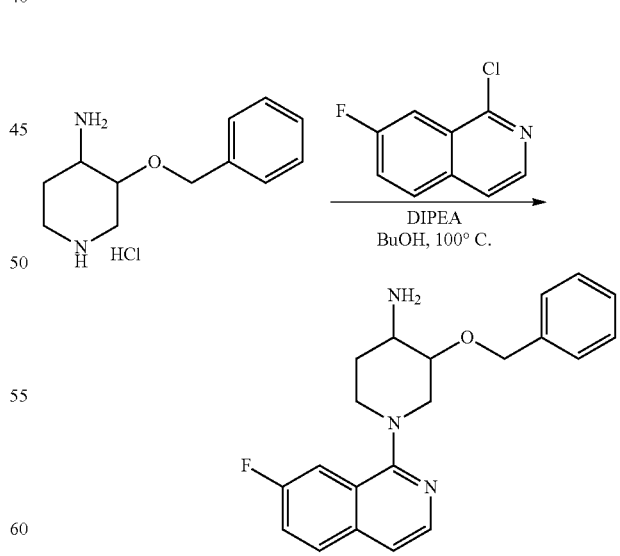

The title compound was prepared according to the procedure described for intermediate 1-(7-fluoroisoquinolin-1-yl)-3-methoxypiperidin-4-amine (see compound 171) using 3-(benzyloxy)piperidin-4-amine dihydrochloride (Y=35%). LS-MS m/z: 352.1 (M+H).

Step 4—Synthesis of 2-({[3-(benzyloxy)-1-(7-fluor-oisoquinolin-1-yl)piperidin-4-yl]amino}methyl)[1]benzopyrano[4,3-b]pyrrol-4(1H)-one

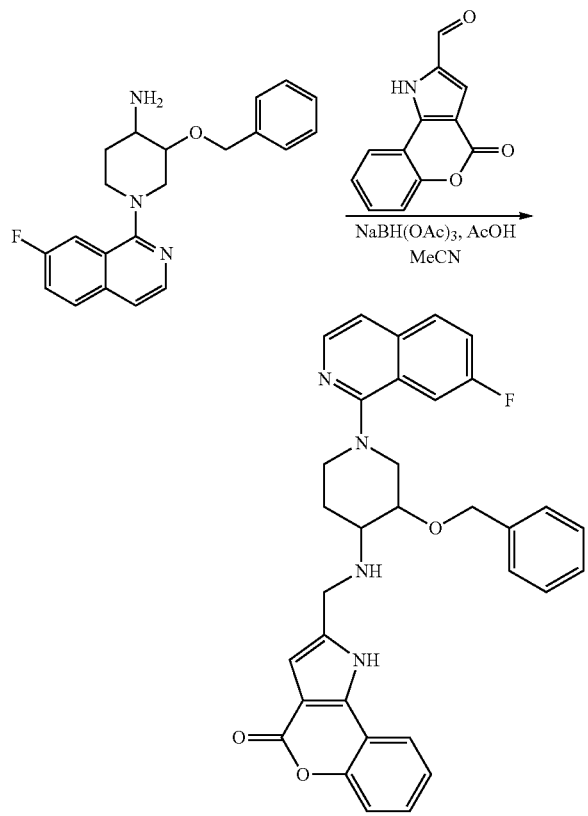

The title compound as a mixture of stereoisomers was prepared according to the procedure described for the synthesis of compound 145 using 3-(benzyloxy)-1-(7-fluoroisoquinolin-1-yl)piperidin-4-amine (Y=45%). LS-MS m/z 549.1 (M+H).

Step 5—Synthesis of 2-({[1-(7-fluoroisoquinolin-1-yl)-3-hydroxypiperidin-4-yl]amino}methyl)[1]benzopyrano[4,3-b]pyrrol-4(1H)-one (compound 186)

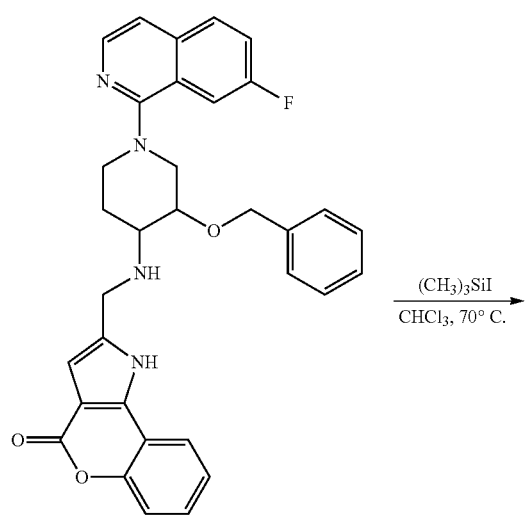

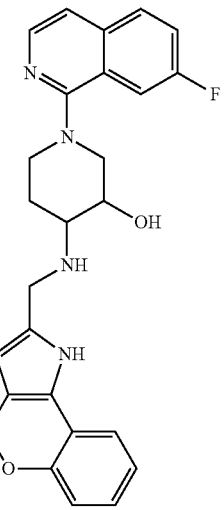

To a stirred solution of 2-({[3-(benzyloxy)-1-(7-fluoroisoquinolin-1-yl)piperidin-4-yl]amino}methyl)[1]benzopyrano[4,3-b]pyrrol-4(1H)-one (mixture of stereoisomers, 200 mg, 0.36 mmol) in chloroform (20 mL) trimethylsilyl iodide (0.729 g, 3.6 mmol) was added slowly at 0-5° C. in a shield tube. The mixture was stirred for 4 h at 70° C. then was diluted with a solution of sodium thiosulfate (30 mL) and filtered. The residue was washed with chloroform (3×15 mL) and petroleum ether (2×20 mL). A purification by flash chromatography (silica gel, 8-10% MeOH in DCM) followed by preparative HPLC separation afforded 2-({[1-(7-fluoroisoquinolin-1-yl)-3-hydroxypiperidin-4-yl]amino}methyl)[1]benzopyrano[4,3-b]pyrrol-4(1H)-one (unassigned stereoisomer, 18 mg, 11% yield) as an off-white solid. LS-MS m/z: 459.2 (M+H).

$^1$H NMR (400 MHz, DMSO d6): δ ppm 12.35 (brs, 1H), 8.09-7.95 (m, 4H), 7.65-7.60 (m, 1H), 7.44-7.35 (m, 4H), 6.57 (s, 1H), 5.03-5.02 (m, 1H), 3.99-3.93 (m, 1H), 3.91-3.72 (m, 2H), 3.69-3.33 (m, 2H), 3.05-3.01 (m, 2H), 2.76-2.67 (m, 1H), 1.89-1.77 (m, 2H).

Preparation of Compound 187

Compound 187 was prepared as described herein below.

Step 1—Synthesis of tert-butyl [1-(1,6-naphthyridin-5-yl)piperidin-4-yl]carbamate

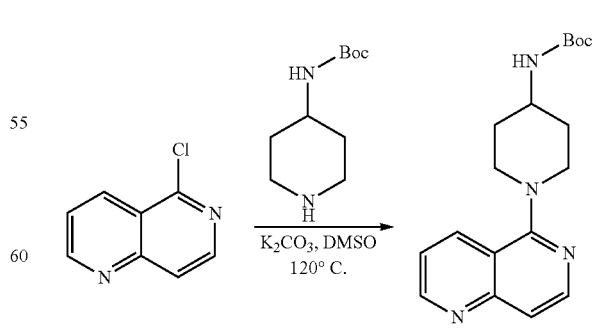

Intermediate tert-butyl [1-(1,6-naphthyridin-5-yl)piperidin-4-yl]carbamate was prepared according to the procedure described for the synthesis of tert-butyl 1-(7-fluoroisoquinolin-1-yl)piperidin-4-yl]carbamate (see compound 145) using 5-chloro-1,6-naphthyridine. Y=82%. LC-MS (M–H⁺)= 329.3

Step 2—Synthesis of 1-(1,6-naphthyridin-5-yl)piperidin-4-amine

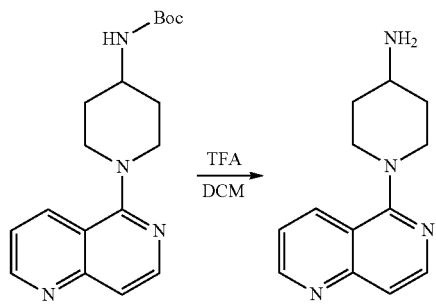 [SMILES: CC(C)(C)OC(=O)NC1CCN(c2nccc3ncccc23)CC1 ; NC1CCN(c2nccc3ncccc23)CC1]

Intermediate 1-(1,6-naphthyridin-5-yl)piperidin-4-amine was prepared according to the procedure described for the synthesis of 1-(7-fluoroisoquinolin-1-yl)piperidin-4-amine (see compound 145) using tert-butyl [1-(1,6-naphthyridin-5-yl)piperidin-4-yl]carbamate. Y=98%. The compound was used without any characterization.

Step 3—Synthesis of 4-chloro-6-fluoro-2-oxo-2H-1-benzopyran-3-carbaldehyde

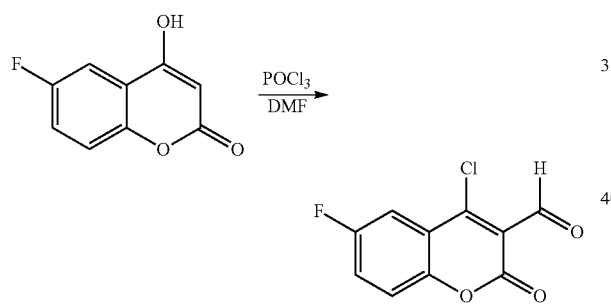

To a stirred volume (25 mL) of DMF, POCl₃ (25 mL) was added in one portion at 0° C. The resulting solution was heated at 50° C. for 0.5 h then a solution of 6-Fluoro-4-hydroxycoumarin (5 g, 27.7 mmol) in DMF (50 mL) was added. The mixture was stirred at 60° C. for 3 h then was poured into ice. After stirring 20 min DCM (50 mL) was added and the organic phase was separated, dried over Na₂SO₄ and concentrated in vacuum to obtain 6.2 g of 4-chloro-6-fluoro-2-oxo-2H-1-benzopyran-3-carbaldehyde, which was used in the next step without further purification.

Step 4—Synthesis of ethyl 8-fluoro-4-oxo-1,4-dihydro[1]benzopyrano [4,3-b]pyrrole-2-carboxylate

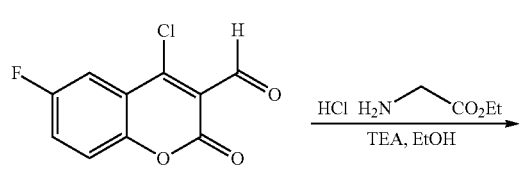

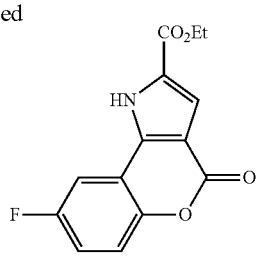

The intermediate ethyl 8-fluoro-4-oxo-1,4-dihydro[1]benzopyrano[4,3-b]pyrrole-2-carboxylate was prepared according to the procedure described for the synthesis of 4-oxo-1,4-dihydro[1]benzopyrano[4,3-b]pyrrole-2-carboxylate (see compound 145) using 4-chloro-6-fluoro-2-oxo-2H-1-benzopyran-3-carbaldehyde (Y=50%). LC-MS (M–H⁺)=276.1

Step 5—Synthesis of 8-fluoro-2-(hydroxymethyl)[1]benzopyrano[4,3-b]pyrrol-4(1H)-one

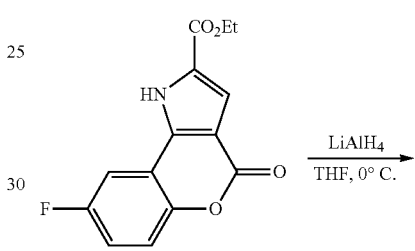

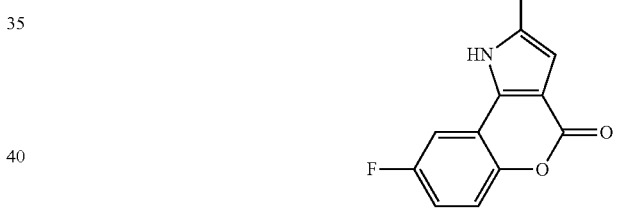

The intermediate 8-fluoro-2-(hydroxymethyl)[1]benzopyrano[4,3-b] pyrrol-4(1H)-one was prepared according to the procedure described for the synthesis of 2-(hydroxymethyl)[1]benzopyrano[4,3-b]pyrrol-4(1H)-one (see compound 145) using 8-fluoro-4-oxo-1,4-dihydro[1]benzopyrano[4,3-b]pyrrole-2-carboxylate. The compound was used in the next step without further characterization. LC-MS (M–H⁺)=234.2

Step 6—Synthesis of 8-fluoro-4-oxo-1,4-dihydro[1]benzopyrano[4,3-b]pyrrole-2-carbaldehyde

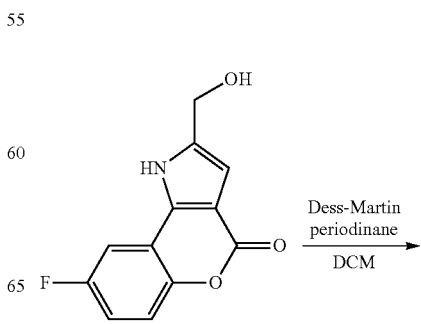

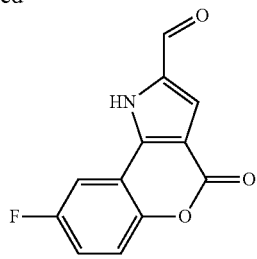

The intermediate 8-fluoro-4-oxo-1,4-dihydro[1]benzopyrano[4,3-b]pyrrole-2-carbaldehyde was prepared according to the procedure described for the synthesis of 4-oxo-1,4-dihydro[1]benzopyrano[4,3-b]pyrrole-2-carbaldehyde (see compound 145) using 8-fluoro-2-(hydroxymethyl)[1]benzopyrano[4,3-b]pyrrol-4(1H)-one. The compound was used in the next step without further characterization. LC-MS (M−H$^+$)=232.2

Step 7—Synthesis of 8-fluoro-2-({[1-(1,6-naphthyridin-5-yl)piperidin-4-yl]amino}methyl)[1]benzopyrano[3,4-b]pyrrol-4(3H)-one (compound 187)

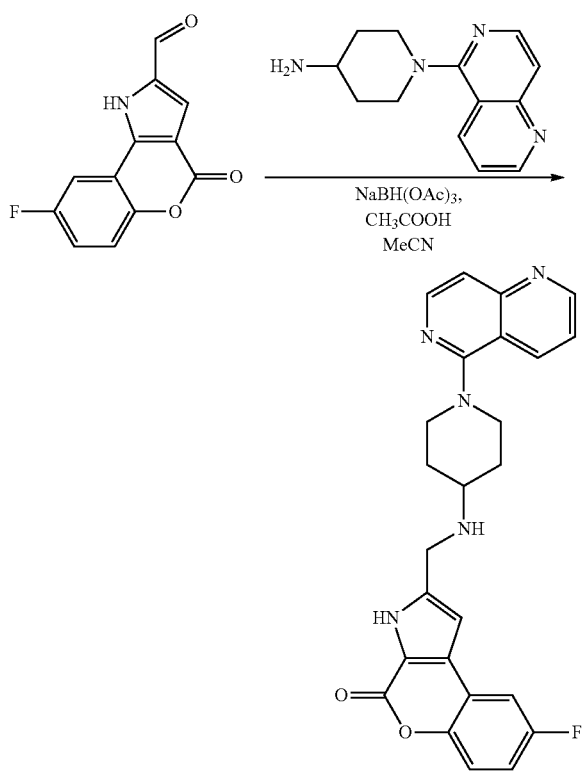

The title compound was prepared according to the procedure described for the synthesis of compound 145 using 8-fluoro-4-oxo-1,4-dihydro[1]benzopyrano[4,3-b]pyrrole-2-carbaldehyde and 1-(1,6-naphthyridin-5-yl)piperidin-4-amine (Y=41%). LC-MS (M−H$^+$)=444.3.

$^1$H NMR (500 MHz, DMSO-d6) δ ppm 1.55-1.69 (m, 2H), 2.03 (d, J=10.15 Hz, 2H), 2.67-2.76 (m, 1H), 3.01 (t, J=11.12 Hz, 2H), 3.77 (d, J=12.90 Hz, 2H), 3.91 (s, 2H), 6.59 (s, 1H), 7.29 (td, J=8.65, 3.02 Hz, 1H), 7.37 (d, J=6.04 Hz, 1H), 7.47 (dd, J=9.06, 4.67 Hz, 1H), 7.57 (dd, J=8.37, 4.25 Hz, 1 H), 7.95 (dd, J=9.06, 3.02 Hz, 1H), 8.26 (d, J=5.76 Hz, 1H), 8.39 (d, J=7.96 Hz, 1H), 8.99 (dd, J=4.39, 1.65 Hz, 1H), 11.96-13.07 (m, 1H).

Preparation of Compound 188

Compound 188 was prepared as described herein below.

Steps 1-2—Synthesis of 1-(6-methoxy-1,5-naphthyridin-4-yl)piperidin-4-amine

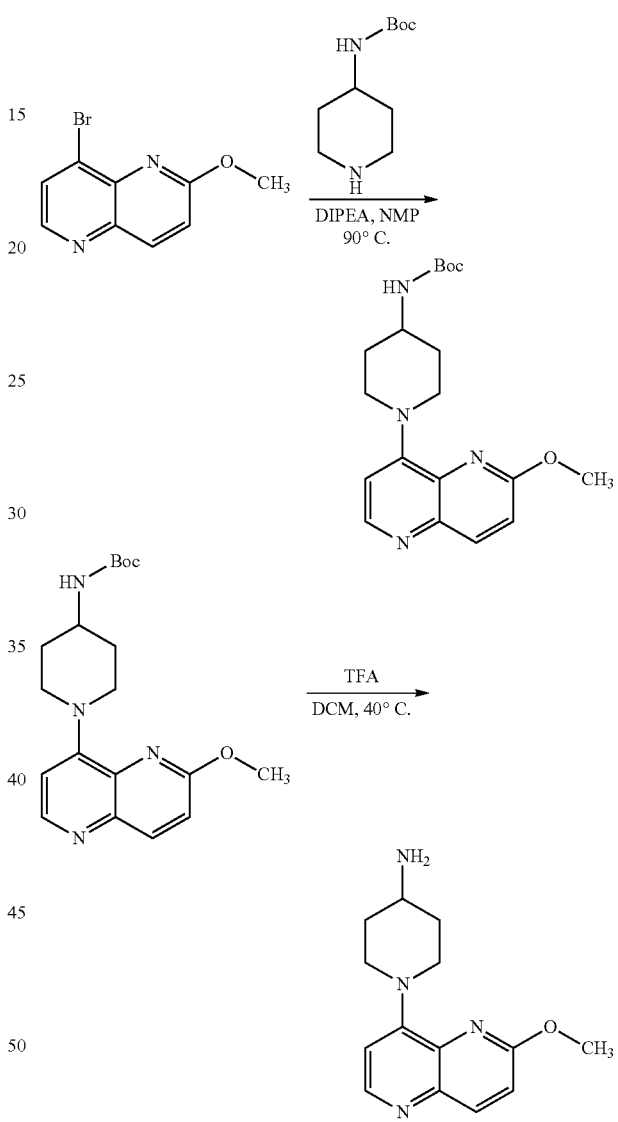

A mixture of 8-Bromo-2-methoxy-1,5-naphthyridine (250 mg, 1 mmol), 4-(N-Boc-amino)piperidine (600 mg, 3 mmol) and DIPEA (44 µL, 0.25 mmol) in NMP (4 mL) was stirred at 90° C. overnight. DCM (20 mL) was added and the mixture was washed with sat. NaHCO$_3$. The solvent was removed in vacuum and the crude material was purified by Si-column eluting with Cy to ethyl acetate 100%. The product was dissolved in DCM (20 mL), TFA was added (4 mL) and the mixture was stirred at 40° C. for 1 h. The solvent was evaporated in vacuum and the residue was purified by SCX column to obtain 265 mg of 1-(6-methoxy-1,5-naphthyridin-4-yl)piperidin-4-amine. LC-MS (M−H+)= 259.2

Step 3—Synthesis of 8-fluoro-2-({[1-(6-methoxy-1,5-naphthyridin-4-yl)piperidin-4-yl]amino}methyl)[1]benzopyrano[3,4-b]pyrrol-4(3H)-one (compound 188)

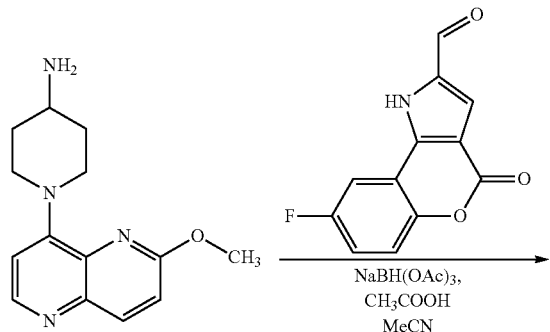

The title compound was prepared according to the procedure described for the synthesis of compound 187 using 1-(6-methoxy-1,5-naphthyridin-4-yl)piperidin-4-amine (Y=23%). LC-MS (M−H+)=474.3.

$^1$H NMR (500 MHz, DMSO-d6) δ ppm 1.48-1.65 (m, 2H), 2.04 (d, J=10.15 Hz, 2H), 2.66-2.79 (m, 1H), 3.00 (t, J=10.84 Hz, 2H), 3.91 (s, 2H), 3.97 (s, 3H), 4.26 (d, J=12.35 Hz, 2H), 6.59 (s, 1H), 6.93 (d, J=5.49 Hz, 1H), 7.16 (d, J=9.06 Hz, 1H), 7.29 (td, J=8.65, 3.02 Hz, 1H), 7.47 (dd, J=9.06, 4.67 Hz, 1H), 7.95 (dd, J=9.06, 3.02 Hz, 1H), 8.13 (d, J=8.78 Hz, 1H), 8.43 (d, J=5.21 Hz, 1H), 11.53-13.13 (m, 1H).

Preparation of Compound 192

Compound 192 was prepared as described herein below.

Steps 1-2—Synthesis of 1-(3-fluoro-6-methoxy-1,5-naphthyridin-4-yl)piperidin-4-amine

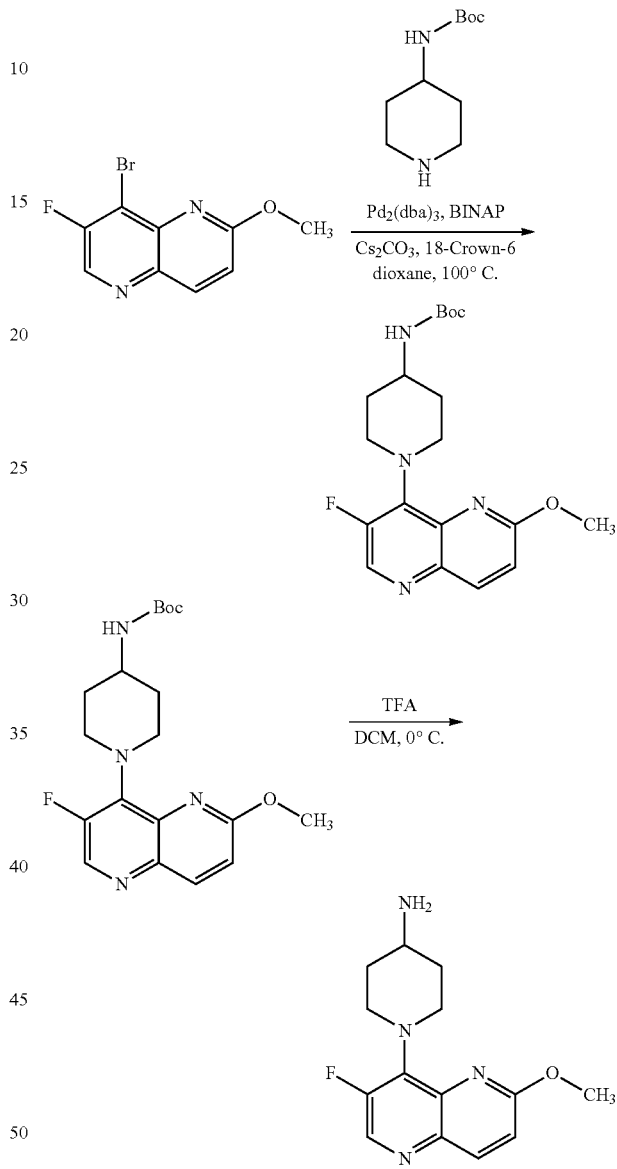

In a vial, 8-bromo-7-fluoro-2-methoxy-1,5-naphthyridine (250 mg, 0.97 mmol), tert-butyl N-(piperidin-4-yl)carbamate (194 mg, 0.97 mmol), tris(dibenzylideneacetone)dipalladium(0) (53 mg, 0.06 mmol), rac-BINAP (37 mg, 0.06 mmol), Cs$_2$CO$_3$ (664 mg, 2.04 mmol) and 18-Crown-6 (26 mg, 0.097 mmol) in dioxane (10 mL) were combined and flushed with N$_2$. The vial was heated to 100° C. while stirring rapidly. After 12 h the solution was filtered, concentrated and the residue was purified via flash chromatography (silica gel, 1% MeOH in DCM) yielding tert-butyl [1-(3-fluoro-6-methoxy-1,5-naphthyridin-4-yl)piperidin-4-yl]carbamate (309 mg, 0.82 mmol, 82% yield) as an orange solid, that was used without further characterization. The compound was dissolved in DCM (20 mL) and cooled to 0° C. TFA (3 mL) was added and the mixture was stirred for 1 h. The solvent was removed and the residue was dissolved in dichloromethane/MeOH and loaded onto an SCX cartridge which was eluted with MeOH and then a 2M solution of ammonia in MeOH. The basic fractions were evaporated to give 1-(3-fluoro-6-methoxy-1,5-naphthyridin-4-yl)piperidin-4-amine (180 mg, 0.66 mmol, 80% yield. LC-MS (M–H+)=277.3

Step 3—Synthesis of 8-fluoro-2-({[1-(3-fluoro-6-methoxy-1,5-naphthyridin-4-yl)piperidin-4-yl]amino}methyl)[1]benzopyrano[3,4-b]pyrrol-4(3H)-one (compound 192)

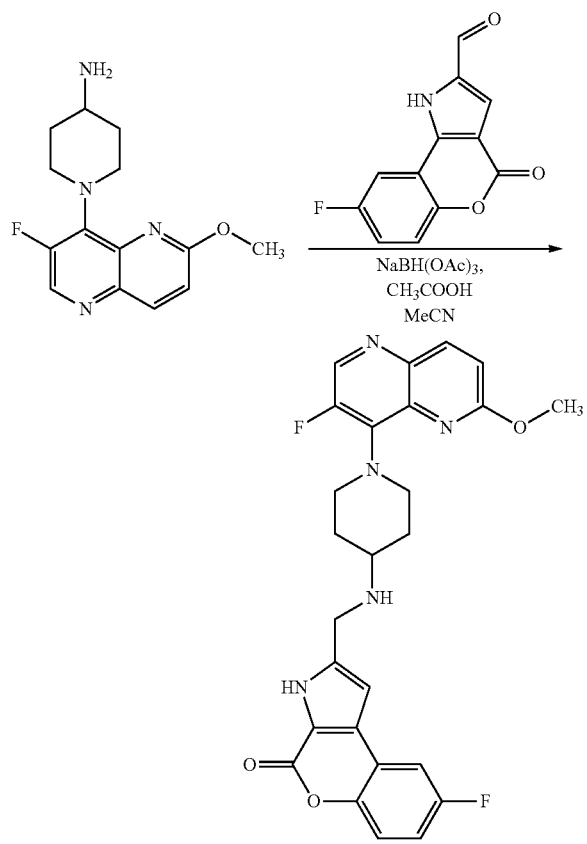

The title compound was prepared according to the procedure described for the synthesis of compound 187 using 1-(3-fluoro-6-methoxy-1,5-naphthyridin-4-yl)piperidin-4-amine (Y=16%). LC-MS (M–H+)=492.1.

$^1$H NMR (400 MHz, METHANOL-d4) δ ppm 1.68-1.82 (m, 2H), 2.12 (d, J=9.29 Hz, 2H), 2.81-2.92 (m, 1H), 3.37 (t, J=12.42 Hz, 2H), 4.02 (s, 2H), 4.04-4.08 (m, 3H), 4.15 (d, J=11.80 Hz, 2H), 6.73 (s, 1H), 7.10 (d, J=9.03 Hz, 1H), 7.22 (td, J=8.72, 2.89 Hz, 1H), 7.44 (dd, J=8.70, 4.52 Hz, 1H), 7.65 (dd, J=8.70, 2.90 Hz, 1H), 8.08 (d, J=9.04 Hz, 1H), 8.42 (d, J=4.77 Hz, 1H).

Preparation of Compound 195

Compound 195 was prepared as described herein below.

Step 1—Synthesis of diethyl {[(6-methoxypyridin-3-yl)amino]methylidene}propanedioate

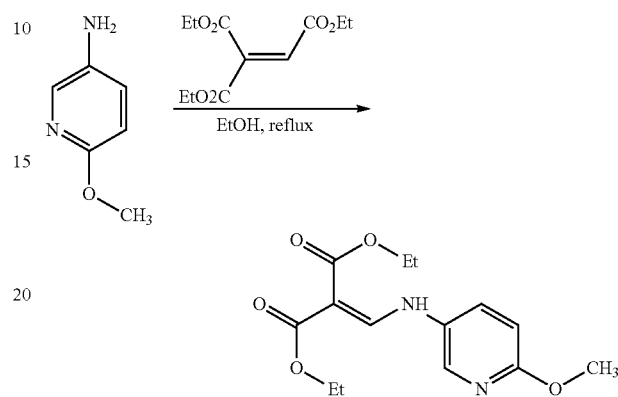

A solution of 6-methoxypyridin-3-amine (5 g, 40.3 mmol) and triethyl ethene-1,1,2-tricarboxylate (8.13 mL, 40.3 mmol) in EtOH (50 mL) was refluxed for 3 h. After cooling the mixture was concentrated under vacuum to give diethyl {[(6-methoxypyridin-3-yl)amino]methylidene}propanedioate as a dark red oil (12 g, quant.), which was used without further purification. LC-MS (M–H$^+$)=295.3

Step 2—Synthesis of ethyl 6-methoxy-4-oxo-1,4-dihydro-1,5-naphthyridine-3-carboxylate

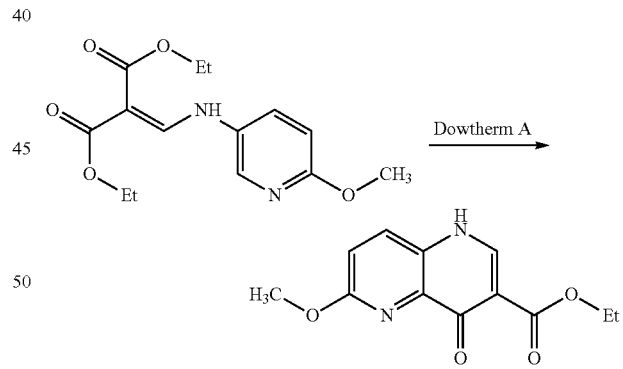

Dowtherm® A (10 mL) was brought to boiling (250° C.) in a 50 mL 3-necked flask fitted with a still-head and a reflux condenser. Diethyl {[(6-methoxypyridin-3-yl)amino]methylidene}propanedioate (2.1 g, 7.2 mmol) was added portion-wise. The mixture was boiled for 15' then it was cooled to room temperature, diluted with Cy (15 mL) and cooled at −20° C. overnight. The brown precipitate was filtered and washed with Cy to obtain a brown solid that was triturated with EtOAc. The suspension was filtered to give ethyl 6-methoxy-4-oxo-1,4-dihydro-1,5-naphthyridine-3-carboxylate as a grey solid (1.04 g, 4.2 mmol, 58% yield). LC-MS (M–H$^+$)=249.2

Step 3—Synthesis of ethyl 4-bromo-6-methoxy-1,5-naphthyridine-3-carboxylate

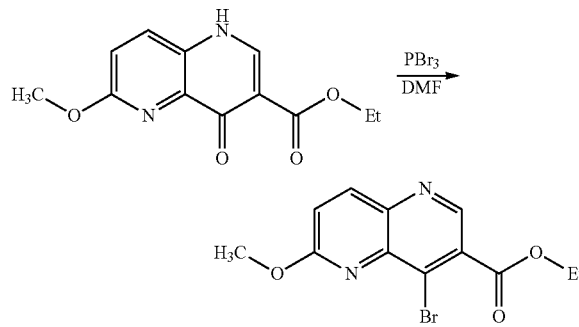

A suspension of ethyl 6-methoxy-4-oxo-1,4-dihydro-1,5-naphthyridine-3-carboxylate (6.3 g, 25.4 mmol) in DMF (20 mL) was stirred under $N_2$ at room temperature. Phosphorus tribromide (2.5 mL, 26.7 mmol) was added drop-wise and the reaction mixture was stirred for additional 30'. The mixture was put in an ice-bath and water (120 mL) was added, followed by sat. $Na_2CO_3$ to pH 7. The solid was filtered under vacuum, washed with water and dried under vacuum. The crude product was purified by NH cartridge (eluent from Cy 100% to Cy/EtOAc 95/5%) to obtain ethyl 4-bromo-6-methoxy-1,5-naphthyridine-3-carboxylate (6.6 g, 21 mmol, 83% yield). LC-MS (M−H$^+$)=311.1

Step 4—Synthesis of 4-bromo-6-methoxy-1,5-naphthyridine-3-carboxylic acid

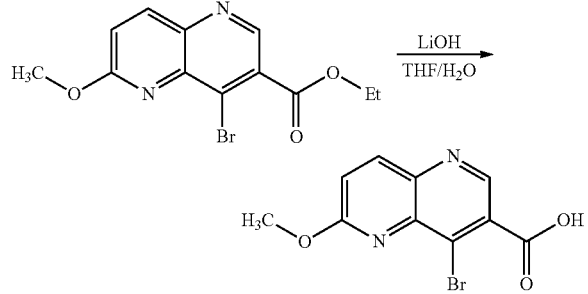

A solution of ethyl 4-bromo-6-methoxy-1,5-naphthyridine-3-carboxylate (500 mg, 1.6 mmol) in THF (4.5 mL) and water (1.5 mL) was treated with LiOH.H2O (201 mg, 4.8 mmol). The mixture was stirred at room temperature for 4 h then was concentrated. The residue was dissolved in water (5 mL) and adjusted to pH 4 with 1N HCl to provide a precipitate, which was filtered and washed with cold water to obtain 4-bromo-6-methoxy-1,5-naphthyridine-3-carboxylic acid (409 mg, 1.45 mmol, 90% yield) as a white solid. LC-MS (M−H$^+$)=283.1

Step 5—Synthesis of 4-chloro-6-methoxy-1,5-naphthyridine-3-carboxamide

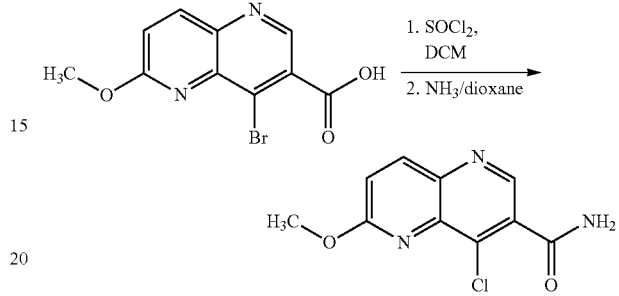

To a solution of 4-bromo-6-methoxy-1,5-naphthyridine-3-carboxylic acid (350 mg, 1.24 mmol) in dry DCM (5 mL), $SOCl_2$ (136 µl, 1.86 mmol) was added and the reaction mixture was stirred for 3 h at room temperature. The mixture was concentrated and the residue was dissolved in 0.5 M ammonia solution in dioxane (7.4 mL, 3.7 mmol). The reaction mixture was stirred for 1 h then was concentrated and the crude 4-chloro-6-methoxy-1,5-naphthyridine-3-carboxamide (0.6 g) was progressed to the next step without further purification. LC-MS (M−H$^+$)=238.2

Step 6—Synthesis of 4-chloro-6-methoxy-1,5-naphthyridine-3-carbonitrile

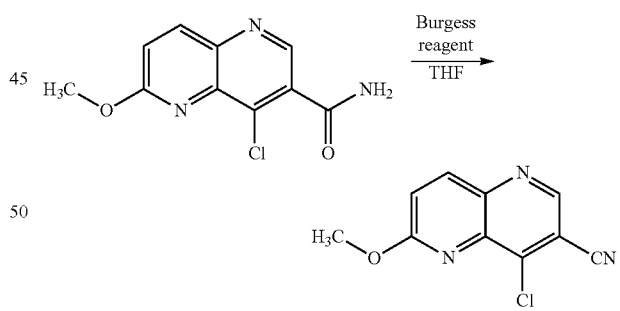

To a suspension of 4-chloro-6-methoxy-1,5-naphthyridine-3-carboxamide (crude 0.6 g, 2.5 mmol) in THF (15 mL), Burgess reagent (1.2 g, 5.0 mmol) was added and the mixture was stirred at room temperature for 1 h. The solvent was removed under vacuum and the residue was purified by chromatography column SNAP-25 eluting with DCM to give 190 mg (0.87 mmol, 35% yield) of 4-chloro-6-methoxy-1,5-naphthyridine-3-carbonitrile. LC-MS (M−H$^+$)= 220.2

Step 7—Synthesis of tert-butyl [1-(3-cyano-6-methoxy-1,5-naphthyridin-4-yl)piperidin-4-yl]carbamate

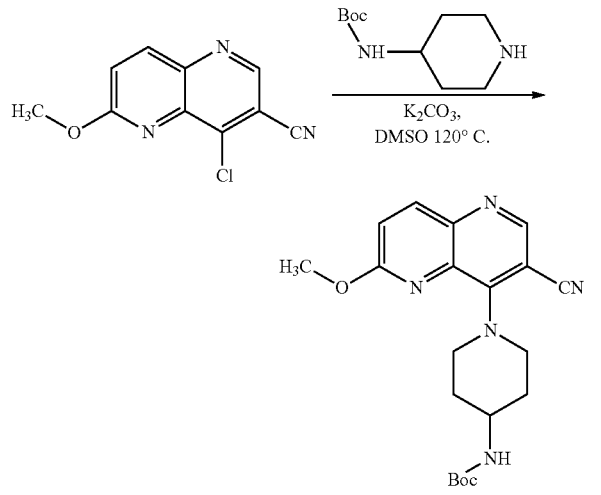

The title intermediate was prepared according to the procedure described for the synthesis of tert-butyl [1-(7-fluoroisoquinolin-1-yl)piperidin-4-yl]carbamate (see compound 145) using 4-chloro-6-methoxy-1,5-naphthyridine-3-carbonitrile. Y=92%. LC-MS (M–H+)=384.4

Step 8—Synthesis of 4-(4-aminopiperidin-1-yl)-6-methoxy-1,5-naphthyridine-3-carbonitrile

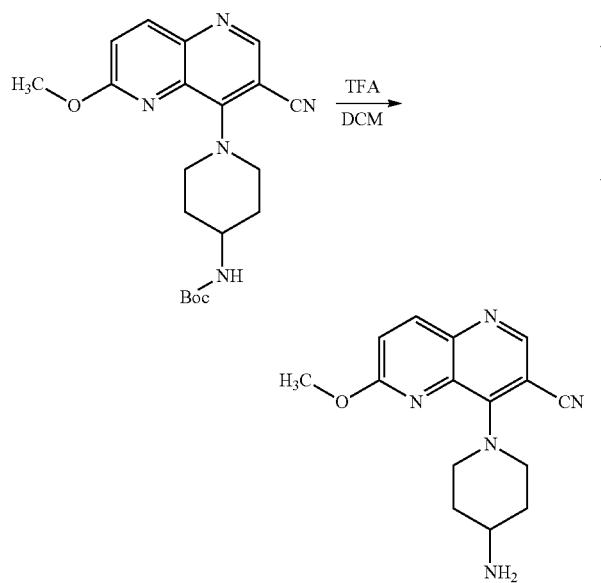

The title compound was prepared according to the procedure described for the synthesis of 1-(7-fluoroisoquinolin-1-yl)piperidin-4-amine (see compound 145) using tert-butyl [1-(3-cyano-6-methoxy-1,5-naphthyridin-4-yl)piperidin-4-yl]carbamate. Y=88%. LC-MS (M–H+)=284.3

Step 9—Synthesis of 4-(4-{[(8-fluoro-4-oxo-3,4-dihydro[1]benzopyrano[3,4-b]pyrrol-2-yl)methyl]amino}piperidin-1-yl)-6-methoxy-1,5-naphthyridine-3-carbonitrile (compound 195)

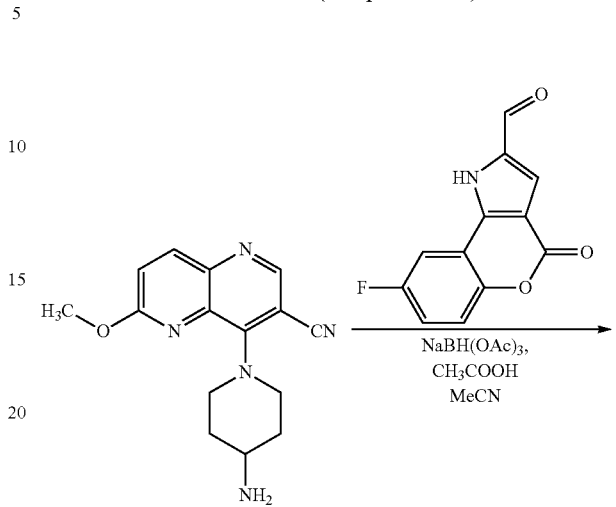

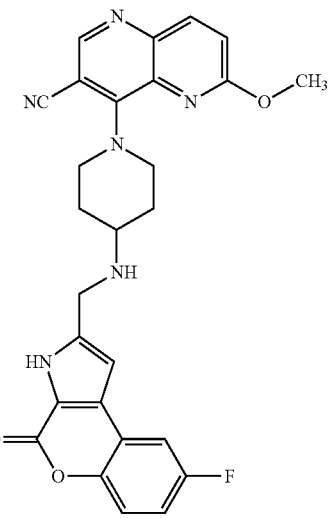

The title compound was prepared according to the procedure described for the synthesis of compound 187 using 4-(4-aminopiperidin-1-yl)-6-methoxy-1,5-naphthyridine-3-carbonitrile (Y=35%). LC-MS (M–H+)=499.4.

$^1$H NMR (400 MHz, DMSO-d6) δ ppm 1.54-1.72 (m, 2H), 2.02-2.14 (m, 2H), 2.63 (br. s., 1H), 2.75-2.87 (m, 1H), 3.52 (t, J=11.07 Hz, 2H), 3.92 (s, 2H), 3.96 (s, 3H), 4.32 (d, J=11.10 Hz, 2H), 6.60 (s, 1H), 7.22-7.35 (m, 2H), 7.47 (dd, J=9.15, 4.66 Hz, 1H), 7.95 (dd, J=9.10, 2.96 Hz, 1H), 8.17 (d, J=8.99 Hz, 1H), 8.57 (s, 1H), 12.50 (br. s., 1H).

Preparation of Compound 196
Compound 196 was prepared as described herein below.

Step 1—Synthesis of 5-chloropyrido[3,4-b]pyrazine

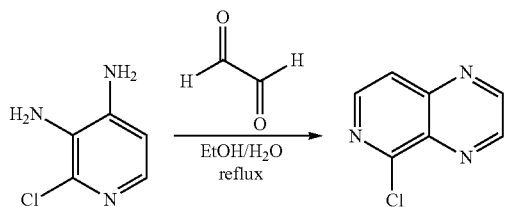

A mixture of 2-chloropyridine-3,4-diamine (1 g, 6.96 mmol) and ethanedial solution (40% wt in water, 3.2 mL, 27.84 mmol) in ethanol (20 mL) was refluxed for 2 hours then was cooled to room temperature. The precipitate was filtered, washed with EtOH and dried in vacuum to give 5-chloropyrido[3,4-b]pyrazine (0.3 g, 1.8 mmol, 26% yield), that was progressed without further purification. LC-MS (M−H+)=166.1

Step 2—Synthesis of tert-butyl [1-(pyrido[3,4-b]pyrazin-5-yl)piperidin-4-yl]carbamate

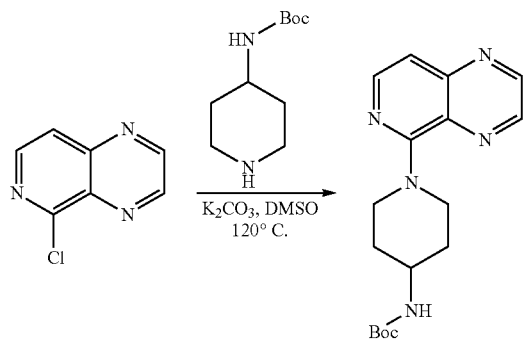

The title intermediate was prepared according to the procedure described for the synthesis of tert-butyl [1-(7-fluoroisoquinolin-1-yl)piperidin-4-yl]carbamate (see compound 145) using 5-chloropyrido[3,4-b]pyrazine. Y=69%. LC-MS (M−H+)=330.4

Step 3—Synthesis of 1-(pyrido[3,4-b]pyrazin-5-yl)piperidin-4-amine

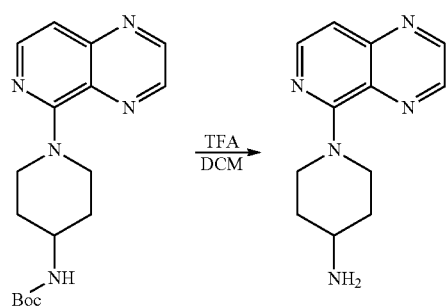

The title compound was prepared according to the procedure described for the synthesis of 1-(7-fluoroisoquinolin-1-yl)piperidin-4-amine (see compound 145) using tert-butyl [1-(pyrido[3,4-b]pyrazin-5-yl)piperidin-4-yl]carbamate. Y=98%. LC-MS (M−H+)=230.3

Step 4—Synthesis of 8-fluoro-2-({[1-(pyrido[3,4-b]pyrazin-5-yl)piperidin-4-yl]amino}methyl)[1]benzopyrano[3,4-b]pyrrol-4(3H)-one (formate salt, compound 196)

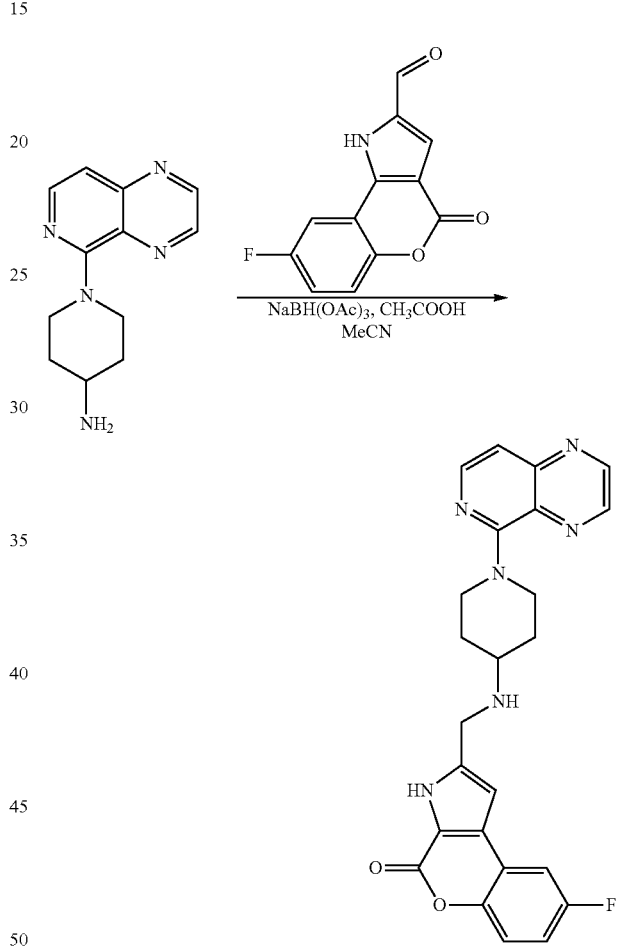

The title compound was prepared according to the procedure described for the synthesis of compound 187 using 1-(pyrido[3,4-b]pyrazin-5-yl)piperidin-4-amine (Y=37%). LC-MS (M−H+)=445.4.

$^1$H NMR (400 MHz, DMSO-d6) δ ppm 1.42-1.61 (m, 2H), 2.02 (d, J=10.30 Hz, 2H), 2.76-2.91 (m, 1H), 3.22 (t, J=11.46 Hz, 2H), 3.96 (s, 2H), 4.80 (d, J=11.50 Hz, 2H), 6.62 (s, 1H), 7.20 (d, J=5.70 Hz, 1H), 7.29 (td, J=8.74, 3.01 Hz, 1H), 7.47 (dd, J=9.10, 4.60 Hz, 1H), 7.95 (dd, J=9.10, 2.96 Hz, 1H), 8.24 (d, J=5.70 Hz, 1H), 8.83 (d, J=1.75 Hz, 1H), 8.98 (d, J=1.75 Hz, 1H).

Preparation of Compound 199

Compound 199 was prepared as described herein below.

Step 1—Synthesis of
5-chloropyrido[3,4-b]pyrazin-3(4H)-one

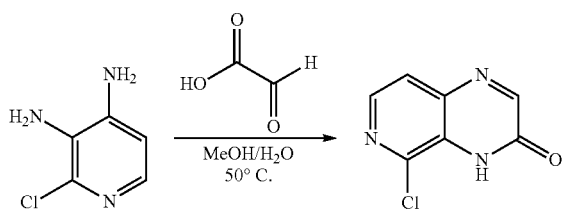 [SMILES: Nc1ccnc(Cl)c1N ; O=CC(=O)O ; O=c1cnc2ccnc(Cl)c2[nH]1]

A mixture of 2-chloropyridine-3,4-diamine (1 g, 6.96 mmol) and glyoxylic acid solution (50% wt in H$_2$O, 0.92 mL, 8.35 mmol) in MeOH (20 mL) was heated in a vial at 50° C. overnight. The mixture was cooled to room temperature and the solvent was removed in vacuum. The residue was triturated with Et$_2$O and the suspension was filtered. The crude product was purified by C-18 chromatography (from 100% water+0.1% formic acid to 80/20 water+0.1% formic acid/MeCN+0.1% formic acid) to give 5-chloropyrido[3,4-b]pyrazin-3(4H)-one (255 mg, 1.4 mmol, 20% yield). LC-MS (M−H+)=182.1

Step 2—Synthesis of
3,5-dichloropyrido[3,4-b]pyrazine

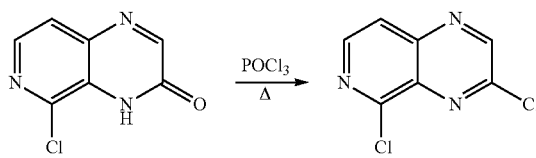

A mixture of 5-chloropyrido[3,4-b]pyrazin-3(4H)-one (200 mg, 1.1 mmol) and phosphorus oxychloride (6 mL) was refluxed for 2 hours. After cooling the solvent was reduced under vacuum. The reaction mixture was carefully poured onto ice and neutralized with a saturated solution of Na$_2$CO$_3$. DCM was added, the organic phase was washed with brine, dried over sodium sulfate and concentrated. The crude material was purified by NH-chromatography (from 100% DCM to 80/20 DCM/EtOAc) to obtain 3,5-dichloropyrido[3,4-b]pyrazine (200 mg, 1 mmol, 91% yield). LC-MS (M−H+)=200.1

Step 3—Synthesis of
5-chloro-3-methoxypyrido[3,4-b]pyrazine

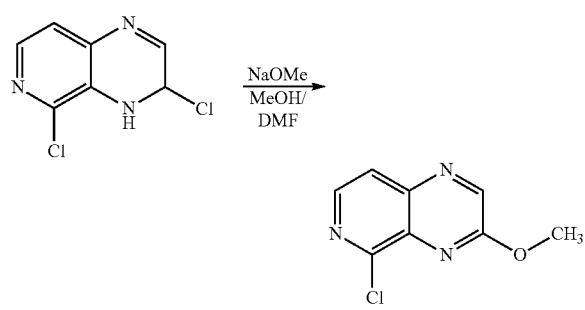

To a solution of 3,5-dichloropyrido[3,4-b]pyrazine (200 mg, 1 mmol) in DMF (3 mL) sodium methoxide (0.5 M solution in MeOH, 2.2 mL, 1.1 mmol) was added, and the reaction was stirred at room temperature for 10 minutes. The solution was diluted with water and extracted with EtOAc. The organic layer was dried over sodium sulfate, filtered and concentrated to afford 5-chloro-3-methoxypyrido[3,4-b]pyrazine (150 mg, 0.77 mmol, 77% yield). LC-MS (M−H+)= 196.1

Step 4—Synthesis of tert-butyl [1-(3-methoxypyrido[3,4-b]pyrazin-5-yl)piperidin-4-yl]carbamate

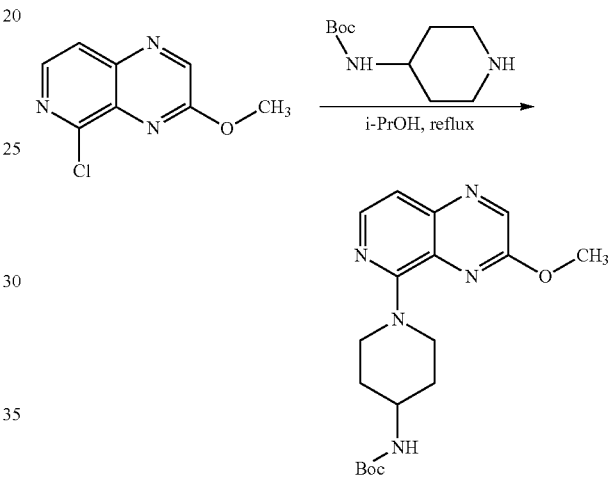

5-chloro-3-methoxypyrido[3,4-b]pyrazine (100 mg, 0.55 mmol) and 4-(N-Boc-amino)piperidine (332 mg, 1.66 mmol) were suspended in isopropanol (5 mL) and stirred under reflux for 2 hours. The reaction solution was concentrated and purified by NH-chromatography (from 100% DCM to 95/5 DCM/MeOH) to obtain tert-butyl [1-(3-methoxypyrido[3,4-b]pyrazin-5-yl)piperidin-4-yl]carbamate (170 mg, 0.47 mmol, 85% yield). LC-MS (M−H+)= 360.4

Step 5—Synthesis of 1-(3-methoxypyrido[3,4-b]pyrazin-5-yl)piperidin-4-amine

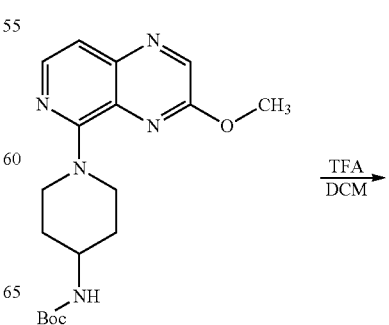

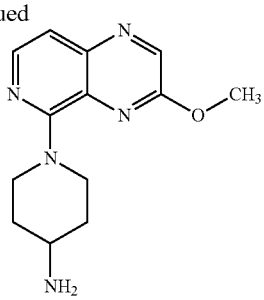

The title compound was prepared according to the procedure described for the synthesis of 1-(7-fluoroisoquinolin-1-yl)piperidin-4-amine (see compound 145) using tert-butyl [1-(3-methoxypyrido[3,4-b]pyrazin-5-yl)piperidin-4-yl]carbamate. Y=91%. LC-MS (M–H+)=260.3

Step 6—Synthesis of 8-fluoro-2-({[1-(3-methoxypyrido[3,4-b]pyrazin-5-yl)piperidin-4-yl]amino}methyl)[1]benzopyrano[3,4-b]pyrrol-4(3H)-one (formate salt, compound 199)

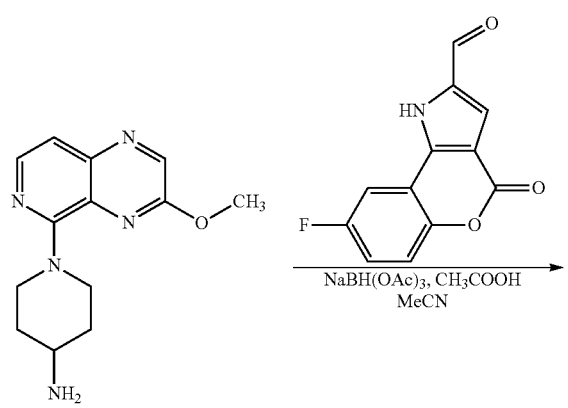

The title compound was prepared according to the procedure described for the synthesis of compound 187 using 1-(3-methoxypyrido[3,4-b]pyrazin-5-yl)piperidin-4-amine (Y=44%). LC-MS (M–H+)=475.2.

$^1$H NMR (400 MHz, DMSO-d6) δ ppm 1.35-1.53 (m, 2H), 1.89-2.02 (m, 2H), 2.69-2.84 (m, 1H), 3.11 (t, J=11.35 Hz, 2H), 3.90 (s, 2H), 3.99 (s, 3H), 4.60-4.71 (m, 2H), 6.57 (s, 1H), 6.98 (d, J=5.67 Hz, 1H), 7.26 (td, J=8.75, 3.03 Hz, 1H), 7.44 (dd, J=9.10, 4.60 Hz, 1H), 7.92 (dd, J=9.10, 3.03 Hz, 1H), 8.13 (d, J=5.48 Hz, 1H), 8.15 (s, 1H), 8.42 (s, 1H), 12.68 (br. s., 1H).

Preparation of Compound 203

Compound 203 was prepared as described herein below.

Step 1—Synthesis of 1-bromo-7-methoxyisoquinolin-3-amine

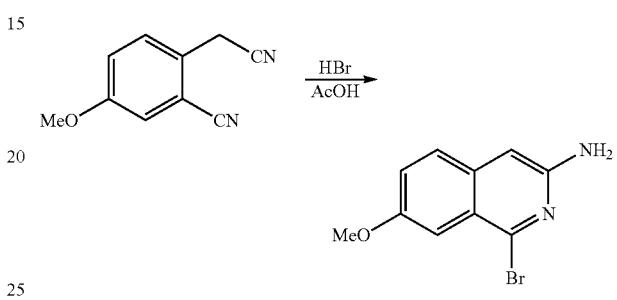

The title intermediate was prepared according to the procedure described for the synthesis of 2-(cyanomethyl)-5-fluorobenzonitrile (see compound 149) using 2-(cyanomethyl)-5-methoxybenzonitrile (Y=17%). LCMS m/z: 253.0 (M+1). $^1$H NMR (300 MHz, DMSO-d6) δ ppm 7.55 (d, J=9.1 Hz, 1H), 7.22 (dd, J=9.0, 2.5 Hz, 1H), 7.14 (d, J=2.5 Hz, 1H), 6.64 (s, 1H), 6.05 (s, 2H), 3.85 (s, 3H).

Step 2—Synthesis of 1-bromo-3-fluoro-7-methoxyisoquinoline

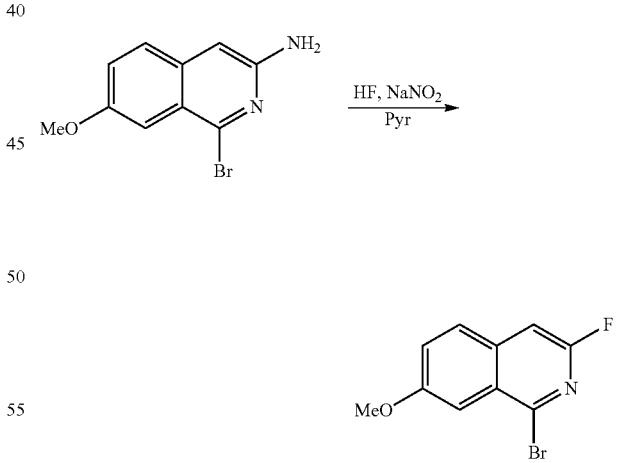

The title intermediate was prepared according to the procedure described for the synthesis of 1-bromo-3,7-difluoroisoquinoline (see compound 149) using 1-bromo-7-methoxyisoquinolin-3-amine (Y=66%). LCMS m/z: 256.0 (M+1).

$^1$H NMR (400 MHz, DMSO-d6) δ ppm 8.01 (d, J=9.0 Hz, 1H), 7.71 (s, 1H), 7.58 (dd, J=9.3, 2.2 Hz, 1H), 7.43 (d, J=2.4 Hz, 1H), 3.96 (s, 3H).

Step 3—Synthesis of 6-fluoro-4-({3-[4-(3-fluoro-7-methoxyisoquinolin-1-yl)piperazin-1-yl]-2-hydroxypropyl}amino)-2H-1-benzopyran-2-one (compound 203)

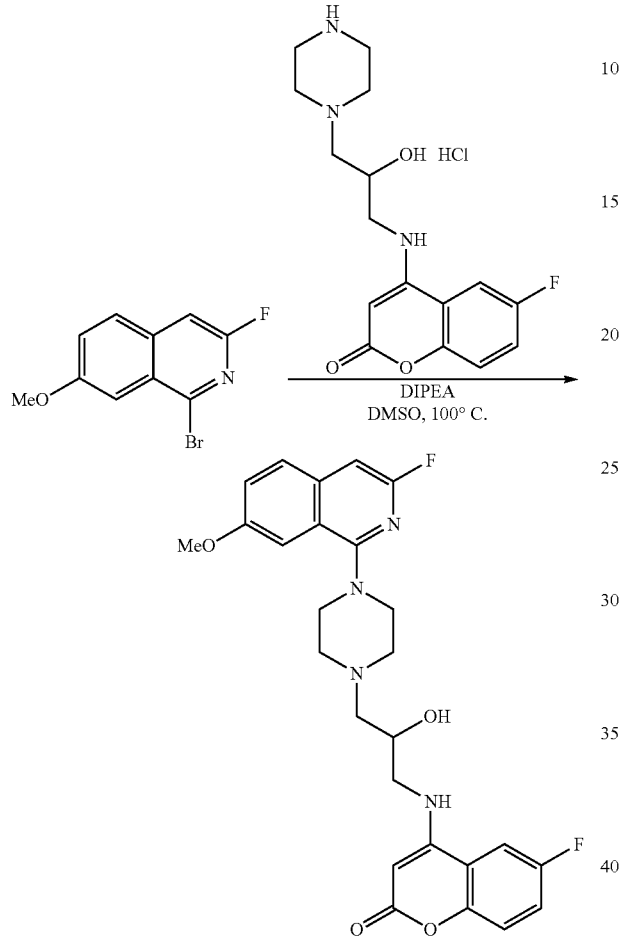

N,N-Diisopropylethylamine (1.7 mL, 9.57 mmol) was added to a stirred suspension of 1-bromo-3-fluoro-7-methoxyisoquinoline (490 mg, 1.91 mmol) and 6-fluoro-4-{[2-hydroxy-3-(piperazin-1-yl)propyl]amino}-2H-1-benzopyran-2-one hydrochloride (prepared as described in the synthesis of compound 166, 754 mg, 1.91 mmol) in DMSO (15 mL). The resulting mixture was stirred at 100° C. for 18 h then was cooled, poured into water (25 mL) and extracted with diethyl ether (3×25 mL) and with DCM (20 mL). The combined organic layers were dried over magnesium sulfate, filtered and concentrated. The crude was absorbed onto silica gel and purified by flash chromatography (DCM/MeOH/NH$_3$) to give 6-fluoro-4-({3-[4-(3-fluoro-7-methoxyisoquinolin-1-yl)piperazin-1-yl]-2-hydroxypropyl}amino)-2H-1-benzopyran-2-one (375 mg, 39% yield) as a beige solid. LCMS m/z: 497.1 (M+1).

$^1$H NMR (400 MHz, DMSO-d6) δ ppm 8.02 (dd, J=10.0, 2.9 Hz, 1H), 7.82 (d, J=9.0 Hz, 1H), 7.71 (t, J=5.5 Hz, 1H), 7.52-7.43 (m, 1H), 7.42-7.33 (m, 2H), 7.28 (d, J=2.4 Hz, 1H), 7.01 (s, 1H), 5.34 (s, 1H), 4.99 (d, J=4.8 Hz, 1H), 4.03-3.92 (m, 1H), 3.89 (s, 3H), 3.48-3.35 (m, 5H), 3.29-3.18 (m, 1H), 2.83-2.68 (m, 4H).

Preparation of Compound 89

Compound 89 was prepared as described hereinbelow, following the synthetic pathway R.

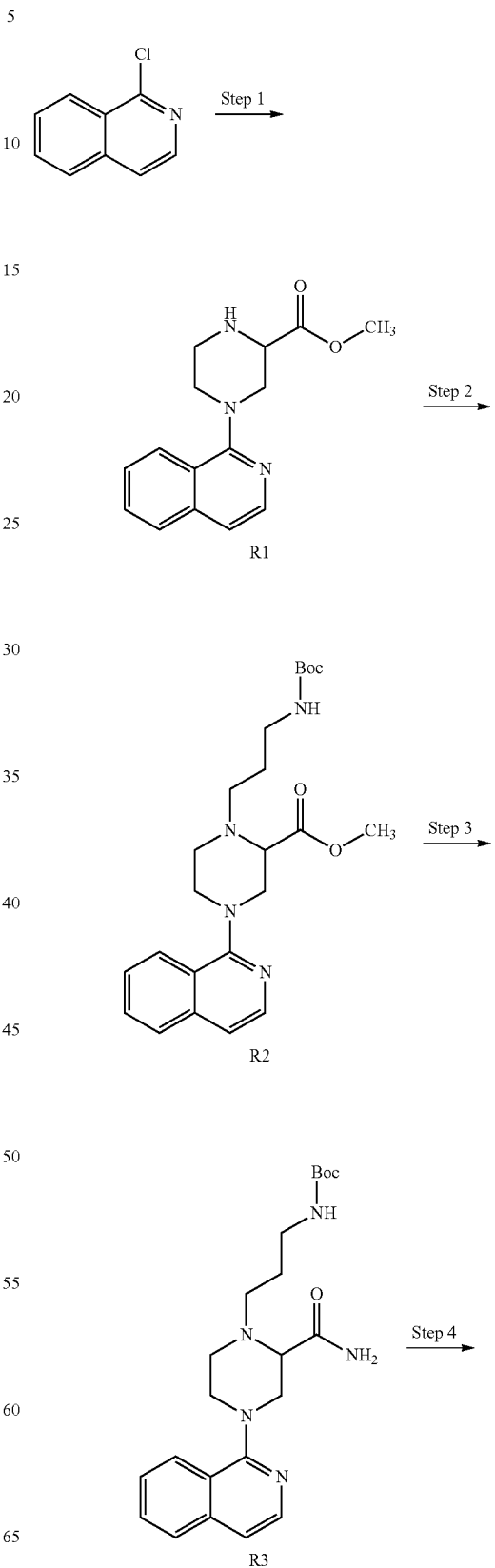

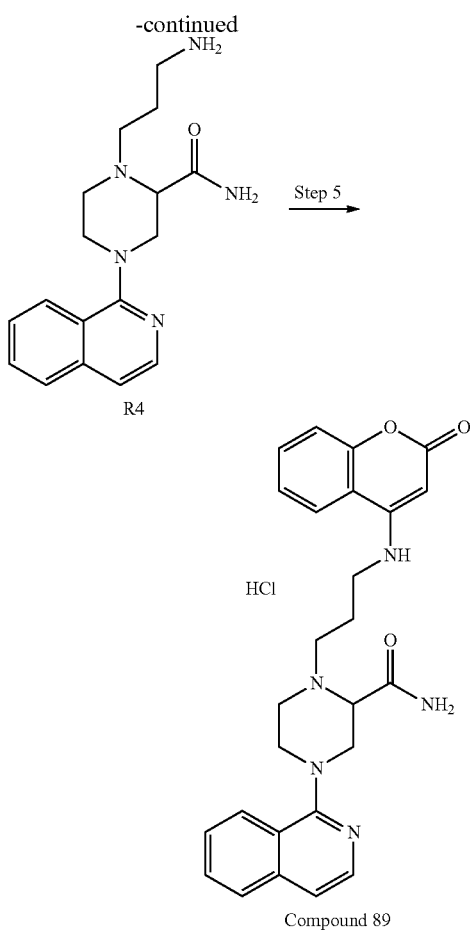

Step 1

A mixture of potassium carbonate (634 mg, 4.6 mmoles, 1.5 eq.), 1-chloroisoquinoline (500 mg, 3.1 mmoles, 1 eq.) and methyl piperazine-2-carboxylate (880 mg, 6.1 mmoles, 2 eq.) in DMSO (4 mL) was heated to 120° C. under microwave irradiation for 5 hours. The reaction was allowed to cool to room temperature. The solid was filtered, washed with water then dried under reduced pressure to give methyl 4-(isoquinolin-1-yl)piperazine-2-carboxylate, intermediate compound R1 (Y=81%).

Step 2

NaH (60% dispersion in mineral oil, 81 mg, 2 mmoles, 1.1 eq.) and tert-butyl N-(3-bromopropyl)carbamate (330 mg, 1.4 mmoles, 0.75 eq.) were added to a stirred solution of intermediate compound R1 (488 mg, 1.8 mmoles, 1 eq.) in anhydrous DMF (6 mL). The mixture was stirred for 4 hours then was quenched with water and extracted with ethyl acetate. The organic phase was dried over sodium sulfate and chromatographed on silica eluting with a gradient of 50-100% EtOAc in petroleum ether to give methyl 1-{3-[(tert-butoxycarbonyl)amino]propyl}-4-(isoquinolin-1-yl)piperazine-2-carboxylate intermediate compound R2 (Y=51%).

Step 3

To a solution of intermediate compound R2 (130 mg, 0.3 mmoles, 1 eq.) in THF/water 9:1 (10 mL) LiOH (13 mg, 0.33 mmoles, 1.1 eq.) was added. The mixture was stirred at 60° C. for 5 hours then was concentrated under reduced pressure. The crude material was dissolved in DMF (2 mL), TEA (62 µL, 0.45 mmoles, 1.5 eq.) was added followed by hexamethyldisilazane (72.4 mg, 0.45 mmoles, 1.5 eq.). The mixture was cooled to 0° C. and HATU (137 mg, 0.36 mmoles, 1.2 eq.) was added. After stirring 3 h at r.t. the solvent was evaporated in vacuum, the residue was dissolved in ethyl acetate and washed with brine. The organic phase was separated, dried and evaporated by vacuum. The crude material was purified by Si-column eluting with ethyl acetate to ethyl acetate/MeOH 95:5 to obtain 90 mg of tert-butyl {3-[2-carbamoyl-4-(isoquinolin-1-yl)piperazin-1-yl]propyl}carbamate, intermediate compound R3 (Y=58%). LC-MS (M−H+)=414.4

Step 4

TFA (1 mL) was added to a solution of intermediate compound R3 (78 mg, 0.2 mmoles, 1 eq.) in dichloromethane (3 mL) at room temperature and the resulting mixture was stirred for 60 minutes. The volatiles were evaporated under reduced pressure then the residue was dissolved in MeOH (2 mL) and loaded onto a preconditioned SCX cartridge (1 g). The SCX was eluted with MeOH and then a 2M solution of ammonia in methanol. The basic fractions were evaporated under reduced pressure to give 56 mg of 1-(3-aminopropyl)-4-(isoquinolin-1-yl)piperazine-2-carboxamide, intermediate compound R4 (Y=quant.). LC-MS (M−H+)=314.2

Step 5

A solution of intermediate compound R4 (56 mg, 0.2 mmoles, 1.1 eq.), triethylamine (37 µL, 0.27 mmoles, 1.5 eq.) and 2-oxo-2H-chromen-4-yl trifluoromethanesulfonate, intermediate compound A1 (53 mg, 0.18 mmoles, 1 eq.) in acetonitrile (2 mL) was heated to 70-C for 1 hour. The reaction mixture was concentrated under reduced pressure and the residue was partitioned between dichloromethane (10 mL) and a brine/sodium bicarbonate mixture (1:1, 10 mL). The mixture was filtered through a hydrophobic frit (Phase Separator) washing with dichloromethane (10 mL). The organic phase was evaporated under reduced pressure and the residue was chromatographed on NH-modified silica gel (2×SNAP 11 in series) eluting with a gradient of 20-100% EtOAc in cyclohexane to give 79 mg of a colorless sticky gum. The product was dissolved in dichloromethane (3 mL) and treated with 1 M HCl solution in diethyl ether (0.46 mL) causing precipitation. The resulting mixture was evaporated under reduced pressure and the residue was triturated with diethyl ether. The solids were dried to give 4-(isoquinolin-1-yl)-1-{3-[(2-oxo-2H-chromen-4-yl)amino]propyl}piperazine-2-carboxamide hydrochloride (compound 89) (Y=25%). LC-MS (M−H⁺)=458.4

Compound 89: 1H NMR (400 MHz, DMSO-d6) δ 10.23 (br. s., 1H), 8.38 (br. s., 1H), 8.19 (d, J=8.5 Hz, 1H), 8.15 (d, J=5.8 Hz, 1H), 8.05 (d, J=7.3 Hz, 1H), 7.99 (br. s., 1H), 7.96 (d, J=8.3 Hz, 1H), 7.83 (t, J=5.8 Hz, 1H), 7.78 (t, J=7.4 Hz, 1H), 7.70-7.64 (m, 1H), 7.64-7.58 (m, 1H), 7.54 (d, J=5.8 Hz, 1H), 7.39-7.29 (m, 2H), 5.29 (s, 1H), 4.49-3.82 (m, 4H), 3.75-3.53 (m, 2H), 3.48-3.19 (m, 6H), 2.24-1.93 (m, 2H)

Biological Assays

Example 1

Inhibition of DNA Gyrase and Topo IV in *E. coli* and *S. aureus*

The above compounds were tested for the inhibition of the enzyme DNA gyrase in a gyrase supercoiling assay and for the inhibition of the enzyme topoisomerase IV in a decatenation assay, in both Gram positive and Gram negative bacteria, according to the following methods.

Both the assays were carried out according to a set-up method modified from the article to Blanche F, et al. "Differential Behaviors of *Staphylococcus aureus* and *Escherichia coli* Type II DNA Topoisomerases", Antimicrob. Agents Chemother., 1996, Vol. 40, No. 12 p. 2714-2720.

The compounds were screened at single concentration (200, 100 or 50 µM), in duplicate.

Ciprofloxacin and novobiocin were used as reference compounds, at single concentration of 200 and 50 µM, respectively.

DNA Gyrase Supercoiling Assay.

Reagents from *S. aureus* and *E. coli* Gyrase Supercoiling Assay kits (Inspiralis, UK) were used. A master mix with a total volume sufficient for the number of reactions to perform was prepared with the following reagents: 5× assay buffer, relaxed pBR322 substrate (0.5 µg/reaction), RNase-DNase free water. Aliquotes of this mix were dispensed in each tube, then 10× compound stock solutions or vehicle control (DMSO), were added to each reaction tube.

Reaction was started with *E. Coli* (2 U/reaction) or *S. aureus* (1 U/reaction) gyrase enzyme addition.

A sample added with an equal volume of dilution buffer was used as negative control (without enzyme).

The reaction tubes were gentle vortexed and incubated 30 minutes at 37° C. Each reaction was stopped by adding 30 µl of Stop Buffer and 30 µl chloroform/isoamyl alcohol (24/1), briefly vortexed for 5-10 seconds and centrifuged at 20000×g for 2 minutes. Samples were loaded onto 1% agarose gel and subjected to electrophoresis for 1 hour at 80V constant voltage in TAE (40 mM Tris-acetate, 2 mM EDTA).

Data acquisition and analysis. Treatment of relaxed pBR322 with DNA gyrase converted the relaxed topoisomers (DNAs of different linking number) to the supercoiled form of the plasmid, which migrates faster on an agarose gel. An upper band might also be visible, which consists of open-circular (nicked) DNA which is present in the relaxed substrate but co-migrates with some of the relaxed topoisomers.

Bands were visualized by ethidium bromide staining (dilution 1:20000) for 30 minutes followed by destaining in distilled water for 10 minutes.

In order to evaluate the compounds activity on the enzyme, the bands of supercoiled DNAs in the gel were photographed by a digital imaging system ImageQuant LAS 4000 (GE Healthcare) according to manufacturer's instructions.

The fluorescent intensity of each band was analyzed by ImageQuant TL software and it was expressed as volume (volume of the uncalibrated quantity of material in the image feature after subtraction of the background intensity by using rolling ball method).

Each band intensity was compared, as percentage, to vehicle sample band intensity, which served as positive control, on the same gel.

Inhibitory activity was expressed as percent of inhibition versus the positive control.

The results are summarized in the following Table 2.

Topoisomerase IV Decatenation Assay

*S. aureus* and *E. coli* Topoisomerase IV decatenation kits (Inspiralis, UK) were used. A master mix with a total volume sufficient for the number of reactions to perform was prepared with the following reagents: 5× assay buffer (50 mM HEPES-KOH (pH 7.6), 100 mM potassium glutamate, 10 mM magnesium acetate, 10 mM DTT, 1 mM ATP, 50 µg/ml albumin), kDNA substrate (200 ng/reaction), RNase-DNase free water. Aliquots of this mix were dispensed in each tube, then 10× compound stock solutions or vehicle control (DMSO), were added in each reaction tube.

Reaction was started with Topoisomerase IV enzyme (0.5 U/reaction) addition.

A sample added with an equal volume of dilution buffer was used as negative control (without enzyme).

The reaction tubes were gentle vortexed and incubated 30 minutes at 37° C. Each reaction was stopped by adding 30 µl of Stop Buffer and 30 µl of chloroform/isoamyl alcohol (24/1), briefly vortexed for 5-10 seconds and centrifuged at 20000×g for 2 minutes. Samples taken from the upper phase were loaded into 1% agarose gel and subjected to electrophoresis for 1 hour at 80V constant voltage in TAE (40 mM Tris-acetate, 2 mM EDTA).

Data acquisition and analysis. Due to the high molecular mass, kDNA could not enter an agarose gel under normal electrophoresis conditions, but remained in the wells. In the presence of Topo IV topoisomerase mini-circles (2.5 Kb) were released from kDNA by decatenation and were quickly and easily resolved in the gel at relatively high voltages.

Bands were visualized by ethidium bromide staining (dil 1:20000) for 30 minutes followed by destaining in distilled water for 10 minutes.

For single concentration screening assay, in order to evaluate the compounds activity on the enzymes, the bands of decatenated DNAs in the gel were photographed by a digital imaging system ImageQuant LAS 4000 (GE Healthcare) according to manufacturer's instructions.

The fluorescent intensity of each band was analyzed by ImageQuant TL software and it was expressed as volume (volume of the uncalibrated quantity of material in the image feature after subtraction of the background intensity by using rolling ball method).

Each band intensity was compared, as percentage, to vehicle sample band intensity, which served as positive control, on the same gel.

Inhibitory activity was expressed as percent of inhibition versus the positive control.

The results are summarized in the following Table 2.

TABLE 2

| | | E. coli | | S. aureus | |
| --- | --- | --- | --- | --- | --- |
| Compound No. | conc. (µM) | % inhibition DNA gyrase | % inhibition Topo IV | % inhibition DNA gyrase | % inhibition Topo IV |
| 27 | 200 | 61 | 53 | n/a | n/a |
| 29 | 200 | 92 | 100 | 86 | n/a |
| 40 | 200 | 54 | 78 | n/a | n/a |
| 44 | 200 | 100 | 100 | 100 | 65 |
| 46 | 200 | 57 | 94 | 100 | n/a |
| 51 | 100 | 100 | 88 | 91 | n/a |
| 52 | 100 | 100 | 96 | 81 | n/a |
| 54 | 100 | 89 | 52 | n/a | n/a |
| 55 | 100 | 94 | 95 | 86 | n/a |
| 56 | 100 | 96 | 79 | 70 | n/a |
| 59 | 100 | 81 | 100 | 90 | 77 |
| 61 | 100 | 92 | 92 | 88 | n/a |
| 62 | 100 | 96 | 71 | 86 | n/a |
| 63 | 100 | 98 | 51 | n/a | n/a |
| 64 | 100 | 93 | 94 | 93 | n/a |
| 65 | 100 | 94 | 80 | 80 | n/a |
| 66 | 100 | 100 | 58 | 87 | n/a |
| 67 | 100 | 89 | 100 | 97 | 100 |
| 69 | 100 | 94 | 51 | 88 | n/a |
| 72 | 100 | 98 | 91 | 97 | 76 |
| 73 | 100 | 85 | n/a | 93 | 49 |
| 77 | 50 | 93 | 73 | 85 | n/a |

TABLE 2-continued

|  |  | E. coli | | S. aureus | |
| --- | --- | --- | --- | --- | --- |
| Compound No. | conc. (µM) | % inhibition DNA gyrase | % inhibition Topo IV | % inhibition DNA gyrase | % inhibition Topo IV |
| 78 | 50 | 89 | 65 | 81 | n/a |
| 79 | 50 | 100 | 100 | 87 | 92 |
| 80 | 50 | 100 | 100 | 92 | 89 |
| 86 | 50 | 96 | 64 | 95 | 53 |
| 88 | 50 | 100 | 100 | 100 | 88 |
| 89 | 50 | 87 | 51 | n/a | n/a |
| 90 | 50 | 93 | 81 | 89 | n/a |
| 91 | 50 | 99 | 95 | 95 | 67 |
| 93 | 50 | 100 | 100 | 95 | 63 |
| 94 | 50 | 100 | 91 | 100 | 88 |
| 95 | 50 | 92 | 53 | 81 | n/a |
| 98 | 50 | 93 | 90 | 90 | n/a |
| 99 | 50 | 98 | 100 | 94 | 92 |
| 100 | 50 | 95 | 76 | 91 | n/a |
| 102 | 50 | 100 | 100 | 100 | 100 |
| 103 | 50 | 98 | 100 | 100 | 100 |
| 104 | 50 | 100 | 100 | 100 | 100 |
| 105 | 50 | 91 | 66 | 100 | n/a |
| 106 | 50 | 100 | 100 | 100 | 68 |
| 108 | 50 | 100 | 76 | 100 | n/a |
| 109 | 50 | 100 | 72 | 100 | n/a |
| 124 | 50 | 79 | 62 | 75 | n/a |
| 125 | 50 | 86 | 68 | 89 | n/a |
| 126 | 50 | 96 | 100 | 95 | 86 |
| 127 | 50 | 89 | 70 | 76 | n/a |
| 131 | 50 | 100 | 100 | 81 | 78 |
| 134 | 50 | 87 | 78 | 71 | n/a |
| 143 | 50 | 96 | 91 | 89 | n/a |
| 144 | 50 | 72 | 85 | 65 | n/a |
| 145 | 50 | 99 | 100 | 97 | n/a |
| 146 | 50 | 91 | 100 | 93 | n/a |
| 147 | 50 | 84 | 74 | 85 | n/a |
| 148 | 50 | 96 | 100 | 100 | 100 |
| 149 | 50 | 90 | 90 | 100 | 100 |
| 150 | 50 | 50 | 50 | 100 | 50 |
| 152 | 50 | 88 | 100 | 100 | 88 |
| 153 | 50 | 72 | 50 | 100 | 61 |
| 155 | 50 | 60 | 0 | 50 | 50 |
| 156 | 50 | 78 | 91 | 89 | 86 |
| 158 | 50 | 95 | 97 | 100 | 100 |
| 159 | 50 | 94 | 98 | 100 | 100 |
| 162 | 50 | 95 | 100 | 100 | 100 |
| 163 | 50 | 80 | 90 | 30 | 100 |
| 166 | 50 | 80 | 90 | 70 | 97 |
| 171 | 50 | 93 | 97 | 100 | 72 |
| 172 | 50 | 94 | 89 | 64 | 39 |
| 177 | 50 | 77 | 74 | 98 | 14 |
| 184 | 50 | 68 | 58 | 83 | 69 |
| 186 | 50 | 70 | 54 | 100 | 87 |
| 187 | 50 | 79 | 82 | 95 | 95 |
| 188 | 50 | 100 | 92 | 97 | 98 |
| 192 | 50 | 70 | 37 | 88 | 76 |
| 195 | 50 | 99 | 100 | 100 | 100 |
| 196 | 50 | 85 | 100 | 83 | 89 |
| 199 | 50 | 90 | 100 | 92 | 100 |
| 203 | 50 | 100 | 100 | 100 | 100 | n/a = not active

The above results showed that the exemplified compounds effectively inhibited both DNA gyrase and Topo IV of E. coli, which is a Gram positive bacteria, and/or S. aureus, which is a Gram negative bacteria.

Example 2

Determination of $IC_{50}$

The compounds that in the above example 1 showed an inhibitory activity higher than selected cut-off (i.e., at least 50% inhibition at single concentration) were further assayed in concentration-response curve (eight half-log concentrations ranging from 0.1 to 300 µM) in order to determine the $IC_{50}$.

The supercoiled or decatenated DNA bands obtained as described in Example 1 were analysed as follows.

Bands were analyzed by gel documentation equipment (Syngene, Cambridge, UK) and quantitated using Syngene Gene Tools software. Raw gel data (fluorescent band volumes) collected from Syngene, GeneTools gel analysis software were converted to a percentage of the 100% control (the fully supercoiled or decatenated DNA band). These data were analyzed using SigmaPlot Version 12.3 (2013). The $IC_{50}$ data were calculated by using the global curve fit non-linear regression tool by selecting the Single, 2 Parameter fit function from the Exponential Decay equation category.

The results are reported in the following table 3.

TABLE 3

|  | E. coli | | S. aureus | |
| --- | --- | --- | --- | --- |
| Compound No. | $IC_{50}$ DNA gyrase | $IC_{50}$ Topo IV | $IC_{50}$ DNA gyrase | $IC_{50}$ Topo IV |
| 29 | 6 | 10 | 20 | — |
| 44 | 0.5 | 10 | 14 | 90 |
| 51 | 0.9 | 2.4 | 4.5 | — |
| 52 | 2.3 | 1.7 | 6.8 | — |
| 55 | 2.1 | 2.6 | 5.6 | — |
| 56 | 4.8 | 13.1 | 33.1 | — |
| 59 | 1.2 | 16.1 | 4.4 | 18.5 |
| 61 | 3.3 | 20.2 | 8.7 | — |
| 62 | 22.3 | 6.7 | 6.9 | — |
| 64 | 20.4 | 16.5 | 5.2 | — |
| 65 | 40.6 | 29.3 | 26.8 | — |
| 66 | 2.3 | 3.2 | 12.1 | — |
| 67 | 0.8 | 1.7 | 2.8 | 11.8 |
| 69 | 12 | 51 | 300 | — |
| 72 | 2.6 | 3.8 | 9.6 | 52 |
| 73 | 66 | — | 43.3 | 136.9 |
| 77 | 6.8 | 3.8 | 13.9 | — |
| 78 | 19.5 | 6.8 | 6.3 | — |
| 79 | 0.6 | 1.2 | 5.2 | 5.5 |
| 80 | 1.2 | 1.3 | 3.9 | 3.1 |
| 86 | 7.6 | 7.8 | 3.7 | 52.8 |
| 88 | 3.2 | 0.9 | 1.1 | 6.7 |
| 89 | 28 | 54 | 33 | — |
| 90 | 8.3 | 15.5 | 9.3 | — |
| 91 | 0.9 | 1.9 | 2.6 | 7.1 |
| 93 | 2.2 | 3.8 | 5.2 | 6.9 |
| 94 | 4.8 | 3.0 | 4.2 | 13.8 |
| 95 | 5.6 | 3.9 | — | — |
| 98 | 5.6 | 8.8 | 4.6 | — |
| 99 | 2.1 | 1.5 | 0.4 | 3.5 |
| 100 | 4.5 | 10.2 | 4.7 | — |
| 102 | 1.8 | 1.1 | 1.5 | 1.7 |
| 103 | 1.1 | 1.3 | 1.6 | 3.0 |
| 104 | 1.5 | 0.4 | 0.6 | 0.3 |
| 105 | 11.4 | 5.6 | 6.6 | — |
| 106 | 2.7 | 2.2 | 1 | 0.6 |
| 108 | 1.0 | 1.8 | 4.8 | — |
| 109 | 5.1 | 5.6 | 20.7 | — |
| 124 | 7.0 | 6.0 | 9.0 | — |
| 125 | 6.3 | 59 | 19 | — |
| 126 | 1.3 | 8.0 | 1.3 | 15 |
| 127 | 2.9 | 52.5 | — | — |
| 134 | 2.8 | 2.5 | 0.81 | 1.72 |
| 148 | 0.42 | 0.12 | 0.024 | 0.05 |
| 149 | 0.1 | 0.14 | 0.018 | 0.04 |
| 150 | 17.1 | 4.24 | 1.02 | 5.89 |
| 152 | 0.66 | 0.85 | 0.31 | 0.53 |
| 153 | 1.42 | 1.34 | 0.49 | 2.3 |
| 155 | 6.31 | — | 8.74 | 7.21 |
| 156 | 2.74 | 0.64 | 1.76 | 1.25 |
| 158 | 1.86 | 0.92 | 0.86 | 2.13 |

TABLE 3-continued

| Compound No. | E. coli IC$_{50}$ DNA gyrase | IC$_{50}$ Topo IV | S. aureus IC$_{50}$ DNA gyrase | IC$_{50}$ Topo IV |
|---|---|---|---|---|
| 159 | 1.65 | 1.04 | 0.51 | 1.09 |
| 162 | 4.85 | 0.95 | 0.88 | 0.31 |
| 163 | 4.4 | 9.89 | 82.7 | 1.22 |
| 166 | 0.15 | 0.2 | 1.13 | 0.3 |
| 187 | 0.19 | 1.57 | 0.16 | 1.37 |
| 188 | 0.09 | 0.3 | 0.015 | 0.2 |
| 192 | 0.08 | 0.13 | 0.017 | 0.1 |
| 195 | 0.14 | 0.3 | 0.1 | 0.1 |
| 196 | 0.79 | 2.54 | 0.16 | 0.39 |

The invention claimed is:

1. A compound of formula (I):

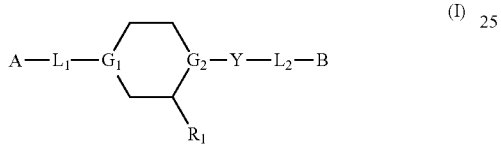

(I)

wherein $G_1$ and $G_2$, identical or different from each other, are CH or N, provided that at least one of $G_1$ and $G_2$ is N;

$R_1$ is hydrogen atom, halogen atom, OH, $(C_{1-3})$alkyl, $(C_{1-3})$alkoxy, $(C_{1-3})$alkyl-OH, —COOR' or —CONR'R", wherein R' and R", identical or different from each other, are hydrogen atom or $(C_{1-3})$alkyl;

$L_1$ is a σ bond, —O— or —NH—;

Y is ethylene, n-propylene, n-butylene, isobutylene, sec-butylene, tert-butylene, pentylene, isopentylene, sec-pentylene, tert-pentylene, neo-pentylene, 3-pentylene, hexylene, isohexylene, —NH—$(C_{1-6})$alkylenyl group or $(C_{4-5})$cycloalkylenyl group, said group being optionally substituted with a hydroxy group or an amino group or a formamido group-(NH—CHO);

$L_2$ is σ bond, —NH— or —NH—$(C_{1-6})$alkylenyl-;

A is a fused bicyclic group having one of the following formulae (II) and (III)

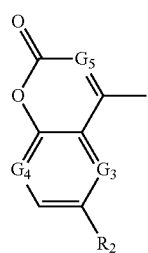

(II)

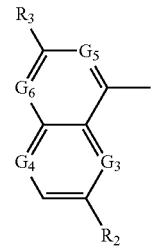

(III)

wherein $G_3$ is N or C(R'), wherein R' is H or $(C_{1-3})$alkyl;

$G_4$, $G_5$, and $G_6$, identical or different from each other, are CH, CF, C—CN, or N, $R_2$ is hydrogen atom, halogen atom, hydroxy, cyano, $(C_{1-3})$alkyl, $(C_{1-3})$alkoxy, $CF_3$, $OCF3$ or NR'R", wherein R' and R", identical or different from each other, are hydrogen atom or $(C_{1-3})$alkyl; and $R_3$ is hydrogen atom, halogen atom, hydroxy, cyano, $(C_{1-3})$alkyl, $(C_{1-3})$alkoxy, trifluoromethyl or NR'R", wherein R' and R" are hydrogen atom or $(C_{1-3})$alkyl;

and

B is a fused bicyclic or tricyclic group having one of the following formulae:

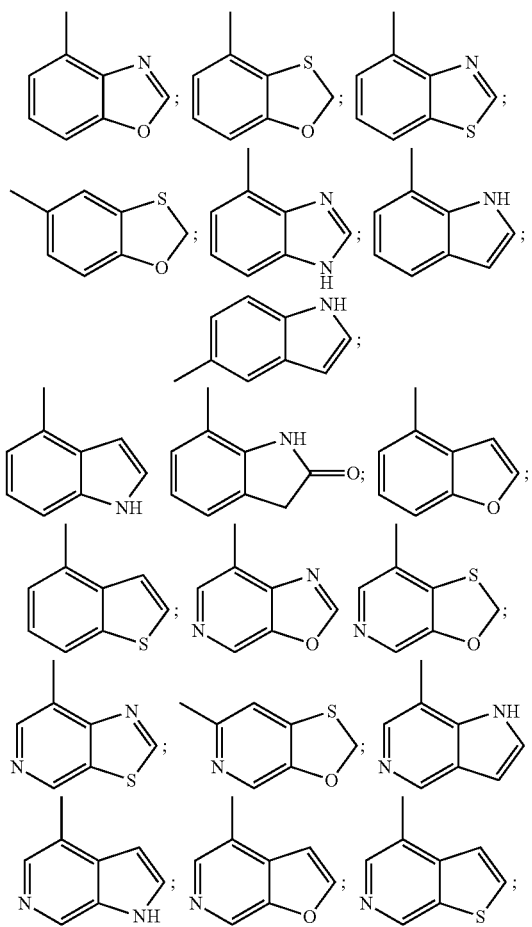

-continued

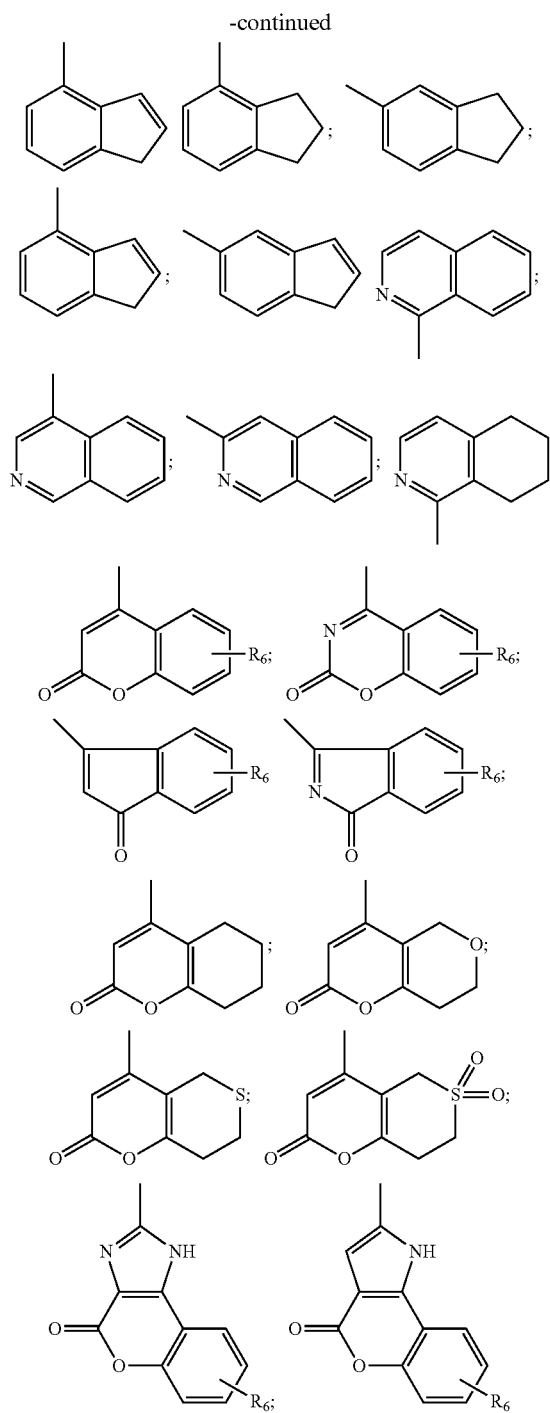

wherein R₆ is hydrogen atom, halogen atom, CF₃, hydroxy or NR'R", wherein R' and R", identical or different from each other, are hydrogen atom or $(C_{1-3})$alkyl, or an addition salt with a pharmaceutically acceptable organic or inorganic acid or base, an enantiomer, N-oxide, or quaternary ammonium salt of said compound of formula (I).

2. The compound, salt, or N-oxide according to claim 1, wherein A is a fused bicyclic ring having one of the following formulae:

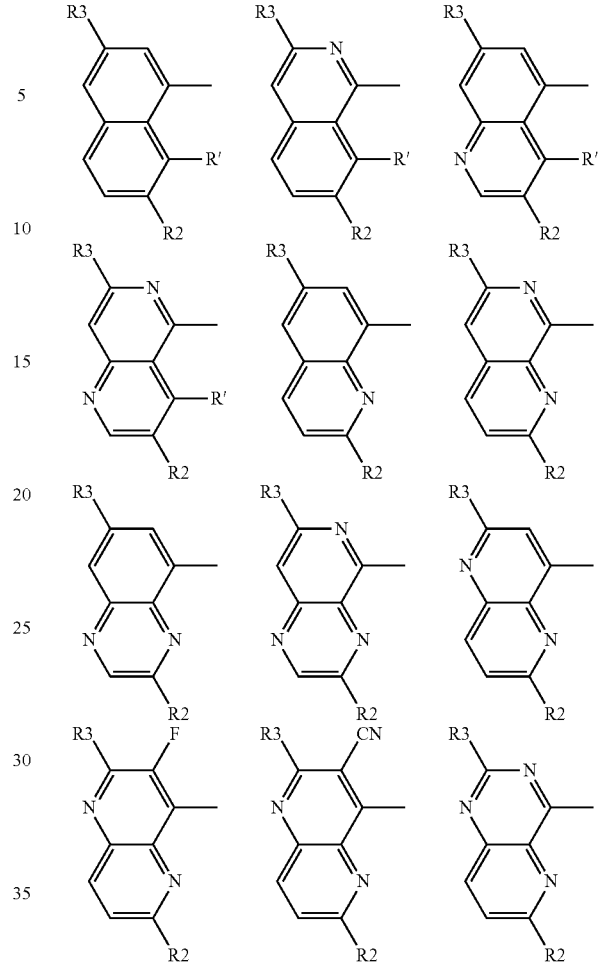

wherein

R' is H or $(C_{1-3})$alkyl

R₂ is hydrogen atom, halogen atom, hydroxy, cyano, $(C_{1-3})$alkyl, $(C_{1-3})$alkoxy, OCF₃ or NR'R", wherein R' and R", identical or different each other, are hydrogen atom or $(C_{1-3})$alkyl; and R₃ is hydrogen atom, halogen atom, hydroxy, cyano, $(C_{1-3})$alkyl, $(C_{1-3})$alkoxy, trifluoromethyl or NR'R", wherein R' and R" are hydrogen atom or $(C_{1-3})$alkyl.

3. The compound, salt, or N-oxide according to claim 1, wherein G3 is N, CH or C(CH₃).

4. The compound, salt, or N-oxide according to claim 1, wherein R₃ is hydrogen atom, halogen atom, cyano, $(C_{1-3})$ alkyl or NR'R", wherein R' and R" are hydrogen atom or $(C_{1-3})$alkyl.

5. The compound, salt, or N-oxide according to claim 1, wherein R₃ is hydrogen atom, F, Cl, cyano, CH₃, NH₂ or N(CH₃)₂.

6. The compound, salt, or N-oxide according to claim 1, wherein said R₁ is hydrogen atom, fluorine atom, chloride atom, OH, $(C_{1-3})$alkyl-OH, —COOR' or —CON(R')(R"), wherein R' and R", identical or different from each other, are hydrogen atom or $(C_{1-3})$alkyl.

7. The compound, salt, or N-oxide according to claim 1, wherein said R₂ is hydrogen atom, halogen atom, cyano, $(C_{1-3})$alkyl, $(C_{1-3})$alkoxy, or NR'R", wherein R' and R", identical or different from each other, are hydrogen atom or $(C_{1-3})$alkyl.

8. The compound, salt, or N-oxide according to claim 1, wherein said Y is ethylene, n-propylene, n-butylene, isobutylene, sec-butylene, tert-butylene, —NH—($C_{1-4}$)alkylenyl group or ($C_{4-5}$)cycloalkylenyl group, said group being optionally substituted with one hydroxy group or an amino group.

9. A pharmaceutical composition, comprising at least one compound of formula (I) according to claim 1, a salt thereof with a pharmaceutically acceptable organic or inorganic acid or base, or an enantiomer thereof, or a quaternary ammonium salt thereof, or a N-oxide thereof, and at least one inert pharmaceutically acceptable excipient.

10. A method for treating a bacterial infection, comprising administering an effective amount of a compound, salt, or N-oxide according to claim 1 to a patient in need thereof.

11. The method according to claim 10, wherein said bacterial infections is selected from the group consisting of a skin infection, a mucosal infection, a gynecological infection, a respiratory tract infection (RTI), a CNS infections, a gastro-intestinal infection, a bone infection, a cardiovascular infection, a sexually transmitted infection, or a urinary tract infection.

* * * * *